(12) United States Patent
Cavet et al.

(10) Patent No.: US 9,200,324 B2
(45) Date of Patent: Dec. 1, 2015

(54) BIOMARKERS AND METHODS FOR MEASURING AND MONITORING INFLAMMATORY DISEASE ACTIVITY

(75) Inventors: Guy L. Cavet, Burlingame, CA (US); Yijing Shen, San Mateo, CA (US); Nicholas Knowlton, Choctaw, OK (US); Michael Centola, Oklahoma City, OK (US)

(73) Assignees: CRESCENDO BIOSCIENCE, South San Francisco, CA (US); OKLAHOMA MEDICAL RESEARCH FOUNDATION, Oklahoma City, OK (US)

( * ) Notice: Subject to any disclaimer, the term of this patent is extended or adjusted under 35 U.S.C. 154(b) by 298 days.

(21) Appl. No.: 12/905,984

(22) Filed: Oct. 15, 2010

(65) Prior Publication Data

US 2011/0137851 A1 Jun. 9, 2011

Related U.S. Application Data

(60) Provisional application No. 61/252,110, filed on Oct. 15, 2009, provisional application No. 61/304,317, filed on Feb. 12, 2010, provisional application No. 61/355,087, filed on Jun. 15, 2010.

(51) Int. Cl.
| | |
|---|---|
| G01N 33/53 | (2006.01) |
| G01N 33/00 | (2006.01) |
| G01N 33/543 | (2006.01) |
| G01N 33/564 | (2006.01) |
| C12Q 1/68 | (2006.01) |
| G06F 19/24 | (2011.01) |

(52) U.S. Cl.
CPC .............. *C12Q 1/6883* (2013.01); *G01N 33/53* (2013.01); *C12Q 2600/118* (2013.01); *C12Q 2600/158* (2013.01); *G01N 2800/102* (2013.01); *G01N 2800/60* (2013.01); *G06F 19/24* (2013.01)

(58) Field of Classification Search
None
See application file for complete search history.

(56) References Cited

U.S. PATENT DOCUMENTS

| 8,058,013 B2 | 11/2011 | Karl et al. |
|---|---|---|
| 2005/0142569 A1 | 6/2005 | Guild et al. |
| 2006/0094056 A1 | 5/2006 | Chappell et al. |
| 2006/0286586 A1 | 12/2006 | Drexhage et al. |
| 2007/0172888 A1 | 7/2007 | Hallermayer et al. |
| 2008/0026485 A1 | 1/2008 | Hueber et al. |
| 2009/0270272 A1 | 10/2009 | Karl et al. |
| 2011/0269633 A1 | 11/2011 | Bilello et al. |
| 2012/0258883 A1 | 10/2012 | Chappell et al. |
| 2014/0005071 A1 | 1/2014 | Chappell et al. |

FOREIGN PATENT DOCUMENTS

| JP | 2007-506100 A | 3/2007 |
|---|---|---|
| JP | 2009-524807 A | 7/2009 |
| JP | 2010-506147 A | 2/2010 |
| JP | 2011-520095 A | 7/2011 |
| WO | WO 2005/029091 A2 | 3/2005 |
| WO | 2007039280 | 4/2007 |
| WO | WO 2007/085411 A | 8/2007 |
| WO | WO 2008/037420 A1 | 4/2008 |
| WO | WO 2009/114627 A2 | 9/2009 |

OTHER PUBLICATIONS

Smolen et al. (Arthritis Research Therapy (2008) vol. 10, pp. 208-219; Published May 2008).*
Hueber et al. (Arthritis & Rheumatism (2005) vol. 52, pp. 2645-2655).*
Coffman et al. Critical Reviews in Clinical Laboratory Sciences (2008) vol. 46, No. 6, pp. 531-562.*
Klooster et al. (Arthritis Research Ther. (2005) vol. 7, pp. R127-R138).*
Wislowska et al. (Rheumatol. International (2007) vol. 27, pp. 947-954).*
Green et al. (Rheumatology (2003) vol. 42, pp. 83-88).*
Senolt et al. (Ann. Rheum. Dis. (2007) vol. 66, pp. 458-463.*
Morel et al. (The Journal of Biol. Chem. (2002) vol. 277, pp. 34679-34691.*
Afuwape et al. (Histol. Histopathol. (2002) vol. 17, pp. 9612-9972.*
Aletaha, D. et al., "Remission and Active Disease in Rheumatoid Arthritis," Arthritis & Rheumatism, Sep. 2005, pp. 2625-2636, vol. 52, No. 9.
"Evidence-Based Rheumatology," ed. M. Matucci Cerinic, Clin. Exp. Rheum. 2002, pp. 443-444, vol. 20, No. 4.
Felson, D.T. et al., "The American College of Rheumatology Preliminary Core Set of Disease Activity Measures for Rheumatoid Arthritis Clinical Trials," Arthritis & Rheumatism, Jun. 1993, pp. 729-740, vol. 36, No. 6.
Felson, D.T. et al., "American College of Rheumatology: Preliminary Definition of Improvement in Rheumatoid Arthritis," Arthritis & Rheumatism, Jun. 1995, pp. 727-735, vol. 38, No. 6.
Fransen, J. et al., "Validity of the Disease Activity Score in Undifferentiated Arthritis," Arthritis Care and Research, Oct. 2010, pp. 1392-1398, vol. 62, No. 10.

(Continued)

*Primary Examiner* — Lori A Clow
(74) *Attorney, Agent, or Firm* — Myriad Genetics, Inc. Intellectual Property Department

(57) ABSTRACT

Biomarkers useful for diagnosing and assessing inflammatory disease are provided, along with kits for measuring their expression. The invention also provides predictive models, based on the biomarkers, as well as computer systems, and software embodiments of the models for scoring and optionally classifying samples. The biomarkers include at least two biomarkers selected from the DAIMRK group and the score is a disease activity index (DAI).

4 Claims, 66 Drawing Sheets

(56) References Cited

OTHER PUBLICATIONS

Gossec, L. et al., "Prognostic Factors for Remission in Early Rheumatoid Arthritis: A Multiparameter Prospective Study," Ann. Rheum. Dis., 2004, pp. 675-680, vol. 63, No. 6.
Grigor, C. et al., "Effect of a Treatment Strategy of Tight Control for Rheumatoid Arthritis (the TICORA Study): A Single-Blind Randomised Controlled Trial," Lancet, 2004, pp. 263-269, vol. 364.
Güler-Yüksel, M. et al., "Changes in Hand and Generalised Bone Mineral Density in Patients with Recent-Onset Rheumatoid Arthritis," Ann. Rheum. Dis. 2009 (Epublication Jan. 20, 2009), pp. 330-336, vol. 68.
Jarvis, J. et al., "Gene-Expression Profiling: Time for Clinical Application?" Lancet, Jan. 15, 2005, pp. 199-200, vol. 365.
Khan, N.A. et al., "Duration of Morning Stiffness in the Assessment of Rheumatoid Arthritis Activity: A Questionable Issue," (Abstract) ACR/ARHP Scientific Meeting 2008, 1 page.
Kroot, E.J.A. et al., "The Prognostic Value of Anti-Cyclic Citrullinated Peptide Antibody in Patients with Recent-Onset Rheumatoid Arthritis," Arthitis & Rheumatism, Aug. 2000, pp. 1831-1835, vol. 43, No. 8.
Mäkinen, H. et al., "Is DAS28 an Appropriate Tool to Assess Remission in Rheumatoid Arthritis?" Ann. Rheum. Dis., 2005, pp. 1410-1413, vol. 64.
Mallya, R.K. et al., "Correlation of Clinical Parameters of Disease Activity in Rheumatoid Arthritis with Serum Concentration of C-Reactive Protein and Erythrocyte Sedimentation Rate," The Journal of Rheumatology, 1982, pp. 224-228, vol. 9, No. 2.
Nadareishvili, Z. et al., "Cardiovascular, Rheumatologic, and Pharmacologic Predictors of Stroke in Patients with Rheumatoid Arthritis: A Nested, Case-Controlled Study," Arthitis Rheum., Aug. 15, 2008, pp. 1090-1096, vol. 59, No. 8.
PCT International Search Report and Written Opinion, PCT Application No. PCT/US10/52970, Dec. 16, 2010, 18 pages.
Pearson, T.A. et al., "Markers of Inflammation and Cardiovascular Disease: Application to Clinical and Public Health Practice: A Statement for Healthcare Professionals From the Centers for Disease Control and Prevention and the American Heart Association," Circulation 2003, pp. 499-511, vol. 107, No. 3.
Pincus, T. et al., "Relative Versus Absolute Goals of Therapies for RA: ACR 20 or ACR 50 Responses Versus Target Values for "Near Remission" of DAS or Single Measures," Clin. Exp. Rheum. 2004, pp. S50-S56, vol. 22, Suppl. 35.
Plant, M.J. et al., "Relationship Between Time-Integrated C-Reactive Protein Levels and Radiologic Progression in Patients with Rheumatoid Arthritis," Arthitis & Rheumatism, Jul. 2000, pp. 1473-1477, vol. 43, No. 7.
Prevoo, M.L.L. et al., "Modified Disease Activity Scores That Include Twenty-Eight-Joint Counts," Arthritis & Rheumatism, Jan. 1995, pp. 44-48, vol. 38, No. 1.
Ridker, P.M. et al., "C-Reactive Protein and Other Markers of Inflammation in the Prediction of Cardiovascular Disease in Women," The New England Journal of Medicine, Mar. 23, 2000, pp. 836-843, vol. 342, No. 12.
Smolen, S. et al., "A Simplified Disease Activity Index for Rheumatoid Arthritis for Use in Clinical Practice," Rheumatology (Oxford), 2003, pp. 244-257, vol. 42.
Stucki, G. et al., "A Self-Administered Rheumatoid Arthritis Disease Activity Index (RADAI) for Epidemiologic Research," Arthritis & Rheumatism, Jun. 1995, pp. 795-798, vol. 38, No. 6.
Van Gestel, A.M. et al., "Validation of Rheumatoid Arthritis Improvement Criteria That Include Simplified Joint Counts," Arthritis & Rheumatism, Oct. 1998, pp. 1845-1850, vol. 41, No. 10.
Van Leeuwen, M. et al., "The Acute-Phase Response in Relation to Radiographic Progression in Early Rheumatoid Arthritis: A Prospective Study During the First Three Years of the Disease," British Journal of Rheumatology, 1993, pp. 9-13, vol. 32 (suppl. 3).
Verstappen, S.M.M. et al., "Intensive Treatment with Methotrexate in Early Rheumatoid Arthritis: Aiming for Remission. Computer Assisted Management in Early Rheumatoid Arthritis (CAMERA, an Open-Label Strategy Trial)," Ann. Rheum. Dis. 2007, pp. 1443-1449, vol. 66.
Wolfe, F., "Comparative Usefulness of C-Reactive Protein and Erythrocyte Sedimentation Rate in Patients with Rheumatoid Arthritis," The Journal of Rheumatology, Aug. 1997, pp. 1477-1485, vol. 24, No. 8.
Wolfe, F., "A Reappraisal of HAQ Disability in Rheumatoid Arthritis," Arthritis & Rheumatism, Dec. 2000, pp. 2751-2761, vol. 43, No. 12.
Chinese First Office Action, Chinese Application No. 201080057651.4, Jun. 21, 2013, 14 pages.
Chinese Second Office Action, Chinese Application No. 201080057651.4, Jan. 13, 2014, 8 pages.
Japanese Office Action, Japanese Application No. 2012-534431, May 28, 2014, 14 pages.
Visser, H. et al., "How to Diagnose Rheumatoid Arthritis Early: A Prediction Model for Persistent (Erosive) Arthritis," Arthritis & Rheumatism, Feb. 2002, pp. 357-365, vol. 46, Issue 2. May be Retrieved at <URL:http://onlinelibrary.wiley.com/doi/10.1002/art.10117/pdf.
Wells, G. et al., "Validation of the 28-Joint Disease Activity Score (DAS28) and European League Against Rheumatism Response Criteria Based on C-Reactive Protein Against Disease Progression in Patients with Rheumatoid Arthritis, and Comparison with the DAS28 Based on Erythrocyte Sedimentation Rate," Ann. Rheum. Dis., 2008, Published Online First May 19, 2008, pp. 954-960, vol. 68. May be Retrieved at <URL:http://ard.bmj.com/content/68/6/954.full.pdf+html>.
Extended European Search Report for Application No. 10824227.2, mailed May 8, 2015.
Toonen et al. "Gene expression profiling in rheumatoid arthritis: Current concepts and future directions", Annals of the Rheumatic Diseases 200812 GB, vol. 67, No. 12, Dec. 2008, pp. 1663-1669.
Van Den Broek et al. "The evolution of biomarkers in rheumatoid arthritis: From clinical research to clinical care", Expert Opinion on Biological Therapy 200811 GB, vol. 8. No. 11, Nov. 2008, pp. 1773-1785.

\* cited by examiner

FIG. 1A

| TWOMRK Set No. | Marker 1 | Marker 2 | AUC | % | r |
|---|---|---|---|---|---|
| 1 | CRP | IL8 | 0.79 | 1.00 | 0.59 |
| 2 | CRP | EGF | 0.77 | 1.00 | 0.57 |
| 3 | SAA1 | EGF | 0.75 | 0.99 | 0.53 |
| 4 | VCAM1 | IL8 | 0.75 | 0.99 | 0.45 |
| 5 | CRP | RETN | 0.75 | 0.98 | 0.48 |
| 6 | SAA1 | IL8 | 0.75 | 0.98 | 0.52 |
| 7 | IL18 | CRP | 0.75 | 1.00 | 0.52 |
| 8 | Calprotectin | IL8 | 0.75 | 0.97 | 0.45 |
| 9 | ICAM1 | IL8 | 0.75 | 0.97 | 0.40 |
| 10 | CRP | LEP | 0.74 | 0.96 | 0.49 |
| 11 | IL8 | CHI3L1 | 0.74 | 0.96 | 0.44 |
| 12 | ICTP | CRP | 0.74 | 0.98 | 0.50 |
| 13 | Keratan sulfate | CRP | 0.73 | 0.96 | 0.50 |
| 14 | IL1RN | IL8 | 0.73 | 0.95 | 0.48 |
| 15 | ICTP | IL1RN | 0.73 | 0.95 | 0.35 |
| 16 | Calprotectin | CRP | 0.73 | 0.95 | 0.48 |
| 17 | LEP | IL8 | 0.73 | 0.94 | 0.41 |
| 18 | EGF | LEP | 0.73 | 0.94 | 0.43 |
| 19 | IL8 | TNFRSF1A | 0.73 | 0.93 | 0.43 |
| 20 | EGF | ICAM1 | 0.73 | 0.93 | 0.39 |
| 21 | EGF | IL8 | 0.72 | 0.92 | 0.43 |
| 22 | CRP | IL1B | 0.72 | 0.92 | 0.49 |
| 23 | CRP | ICAM1 | 0.72 | 0.91 | 0.44 |
| 24 | CRP | CCL22 | 0.72 | 0.91 | 0.47 |
| 25 | CRP | APOA1 | 0.72 | 0.90 | 0.46 |
| 26 | IL8 | IL6 | 0.72 | 0.90 | 0.43 |
| 27 | CRP | TNFRSF1A | 0.72 | 0.90 | 0.47 |
| 28 | IL1RN | EGF | 0.71 | 0.89 | 0.43 |
| 29 | EGF | VCAM1 | 0.71 | 0.89 | 0.42 |
| 30 | CRP | VEGFA | 0.71 | 0.88 | 0.45 |
| 31 | CRP | APOC3 | 0.71 | 0.88 | 0.45 |
| 32 | CRP | MMP3 | 0.71 | 0.87 | 0.43 |
| 33 | CRP | IL6 | 0.71 | 0.87 | 0.45 |
| 34 | CRP | CHI3L1 | 0.71 | 0.86 | 0.45 |
| 35 | CRP | VCAM1 | 0.71 | 0.86 | 0.46 |
| 36 | CRP | IL6R | 0.71 | 0.85 | 0.45 |
| 37 | EGF | CHI3L1 | 0.71 | 0.85 | 0.41 |
| 38 | APOA1 | IL8 | 0.71 | 0.84 | 0.40 |

| TWOMRK Set No. | Marker 1 | Marker 2 | AUC | % | r |
|---|---|---|---|---|---|
| 39 | CRP | MMP1 | 0.71 | 0.84 | 0.44 |
| 40 | MMP3 | IL8 | 0.71 | 0.83 | 0.39 |
| 41 | CRP | SAA1 | 0.71 | 0.83 | 0.46 |
| 42 | IL8 | CCL22 | 0.70 | 0.82 | 0.37 |
| 43 | SAA1 | RETN | 0.70 | 0.82 | 0.41 |
| 44 | ICTP | Calprotectin | 0.70 | 0.93 | 0.41 |
| 45 | Calprotectin | EGF | 0.70 | 0.81 | 0.39 |
| 46 | IL1RN | CRP | 0.70 | 0.81 | 0.45 |
| 47 | IL18 | SAA1 | 0.70 | 0.92 | 0.39 |
| 48 | IL8 | IL6R | 0.70 | 0.80 | 0.37 |
| 49 | EGF | MMP1 | 0.70 | 0.80 | 0.39 |
| 50 | SAA1 | LEP | 0.70 | 0.80 | 0.41 |
| 51 | IL8 | APOC3 | 0.70 | 0.79 | 0.37 |
| 52 | RETN | IL8 | 0.70 | 0.79 | 0.39 |
| 53 | EGF | APOA1 | 0.70 | 0.78 | 0.39 |
| 54 | EGF | TNFRSF1A | 0.70 | 0.78 | 0.41 |
| 55 | IL18 | Calprotectin | 0.70 | 0.90 | 0.41 |
| 56 | ICAM1 | LEP | 0.69 | 0.77 | 0.29 |
| 57 | IL8 | IL1B | 0.69 | 0.77 | 0.38 |
| 58 | EGF | MMP3 | 0.69 | 0.76 | 0.39 |
| 59 | EGF | IL1B | 0.69 | 0.76 | 0.40 |
| 60 | LEP | VCAM1 | 0.69 | 0.75 | 0.36 |
| 61 | Keratan sulfate | Calprotectin | 0.69 | 0.89 | 0.41 |
| 62 | EGF | IL6 | 0.69 | 0.75 | 0.39 |
| 63 | EGF | APOC3 | 0.69 | 0.74 | 0.37 |
| 64 | EGF | VEGFA | 0.69 | 0.74 | 0.42 |
| 65 | EGF | RETN | 0.69 | 0.73 | 0.39 |
| 66 | IL8 | VEGFA | 0.69 | 0.73 | 0.38 |
| 67 | SAA1 | IL1B | 0.69 | 0.72 | 0.42 |
| 68 | EGF | CCL22 | 0.69 | 0.72 | 0.39 |
| 69 | IL8 | MMP1 | 0.69 | 0.71 | 0.37 |
| 70 | EGF | IL6R | 0.69 | 0.71 | 0.38 |
| 71 | ICTP | LEP | 0.69 | 0.88 | 0.32 |
| 72 | LEP | IL1B | 0.69 | 0.70 | 0.32 |
| 73 | ICTP | CHI3L1 | 0.68 | 0.87 | 0.30 |
| 74 | Keratan sulfate | IL1RN | 0.68 | 0.86 | 0.35 |
| 75 | SAA1 | VCAM1 | 0.68 | 0.70 | 0.40 |
| 76 | LEP | APOA1 | 0.68 | 0.70 | 0.34 |
| 77 | SAA1 | APOA1 | 0.68 | 0.69 | 0.39 |

FIG. 1B

| TWOMRK Set No. | Marker 1 | Marker 2 | AUC | % | r |
|---|---|---|---|---|---|
| 78 | ICTP | SAA1 | 0.68 | 0.85 | 0.37 |
| 79 | IL18 | CHI3L1 | 0.68 | 0.83 | 0.34 |
| 80 | ICAM1 | IL1B | 0.68 | 0.69 | 0.31 |
| 81 | Keratan sulfate | CHI3L1 | 0.67 | 0.82 | 0.34 |
| 82 | IL1RN | SAA1 | 0.67 | 0.68 | 0.39 |
| 83 | VCAM1 | IL1B | 0.67 | 0.68 | 0.38 |
| 84 | SAA1 | ICAM1 | 0.67 | 0.67 | 0.35 |
| 85 | SAA1 | CCL22 | 0.67 | 0.67 | 0.40 |
| 86 | SAA1 | VEGFA | 0.67 | 0.66 | 0.37 |
| 87 | Calprotectin | SAA1 | 0.67 | 0.66 | 0.39 |
| 88 | VCAM1 | RETN | 0.67 | 0.65 | 0.31 |
| 89 | LEP | CHI3L1 | 0.67 | 0.65 | 0.28 |
| 90 | IL18 | IL1RN | 0.66 | 0.81 | 0.34 |
| 91 | IL18 | EGF | 0.66 | 0.80 | 0.29 |
| 92 | SAA1 | APOC3 | 0.66 | 0.64 | 0.38 |
| 93 | SAA1 | CHI3L1 | 0.66 | 0.64 | 0.37 |
| 94 | ICTP | VCAM1 | 0.66 | 0.77 | 0.26 |
| 95 | LEP | TNFRSF1A | 0.66 | 0.63 | 0.28 |
| 96 | ICTP | VEGFA | 0.66 | 0.75 | 0.25 |
| 97 | ICTP | ICAM1 | 0.66 | 0.74 | 0.25 |
| 98 | Keratan sulfate | LEP | 0.66 | 0.73 | 0.30 |
| 99 | Keratan sulfate | TNFRSF1A | 0.66 | 0.71 | 0.29 |
| 100 | SAA1 | IL6R | 0.66 | 0.63 | 0.37 |
| 101 | SAA1 | MMP3 | 0.66 | 0.62 | 0.36 |
| 102 | APOA1 | VCAM1 | 0.66 | 0.62 | 0.32 |
| 103 | SAA1 | IL6 | 0.66 | 0.61 | 0.36 |
| 104 | ICAM1 | RETN | 0.66 | 0.61 | 0.25 |
| 105 | LEP | RETN | 0.66 | 0.60 | 0.25 |
| 106 | SAA1 | TNFRSF1A | 0.66 | 0.60 | 0.37 |
| 107 | ICTP | TNFRSF1A | 0.66 | 0.70 | 0.24 |
| 108 | ICAM1 | MMP3 | 0.66 | 0.60 | 0.25 |
| 109 | ICAM1 | VCAM1 | 0.66 | 0.59 | 0.26 |
| 110 | ICTP | EGF | 0.66 | 0.69 | 0.26 |
| 111 | Keratan sulfate | VCAM1 | 0.66 | 0.68 | 0.29 |
| 112 | Keratan sulfate | EGF | 0.66 | 0.67 | 0.30 |
| 113 | CHI3L1 | IL1B | 0.66 | 0.59 | 0.33 |
| 114 | SAA1 | MMP1 | 0.66 | 0.58 | 0.37 |
| 115 | LEP | MMP3 | 0.66 | 0.58 | 0.30 |
| 116 | ICAM1 | CHI3L1 | 0.65 | 0.57 | 0.23 |

FIG. 1C

| TWOMRK Set No. | Marker 1 | Marker 2 | AUC | % | r |
|---|---|---|---|---|---|
| 117 | ICAM1 | IL6R | 0.65 | 0.57 | 0.28 |
| 118 | IL18 | VEGFA | 0.65 | 0.64 | 0.31 |
| 119 | Keratan sulfate | SAA1 | 0.65 | 0.63 | 0.34 |
| 120 | IL18 | APOC3 | 0.65 | 0.62 | 0.28 |
| 121 | Calprotectin | ICAM1 | 0.65 | 0.56 | 0.25 |
| 122 | IL18 | LEP | 0.65 | 0.61 | 0.32 |
| 123 | IL1RN | ICAM1 | 0.65 | 0.56 | 0.26 |
| 124 | ICTP | APOC3 | 0.65 | 0.60 | 0.24 |
| 125 | LEP | MMP1 | 0.65 | 0.55 | 0.26 |
| 126 | ICTP | IL6 | 0.65 | 0.58 | 0.31 |
| 127 | MMP3 | VCAM1 | 0.65 | 0.55 | 0.30 |
| 128 | IL1RN | IL1B | 0.65 | 0.54 | 0.36 |
| 129 | IL18 | VCAM1 | 0.65 | 0.57 | 0.29 |
| 130 | ICAM1 | IL6 | 0.65 | 0.54 | 0.25 |
| 131 | IL18 | IL6 | 0.65 | 0.56 | 0.31 |
| 132 | LEP | IL6R | 0.64 | 0.53 | 0.25 |
| 133 | IL18 | ICAM1 | 0.64 | 0.55 | 0.28 |
| 134 | ICAM1 | APOA1 | 0.64 | 0.53 | 0.25 |
| 135 | IL1B | TNFRSF1A | 0.64 | 0.52 | 0.30 |
| 136 | IL1RN | LEP | 0.64 | 0.52 | 0.28 |
| 137 | IL18 | TNFRSF1A | 0.64 | 0.54 | 0.27 |
| 138 | IL1RN | VCAM1 | 0.64 | 0.51 | 0.30 |
| 139 | ICAM1 | TNFRSF1A | 0.64 | 0.51 | 0.25 |
| 140 | Keratan sulfate | ICAM1 | 0.64 | 0.52 | 0.28 |
| 141 | VCAM1 | CCL22 | 0.64 | 0.50 | 0.31 |
| 142 | VCAM1 | IL6R | 0.64 | 0.50 | 0.30 |
| 143 | IL18 | MMP1 | 0.64 | 0.51 | 0.26 |
| 144 | Calprotectin | LEP | 0.64 | 0.50 | 0.25 |
| 145 | Calprotectin | VCAM1 | 0.64 | 0.49 | 0.31 |
| 146 | ICTP | IL1B | 0.64 | 0.50 | 0.23 |
| 147 | VCAM1 | CHI3L1 | 0.64 | 0.49 | 0.29 |
| 148 | ICAM1 | VEGFA | 0.64 | 0.48 | 0.24 |
| 149 | ICAM1 | CCL22 | 0.64 | 0.48 | 0.26 |
| 150 | RETN | CHI3L1 | 0.64 | 0.47 | 0.18 |
| 151 | VCAM1 | IL6 | 0.64 | 0.47 | 0.28 |
| 152 | ICTP | MMP3 | 0.64 | 0.48 | 0.23 |
| 153 | ICTP | IL6R | 0.64 | 0.46 | 0.21 |
| 154 | LEP | CCL22 | 0.64 | 0.46 | 0.24 |
| 155 | ICAM1 | MMP1 | 0.64 | 0.46 | 0.25 |

FIG. 1D

| TWO.MRK Set No. | Marker 1 | Marker 2 | AUC | % | r |
|---|---|---|---|---|---|
| 156 | LEP | IL6 | 0.64 | 0.45 | 0.28 |
| 157 | LEP | VEGFA | 0.64 | 0.45 | 0.24 |
| 158 | ICAM1 | APOC3 | 0.64 | 0.44 | 0.25 |
| 159 | LEP | APOC3 | 0.64 | 0.44 | 0.23 |
| 160 | VCAM1 | TNFRSF1A | 0.63 | 0.43 | 0.28 |
| 161 | VCAM1 | VEGFA | 0.63 | 0.43 | 0.29 |
| 162 | Keratan sulfate | VEGFA | 0.63 | 0.43 | 0.28 |
| 163 | ICTP | CCL22 | 0.63 | 0.42 | 0.23 |
| 164 | ICTP | MMP1 | 0.63 | 0.40 | 0.22 |
| 165 | VCAM1 | MMP1 | 0.63 | 0.42 | 0.29 |
| 166 | IL18 | IL8 | 0.63 | 0.38 | 0.31 |
| 167 | APOA1 | IL1B | 0.63 | 0.42 | 0.30 |
| 168 | IL1RN | RETN | 0.63 | 0.41 | 0.25 |
| 169 | IL18 | IL6R | 0.63 | 0.36 | 0.25 |
| 170 | Calprotectin | IL1B | 0.63 | 0.41 | 0.27 |
| 171 | IL18 | IL1B | 0.63 | 0.33 | 0.25 |
| 172 | MMP3 | IL1B | 0.63 | 0.40 | 0.29 |
| 173 | Keratan sulfate | APOC3 | 0.63 | 0.32 | 0.25 |
| 174 | VCAM1 | APOC3 | 0.62 | 0.40 | 0.27 |
| 175 | RETN | TNFRSF1A | 0.62 | 0.40 | 0.20 |
| 176 | ICTP | IL8 | 0.62 | 0.30 | 0.27 |
| 177 | Keratan sulfate | IL6 | 0.62 | 0.27 | 0.32 |
| 178 | APOA1 | CHI3L1 | 0.62 | 0.39 | 0.24 |
| 179 | ICTP | RETN | 0.62 | 0.26 | 0.29 |
| 180 | IL18 | CCL22 | 0.62 | 0.25 | 0.25 |
| 181 | MMP3 | CHI3L1 | 0.62 | 0.39 | 0.18 |
| 182 | IL18 | MMP3 | 0.62 | 0.24 | 0.24 |
| 183 | Keratan sulfate | RETN | 0.62 | 0.23 | 0.31 |
| 184 | IL6 | IL1B | 0.62 | 0.38 | 0.27 |
| 185 | IL1B | IL6R | 0.61 | 0.38 | 0.24 |
| 186 | CCL22 | IL1B | 0.61 | 0.37 | 0.25 |
| 187 | IL1RN | APOA1 | 0.61 | 0.37 | 0.26 |
| 188 | IL18 | APOA1 | 0.61 | 0.18 | 0.26 |
| 189 | IL1B | APOC3 | 0.61 | 0.36 | 0.25 |
| 190 | IL1RN | CHI3L1 | 0.61 | 0.36 | 0.21 |
| 191 | Keratan sulfate | IL6R | 0.61 | 0.17 | 0.24 |
| 192 | IL1B | MMP1 | 0.61 | 0.35 | 0.24 |
| 193 | IL18 | RETN | 0.61 | 0.15 | 0.31 |
| 194 | Calprotectin | CHI3L1 | 0.61 | 0.35 | 0.16 |

FIG. 1E

| TWOMRK Set No. | Marker 1 | Marker 2 | AUC | % | r |
|---|---|---|---|---|---|
| 195 | IL1RN | MMP3 | 0.61 | 0.34 | 0.22 |
| 196 | Keratan sulfate | IL8 | 0.61 | 0.14 | 0.30 |
| 197 | RETN | IL1B | 0.61 | 0.34 | 0.25 |
| 198 | IL1RN | TNFRSF1A | 0.61 | 0.33 | 0.23 |
| 199 | APOA1 | TNFRSF1A | 0.61 | 0.33 | 0.24 |
| 200 | VEGFA | IL1B | 0.60 | 0.32 | 0.24 |
| 201 | Keratan sulfate | IL1B | 0.60 | 0.11 | 0.23 |
| 202 | ICTP | APOA1 | 0.60 | 0.10 | 0.21 |
| 203 | Keratan sulfate | MMP1 | 0.60 | 0.08 | 0.23 |
| 204 | Keratan sulfate | APOA1 | 0.60 | 0.07 | 0.27 |
| 205 | CHI3L1 | TNFRSF1A | 0.60 | 0.32 | 0.18 |
| 206 | CHI3L1 | IL6R | 0.60 | 0.31 | 0.16 |
| 207 | MMP3 | TNFRSF1A | 0.60 | 0.31 | 0.18 |
| 208 | Keratan sulfate | MMP3 | 0.60 | 0.04 | 0.23 |

| THREEMRK Set No. | Marker 1 | Marker 2 | Marker 3 | AUC | % | r |
|---|---|---|---|---|---|---|
| 1 | LEP | IL1B | SAA1 | 0.72 | 0.81 | 0.46 |
| 2 | LEP | APOA1 | SAA1 | 0.71 | 0.78 | 0.44 |
| 3 | LEP | RETN | VCAM1 | 0.71 | 0.76 | 0.37 |
| 4 | ICAM1 | IL1B | LEP | 0.71 | 0.75 | 0.35 |
| 5 | EGF | IL1B | TNFRSF1A | 0.71 | 0.74 | 0.43 |
| 6 | ICAM1 | LEP | RETN | 0.71 | 0.73 | 0.31 |
| 7 | ICAM1 | LEP | SAA1 | 0.71 | 0.73 | 0.39 |
| 8 | LEP | CCL22 | SAA1 | 0.71 | 0.72 | 0.43 |
| 9 | ICAM1 | APOA1 | LEP | 0.71 | 0.72 | 0.34 |
| 10 | CHI3L1 | IL1B | SAA1 | 0.70 | 0.70 | 0.43 |
| 11 | IL8 | APOC3 | RETN | 0.70 | 0.70 | 0.40 |
| 12 | APOA1 | VCAM1 | LEP | 0.70 | 0.70 | 0.40 |
| 13 | LEP | IL1B | VCAM1 | 0.70 | 0.70 | 0.41 |
| 14 | EGF | MMP3 | TNFRSF1A | 0.70 | 0.70 | 0.42 |
| 15 | IL1 | LEP | SAA1 | 0.70 | 0.69 | 0.42 |
| 16 | ICAM1 | IL1B | SAA1 | 0.70 | 0.69 | 0.43 |
| 17 | LEP | IL6R | SAA1 | 0.70 | 0.69 | 0.42 |
| 18 | CCL22 | TNFRSF1A | EGF | 0.70 | 0.69 | 0.41 |
| 19 | LEP | TNFRSF1A | SAA1 | 0.70 | 0.68 | 0.42 |
| 20 | LEP | VCAM1 | SAA1 | 0.70 | 0.68 | 0.41 |
| 21 | ICAM1 | IL6R | LEP | 0.70 | 0.68 | 0.31 |
| 22 | LEP | VCAM1 | VEGFA | 0.70 | 0.68 | 0.37 |
| 23 | LEP | CHI3L1 | SAA1 | 0.70 | 0.68 | 0.41 |
| 24 | Calprotectin | LEP | SAA1 | 0.70 | 0.67 | 0.42 |
| 25 | LEP | APOC3 | SAA1 | 0.70 | 0.67 | 0.42 |
| 26 | CCL22 | IL1B | SAA1 | 0.70 | 0.67 | 0.45 |
| 27 | ICAM1 | LEP | MMP3 | 0.70 | 0.67 | 0.33 |
| 28 | Calprotectin | ICAM1 | LEP | 0.70 | 0.67 | 0.31 |
| 29 | SAA1 | IL1B | VCAM1 | 0.70 | 0.67 | 0.43 |
| 30 | IL8 | APOC3 | VEGFA | 0.70 | 0.66 | 0.41 |
| 31 | EGF | IL1B | MMP1 | 0.70 | 0.66 | 0.42 |
| 32 | EGF | APOA1 | MMP3 | 0.70 | 0.66 | 0.40 |
| 33 | APOA1 | MMP1 | EGF | 0.70 | 0.66 | 0.40 |
| 34 | LEP | VEGFA | SAA1 | 0.70 | 0.66 | 0.41 |
| 35 | LEP | MMP1 | SAA1 | 0.70 | 0.66 | 0.41 |
| 36 | EGF | MMP1 | MMP3 | 0.70 | 0.66 | 0.40 |
| 37 | EGF | CCL22 | MMP3 | 0.70 | 0.66 | 0.42 |
| 38 | LEP | IL6 | SAA1 | 0.70 | 0.65 | 0.41 |

| THREEMRK Set No. | Marker 1 | Marker 2 | Marker 3 | AUC | % | r |
|---|---|---|---|---|---|---|
| 39 | IL6R | APOC3 | IL8 | 0.70 | 0.65 | 0.36 |
| 40 | EGF | IL6R | MMP3 | 0.70 | 0.65 | 0.40 |
| 41 | LEP | MMP3 | SAA1 | 0.70 | 0.65 | 0.41 |
| 42 | APOA1 | IL1B | EGF | 0.69 | 0.65 | 0.41 |
| 43 | APOA1 | IL1B | SAA1 | 0.69 | 0.65 | 0.45 |
| 44 | IL1 | IL1B | SAA1 | 0.69 | 0.65 | 0.46 |
| 45 | IL8 | IL1B | VEGFA | 0.69 | 0.65 | 0.41 |
| 46 | EGF | TNFRSF1A | VEGFA | 0.69 | 0.65 | 0.42 |
| 47 | EGF | MMP3 | RETN | 0.69 | 0.64 | 0.40 |
| 48 | IL1B | APOC3 | IL8 | 0.69 | 0.64 | 0.37 |
| 49 | SAA1 | IL1B | VEGFA | 0.69 | 0.64 | 0.43 |
| 50 | CHI3L1 | IL1B | LEP | 0.69 | 0.64 | 0.36 |
| 51 | ICAM1 | LEP | VCAM1 | 0.69 | 0.64 | 0.34 |
| 52 | EGF | MMP1 | TNFRSF1A | 0.69 | 0.64 | 0.40 |
| 53 | IL8 | IL1B | RETN | 0.69 | 0.64 | 0.41 |
| 54 | LEP | IL6R | VCAM1 | 0.69 | 0.63 | 0.36 |
| 55 | IL8 | IL6R | RETN | 0.69 | 0.63 | 0.39 |
| 56 | APOA1 | TNFRSF1A | EGF | 0.69 | 0.63 | 0.42 |
| 57 | APOA1 | IL6R | EGF | 0.69 | 0.63 | 0.39 |
| 58 | LEP | CHI3L1 | VCAM1 | 0.69 | 0.63 | 0.36 |
| 59 | APOA1 | CCL22 | EGF | 0.69 | 0.63 | 0.40 |
| 60 | EGF | IL1B | RETN | 0.69 | 0.63 | 0.42 |
| 61 | ICAM1 | CHI3L1 | LEP | 0.69 | 0.63 | 0.31 |
| 62 | APOC3 | TNFRSF1A | EGF | 0.69 | 0.62 | 0.39 |
| 63 | EGF | MMP3 | VEGFA | 0.69 | 0.62 | 0.41 |
| 64 | LEP | CHI3L1 | RETN | 0.69 | 0.62 | 0.30 |
| 65 | IL1B | IL6R | SAA1 | 0.69 | 0.62 | 0.43 |
| 66 | IL1B | TNFRSF1A | SAA1 | 0.69 | 0.62 | 0.43 |
| 67 | APOA1 | RETN | EGF | 0.69 | 0.62 | 0.40 |
| 68 | EGF | IL1B | VEGFA | 0.69 | 0.62 | 0.42 |
| 69 | EGF | IL1B | IL6R | 0.69 | 0.62 | 0.40 |
| 70 | LEP | TNFRSF1A | VCAM1 | 0.69 | 0.62 | 0.36 |
| 71 | IL8 | IL6R | VEGFA | 0.69 | 0.62 | 0.40 |
| 72 | EGF | IL1B | MMP3 | 0.69 | 0.61 | 0.42 |
| 73 | IL8 | VEGFA | RETN | 0.69 | 0.61 | 0.42 |
| 74 | IL6 | IL1B | SAA1 | 0.69 | 0.61 | 0.44 |
| 75 | EGF | APOC3 | IL1B | 0.69 | 0.61 | 0.39 |
| 76 | IL6R | MMP1 | IL8 | 0.69 | 0.61 | 0.37 |
| 77 | MMP3 | IL1B | SAA1 | 0.69 | 0.61 | 0.43 |

FIG. 2B

| THREEMRK Set No. | Marker 1 | Marker 2 | Marker 3 | AUC | % | r |
|---|---|---|---|---|---|---|
| 78 | IL1B | IL6R | IL8 | 0.69 | 0.61 | 0.38 |
| 79 | IL1B | MMP1 | IL8 | 0.69 | 0.61 | 0.39 |
| 80 | Calprotectin | IL1B | SAA1 | 0.69 | 0.61 | 0.44 |
| 81 | IL8 | MMP1 | RETN | 0.69 | 0.61 | 0.40 |
| 82 | EGF | IL6 | MMP3 | 0.69 | 0.61 | 0.41 |
| 83 | EGF | IL6 | VEGFA | 0.69 | 0.61 | 0.42 |
| 84 | APOA1 | APOC3 | EGF | 0.69 | 0.61 | 0.38 |
| 85 | EGF | IL6 | TNFRSF1A | 0.69 | 0.60 | 0.42 |
| 86 | APOA1 | VEGFA | EGF | 0.69 | 0.60 | 0.42 |
| 87 | CCL22 | IL1B | EGF | 0.69 | 0.60 | 0.41 |
| 88 | ICAM1 | LEP | TNFRSF1A | 0.69 | 0.60 | 0.32 |
| 89 | ICAM1 | LEP | VEGFA | 0.69 | 0.60 | 0.29 |
| 90 | EGF | APOC3 | VEGFA | 0.69 | 0.60 | 0.40 |
| 91 | EGF | IL1B | IL6 | 0.69 | 0.60 | 0.42 |
| 92 | EGF | APOC3 | MMP3 | 0.69 | 0.60 | 0.38 |
| 93 | EGF | RETN | TNFRSF1A | 0.69 | 0.60 | 0.40 |
| 94 | EGF | MMP1 | VEGFA | 0.69 | 0.60 | 0.41 |
| 95 | ICAM1 | IL6 | LEP | 0.69 | 0.60 | 0.31 |
| 96 | Calprotectin | LEP | VCAM1 | 0.69 | 0.60 | 0.35 |
| 97 | CCL22 | MMP1 | EGF | 0.69 | 0.60 | 0.40 |
| 98 | EGF | IL6R | TNFRSF1A | 0.69 | 0.59 | 0.39 |
| 99 | ICAM1 | APOA1 | SAA1 | 0.69 | 0.59 | 0.38 |
| 100 | EGF | IL6R | MMP1 | 0.69 | 0.59 | 0.39 |
| 101 | Calprotectin | SAA1 | VCAM1 | 0.69 | 0.59 | 0.40 |
| 102 | ICAM1 | LEP | MMP1 | 0.68 | 0.59 | 0.30 |
| 103 | APOA1 | CHI3L1 | LEP | 0.68 | 0.59 | 0.35 |
| 104 | ICAM1 | APOC3 | LEP | 0.68 | 0.59 | 0.29 |
| 105 | LEP | MMP3 | VCAM1 | 0.68 | 0.59 | 0.36 |
| 106 | IL1B | APOC3 | SAA1 | 0.68 | 0.59 | 0.43 |
| 107 | IL1B | TNFRSF1A | LEP | 0.68 | 0.59 | 0.34 |
| 108 | EGF | IL6R | VEGFA | 0.68 | 0.59 | 0.41 |
| 109 | Calprotectin | IL1B | LEP | 0.68 | 0.59 | 0.34 |
| 110 | APOC3 | MMP1 | IL8 | 0.68 | 0.58 | 0.37 |
| 111 | IL1 | LEP | VCAM1 | 0.68 | 0.58 | 0.35 |
| 112 | CHI3L1 | IL1B | ICAM1 | 0.68 | 0.58 | 0.33 |
| 113 | IL8 | MMP1 | VEGFA | 0.68 | 0.58 | 0.41 |
| 114 | ICAM1 | VEGFA | SAA1 | 0.68 | 0.58 | 0.35 |
| 115 | LEP | MMP1 | VCAM1 | 0.68 | 0.58 | 0.35 |
| 116 | Calprotectin | APOA1 | SAA1 | 0.68 | 0.58 | 0.42 |

FIG. 2C

| THREEMRK Set No. | Marker 1 | Marker 2 | Marker 3 | AUC | % | r |
|---|---|---|---|---|---|---|
| 117 | CCL22 | IL6R | EGF | 0.68 | 0.58 | 0.38 |
| 118 | ICAM1 | CCL22 | LEP | 0.68 | 0.58 | 0.30 |
| 119 | IL1B | MMP1 | SAA1 | 0.68 | 0.58 | 0.42 |
| 120 | APOA1 | IL6 | EGF | 0.68 | 0.58 | 0.41 |
| 121 | LEP | IL1B | MMP3 | 0.68 | 0.58 | 0.36 |
| 122 | EGF | APOC3 | IL6R | 0.68 | 0.58 | 0.37 |
| 123 | EGF | IL6 | IL6R | 0.68 | 0.57 | 0.41 |
| 124 | EGF | IL6 | MMP1 | 0.68 | 0.57 | 0.40 |
| 125 | EGF | CCL22 | VEGFA | 0.68 | 0.57 | 0.41 |
| 126 | ICAM1 | IL1B | VCAM1 | 0.68 | 0.57 | 0.35 |
| 127 | LEP | IL6 | VCAM1 | 0.68 | 0.57 | 0.36 |
| 128 | EGF | IL6 | RETN | 0.68 | 0.57 | 0.41 |
| 129 | LEP | APOC3 | VCAM1 | 0.68 | 0.57 | 0.36 |
| 130 | ICAM1 | LEP | IL1 | 0.68 | 0.57 | 0.31 |
| 131 | EGF | CCL22 | RETN | 0.68 | 0.57 | 0.40 |
| 132 | APOC3 | MMP1 | EGF | 0.68 | 0.57 | 0.37 |
| 133 | EGF | CCL22 | IL6 | 0.68 | 0.57 | 0.41 |
| 134 | IL1B | APOC3 | LEP | 0.68 | 0.57 | 0.32 |
| 135 | LEP | CCL22 | VCAM1 | 0.68 | 0.57 | 0.36 |
| 136 | LEP | IL1B | VEGFA | 0.68 | 0.56 | 0.32 |
| 137 | EGF | IL6R | RETN | 0.68 | 0.56 | 0.38 |
| 138 | ICAM1 | IL6 | SAA1 | 0.68 | 0.56 | 0.36 |
| 139 | IL1B | IL6R | LEP | 0.68 | 0.56 | 0.33 |
| 140 | EGF | APOC3 | IL6 | 0.68 | 0.56 | 0.39 |
| 141 | LEP | APOA1 | MMP3 | 0.68 | 0.56 | 0.35 |
| 142 | CCL22 | APOC3 | EGF | 0.68 | 0.56 | 0.38 |
| 143 | MMP3 | VCAM1 | SAA1 | 0.68 | 0.56 | 0.38 |
| 144 | SAA1 | CCL22 | VEGFA | 0.68 | 0.56 | 0.40 |
| 145 | APOA1 | IL1B | LEP | 0.68 | 0.56 | 0.37 |
| 146 | LEP | MMP3 | RETN | 0.68 | 0.56 | 0.30 |
| 147 | APOA1 | VEGFA | LEP | 0.68 | 0.56 | 0.33 |
| 148 | Calprotectin | APOA1 | LEP | 0.68 | 0.56 | 0.32 |
| 149 | EGF | MMP1 | RETN | 0.68 | 0.55 | 0.38 |
| 150 | CHI3L1 | CCL22 | SAA1 | 0.68 | 0.55 | 0.40 |
| 151 | MMP3 | IL1B | VCAM1 | 0.68 | 0.55 | 0.38 |
| 152 | EGF | APOC3 | RETN | 0.68 | 0.55 | 0.38 |
| 153 | SAA1 | APOC3 | VCAM1 | 0.68 | 0.55 | 0.40 |
| 154 | ICAM1 | CHI3L1 | RETN | 0.68 | 0.55 | 0.25 |
| 155 | APOA1 | IL1B | VCAM1 | 0.68 | 0.55 | 0.40 |

FIG. 2D

| THREEMRK Set No. | Marker 1 | Marker 2 | Marker 3 | AUC | % | r |
|---|---|---|---|---|---|---|
| 156 | Calprotectin | ICAM1 | SAA1 | 0.68 | 0.55 | 0.37 |
| 157 | EGF | RETN | VEGFA | 0.68 | 0.55 | 0.40 |
| 158 | LEP | IL1B | RETN | 0.68 | 0.55 | 0.33 |
| 159 | APOA1 | APOC3 | SAA1 | 0.68 | 0.55 | 0.41 |
| 160 | IL1B | MMP1 | LEP | 0.68 | 0.55 | 0.32 |
| 161 | APOA1 | VCAM1 | SAA1 | 0.68 | 0.55 | 0.39 |
| 162 | Calprotectin | APOC3 | SAA1 | 0.67 | 0.54 | 0.40 |
| 163 | APOA1 | RETN | LEP | 0.67 | 0.54 | 0.31 |
| 164 | MMP3 | RETN | VCAM1 | 0.67 | 0.54 | 0.32 |
| 165 | IL1 | SAA1 | VCAM1 | 0.67 | 0.54 | 0.39 |
| 166 | ICAM1 | IL1B | TNFRSF1A | 0.67 | 0.54 | 0.32 |
| 167 | ICAM1 | TNFRSF1A | SAA1 | 0.67 | 0.54 | 0.36 |
| 168 | SAA1 | VCAM1 | VEGFA | 0.67 | 0.54 | 0.39 |
| 169 | APOA1 | VEGFA | SAA1 | 0.67 | 0.54 | 0.39 |
| 170 | IL1 | RETN | VCAM1 | 0.67 | 0.54 | 0.34 |
| 171 | ICAM1 | IL1B | IL6R | 0.67 | 0.54 | 0.31 |
| 172 | IL1 | APOC3 | SAA1 | 0.67 | 0.54 | 0.38 |
| 173 | SAA1 | APOC3 | VEGFA | 0.67 | 0.54 | 0.38 |
| 174 | ICAM1 | VCAM1 | SAA1 | 0.67 | 0.54 | 0.36 |
| 175 | Calprotectin | IL1 | SAA1 | 0.67 | 0.53 | 0.40 |
| 176 | ICAM1 | RETN | TNFRSF1A | 0.67 | 0.53 | 0.27 |
| 177 | IL6 | IL1B | LEP | 0.67 | 0.53 | 0.34 |
| 178 | RETN | CHI3L1 | VCAM1 | 0.67 | 0.53 | 0.31 |
| 179 | ICAM1 | CHI3L1 | SAA1 | 0.67 | 0.53 | 0.35 |
| 180 | ICAM1 | IL1B | MMP3 | 0.67 | 0.53 | 0.34 |
| 181 | APOA1 | CCL22 | SAA1 | 0.67 | 0.53 | 0.42 |
| 182 | LEP | CHI3L1 | VEGFA | 0.67 | 0.53 | 0.30 |
| 183 | Calprotectin | SAA1 | VEGFA | 0.67 | 0.53 | 0.39 |
| 184 | SAA1 | CCL22 | VCAM1 | 0.67 | 0.53 | 0.40 |
| 185 | CCL22 | APOC3 | SAA1 | 0.67 | 0.53 | 0.39 |
| 186 | APOA1 | TNFRSF1A | LEP | 0.67 | 0.53 | 0.34 |
| 187 | Calprotectin | CHI3L1 | SAA1 | 0.67 | 0.53 | 0.39 |
| 188 | IL1 | ICAM1 | SAA1 | 0.67 | 0.52 | 0.36 |
| 189 | APOA1 | MMP1 | LEP | 0.67 | 0.52 | 0.32 |
| 190 | ICAM1 | RETN | VCAM1 | 0.67 | 0.52 | 0.30 |
| 191 | SAA1 | IL6 | VCAM1 | 0.67 | 0.52 | 0.38 |
| 192 | SAA1 | MMP1 | VCAM1 | 0.67 | 0.52 | 0.39 |
| 193 | CHI3L1 | IL1B | VCAM1 | 0.67 | 0.52 | 0.37 |
| 194 | Calprotectin | ICAM1 | IL1B | 0.67 | 0.52 | 0.32 |

FIG. 2E

| THREEMRK Set No. | Marker 1 | Marker 2 | Marker 3 | AUC | % | r |
|---|---|---|---|---|---|---|
| 195 | MMP3 | CCL22 | SAA1 | 0.67 | 0.52 | 0.40 |
| 196 | ICAM1 | CCL22 | SAA1 | 0.67 | 0.52 | 0.36 |
| 197 | IL1 | SAA1 | VEGFA | 0.67 | 0.52 | 0.38 |
| 198 | IL6 | CCL22 | SAA1 | 0.67 | 0.52 | 0.39 |
| 199 | IL1 | LEP | RETN | 0.67 | 0.52 | 0.33 |
| 200 | APOA1 | IL1B | ICAM1 | 0.67 | 0.52 | 0.34 |
| 201 | SAA1 | IL6R | VCAM1 | 0.67 | 0.51 | 0.39 |
| 202 | LEP | RETN | TNFRSF1A | 0.67 | 0.51 | 0.29 |
| 203 | Calprotectin | IL1B | VCAM1 | 0.67 | 0.51 | 0.38 |
| 204 | Calprotectin | MMP3 | SAA1 | 0.67 | 0.51 | 0.39 |
| 205 | APOA1 | RETN | VCAM1 | 0.67 | 0.51 | 0.33 |
| 206 | IL1 | CHI3L1 | RETN | 0.67 | 0.51 | 0.27 |
| 207 | ICAM1 | IL1B | IL1 | 0.67 | 0.51 | 0.35 |
| 208 | SAA1 | CHI3L1 | VCAM1 | 0.67 | 0.51 | 0.39 |
| 209 | ICAM1 | IL6R | SAA1 | 0.67 | 0.51 | 0.35 |
| 210 | CCL22 | IL1B | VCAM1 | 0.67 | 0.51 | 0.38 |
| 211 | IL1 | IL1B | LEP | 0.67 | 0.51 | 0.38 |
| 212 | IL1 | IL1B | VCAM1 | 0.67 | 0.51 | 0.39 |
| 213 | ICAM1 | MMP1 | SAA1 | 0.67 | 0.51 | 0.35 |
| 214 | IL1 | APOA1 | LEP | 0.67 | 0.50 | 0.34 |
| 215 | CCL22 | TNFRSF1A | SAA1 | 0.67 | 0.50 | 0.39 |
| 216 | MMP3 | APOC3 | SAA1 | 0.67 | 0.50 | 0.39 |
| 217 | IL1 | APOA1 | SAA1 | 0.67 | 0.50 | 0.40 |
| 218 | ICAM1 | MMP3 | SAA1 | 0.67 | 0.50 | 0.37 |
| 219 | IL1B | MMP1 | VCAM1 | 0.67 | 0.50 | 0.38 |
| 220 | Calprotectin | IL6 | SAA1 | 0.67 | 0.50 | 0.38 |
| 221 | ICAM1 | MMP3 | RETN | 0.67 | 0.50 | 0.27 |
| 222 | APOA1 | IL6 | SAA1 | 0.67 | 0.50 | 0.39 |
| 223 | CCL22 | IL1B | ICAM1 | 0.67 | 0.50 | 0.31 |
| 224 | LEP | CHI3L1 | MMP3 | 0.67 | 0.50 | 0.30 |
| 225 | IL6 | IL1B | VCAM1 | 0.67 | 0.50 | 0.37 |
| 226 | RETN | IL1B | VCAM1 | 0.67 | 0.50 | 0.36 |
| 227 | CHI3L1 | IL1B | TNFRSF1A | 0.67 | 0.49 | 0.32 |
| 228 | SAA1 | CHI3L1 | VEGFA | 0.67 | 0.49 | 0.37 |
| 229 | IL1 | CCL22 | SAA1 | 0.67 | 0.49 | 0.40 |
| 230 | APOA1 | IL6R | LEP | 0.67 | 0.49 | 0.32 |
| 231 | IL1 | SAA1 | TNFRSF1A | 0.67 | 0.49 | 0.38 |
| 232 | ICAM1 | APOC3 | IL1B | 0.67 | 0.49 | 0.32 |
| 233 | RETN | IL6R | VCAM1 | 0.67 | 0.49 | 0.31 |

FIG. 2F

| THREEMRK Set No. | Marker 1 | Marker 2 | Marker 3 | AUC | % | r |
|---|---|---|---|---|---|---|
| 234 | CCL22 | MMP1 | SAA1 | 0.67 | 0.49 | 0.40 |
| 235 | APOA1 | CHI3L1 | SAA1 | 0.66 | 0.49 | 0.39 |
| 236 | SAA1 | TNFRSF1A | VCAM1 | 0.66 | 0.49 | 0.39 |
| 237 | IL1 | IL6R | SAA1 | 0.66 | 0.49 | 0.39 |
| 238 | CCL22 | IL1B | LEP | 0.66 | 0.49 | 0.31 |
| 239 | CCL22 | IL6R | SAA1 | 0.66 | 0.49 | 0.40 |
| 240 | APOA1 | VCAM1 | ICAM1 | 0.66 | 0.48 | 0.30 |
| 241 | Calprotectin | MMP1 | SAA1 | 0.66 | 0.48 | 0.38 |
| 242 | APOA1 | MMP1 | SAA1 | 0.66 | 0.48 | 0.39 |
| 243 | Calprotectin | IL6R | SAA1 | 0.66 | 0.48 | 0.39 |
| 244 | ICAM1 | APOC3 | SAA1 | 0.66 | 0.48 | 0.35 |
| 245 | IL6 | APOC3 | SAA1 | 0.66 | 0.48 | 0.38 |
| 246 | CHI3L1 | APOC3 | SAA1 | 0.66 | 0.48 | 0.37 |
| 247 | IL6R | APOC3 | SAA1 | 0.66 | 0.48 | 0.38 |
| 248 | APOA1 | IL6R | SAA1 | 0.66 | 0.48 | 0.39 |
| 249 | LEP | MMP3 | TNFRSF1A | 0.66 | 0.48 | 0.30 |
| 250 | IL1B | IL6R | VCAM1 | 0.66 | 0.48 | 0.36 |
| 251 | ICAM1 | IL1B | MMP1 | 0.66 | 0.48 | 0.30 |
| 252 | SAA1 | TNFRSF1A | VEGFA | 0.66 | 0.48 | 0.36 |
| 253 | Calprotectin | CCL22 | SAA1 | 0.66 | 0.47 | 0.40 |
| 254 | SAA1 | MMP1 | VEGFA | 0.66 | 0.47 | 0.37 |
| 255 | ICAM1 | RETN | IL1 | 0.66 | 0.47 | 0.27 |
| 256 | ICAM1 | IL1B | RETN | 0.66 | 0.47 | 0.30 |
| 257 | APOA1 | VCAM1 | IL1 | 0.66 | 0.47 | 0.34 |
| 258 | ICAM1 | MMP3 | VCAM1 | 0.66 | 0.47 | 0.30 |
| 259 | APOA1 | CCL22 | LEP | 0.66 | 0.47 | 0.32 |
| 260 | CHI3L1 | CCL22 | LEP | 0.66 | 0.47 | 0.29 |
| 261 | IL1 | MMP3 | SAA1 | 0.66 | 0.47 | 0.38 |
| 262 | APOA1 | CHI3L1 | IL1B | 0.66 | 0.47 | 0.35 |
| 263 | IL1B | TNFRSF1A | VCAM1 | 0.66 | 0.47 | 0.37 |
| 264 | Calprotectin | SAA1 | TNFRSF1A | 0.66 | 0.47 | 0.37 |
| 265 | MMP3 | CHI3L1 | SAA1 | 0.66 | 0.47 | 0.37 |
| 266 | RETN | TNFRSF1A | VCAM1 | 0.66 | 0.46 | 0.31 |
| 267 | SAA1 | IL6R | VEGFA | 0.66 | 0.46 | 0.36 |
| 268 | APOA1 | APOC3 | LEP | 0.66 | 0.46 | 0.31 |
| 269 | Calprotectin | RETN | VCAM1 | 0.66 | 0.46 | 0.30 |
| 270 | MMP1 | TNFRSF1A | SAA1 | 0.66 | 0.46 | 0.38 |
| 271 | VCAM1 | IL1B | VEGFA | 0.66 | 0.46 | 0.36 |
| 272 | APOA1 | CHI3L1 | ICAM1 | 0.66 | 0.46 | 0.28 |

FIG. 2G

| THREEMRK Set No. | Marker 1 | Marker 2 | Marker 3 | AUC | % | r |
|---|---|---|---|---|---|---|
| 273 | IL1B | APOC3 | VCAM1 | 0.66 | 0.46 | 0.36 |
| 274 | APOC3 | TNFRSF1A | SAA1 | 0.66 | 0.46 | 0.38 |
| 275 | CHI3L1 | TNFRSF1A | LEP | 0.66 | 0.46 | 0.29 |
| 276 | ICAM1 | IL1B | VEGFA | 0.66 | 0.46 | 0.30 |
| 277 | ICAM1 | IL1B | IL6 | 0.66 | 0.46 | 0.31 |
| 278 | IL6 | CHI3L1 | SAA1 | 0.66 | 0.46 | 0.36 |
| 279 | CHI3L1 | MMP1 | LEP | 0.66 | 0.45 | 0.27 |
| 280 | IL6 | CHI3L1 | LEP | 0.66 | 0.45 | 0.29 |
| 281 | IL1 | RETN | TNFRSF1A | 0.66 | 0.45 | 0.27 |
| 282 | APOA1 | TNFRSF1A | SAA1 | 0.66 | 0.45 | 0.39 |
| 283 | CHI3L1 | IL1B | RETN | 0.66 | 0.45 | 0.32 |
| 284 | Calprotectin | CHI3L1 | LEP | 0.66 | 0.45 | 0.27 |
| 285 | CHI3L1 | TNFRSF1A | RETN | 0.66 | 0.45 | 0.22 |
| 286 | CHI3L1 | IL6R | SAA1 | 0.66 | 0.45 | 0.36 |
| 287 | Calprotectin | LEP | RETN | 0.66 | 0.45 | 0.26 |
| 288 | MMP3 | APOA1 | SAA1 | 0.66 | 0.45 | 0.38 |
| 289 | CHI3L1 | TNFRSF1A | SAA1 | 0.66 | 0.45 | 0.36 |
| 290 | CHI3L1 | APOC3 | LEP | 0.66 | 0.45 | 0.28 |
| 291 | ICAM1 | CHI3L1 | MMP3 | 0.66 | 0.45 | 0.25 |
| 292 | RETN | CCL22 | VCAM1 | 0.66 | 0.44 | 0.32 |
| 293 | IL1 | CHI3L1 | LEP | 0.66 | 0.44 | 0.31 |
| 294 | APOA1 | VCAM1 | MMP3 | 0.66 | 0.44 | 0.33 |
| 295 | IL6 | VEGFA | SAA1 | 0.66 | 0.44 | 0.36 |
| 296 | APOA1 | IL6 | LEP | 0.66 | 0.44 | 0.33 |
| 297 | Calprotectin | ICAM1 | RETN | 0.66 | 0.44 | 0.23 |
| 298 | RETN | IL6 | VCAM1 | 0.66 | 0.44 | 0.30 |
| 299 | ICAM1 | APOC3 | VCAM1 | 0.66 | 0.44 | 0.29 |
| 300 | MMP3 | VEGFA | SAA1 | 0.66 | 0.44 | 0.36 |
| 301 | IL6R | TNFRSF1A | LEP | 0.66 | 0.44 | 0.28 |
| 302 | APOC3 | MMP1 | SAA1 | 0.66 | 0.44 | 0.37 |
| 303 | ICAM1 | IL6R | VCAM1 | 0.66 | 0.44 | 0.28 |
| 304 | IL1 | IL6 | SAA1 | 0.66 | 0.44 | 0.37 |
| 305 | IL1 | CHI3L1 | SAA1 | 0.66 | 0.43 | 0.36 |
| 306 | IL1 | MMP1 | SAA1 | 0.66 | 0.43 | 0.37 |
| 307 | CHI3L1 | IL6R | LEP | 0.65 | 0.43 | 0.27 |
| 308 | MMP3 | IL6R | SAA1 | 0.65 | 0.43 | 0.37 |
| 309 | CHI3L1 | IL1B | IL6R | 0.65 | 0.43 | 0.32 |
| 310 | ICAM1 | MMP3 | IL1 | 0.65 | 0.43 | 0.28 |
| 311 | LEP | IL6 | RETN | 0.65 | 0.43 | 0.28 |

FIG. 2H

| THREEMRK Set No. | Marker 1 | Marker 2 | Marker 3 | AUC | % | r |
|---|---|---|---|---|---|---|
| 312 | APOA1 | VCAM1 | Calprotectin | 0.65 | 0.43 | 0.31 |
| 313 | Calprotectin | LEP | TNFRSF1A | 0.65 | 0.43 | 0.28 |
| 314 | IL6R | TNFRSF1A | SAA1 | 0.65 | 0.43 | 0.36 |
| 315 | CHI3L1 | IL1B | VEGFA | 0.65 | 0.43 | 0.32 |
| 316 | ICAM1 | IL6R | RETN | 0.65 | 0.43 | 0.24 |
| 317 | APOA1 | TNFRSF1A | VCAM1 | 0.65 | 0.43 | 0.31 |
| 318 | LEP | APOC3 | MMP3 | 0.65 | 0.42 | 0.28 |
| 319 | APOA1 | IL6R | VCAM1 | 0.65 | 0.42 | 0.32 |
| 320 | IL6 | IL6R | SAA1 | 0.65 | 0.42 | 0.36 |
| 321 | LEP | TNFRSF1A | VEGFA | 0.65 | 0.42 | 0.27 |
| 322 | APOA1 | RETN | ICAM1 | 0.65 | 0.42 | 0.26 |
| 323 | MMP3 | TNFRSF1A | SAA1 | 0.65 | 0.42 | 0.37 |
| 324 | CHI3L1 | IL1B | IL1 | 0.65 | 0.42 | 0.36 |
| 325 | APOA1 | CHI3L1 | VCAM1 | 0.65 | 0.42 | 0.31 |
| 326 | IL1 | IL1B | MMP3 | 0.65 | 0.42 | 0.38 |
| 327 | MMP3 | IL6 | SAA1 | 0.65 | 0.42 | 0.37 |
| 328 | LEP | MMP1 | RETN | 0.65 | 0.42 | 0.25 |
| 329 | ICAM1 | IL6R | MMP3 | 0.65 | 0.42 | 0.27 |
| 330 | LEP | RETN | VEGFA | 0.65 | 0.42 | 0.25 |
| 331 | Calprotectin | LEP | MMP3 | 0.65 | 0.41 | 0.27 |
| 332 | IL1 | IL1B | RETN | 0.65 | 0.41 | 0.35 |
| 333 | IL1 | LEP | MMP3 | 0.65 | 0.41 | 0.30 |
| 334 | CHI3L1 | IL1B | MMP1 | 0.65 | 0.41 | 0.32 |
| 335 | IL1 | LEP | TNFRSF1A | 0.65 | 0.41 | 0.29 |
| 336 | APOA1 | CCL22 | VCAM1 | 0.65 | 0.41 | 0.33 |
| 337 | RETN | APOC3 | VCAM1 | 0.65 | 0.41 | 0.30 |
| 338 | RETN | VEGFA | VCAM1 | 0.65 | 0.41 | 0.31 |
| 339 | ICAM1 | APOA1 | MMP3 | 0.65 | 0.41 | 0.28 |
| 340 | APOA1 | IL6R | ICAM1 | 0.65 | 0.41 | 0.28 |
| 341 | CHI3L1 | MMP1 | SAA1 | 0.65 | 0.41 | 0.35 |
| 342 | Calprotectin | CHI3L1 | IL1B | 0.65 | 0.41 | 0.31 |
| 343 | CHI3L1 | CCL22 | IL1B | 0.65 | 0.41 | 0.31 |
| 344 | IL6R | MMP1 | SAA1 | 0.65 | 0.40 | 0.36 |
| 345 | CHI3L1 | IL1B | IL6 | 0.65 | 0.40 | 0.32 |
| 346 | Calprotectin | ICAM1 | VCAM1 | 0.65 | 0.40 | 0.27 |
| 347 | IL6 | MMP1 | SAA1 | 0.65 | 0.40 | 0.36 |
| 348 | MMP3 | MMP1 | SAA1 | 0.65 | 0.40 | 0.36 |
| 349 | MMP3 | IL6R | VCAM1 | 0.65 | 0.40 | 0.30 |
| 350 | IL1B | TNFRSF1A | IL1 | 0.65 | 0.40 | 0.36 |

FIG. 21

| THREEMRK Set No. | Marker 1 | Marker 2 | Marker 3 | AUC | % | r |
|---|---|---|---|---|---|---|
| 351 | ICAM1 | IL6 | VCAM1 | 0.65 | 0.40 | 0.26 |
| 352 | MMP3 | CHI3L1 | RETN | 0.65 | 0.40 | 0.19 |
| 353 | APOA1 | IL1B | TNFRSF1A | 0.65 | 0.40 | 0.33 |
| 354 | CCL22 | TNFRSF1A | LEP | 0.65 | 0.40 | 0.27 |
| 355 | APOA1 | APOC3 | VCAM1 | 0.65 | 0.40 | 0.32 |
| 356 | ICAM1 | VCAM1 | IL1 | 0.65 | 0.40 | 0.29 |
| 357 | CHI3L1 | APOC3 | IL1B | 0.65 | 0.39 | 0.31 |
| 358 | ICAM1 | MMP3 | VEGFA | 0.65 | 0.39 | 0.27 |
| 359 | Calprotectin | MMP3 | VCAM1 | 0.65 | 0.39 | 0.30 |
| 360 | LEP | IL6R | RETN | 0.65 | 0.39 | 0.24 |
| 361 | APOC3 | TNFRSF1A | LEP | 0.65 | 0.39 | 0.27 |
| 362 | MMP3 | TNFRSF1A | VCAM1 | 0.65 | 0.39 | 0.30 |
| 363 | IL6 | TNFRSF1A | SAA1 | 0.65 | 0.39 | 0.36 |
| 364 | RETN | MMP1 | VCAM1 | 0.65 | 0.39 | 0.30 |
| 365 | ICAM1 | TNFRSF1A | VCAM1 | 0.65 | 0.39 | 0.27 |
| 366 | APOA1 | TNFRSF1A | ICAM1 | 0.65 | 0.39 | 0.27 |
| 367 | IL1B | IL6R | TNFRSF1A | 0.65 | 0.39 | 0.29 |
| 368 | CHI3L1 | IL1B | MMP3 | 0.65 | 0.39 | 0.32 |
| 369 | MMP3 | MMP1 | VCAM1 | 0.65 | 0.39 | 0.30 |
| 370 | ICAM1 | MMP1 | RETN | 0.65 | 0.38 | 0.24 |
| 371 | APOA1 | IL1B | IL1 | 0.65 | 0.38 | 0.39 |
| 372 | ICAM1 | MMP3 | TNFRSF1A | 0.65 | 0.38 | 0.26 |
| 373 | IL1 | MMP3 | RETN | 0.65 | 0.38 | 0.26 |
| 374 | Calprotectin | APOA1 | ICAM1 | 0.65 | 0.38 | 0.26 |
| 375 | ICAM1 | CHI3L1 | VCAM1 | 0.65 | 0.38 | 0.26 |
| 376 | MMP3 | APOC3 | VCAM1 | 0.65 | 0.38 | 0.30 |
| 377 | LEP | APOC3 | RETN | 0.65 | 0.38 | 0.23 |
| 378 | ICAM1 | RETN | VEGFA | 0.65 | 0.38 | 0.24 |

| FOURMRK Set No. | Marker 1 | Marker 2 | Marker 3 | Marker 4 | AUC | % | r |
|---|---|---|---|---|---|---|---|
| 1 | APOA1 | CHI3L1 | LEP | RETN | 0.71 | 0.66 | 0.36 |
| 2 | Calprotectin | LEP | SAA1 | VEGFA | 0.71 | 0.66 | 0.42 |
| 3 | APOA1 | CCL22 | IL1B | SAA1 | 0.71 | 0.65 | 0.47 |
| 4 | IL6 | VEGFA | LEP | SAA1 | 0.71 | 0.64 | 0.42 |
| 5 | LEP | MMP3 | SAA1 | VEGFA | 0.71 | 0.64 | 0.41 |
| 6 | APOA1 | CHI3L1 | IL1B | LEP | 0.71 | 0.64 | 0.41 |
| 7 | LEP | APOC3 | SAA1 | VEGFA | 0.71 | 0.63 | 0.41 |
| 8 | ICAM1 | LEP | MMP3 | VCAM1 | 0.71 | 0.63 | 0.35 |
| 9 | ICAM1 | LEP | MMP3 | VEGFA | 0.70 | 0.60 | 0.34 |
| 10 | CCL22 | IL1B | SAA1 | VCAM1 | 0.70 | 0.60 | 0.46 |
| 11 | APOA1 | IL1B | SAA1 | VEGFA | 0.70 | 0.60 | 0.44 |
| 12 | APOC3 | MMP1 | LEP | SAA1 | 0.70 | 0.59 | 0.42 |
| 13 | CHI3L1 | IL1B | LEP | RETN | 0.70 | 0.58 | 0.35 |
| 14 | Calprotectin | IL1B | SAA1 | VCAM1 | 0.70 | 0.58 | 0.45 |
| 15 | Calprotectin | IL6 | LEP | SAA1 | 0.70 | 0.58 | 0.41 |
| 16 | LEP | CHI3L1 | SAA1 | VEGFA | 0.70 | 0.58 | 0.41 |
| 17 | Calprotectin | CHI3L1 | LEP | SAA1 | 0.70 | 0.58 | 0.42 |
| 18 | IL1RN | IL1B | SAA1 | VCAM1 | 0.70 | 0.57 | 0.46 |
| 19 | Calprotectin | LEP | MMP3 | SAA1 | 0.70 | 0.57 | 0.42 |
| 20 | APOA1 | IL1B | EGF | MMP1 | 0.70 | 0.57 | 0.43 |
| 21 | IL1B | APOC3 | SAA1 | VCAM1 | 0.70 | 0.57 | 0.44 |
| 22 | CHI3L1 | APOC3 | LEP | SAA1 | 0.70 | 0.57 | 0.41 |
| 23 | APOA1 | IL1B | SAA1 | VCAM1 | 0.70 | 0.57 | 0.45 |
| 24 | EGF | MMP1 | MMP3 | VEGFA | 0.70 | 0.57 | 0.42 |
| 25 | APOA1 | IL1B | EGF | IL6R | 0.70 | 0.57 | 0.41 |
| 26 | IL1B | TNFRSF1A | SAA1 | VEGFA | 0.70 | 0.57 | 0.45 |
| 27 | APOA1 | IL1B | IL1RN | SAA1 | 0.70 | 0.57 | 0.46 |
| 28 | EGF | CCL22 | MMP3 | RETN | 0.70 | 0.57 | 0.42 |
| 29 | Calprotectin | LEP | MMP1 | SAA1 | 0.70 | 0.57 | 0.41 |
| 30 | CHI3L1 | CCL22 | IL1B | LEP | 0.70 | 0.57 | 0.37 |
| 31 | IL1B | IL6R | SAA1 | VCAM1 | 0.70 | 0.56 | 0.44 |
| 32 | Calprotectin | APOC3 | LEP | SAA1 | 0.70 | 0.56 | 0.42 |
| 33 | APOA1 | CCL22 | EGF | MMP3 | 0.70 | 0.56 | 0.42 |
| 34 | APOA1 | RETN | EGF | TNFRSF1A | 0.70 | 0.56 | 0.40 |
| 35 | IL1B | IL6R | SAA1 | VEGFA | 0.70 | 0.56 | 0.42 |
| 36 | CCL22 | IL1B | EGF | MMP3 | 0.70 | 0.56 | 0.44 |
| 37 | APOA1 | APOC3 | EGF | TNFRSF1A | 0.70 | 0.56 | 0.40 |
| 38 | APOA1 | IL1B | SAA1 | TNFRSF1A | 0.70 | 0.56 | 0.45 |

| FOURMRK Set No. | Marker 1 | Marker 2 | Marker 3 | Marker 4 | AUC | % | r |
|---|---|---|---|---|---|---|---|
| 39 | LEP | MMP1 | MMP3 | SAA1 | 0.70 | 0.56 | 0.39 |
| 40 | APOA1 | IL1B | EGF | MMP3 | 0.70 | 0.55 | 0.44 |
| 41 | APOA1 | APOC3 | EGF | MMP3 | 0.70 | 0.55 | 0.40 |
| 42 | IL1RN | CHI3L1 | LEP | RETN | 0.70 | 0.55 | 0.33 |
| 43 | CCL22 | IL1B | SAA1 | VEGFA | 0.70 | 0.55 | 0.45 |
| 44 | APOA1 | IL6R | EGF | TNFRSF1A | 0.70 | 0.55 | 0.40 |
| 45 | LEP | APOC3 | MMP3 | SAA1 | 0.70 | 0.55 | 0.41 |
| 46 | EGF | APOC3 | MMP3 | VEGFA | 0.70 | 0.55 | 0.41 |
| 47 | IL1B | MMP1 | IL1RN | SAA1 | 0.70 | 0.55 | 0.45 |
| 48 | APOA1 | IL1B | MMP3 | SAA1 | 0.70 | 0.55 | 0.45 |
| 49 | EGF | IL1B | MMP3 | RETN | 0.70 | 0.55 | 0.43 |
| 50 | Calprotectin | CCL22 | IL1B | SAA1 | 0.70 | 0.54 | 0.44 |
| 51 | SAA1 | IL1B | VCAM1 | VEGFA | 0.70 | 0.54 | 0.43 |
| 52 | IL1B | APOC3 | SAA1 | VEGFA | 0.70 | 0.54 | 0.43 |
| 53 | IL6 | IL1B | IL1RN | SAA1 | 0.70 | 0.54 | 0.45 |
| 54 | EGF | IL1B | IL6R | MMP3 | 0.70 | 0.54 | 0.42 |

| Set No. | Marker 1 | Marker 2 | Marker 3 | Marker 4 | Marker 5 | AUC | % | r |
|---|---|---|---|---|---|---|---|---|
| 1 | IL1RN | LEP | MMP3 | RETN | TNFRSF1A | 0.71 | 0.66 | 0.34 |
| 2 | IL1RN | CHI3L1 | LEP | MMP3 | RETN | 0.71 | 0.65 | 0.34 |
| 3 | CCL22 | IL1B | IL1RN | SAA1 | VEGFA | 0.70 | 0.62 | 0.45 |
| 4 | IL1RN | IL1B | SAA1 | VCAM1 | VEGFA | 0.70 | 0.61 | 0.46 |
| 5 | APOA1 | APOC3 | IL1B | SAA1 | VCAM1 | 0.70 | 0.60 | 0.44 |
| 6 | CHI3L1 | APOC3 | IL6 | LEP | SAA1 | 0.70 | 0.60 | 0.40 |
| 7 | APOA1 | RETN | IL1RN | LEP | MMP3 | 0.70 | 0.60 | 0.38 |
| 8 | APOA1 | APOC3 | EGF | IL1B | MMP3 | 0.70 | 0.60 | 0.42 |
| 9 | APOA1 | IL6R | EGF | MMP1 | MMP3 | 0.70 | 0.60 | 0.40 |
| 10 | APOC3 | MMP1 | IL1B | SAA1 | VCAM1 | 0.70 | 0.59 | 0.45 |
| 11 | IL6 | IL1B | SAA1 | VCAM1 | VEGFA | 0.70 | 0.59 | 0.43 |
| 12 | APOA1 | RETN | IL1RN | LEP | TNFRSF1A | 0.70 | 0.58 | 0.36 |
| 13 | IL1B | IL6R | SAA1 | TNFRSF1A | VCAM1 | 0.70 | 0.58 | 0.43 |
| 14 | APOA1 | IL1B | SAA1 | TNFRSF1A | VCAM1 | 0.70 | 0.58 | 0.44 |
| 15 | IL6 | IL1B | MMP3 | SAA1 | VCAM1 | 0.70 | 0.58 | 0.42 |
| 16 | IL1RN | IL1B | MMP3 | SAA1 | VEGFA | 0.70 | 0.58 | 0.44 |
| 17 | APOA1 | APOC3 | EGF | MMP1 | TNFRSF1A | 0.70 | 0.57 | 0.41 |
| 18 | IL1B | MMP1 | SAA1 | VCAM1 | VEGFA | 0.70 | 0.57 | 0.43 |
| 19 | Calprotectin | IL1B | IL1RN | SAA1 | VEGFA | 0.70 | 0.57 | 0.46 |
| 20 | EGF | APOC3 | IL1B | MMP3 | VEGFA | 0.70 | 0.57 | 0.43 |
| 21 | IL1B | IL6R | IL1RN | SAA1 | VEGFA | 0.70 | 0.57 | 0.44 |
| 22 | APOA1 | IL1B | IL1RN | SAA1 | VCAM1 | 0.70 | 0.57 | 0.46 |
| 23 | EGF | IL1B | IL6 | IL6R | MMP3 | 0.70 | 0.57 | 0.44 |
| 24 | APOA1 | RETN | LEP | MMP3 | TNFRSF1A | 0.70 | 0.57 | 0.35 |
| 25 | APOA1 | IL1B | IL6R | SAA1 | VCAM1 | 0.70 | 0.56 | 0.45 |
| 26 | APOA1 | IL1B | MMP3 | SAA1 | VCAM1 | 0.70 | 0.56 | 0.44 |
| 27 | CCL22 | IL1B | IL6 | SAA1 | VEGFA | 0.70 | 0.56 | 0.43 |
| 28 | CHI3L1 | CCL22 | IL1B | IL6R | LEP | 0.70 | 0.56 | 0.35 |
| 29 | IL1B | APOC3 | IL6R | SAA1 | VCAM1 | 0.70 | 0.56 | 0.43 |
| 30 | Calprotectin | IL6R | LEP | MMP3 | VCAM1 | 0.70 | 0.56 | 0.36 |
| 31 | IL1B | TNFRSF1A | SAA1 | VCAM1 | VEGFA | 0.70 | 0.56 | 0.44 |
| 32 | APOA1 | CCL22 | EGF | IL1B | MMP3 | 0.70 | 0.56 | 0.44 |
| 33 | CHI3L1 | IL6R | LEP | MMP3 | RETN | 0.70 | 0.56 | 0.30 |
| 34 | CHI3L1 | IL1B | LEP | MMP3 | TNFRSF1A | 0.70 | 0.56 | 0.38 |
| 35 | CHI3L1 | TNFRSF1A | IL1RN | LEP | RETN | 0.70 | 0.56 | 0.32 |
| 36 | CHI3L1 | IL1B | IL1RN | RETN | VCAM1 | 0.70 | 0.56 | 0.41 |
| 37 | CHI3L1 | APOC3 | LEP | MMP3 | SAA1 | 0.70 | 0.56 | 0.40 |
| 38 | IL1B | IL6R | IL1RN | MMP3 | SAA1 | 0.70 | 0.56 | 0.45 |

| Set No. | Marker 1 | Marker 2 | Marker 3 | Marker 4 | Marker 5 | AUC | % | r |
|---|---|---|---|---|---|---|---|---|
| 39 | IL1B | IL6R | IL8 | RETN | VEGFA | 0.70 | 0.56 | 0.43 |
| 40 | APOA1 | APOC3 | EGF | MMP3 | VEGFA | 0.70 | 0.56 | 0.41 |
| 41 | APOA1 | IL1B | IL1RN | LEP | RETN | 0.70 | 0.56 | 0.42 |
| 42 | CCL22 | IL1B | EGF | MMP3 | VEGFA | 0.70 | 0.55 | 0.45 |
| 43 | APOA1 | IL1B | MMP1 | SAA1 | VCAM1 | 0.70 | 0.55 | 0.45 |
| 44 | APOA1 | IL1B | EGF | IL6R | MMP3 | 0.70 | 0.55 | 0.43 |

| SIXMRK Set No. | Marker 1 | Marker 2 | Marker 3 | Marker 4 | Marker 5 | Marker 6 | AUC | % | r |
|---|---|---|---|---|---|---|---|---|---|
| 1 | APOA1 | IL1B | IL6R | IL1RN | SAA1 | VCAM1 | 0.71 | 0.59 | 0.46 |
| 2 | APOA1 | RETN | ICAM1 | IL1RN | MMP3 | TNFRSF1A | 0.71 | 0.58 | 0.32 |
| 3 | CHI3L1 | IL6R | IL1RN | LEP | RETN | TNFRSF1A | 0.71 | 0.57 | 0.34 |
| 4 | APOA1 | IL6 | IL1RN | LEP | RETN | TNFRSF1A | 0.71 | 0.56 | 0.38 |
| 5 | IL1B | APOC3 | IL6 | IL1RN | SAA1 | VCAM1 | 0.71 | 0.55 | 0.46 |
| 6 | CCL22 | IL1B | IL6 | MMP3 | SAA1 | VEGFA | 0.71 | 0.55 | 0.44 |
| 7 | APOA1 | IL1B | Calprotectin | IL1RN | SAA1 | TNFRSF1A | 0.70 | 0.54 | 0.48 |
| 8 | APOA1 | IL1B | IL1RN | MMP1 | SAA1 | VCAM1 | 0.70 | 0.53 | 0.47 |
| 9 | APOA1 | APOC3 | CCL22 | EGF | MMP1 | MMP3 | 0.70 | 0.53 | 0.43 |
| 10 | APOA1 | IL1B | Calprotectin | IL1RN | MMP1 | SAA1 | 0.70 | 0.53 | 0.48 |
| 11 | APOA1 | CCL22 | IL6R | LEP | RETN | TNFRSF1A | 0.70 | 0.52 | 0.34 |
| 12 | Calprotectin | APOC3 | CHI3L1 | IL1B | LEP | VEGFA | 0.70 | 0.52 | 0.37 |
| 13 | APOA1 | IL1B | IL1RN | LEP | RETN | TNFRSF1A | 0.70 | 0.51 | 0.42 |
| 14 | Calprotectin | CCL22 | IL1B | IL6 | SAA1 | VEGFA | 0.70 | 0.51 | 0.45 |
| 15 | APOA1 | RETN | IL1RN | LEP | TNFRSF1A | VEGFA | 0.70 | 0.51 | 0.36 |
| 16 | APOA1 | CCL22 | EGF | IL1B | IL6R | MMP3 | 0.70 | 0.50 | 0.45 |
| 17 | APOA1 | IL1B | MMP3 | SAA1 | TNFRSF1A | VCAM1 | 0.70 | 0.50 | 0.44 |
| 18 | CHI3L1 | TNFRSF1A | ICAM1 | IL1RN | MMP3 | RETN | 0.70 | 0.50 | 0.30 |
| 19 | APOA1 | IL1B | Calprotectin | IL6R | IL1RN | SAA1 | 0.70 | 0.50 | 0.47 |
| 20 | IL1B | IL6R | SAA1 | TNFRSF1A | VCAM1 | VEGFA | 0.70 | 0.49 | 0.42 |
| 21 | Calprotectin | IL1B | IL1RN | MMP3 | SAA1 | VEGFA | 0.70 | 0.49 | 0.45 |
| 22 | EGF | IL1B | IL6R | MMP1 | MMP3 | VEGFA | 0.70 | 0.49 | 0.43 |
| 23 | Calprotectin | IL1B | IL6R | LEP | RETN | TNFRSF1A | 0.70 | 0.49 | 0.34 |
| 24 | APOC3 | MMP1 | IL1B | IL6R | SAA1 | VCAM1 | 0.70 | 0.49 | 0.43 |
| 25 | APOA1 | APOC3 | EGF | IL6R | RETN | TNFRSF1A | 0.70 | 0.49 | 0.41 |
| 26 | CHI3L1 | IL1B | IL1RN | RETN | VCAM1 | VEGFA | 0.70 | 0.49 | 0.42 |

| SIXMRK Set No. | Marker 1 | Marker 2 | Marker 3 | Marker 4 | Marker 5 | Marker 6 | AUC | % | r |
|---|---|---|---|---|---|---|---|---|---|
| 27 | APOA1 | CCL22 | EGF | IL1B | MMP1 | MMP3 | 0.70 | 0.49 | 0.46 |
| 28 | IL1B | APOC3 | IL6R | SAA1 | VCAM1 | VEGFA | 0.70 | 0.49 | 0.44 |
| 29 | CHI3L1 | IL1B | IL6R | LEP | MMP1 | MMP3 | 0.70 | 0.49 | 0.38 |
| 30 | APOA1 | IL6 | IL6R | LEP | RETN | TNFRSF1A | 0.70 | 0.48 | 0.36 |
| 31 | ICAM1 | IL1B | IL1RN | MMP3 | RETN | VCAM1 | 0.70 | 0.48 | 0.39 |
| 32 | CHI3L1 | CCL22 | IL1B | IL6 | LEP | VEGFA | 0.70 | 0.48 | 0.36 |
| 33 | APOA1 | CHI3L1 | ICAM1 | IL1B | RETN | VCAM1 | 0.70 | 0.48 | 0.38 |
| 34 | APOA1 | RETN | Calprotectin | IL1RN | LEP | TNFRSF1A | 0.70 | 0.48 | 0.36 |
| 35 | EGF | IL1B | IL6 | MMP1 | MMP3 | VEGFA | 0.70 | 0.48 | 0.42 |
| 36 | APOC3 | TNFRSF1A | ICAM1 | IL6R | LEP | MMP3 | 0.70 | 0.48 | 0.32 |
| 37 | CHI3L1 | IL1B | ICAM1 | MMP3 | RETN | VCAM1 | 0.70 | 0.48 | 0.36 |
| 38 | CHI3L1 | IL6R | ICAM1 | LEP | MMP1 | MMP3 | 0.70 | 0.48 | 0.34 |
| 39 | CCL22 | APOC3 | IL1B | IL6 | IL1RN | SAA1 | 0.70 | 0.48 | 0.46 |
| 40 | APOA1 | IL1B | Calprotectin | MMP3 | SAA1 | TNFRSF1A | 0.70 | 0.48 | 0.46 |
| 41 | APOA1 | APOC3 | EGF | IL6 | IL6R | TNFRSF1A | 0.70 | 0.48 | 0.43 |
| 42 | APOA1 | IL6R | IL1RN | LEP | RETN | TNFRSF1A | 0.70 | 0.48 | 0.36 |
| 43 | APOA1 | CCL22 | EGF | IL1B | MMP3 | VEGFA | 0.70 | 0.48 | 0.44 |
| 44 | APOC3 | MMP1 | EGF | MMP3 | RETN | VEGFA | 0.70 | 0.47 | 0.41 |
| 45 | Calprotectin | CCL22 | LEP | MMP3 | TNFRSF1A | VCAM1 | 0.70 | 0.47 | 0.37 |
| 46 | ICAM1 | IL6R | IL1RN | LEP | MMP1 | MMP3 | 0.70 | 0.47 | 0.31 |
| 47 | Calprotectin | CHI3L1 | IL1RN | LEP | MMP1 | RETN | 0.70 | 0.47 | 0.33 |
| 48 | APOA1 | IL1B | IL6 | IL1RN | SAA1 | VCAM1 | 0.70 | 0.47 | 0.44 |
| 49 | APOA1 | IL6R | IL6 | MMP3 | RETN | VCAM1 | 0.70 | 0.47 | 0.37 |
| 50 | IL1B | TNFRSF1A | IL1RN | MMP3 | SAA1 | VEGFA | 0.70 | 0.47 | 0.43 |
| 51 | CCL22 | IL1B | IL6 | IL1RN | MMP1 | SAA1 | 0.70 | 0.47 | 0.46 |
| 52 | APOA1 | APOC3 | CCL22 | EGF | MMP3 | RETN | 0.70 | 0.47 | 0.41 |
| 53 | APOA1 | IL6 | LEP | RETN | TNFRSF1A | VEGFA | 0.70 | 0.47 | 0.35 |
| 54 | APOA1 | MMP1 | Calprotectin | LEP | MMP3 | RETN | 0.70 | 0.47 | 0.34 |

FIG. 5B

| SIXMRK Set No. | Marker 1 | Marker 2 | Marker 3 | Marker 4 | Marker 5 | Marker 6 | AUC | % | r |
|---|---|---|---|---|---|---|---|---|---|
| 55 | APOA1 | IL6R | LEP | MMP3 | RETN | TNFRSF1A | 0.70 | 0.47 | 0.34 |
| 56 | APOC3 | TNFRSF1A | IL1B | IL6R | SAA1 | VCAM1 | 0.70 | 0.47 | 0.42 |
| 57 | CHI3L1 | IL6R | LEP | MMP3 | RETN | VEGFA | 0.70 | 0.47 | 0.30 |
| 58 | APOA1 | CHI3L1 | Calprotectin | CCL22 | SAA1 | VEGFA | 0.70 | 0.47 | 0.42 |
| 59 | APOA1 | IL1B | Calprotectin | LEP | RETN | TNFRSF1A | 0.70 | 0.47 | 0.39 |
| 60 | CCL22 | APOC3 | IL1B | IL6 | SAA1 | VEGFA | 0.70 | 0.46 | 0.44 |
| 61 | CHI3L1 | IL6R | ICAM1 | LEP | TNFRSF1A | VCAM1 | 0.70 | 0.46 | 0.34 |
| 62 | APOA1 | IL1B | IL6 | SAA1 | TNFRSF1A | VCAM1 | 0.70 | 0.46 | 0.45 |
| 63 | Calprotectin | APOC3 | CHI3L1 | IL1RN | LEP | RETN | 0.70 | 0.46 | 0.32 |
| 64 | CCL22 | TNFRSF1A | ICAM1 | LEP | VCAM1 | VEGFA | 0.70 | 0.46 | 0.33 |
| 65 | APOA1 | CCL22 | EGF | MMP3 | RETN | VEGFA | 0.70 | 0.46 | 0.43 |
| 66 | IL1B | IL6R | IL1RN | LEP | MMP3 | RETN | 0.70 | 0.46 | 0.39 |
| 67 | IL6R | TNFRSF1A | LEP | MMP3 | VCAM1 | VEGFA | 0.70 | 0.46 | 0.35 |
| 68 | APOC3 | TNFRSF1A | CCL22 | IL1B | IL1RN | SAA1 | 0.70 | 0.46 | 0.46 |
| 69 | Calprotectin | CHI3L1 | IL1B | IL6R | LEP | TNFRSF1A | 0.70 | 0.46 | 0.35 |
| 70 | Calprotectin | APOC3 | IL1B | IL1RN | SAA1 | VEGFA | 0.70 | 0.46 | 0.45 |
| 71 | APOA1 | IL1B | EGF | IL6 | MMP1 | MMP3 | 0.70 | 0.46 | 0.45 |
| 72 | Calprotectin | APOC3 | CHI3L1 | IL1B | IL6R | LEP | 0.70 | 0.46 | 0.34 |
| 73 | CHI3L1 | MMP1 | IL6 | LEP | MMP3 | SAA1 | 0.70 | 0.45 | 0.39 |
| 74 | CCL22 | IL6R | EGF | MMP1 | MMP3 | VEGFA | 0.70 | 0.45 | 0.43 |
| 75 | IL1B | MMP1 | IL1RN | SAA1 | TNFRSF1A | VCAM1 | 0.70 | 0.45 | 0.46 |
| 76 | IL6 | IL1B | IL1B | MMP3 | SAA1 | VEGFA | 0.70 | 0.45 | 0.44 |
| 77 | IL6 | IL1B | IL1RN | MMP3 | MMP1 | VCAM1 | 0.70 | 0.45 | 0.45 |
| 78 | APOA1 | RETN | Calprotectin | LEP | MMP3 | TNFRSF1A | 0.70 | 0.45 | 0.35 |
| 79 | APOA1 | CHI3L1 | IL1B | IL1RN | RETN | VCAM1 | 0.70 | 0.45 | 0.41 |
| 80 | APOA1 | RETN | IL1RN | MMP3 | TNFRSF1A | VCAM1 | 0.70 | 0.45 | 0.36 |
| 81 | EGF | APOC3 | IL1B | IL6R | MMP3 | VEGFA | 0.70 | 0.45 | 0.42 |
| 82 | Calprotectin | CHI3L1 | CCL22 | IL1B | IL6R | LEP | 0.70 | 0.45 | 0.34 |

FIG. 5C

| SIXMRK Set No. | Marker 1 | Marker 2 | Marker 3 | Marker 4 | Marker 5 | Marker 6 | AUC | % | r |
|---|---|---|---|---|---|---|---|---|---|
| 83 | IL1B | APOC3 | IL1RN | MMP3 | SAA1 | VCAM1 | 0.70 | 0.45 | 0.43 |
| 84 | APOA1 | RETN | ICAM1 | IL1RN | TNFRSF1A | VCAM1 | 0.70 | 0.45 | 0.33 |

| TWOMRK Set No. | Marker 1 | Marker 2 | AUC | % | r |
|---|---|---|---|---|---|
| 1 | CCL22 | IL6 | 0.85 | 1 | 0.68 |
| 2 | CRP | IL6 | 0.85 | 0.99 | 0.7 |
| 3 | IL1B | IL6 | 0.85 | 0.99 | 0.68 |
| 4 | IL6 | IL1RN | 0.85 | 0.98 | 0.67 |
| 5 | IL6 | SAA1 | 0.85 | 0.98 | 0.68 |
| 6 | CRP | ICAM1 | 0.84 | 0.92 | 0.65 |
| 7 | CRP | RETN | 0.84 | 0.93 | 0.64 |
| 8 | EGF | IL6 | 0.84 | 0.95 | 0.68 |
| 9 | ICAM1 | IL6 | 0.84 | 0.94 | 0.66 |
| 10 | IL6 | calprotectin | 0.84 | 0.91 | 0.67 |
| 11 | IL6 | IL8 | 0.84 | 0.93 | 0.67 |
| 12 | IL6 | LEP | 0.84 | 0.92 | 0.66 |
| 13 | IL6 | MMP1 | 0.84 | 0.97 | 0.67 |
| 14 | IL6 | MMP3 | 0.84 | 0.91 | 0.67 |
| 15 | IL6 | pyridinoline | 0.84 | 0.96 | 0.67 |
| 16 | IL6 | RETN | 0.84 | 0.96 | 0.67 |
| 17 | IL6 | TNFRSF1A | 0.84 | 0.95 | 0.66 |
| 18 | IL6 | VCAM1 | 0.84 | 0.97 | 0.66 |
| 19 | IL6 | VEGFA | 0.84 | 0.94 | 0.67 |
| 20 | CCL22 | CRP | 0.83 | 0.86 | 0.64 |
| 21 | CRP | calprotectin | 0.83 | 0.88 | 0.64 |
| 22 | CRP | CHI3L1 | 0.83 | 0.87 | 0.64 |
| 23 | CRP | IL1B | 0.83 | 0.87 | 0.64 |
| 24 | CRP | IL1RN | 0.83 | 0.84 | 0.64 |
| 25 | CRP | IL8 | 0.83 | 0.89 | 0.66 |
| 26 | CRP | MMP3 | 0.83 | 0.86 | 0.64 |
| 27 | CRP | pyridinoline | 0.83 | 0.88 | 0.65 |
| 28 | CRP | TNFRSF1A | 0.83 | 0.85 | 0.64 |
| 29 | CRP | VEGFA | 0.83 | 0.89 | 0.65 |
| 30 | IL6 | CHI3L1 | 0.83 | 0.85 | 0.67 |
| 31 | IL6R | IL6 | 0.83 | 0.9 | 0.65 |
| 32 | SAA1 | calprotectin | 0.83 | 0.84 | 0.63 |
| 33 | CRP | EGF | 0.82 | 0.82 | 0.64 |
| 34 | CRP | IL6R | 0.82 | 0.81 | 0.63 |
| 35 | CRP | LEP | 0.82 | 0.81 | 0.64 |
| 36 | CRP | MMP1 | 0.82 | 0.83 | 0.64 |
| 37 | CRP | SAA1 | 0.82 | 0.8 | 0.64 |
| 38 | CRP | VCAM1 | 0.82 | 0.82 | 0.63 |

| 39 | IL1B | SAA1 | 0.82 | 0.79 | 0.61 |
|---|---|---|---|---|---|
| 40 | MMP3 | SAA1 | 0.82 | 0.83 | 0.61 |
| 41 | CCL22 | SAA1 | 0.81 | 0.76 | 0.6 |
| 42 | ICAM1 | SAA1 | 0.81 | 0.79 | 0.61 |
| 43 | IL8 | SAA1 | 0.81 | 0.77 | 0.62 |
| 44 | SAA1 | CHI3L1 | 0.81 | 0.78 | 0.59 |
| 45 | SAA1 | LEP | 0.81 | 0.77 | 0.59 |
| 46 | SAA1 | pyridinoline | 0.81 | 0.78 | 0.61 |
| 47 | SAA1 | RETN | 0.81 | 0.76 | 0.6 |
| 48 | calprotectin | CHI3L1 | 0.80 | 0.72 | 0.55 |
| 49 | EGF | SAA1 | 0.80 | 0.75 | 0.61 |
| 50 | IL6R | SAA1 | 0.80 | 0.74 | 0.59 |
| 51 | MMP1 | SAA1 | 0.80 | 0.75 | 0.59 |
| 52 | SAA1 | IL1RN | 0.80 | 0.73 | 0.6 |
| 53 | SAA1 | TNFRSF1A | 0.80 | 0.73 | 0.6 |
| 54 | SAA1 | VCAM1 | 0.80 | 0.74 | 0.6 |
| 55 | SAA1 | VEGFA | 0.80 | 0.72 | 0.61 |
| 56 | calprotectin | LEP | 0.79 | 0.68 | 0.53 |
| 57 | ICAM1 | calprotectin | 0.79 | 0.69 | 0.53 |
| 58 | IL1B | calprotectin | 0.79 | 0.71 | 0.56 |
| 59 | IL6R | calprotectin | 0.79 | 0.71 | 0.52 |
| 60 | TNFRSF1A | calprotectin | 0.79 | 0.69 | 0.53 |
| 61 | VEGFA | calprotectin | 0.79 | 0.7 | 0.53 |
| 62 | calprotectin | interleukin | 0.78 | 0.66 | 0.52 |
| 63 | calprotectin | pyridinoline | 0.78 | 0.65 | 0.53 |
| 64 | calprotectin | RETN | 0.78 | 0.65 | 0.52 |
| 65 | CCL22 | calprotectin | 0.78 | 0.67 | 0.52 |
| 66 | EGF | calprotectin | 0.78 | 0.64 | 0.52 |
| 67 | MMP1 | calprotectin | 0.78 | 0.66 | 0.54 |
| 68 | MMP3 | calprotectin | 0.78 | 0.67 | 0.55 |
| 69 | VCAM1 | calprotectin | 0.78 | 0.68 | 0.52 |
| 70 | IL8 | calprotectin | 0.77 | 0.64 | 0.54 |
| 71 | MMP3 | CHI3L1 | 0.76 | 0.63 | 0.5 |
| 72 | IL1B | MMP3 | 0.75 | 0.62 | 0.52 |
| 73 | IL8 | MMP3 | 0.75 | 0.63 | 0.52 |
| 74 | IL1B | IL8 | 0.74 | 0.61 | 0.5 |
| 75 | MMP1 | MMP3 | 0.74 | 0.59 | 0.47 |
| 76 | MMP3 | pyridinoline | 0.74 | 0.62 | 0.46 |
| 77 | MMP3 | RETN | 0.74 | 0.6 | 0.48 |
| 78 | MMP3 | TNFRSF1A | 0.74 | 0.61 | 0.48 |
| 79 | EGF | MMP3 | 0.73 | 0.56 | 0.45 |

FIG. 16B

| | | | | | |
|---|---|---|---|---|---|
| 80 | ICAM1 | MMP3 | 0.73 | 0.57 | 0.46 |
| 81 | IL6R | MMP3 | 0.73 | 0.58 | 0.45 |
| 82 | MMP3 | IL1RN | 0.73 | 0.57 | 0.45 |
| 83 | MMP3 | LEP | 0.73 | 0.56 | 0.47 |
| 84 | MMP3 | VCAM1 | 0.73 | 0.58 | 0.46 |
| 85 | MMP3 | VEGFA | 0.73 | 0.59 | 0.47 |
| 86 | CCL22 | IL1B | 0.72 | 0.55 | 0.39 |
| 87 | CCL22 | IL8 | 0.72 | 0.54 | 0.46 |
| 88 | CCL22 | MMP3 | 0.72 | 0.54 | 0.45 |
| 89 | IL1B | CHI3L1 | 0.72 | 0.53 | 0.45 |
| 90 | IL8 | CHI3L1 | 0.72 | 0.55 | 0.47 |
| 91 | IL1B | MMP1 | 0.71 | 0.52 | 0.42 |
| 92 | IL1B | VEGFA | 0.71 | 0.52 | 0.4 |
| 93 | IL8 | MMP1 | 0.71 | 0.53 | 0.47 |
| 94 | IL8 | RETN | 0.71 | 0.51 | 0.44 |
| 95 | CCL22 | CHI3L1 | 0.70 | 0.51 | 0.39 |
| 96 | ICAM1 | IL1B | 0.70 | 0.49 | 0.4 |
| 97 | ICAM1 | IL8 | 0.70 | 0.48 | 0.44 |
| 98 | IL1B | IL1RN | 0.70 | 0.47 | 0.38 |
| 99 | IL1B | IL6R | 0.70 | 0.5 | 0.4 |
| 100 | IL1B | TNFRSF1A | 0.70 | 0.47 | 0.41 |
| 101 | IL8 | IL1RN | 0.70 | 0.46 | 0.42 |
| 102 | IL8 | pyridinoline | 0.70 | 0.46 | 0.42 |
| 103 | IL8 | VEGFA | 0.70 | 0.45 | 0.42 |
| 104 | MMP1 | CHI3L1 | 0.70 | 0.48 | 0.4 |
| 105 | TNFRSF1A | CHI3L1 | 0.70 | 0.49 | 0.4 |
| 106 | CHI3L1 | RETN | 0.69 | 0.42 | 0.38 |
| 107 | EGF | IL1B | 0.69 | 0.44 | 0.38 |
| 108 | EGF | IL8 | 0.69 | 0.41 | 0.42 |
| 109 | ICAM1 | CHI3L1 | 0.69 | 0.42 | 0.38 |
| 110 | IL1B | LEP | 0.69 | 0.41 | 0.36 |
| 111 | IL1B | pyridinoline | 0.69 | 0.43 | 0.38 |
| 112 | IL1B | VCAM1 | 0.69 | 0.44 | 0.37 |
| 113 | IL6R | CHI3L1 | 0.69 | 0.39 | 0.38 |
| 114 | IL6R | IL8 | 0.69 | 0.4 | 0.42 |
| 115 | IL8 | LEP | 0.69 | 0.39 | 0.41 |
| 116 | IL8 | TNFRSF1A | 0.69 | 0.45 | 0.43 |
| 117 | IL8 | VCAM1 | 0.69 | 0.38 | 0.41 |
| 118 | VEGFA | CHI3L1 | 0.69 | 0.43 | 0.39 |
| 119 | CHI3L1 | IL1RN | 0.68 | 0.36 | 0.37 |
| 120 | CHI3L1 | LEP | 0.68 | 0.35 | 0.37 |

FIG. 16C

| | | | | | |
|---|---|---|---|---|---|
| 121 | CHI3L1 | pyridinoline | 0.68 | 0.37 | 0.38 |
| 122 | EGF | CHI3L1 | 0.68 | 0.37 | 0.39 |
| 123 | IL1B | RETN | 0.68 | 0.38 | 0.37 |
| 124 | VCAM1 | CHI3L1 | 0.68 | 0.36 | 0.37 |
| 125 | IL6R | TNFRSF1A | 0.67 | 0.35 | 0.34 |
| 126 | MMP1 | VEGFA | 0.67 | 0.34 | 0.34 |
| 127 | TNFRSF1A | VEGFA | 0.67 | 0.34 | 0.34 |
| 128 | CCL22 | VEGFA | 0.66 | 0.33 | 0.27 |
| 129 | MMP1 | RETN | 0.66 | 0.32 | 0.34 |
| 130 | MMP1 | TNFRSF1A | 0.66 | 0.33 | 0.36 |
| 131 | TNFRSF1A | pyridinoline | 0.66 | 0.32 | 0.34 |
| 132 | CCL22 | TNFRSF1A | 0.65 | 0.31 | 0.34 |
| 133 | ICAM1 | MMP1 | 0.65 | 0.29 | 0.32 |
| 134 | ICAM1 | TNFRSF1A | 0.65 | 0.31 | 0.32 |
| 135 | ICAM1 | VEGFA | 0.65 | 0.28 | 0.27 |
| 136 | MMP1 | pyridinoline | 0.65 | 0.29 | 0.33 |
| 137 | TNFRSF1A | VCAM1 | 0.65 | 0.27 | 0.33 |
| 138 | VEGFA | IL1RN | 0.65 | 0.3 | 0.24 |
| 139 | VEGFA | pyridinoline | 0.65 | 0.28 | 0.29 |
| 140 | CCL22 | MMP1 | 0.64 | 0.27 | 0.31 |
| 141 | EGF | MMP1 | 0.64 | 0.23 | 0.34 |
| 142 | EGF | TNFRSF1A | 0.64 | 0.25 | 0.34 |
| 143 | IL6R | MMP1 | 0.64 | 0.26 | 0.32 |
| 144 | MMP1 | IL1RN | 0.64 | 0.25 | 0.31 |
| 145 | TNFRSF1A | RETN | 0.64 | 0.24 | 0.32 |
| 146 | VCAM1 | VEGFA | 0.64 | 0.24 | 0.25 |
| 147 | VEGFA | LEP | 0.64 | 0.26 | 0.24 |
| 148 | IL6R | VEGFA | 0.63 | 0.22 | 0.24 |
| 149 | MMP1 | LEP | 0.63 | 0.21 | 0.3 |
| 150 | MMP1 | VCAM1 | 0.63 | 0.22 | 0.31 |
| 151 | TNFRSF1A | IL1RN | 0.63 | 0.23 | 0.31 |
| 152 | VEGFA | RETN | 0.63 | 0.21 | 0.26 |
| 153 | CCL22 | ICAM1 | 0.62 | 0.19 | 0.2 |
| 154 | EGF | VEGFA | 0.62 | 0.19 | 0.24 |
| 155 | TNFRSF1A | LEP | 0.62 | 0.2 | 0.31 |
| 156 | ICAM1 | pyridinoline | 0.60 | 0.18 | 0.23 |
| 157 | ICAM1 | RETN | 0.60 | 0.18 | 0.22 |

| THREEMRK Set No. | Marker 1 | Marker 2 | Marker 3 | AUC | % | r |
|---|---|---|---|---|---|---|
| 1 | IL8 | TNFRSF1A | VEGFA | 0.72 | 0.49 | 0.40 |
| 2 | IL8 | pyridinoline | VEGFA | 0.71 | 0.47 | 0.42 |
| 3 | IL8 | pyridinoline | TNFRSF1A | 0.71 | 0.46 | 0.41 |
| 4 | IL6R | IL8 | VEGFA | 0.71 | 0.45 | 0.41 |
| 5 | ICAM1 | IL8 | VEGFA | 0.70 | 0.44 | 0.43 |
| 6 | ICAM1 | IL8 | TNFRSF1A | 0.70 | 0.44 | 0.42 |
| 7 | IL1B | LEP | TNFRSF1A | 0.70 | 0.44 | 0.40 |
| 8 | IL6R | CHI3L1 | VEGFA | 0.70 | 0.42 | 0.34 |
| 9 | EGF | IL1B | pyridinoline | 0.70 | 0.42 | 0.38 |
| 10 | IL1B | RETN | TNFRSF1A | 0.70 | 0.41 | 0.41 |
| 11 | IL8 | IL1RN | VEGFA | 0.70 | 0.41 | 0.43 |
| 12 | EGF | IL8 | VEGFA | 0.70 | 0.40 | 0.42 |
| 13 | CHI3L1 | RETN | ICAM1 | 0.70 | 0.40 | 0.37 |
| 14 | IL8 | IL1RN | TNFRSF1A | 0.70 | 0.39 | 0.41 |
| 15 | CHI3L1 | IL1RN | IL6R | 0.70 | 0.39 | 0.32 |
| 16 | IL1B | pyridinoline | TNFRSF1A | 0.70 | 0.39 | 0.41 |
| 17 | IL1B | TNFRSF1A | VCAM1 | 0.69 | 0.38 | 0.39 |
| 18 | ICAM1 | IL8 | LEP | 0.69 | 0.38 | 0.41 |
| 19 | EGF | ICAM1 | IL8 | 0.69 | 0.38 | 0.41 |
| 20 | ICAM1 | IL8 | pyridinoline | 0.69 | 0.37 | 0.40 |
| 21 | EGF | IL1B | LEP | 0.69 | 0.37 | 0.36 |
| 22 | ICAM1 | IL6R | IL8 | 0.69 | 0.37 | 0.41 |
| 23 | EGF | IL8 | TNFRSF1A | 0.69 | 0.37 | 0.42 |
| 24 | EGF | IL1B | TNFRSF1A | 0.69 | 0.37 | 0.41 |
| 25 | ICAM1 | IL8 | IL1RN | 0.69 | 0.36 | 0.43 |
| 26 | IL6R | CHI3L1 | VCAM1 | 0.69 | 0.36 | 0.36 |
| 27 | ICAM1 | IL8 | VCAM1 | 0.69 | 0.36 | 0.39 |
| 28 | CHI3L1 | RETN | EGF | 0.69 | 0.35 | 0.38 |
| 29 | CHI3L1 | RETN | VEGFA | 0.69 | 0.35 | 0.35 |
| 30 | IL8 | VCAM1 | VEGFA | 0.69 | 0.35 | 0.38 |
| 31 | ICAM1 | CHI3L1 | IL6R | 0.69 | 0.35 | 0.35 |
| 32 | ICAM1 | CHI3L1 | VEGFA | 0.69 | 0.34 | 0.37 |
| 33 | EGF | IL8 | IL1RN | 0.69 | 0.34 | 0.41 |
| 34 | CHI3L1 | pyridinoline | VEGFA | 0.69 | 0.34 | 0.37 |
| 35 | IL8 | TNFRSF1A | VCAM1 | 0.69 | 0.34 | 0.42 |
| 36 | IL6R | IL8 | TNFRSF1A | 0.69 | 0.34 | 0.40 |
| 37 | EGF | CHI3L1 | VEGFA | 0.69 | 0.33 | 0.37 |
| 38 | IL6R | IL8 | pyridinoline | 0.69 | 0.33 | 0.40 |

| | | | | | | |
|---|---|---|---|---|---|---|
| 39 | IL8 | IL1RN | pyridinoline | 0.69 | 0.33 | 0.40 |
| 40 | IL8 | LEP | VEGFA | 0.69 | 0.33 | 0.41 |
| 41 | IL1B | IL1RN | TNFRSF1A | 0.69 | 0.33 | 0.38 |
| 42 | IL1B | IL1RN | pyridinoline | 0.69 | 0.33 | 0.36 |
| 43 | IL1B | LEP | pyridinoline | 0.69 | 0.33 | 0.36 |
| 44 | CHI3L1 | pyridinoline | VCAM1 | 0.69 | 0.33 | 0.37 |
| 45 | CHI3L1 | pyridinoline | EGF | 0.69 | 0.32 | 0.39 |
| 46 | CHI3L1 | RETN | IL6R | 0.69 | 0.32 | 0.34 |
| 47 | ICAM1 | CHI3L1 | VCAM1 | 0.68 | 0.32 | 0.35 |
| 48 | CHI3L1 | LEP | VEGFA | 0.68 | 0.32 | 0.34 |
| 49 | EGF | CHI3L1 | IL6R | 0.68 | 0.31 | 0.36 |
| 50 | CHI3L1 | RETN | VCAM1 | 0.68 | 0.31 | 0.35 |
| 51 | CHI3L1 | IL1RN | VEGFA | 0.68 | 0.31 | 0.37 |
| 52 | CHI3L1 | IL1RN | ICAM1 | 0.68 | 0.31 | 0.35 |
| 53 | IL6R | IL8 | LEP | 0.68 | 0.30 | 0.39 |
| 54 | VCAM1 | CHI3L1 | VEGFA | 0.68 | 0.30 | 0.35 |
| 55 | CHI3L1 | LEP | ICAM1 | 0.68 | 0.30 | 0.37 |
| 56 | IL8 | LEP | TNFRSF1A | 0.68 | 0.30 | 0.40 |
| 57 | EGF | CHI3L1 | ICAM1 | 0.68 | 0.29 | 0.37 |
| 58 | CHI3L1 | pyridinoline | IL6R | 0.68 | 0.29 | 0.36 |
| 59 | EGF | IL1B | VCAM1 | 0.68 | 0.29 | 0.35 |
| 60 | CHI3L1 | pyridinoline | ICAM1 | 0.68 | 0.29 | 0.34 |
| 61 | IL1B | pyridinoline | VCAM1 | 0.68 | 0.29 | 0.35 |
| 62 | IL8 | IL1RN | LEP | 0.68 | 0.29 | 0.39 |
| 63 | CHI3L1 | IL1RN | RETN | 0.68 | 0.29 | 0.33 |
| 64 | CHI3L1 | pyridinoline | RETN | 0.68 | 0.28 | 0.37 |
| 65 | CHI3L1 | LEP | pyridinoline | 0.68 | 0.28 | 0.37 |
| 66 | CHI3L1 | IL1RN | pyridinoline | 0.68 | 0.28 | 0.35 |
| 67 | IL6R | IL8 | IL1RN | 0.68 | 0.28 | 0.40 |
| 68 | EGF | IL8 | pyridinoline | 0.68 | 0.28 | 0.38 |
| 69 | EGF | IL1B | RETN | 0.68 | 0.28 | 0.35 |
| 70 | IL1B | IL1RN | LEP | 0.68 | 0.27 | 0.32 |
| 71 | IL8 | pyridinoline | VCAM1 | 0.68 | 0.27 | 0.39 |
| 72 | IL8 | LEP | pyridinoline | 0.68 | 0.27 | 0.37 |
| 73 | CHI3L1 | IL1RN | LEP | 0.68 | 0.27 | 0.34 |
| 74 | EGF | IL8 | LEP | 0.68 | 0.27 | 0.38 |
| 75 | IL6R | IL8 | VCAM1 | 0.68 | 0.27 | 0.39 |
| 76 | EGF | CHI3L1 | VCAM1 | 0.68 | 0.27 | 0.36 |
| 77 | EGF | IL6R | IL8 | 0.68 | 0.27 | 0.39 |
| 78 | CHI3L1 | LEP | RETN | 0.68 | 0.26 | 0.35 |
| 79 | CHI3L1 | IL1RN | VCAM1 | 0.68 | 0.26 | 0.33 |

FIG. 17B

| 80 | IL1B | pyridinoline | RETN | 0.68 | 0.26 | 0.35 |
|---|---|---|---|---|---|---|
| 81 | IL1B | IL1RN | RETN | 0.67 | 0.26 | 0.36 |
| 82 | IL8 | IL1RN | VCAM1 | 0.67 | 0.26 | 0.41 |
| 83 | CHI3L1 | IL1RN | EGF | 0.67 | 0.26 | 0.37 |
| 84 | EGF | IL8 | VCAM1 | 0.67 | 0.26 | 0.37 |
| 85 | MMP1 | TNFRSF1A | VEGFA | 0.67 | 0.25 | 0.34 |
| 86 | IL6R | MMP1 | TNFRSF1A | 0.67 | 0.25 | 0.34 |
| 87 | IL6R | TNFRSF1A | VEGFA | 0.67 | 0.25 | 0.33 |
| 88 | CCL22 | TNFRSF1A | VEGFA | 0.67 | 0.25 | 0.31 |
| 89 | CHI3L1 | LEP | IL6R | 0.67 | 0.25 | 0.34 |
| 90 | IL1B | LEP | VCAM1 | 0.67 | 0.25 | 0.33 |
| 91 | CHI3L1 | LEP | VCAM1 | 0.67 | 0.25 | 0.35 |
| 92 | IL1B | IL1RN | VCAM1 | 0.67 | 0.25 | 0.36 |
| 93 | EGF | IL1B | IL1RN | 0.67 | 0.24 | 0.35 |
| 94 | CCL22 | IL6R | TNFRSF1A | 0.67 | 0.24 | 0.32 |
| 95 | CCL22 | MMP1 | VEGFA | 0.67 | 0.24 | 0.31 |
| 96 | CCL22 | ICAM1 | TNFRSF1A | 0.67 | 0.24 | 0.32 |
| 97 | IL8 | LEP | VCAM1 | 0.67 | 0.24 | 0.39 |
| 98 | CHI3L1 | LEP | EGF | 0.67 | 0.24 | 0.37 |
| 99 | IL1B | RETN | VCAM1 | 0.66 | 0.24 | 0.34 |
| 100 | ICAM1 | MMP1 | pyridinoline | 0.66 | 0.24 | 0.30 |
| 101 | IL6R | pyridinoline | TNFRSF1A | 0.66 | 0.24 | 0.32 |
| 102 | IL6R | IL1RN | TNFRSF1A | 0.66 | 0.23 | 0.30 |
| 103 | EGF | MMP1 | VEGFA | 0.66 | 0.23 | 0.36 |
| 104 | IL6R | TNFRSF1A | VCAM1 | 0.66 | 0.23 | 0.30 |
| 105 | ICAM1 | IL6R | TNFRSF1A | 0.66 | 0.23 | 0.32 |
| 106 | IL1B | LEP | RETN | 0.66 | 0.23 | 0.31 |
| 107 | MMP1 | RETN | VEGFA | 0.66 | 0.23 | 0.32 |
| 108 | TNFRSF1A | VCAM1 | VEGFA | 0.66 | 0.23 | 0.32 |
| 109 | MMP1 | pyridinoline | TNFRSF1A | 0.66 | 0.23 | 0.34 |
| 110 | CCL22 | MMP1 | RETN | 0.66 | 0.23 | 0.32 |
| 111 | IL6R | RETN | TNFRSF1A | 0.66 | 0.22 | 0.30 |
| 112 | IL6R | MMP1 | VEGFA | 0.66 | 0.22 | 0.30 |
| 113 | ICAM1 | MMP1 | TNFRSF1A | 0.66 | 0.22 | 0.33 |
| 114 | MMP1 | TNFRSF1A | VCAM1 | 0.66 | 0.22 | 0.35 |
| 115 | MMP1 | VCAM1 | VEGFA | 0.66 | 0.22 | 0.31 |
| 116 | MMP1 | pyridinoline | VEGFA | 0.65 | 0.22 | 0.32 |
| 117 | EGF | IL6R | TNFRSF1A | 0.65 | 0.22 | 0.33 |
| 118 | MMP1 | RETN | TNFRSF1A | 0.65 | 0.22 | 0.34 |
| 119 | ICAM1 | MMP1 | VEGFA | 0.65 | 0.22 | 0.32 |
| 120 | CCL22 | ICAM1 | MMP1 | 0.65 | 0.21 | 0.33 |

FIG. 17C

| | | | | | | |
|---|---|---|---|---|---|---|
| | 121 | MMP1 | LEP | TNFRSF1A | 0.65 | 0.21 | 0.33 |
| | 122 | ICAM1 | TNFRSF1A | VEGFA | 0.65 | 0.21 | 0.31 |
| | 123 | TNFRSF1A | IL1RN | VEGFA | 0.65 | 0.21 | 0.31 |
| | 124 | EGF | MMP1 | TNFRSF1A | 0.65 | 0.21 | 0.37 |
| | 125 | TNFRSF1A | RETN | VEGFA | 0.65 | 0.21 | 0.30 |
| | 126 | MMP1 | LEP | VEGFA | 0.65 | 0.21 | 0.29 |
| | 127 | TNFRSF1A | pyridinoline | VEGFA | 0.65 | 0.21 | 0.31 |
| | 128 | CCL22 | MMP1 | TNFRSF1A | 0.65 | 0.21 | 0.32 |
| | 129 | IL6R | LEP | TNFRSF1A | 0.65 | 0.20 | 0.32 |
| | 130 | CCL22 | IL6R | VEGFA | 0.65 | 0.20 | 0.22 |
| | 131 | TNFRSF1A | LEP | VEGFA | 0.65 | 0.20 | 0.31 |
| | 132 | CCL22 | RETN | VEGFA | 0.65 | 0.20 | 0.26 |
| | 133 | CCL22 | IL1RN | VEGFA | 0.65 | 0.20 | 0.20 |
| | 134 | ICAM1 | pyridinoline | TNFRSF1A | 0.65 | 0.20 | 0.31 |
| | 135 | CCL22 | MMP1 | pyridinoline | 0.65 | 0.20 | 0.30 |
| | 136 | ICAM1 | IL6R | MMP1 | 0.65 | 0.20 | 0.30 |
| | 137 | IL6R | MMP1 | RETN | 0.65 | 0.20 | 0.30 |
| | 138 | MMP1 | RETN | VCAM1 | 0.65 | 0.19 | 0.29 |
| | 139 | CCL22 | LEP | VEGFA | 0.65 | 0.19 | 0.23 |
| | 140 | CCL22 | pyridinoline | TNFRSF1A | 0.65 | 0.19 | 0.29 |
| | 141 | MMP1 | IL1RN | TNFRSF1A | 0.65 | 0.19 | 0.31 |
| | 142 | EGF | MMP1 | RETN | 0.65 | 0.19 | 0.33 |
| | 143 | MMP1 | IL1RN | VEGFA | 0.64 | 0.19 | 0.30 |
| | 144 | LEP | RETN | MMP1 | 0.64 | 0.19 | 0.30 |
| | 145 | EGF | TNFRSF1A | VEGFA | 0.64 | 0.19 | 0.31 |
| | 146 | ICAM1 | TNFRSF1A | VCAM1 | 0.64 | 0.19 | 0.30 |
| | 147 | ICAM1 | pyridinoline | VEGFA | 0.64 | 0.18 | 0.28 |
| | 148 | CCL22 | ICAM1 | VEGFA | 0.64 | 0.18 | 0.25 |
| | 149 | CCL22 | TNFRSF1A | VCAM1 | 0.64 | 0.18 | 0.30 |
| | 150 | CCL22 | pyridinoline | VEGFA | 0.64 | 0.18 | 0.27 |
| | 151 | IL6R | pyridinoline | VEGFA | 0.64 | 0.18 | 0.25 |
| | 152 | IL1RN | pyridinoline | VEGFA | 0.64 | 0.18 | 0.24 |
| | 153 | pyridinoline | RETN | TNFRSF1A | 0.64 | 0.18 | 0.29 |
| | 154 | TNFRSF1A | pyridinoline | VCAM1 | 0.64 | 0.18 | 0.31 |
| | 155 | EGF | ICAM1 | MMP1 | 0.64 | 0.18 | 0.35 |
| | 156 | IL6R | MMP1 | pyridinoline | 0.64 | 0.17 | 0.31 |
| | 157 | TNFRSF1A | LEP | VCAM1 | 0.64 | 0.17 | 0.32 |
| | 158 | EGF | pyridinoline | TNFRSF1A | 0.64 | 0.17 | 0.32 |
| | 159 | IL1RN | RETN | MMP1 | 0.64 | 0.17 | 0.29 |
| | 160 | CCL22 | EGF | TNFRSF1A | 0.64 | 0.17 | 0.32 |
| | 161 | IL1RN | pyridinoline | TNFRSF1A | 0.64 | 0.17 | 0.29 |

FIG. 17D

| | | | | | | |
|---|---|---|---|---|---|---|
| 162 | EGF | TNFRSF1A | VCAM1 | 0.64 | 0.17 | 0.32 |
| 163 | LEP | pyridinoline | VEGFA | 0.64 | 0.17 | 0.25 |
| 164 | CCL22 | RETN | TNFRSF1A | 0.64 | 0.17 | 0.30 |
| 165 | EGF | ICAM1 | TNFRSF1A | 0.64 | 0.17 | 0.30 |
| 166 | CCL22 | EGF | VEGFA | 0.64 | 0.16 | 0.24 |
| 167 | ICAM1 | MMP1 | RETN | 0.64 | 0.16 | 0.28 |
| 168 | CCL22 | LEP | MMP1 | 0.64 | 0.16 | 0.27 |
| 169 | EGF | MMP1 | pyridinoline | 0.63 | 0.16 | 0.33 |
| 170 | ICAM1 | LEP | TNFRSF1A | 0.63 | 0.16 | 0.27 |
| 171 | ICAM1 | IL1RN | VEGFA | 0.63 | 0.16 | 0.22 |
| 172 | ICAM1 | LEP | MMP1 | 0.63 | 0.16 | 0.26 |
| 173 | ICAM1 | MMP1 | VCAM1 | 0.63 | 0.16 | 0.28 |
| 174 | CCL22 | LEP | TNFRSF1A | 0.63 | 0.16 | 0.29 |
| 175 | CCL22 | IL1RN | TNFRSF1A | 0.63 | 0.15 | 0.31 |
| 176 | CCL22 | VCAM1 | VEGFA | 0.63 | 0.15 | 0.24 |
| 177 | ICAM1 | RETN | TNFRSF1A | 0.63 | 0.15 | 0.31 |
| 178 | EGF | IL6R | MMP1 | 0.63 | 0.15 | 0.31 |
| 179 | IL6R | IL1RN | MMP1 | 0.63 | 0.15 | 0.27 |
| 180 | TNFRSF1A | RETN | VCAM1 | 0.63 | 0.15 | 0.30 |
| 181 | IL6R | MMP1 | VCAM1 | 0.63 | 0.15 | 0.27 |
| 182 | ICAM1 | LEP | VEGFA | 0.63 | 0.15 | 0.21 |
| 183 | MMP1 | pyridinoline | RETN | 0.63 | 0.15 | 0.30 |
| 184 | TNFRSF1A | IL1RN | VCAM1 | 0.63 | 0.14 | 0.29 |
| 185 | VCAM1 | pyridinoline | VEGFA | 0.63 | 0.14 | 0.26 |
| 186 | ICAM1 | RETN | VEGFA | 0.63 | 0.14 | 0.22 |
| 187 | LEP | pyridinoline | MMP1 | 0.63 | 0.14 | 0.29 |
| 188 | EGF | pyridinoline | VEGFA | 0.63 | 0.14 | 0.27 |
| 189 | LEP | pyridinoline | TNFRSF1A | 0.63 | 0.14 | 0.28 |
| 190 | CCL22 | pyridinoline | RETN | 0.63 | 0.14 | 0.24 |
| 191 | ICAM1 | IL6R | VEGFA | 0.63 | 0.14 | 0.22 |
| 192 | MMP1 | IL1RN | VCAM1 | 0.63 | 0.14 | 0.24 |
| 193 | IL1RN | RETN | TNFRSF1A | 0.63 | 0.13 | 0.29 |
| 194 | IL6R | IL1RN | VEGFA | 0.63 | 0.13 | 0.20 |
| 195 | CCL22 | MMP1 | VCAM1 | 0.63 | 0.13 | 0.26 |
| 196 | MMP1 | pyridinoline | VCAM1 | 0.63 | 0.13 | 0.30 |
| 197 | ICAM1 | IL1RN | MMP1 | 0.63 | 0.13 | 0.27 |
| 198 | IL1RN | pyridinoline | MMP1 | 0.62 | 0.13 | 0.27 |
| 199 | EGF | ICAM1 | VEGFA | 0.62 | 0.13 | 0.22 |
| 200 | EGF | MMP1 | VCAM1 | 0.62 | 0.13 | 0.32 |
| 201 | CCL22 | EGF | MMP1 | 0.62 | 0.13 | 0.32 |
| 202 | ICAM1 | VCAM1 | VEGFA | 0.62 | 0.12 | 0.22 |

FIG. 17E

| 203 | EGF | IL1RN | TNFRSF1A | 0.62 | 0.12 | 0.31 |
|---|---|---|---|---|---|---|
| 204 | ICAM1 | IL1RN | TNFRSF1A | 0.62 | 0.12 | 0.29 |
| 205 | CCL22 | IL6R | MMP1 | 0.62 | 0.12 | 0.28 |
| 206 | IL1RN | LEP | VEGFA | 0.62 | 0.12 | 0.19 |
| 207 | IL6R | VCAM1 | VEGFA | 0.62 | 0.12 | 0.20 |
| 208 | EGF | LEP | VEGFA | 0.62 | 0.12 | 0.21 |
| 209 | IL1RN | LEP | TNFRSF1A | 0.62 | 0.12 | 0.29 |
| 210 | EGF | IL6R | VEGFA | 0.62 | 0.12 | 0.21 |
| 211 | EGF | IL1RN | VEGFA | 0.62 | 0.11 | 0.21 |
| 212 | CCL22 | IL1RN | MMP1 | 0.62 | 0.11 | 0.28 |
| 213 | CCL22 | ICAM1 | RETN | 0.62 | 0.11 | 0.21 |
| 214 | CCL22 | ICAM1 | pyridinoline | 0.62 | 0.11 | 0.22 |
| 215 | EGF | VCAM1 | VEGFA | 0.62 | 0.11 | 0.22 |
| 216 | IL6R | RETN | VEGFA | 0.62 | 0.11 | 0.23 |
| 217 | pyridinoline | RETN | VEGFA | 0.62 | 0.11 | 0.24 |
| 218 | EGF | RETN | TNFRSF1A | 0.62 | 0.11 | 0.29 |
| 219 | VCAM1 | RETN | VEGFA | 0.62 | 0.11 | 0.23 |
| 220 | IL6R | LEP | VEGFA | 0.62 | 0.10 | 0.19 |
| 221 | EGF | LEP | TNFRSF1A | 0.62 | 0.10 | 0.29 |
| 222 | EGF | LEP | MMP1 | 0.61 | 0.10 | 0.31 |
| 223 | VCAM1 | LEP | VEGFA | 0.61 | 0.10 | 0.19 |
| 224 | LEP | RETN | VEGFA | 0.61 | 0.10 | 0.22 |
| 225 | LEP | RETN | TNFRSF1A | 0.61 | 0.10 | 0.27 |
| 226 | MMP1 | LEP | VCAM1 | 0.61 | 0.10 | 0.27 |
| 227 | IL6R | LEP | MMP1 | 0.61 | 0.10 | 0.29 |
| 228 | EGF | IL1RN | MMP1 | 0.61 | 0.10 | 0.28 |
| 229 | EGF | RETN | VEGFA | 0.61 | 0.09 | 0.22 |
| 230 | IL1RN | RETN | VEGFA | 0.61 | 0.09 | 0.19 |
| 231 | VCAM1 | IL1RN | VEGFA | 0.61 | 0.09 | 0.18 |
| 232 | IL1RN | LEP | MMP1 | 0.60 | 0.09 | 0.26 |
| 233 | CCL22 | ICAM1 | IL6R | 0.60 | 0.09 | 0.15 |
| 234 | ICAM1 | pyridinoline | RETN | 0.60 | 0.09 | 0.23 |
| 235 | ICAM1 | LEP | pyridinoline | 0.60 | 0.09 | 0.21 |
| 236 | CCL22 | ICAM1 | VCAM1 | 0.60 | 0.09 | 0.16 |

| FOURMRK Set No. | Marker 1 | Marker 2 | Marker 3 | Marker 4 | AUC | % | r |
|---|---|---|---|---|---|---|---|
| 1 | IL1B | RETN | TNFRSF1A | VCAM1 | 0.70 | 0.33 | 0.40 |
| 2 | CHI3L1 | pyridinoline | EGF | VEGFA | 0.70 | 0.32 | 0.38 |
| 3 | IL1B | IL1RN | TNFRSF1A | VCAM1 | 0.69 | 0.31 | 0.39 |
| 4 | ICAM1 | IL6R | IL8 | IL1RN | 0.69 | 0.29 | 0.41 |
| 5 | CHI3L1 | pyridinoline | RETN | VEGFA | 0.69 | 0.29 | 0.38 |
| 6 | EGF | ICAM1 | IL8 | pyridinoline | 0.69 | 0.29 | 0.41 |
| 7 | IL1B | pyridinoline | RETN | TNFRSF1A | 0.69 | 0.29 | 0.41 |
| 8 | EGF | CHI3L1 | ICAM1 | VCAM1 | 0.69 | 0.29 | 0.39 |
| 9 | EGF | IL8 | IL1RN | VEGFA | 0.69 | 0.29 | 0.42 |
| 10 | ICAM1 | IL8 | pyridinoline | VCAM1 | 0.69 | 0.28 | 0.40 |
| 11 | IL6R | MMP1 | TNFRSF1A | VEGFA | 0.69 | 0.28 | 0.35 |
| 12 | CHI3L1 | pyridinoline | IL6R | VCAM1 | 0.69 | 0.28 | 0.36 |
| 13 | EGF | IL1B | IL1RN | TNFRSF1A | 0.69 | 0.28 | 0.41 |
| 14 | EGF | IL8 | VCAM1 | VEGFA | 0.69 | 0.28 | 0.41 |
| 15 | CHI3L1 | pyridinoline | VCAM1 | VEGFA | 0.69 | 0.28 | 0.36 |
| 16 | IL8 | IL1RN | VCAM1 | VEGFA | 0.69 | 0.27 | 0.41 |
| 17 | EGF | ICAM1 | IL8 | VCAM1 | 0.69 | 0.27 | 0.41 |
| 18 | IL6R | IL8 | TNFRSF1A | VCAM1 | 0.69 | 0.26 | 0.40 |
| 19 | IL6R | IL8 | LEP | TNFRSF1A | 0.69 | 0.26 | 0.41 |
| 20 | EGF | CHI3L1 | ICAM1 | VEGFA | 0.69 | 0.26 | 0.37 |
| 21 | CHI3L1 | pyridinoline | EGF | ICAM1 | 0.69 | 0.26 | 0.38 |
| 22 | ICAM1 | IL8 | LEP | VCAM1 | 0.69 | 0.26 | 0.40 |
| 23 | IL1B | pyridinoline | TNFRSF1A | VCAM1 | 0.69 | 0.25 | 0.40 |
| 24 | CHI3L1 | RETN | IL6R | VCAM1 | 0.69 | 0.25 | 0.37 |
| 25 | IL6R | IL8 | IL1RN | TNFRSF1A | 0.68 | 0.25 | 0.41 |
| 26 | EGF | IL1B | RETN | TNFRSF1A | 0.68 | 0.25 | 0.41 |
| 27 | EGF | IL1B | TNFRSF1A | VCAM1 | 0.68 | 0.25 | 0.40 |
| 28 | ICAM1 | IL8 | IL1RN | pyridinoline | 0.68 | 0.25 | 0.41 |
| 29 | CHI3L1 | IL1RN | ICAM1 | pyridinoline | 0.68 | 0.25 | 0.37 |
| 30 | CHI3L1 | pyridinoline | ICAM1 | VEGFA | 0.68 | 0.25 | 0.36 |
| 31 | CHI3L1 | RETN | ICAM1 | VEGFA | 0.68 | 0.25 | 0.35 |
| 32 | ICAM1 | IL6R | IL8 | pyridinoline | 0.68 | 0.25 | 0.40 |
| 33 | IL8 | IL1RN | TNFRSF1A | VCAM1 | 0.68 | 0.24 | 0.41 |
| 34 | EGF | IL8 | IL1RN | TNFRSF1A | 0.68 | 0.24 | 0.42 |
| 35 | CHI3L1 | pyridinoline | ICAM1 | RETN | 0.68 | 0.24 | 0.35 |
| 36 | CHI3L1 | IL1RN | EGF | RETN | 0.68 | 0.24 | 0.39 |
| 37 | CHI3L1 | RETN | ICAM1 | VCAM1 | 0.68 | 0.24 | 0.36 |
| 38 | EGF | ICAM1 | IL8 | IL1RN | 0.68 | 0.24 | 0.42 |

| 39 | IL8 | IL1RN | LEP | pyridinoline | 0.68 | 0.24 | 0.40 |
|---|---|---|---|---|---|---|---|
| 40 | IL8 | IL1RN | LEP | VEGFA | 0.68 | 0.24 | 0.40 |
| 41 | IL1B | IL1RN | pyridinoline | TNFRSF1A | 0.68 | 0.23 | 0.39 |
| 42 | EGF | IL8 | TNFRSF1A | VCAM1 | 0.68 | 0.23 | 0.42 |
| 43 | IL6R | pyridinoline | TNFRSF1A | VEGFA | 0.68 | 0.23 | 0.33 |
| 44 | ICAM1 | IL8 | IL1RN | VCAM1 | 0.68 | 0.23 | 0.41 |
| 45 | ICAM1 | IL8 | LEP | pyridinoline | 0.68 | 0.23 | 0.39 |
| 46 | CHI3L1 | LEP | EGF | ICAM1 | 0.68 | 0.23 | 0.37 |
| 47 | EGF | ICAM1 | IL8 | LEP | 0.68 | 0.22 | 0.40 |
| 48 | ICAM1 | CHI3L1 | VCAM1 | VEGFA | 0.68 | 0.22 | 0.35 |
| 49 | CHI3L1 | LEP | ICAM1 | VEGFA | 0.68 | 0.22 | 0.34 |
| 50 | CHI3L1 | RETN | EGF | VEGFA | 0.68 | 0.22 | 0.36 |
| 51 | CHI3L1 | IL1RN | RETN | VEGFA | 0.68 | 0.22 | 0.35 |
| 52 | ICAM1 | CHI3L1 | IL6R | VCAM1 | 0.68 | 0.22 | 0.35 |
| 53 | CHI3L1 | pyridinoline | ICAM1 | VCAM1 | 0.68 | 0.22 | 0.36 |
| 54 | IL1B | IL1RN | LEP | pyridinoline | 0.68 | 0.22 | 0.34 |
| 55 | EGF | IL8 | LEP | VEGFA | 0.68 | 0.21 | 0.39 |
| 56 | CHI3L1 | pyridinoline | ICAM1 | IL6R | 0.68 | 0.21 | 0.35 |
| 57 | EGF | CHI3L1 | IL6R | VCAM1 | 0.68 | 0.21 | 0.36 |
| 58 | CCL22 | IL6R | TNFRSF1A | VEGFA | 0.68 | 0.21 | 0.31 |
| 59 | IL8 | LEP | TNFRSF1A | VCAM1 | 0.68 | 0.21 | 0.41 |
| 60 | ICAM1 | IL6R | IL8 | VCAM1 | 0.68 | 0.21 | 0.40 |
| 61 | CHI3L1 | RETN | ICAM1 | IL6R | 0.68 | 0.21 | 0.35 |
| 62 | CHI3L1 | RETN | VCAM1 | VEGFA | 0.68 | 0.21 | 0.35 |
| 63 | IL8 | LEP | VCAM1 | VEGFA | 0.68 | 0.21 | 0.38 |
| 64 | CHI3L1 | RETN | EGF | ICAM1 | 0.68 | 0.21 | 0.37 |
| 65 | IL8 | IL1RN | LEP | TNFRSF1A | 0.68 | 0.21 | 0.40 |
| 66 | CCL22 | MMP1 | pyridinoline | VEGFA | 0.68 | 0.21 | 0.34 |
| 67 | EGF | IL1B | IL1RN | VCAM1 | 0.68 | 0.20 | 0.32 |
| 68 | CHI3L1 | LEP | pyridinoline | VEGFA | 0.68 | 0.20 | 0.35 |
| 69 | IL6R | IL8 | IL1RN | pyridinoline | 0.68 | 0.20 | 0.39 |
| 70 | CHI3L1 | IL1RN | EGF | pyridinoline | 0.68 | 0.20 | 0.37 |
| 71 | CHI3L1 | IL1RN | EGF | VEGFA | 0.68 | 0.20 | 0.35 |
| 72 | CHI3L1 | LEP | RETN | VEGFA | 0.68 | 0.20 | 0.35 |
| 73 | CHI3L1 | IL1RN | ICAM1 | IL6R | 0.68 | 0.20 | 0.35 |
| 74 | CHI3L1 | pyridinoline | EGF | IL6R | 0.68 | 0.20 | 0.37 |
| 75 | CHI3L1 | IL1RN | pyridinoline | RETN | 0.68 | 0.20 | 0.36 |
| 76 | CHI3L1 | pyridinoline | IL6R | RETN | 0.68 | 0.20 | 0.36 |
| 77 | ICAM1 | IL6R | IL8 | LEP | 0.68 | 0.20 | 0.38 |
| 78 | IL8 | IL1RN | pyridinoline | VCAM1 | 0.68 | 0.20 | 0.39 |
| 79 | MMP1 | TNFRSF1A | VCAM1 | VEGFA | 0.67 | 0.19 | 0.34 |

FIG. 18B

| | | | | | | | |
|---|---|---|---|---|---|---|---|
| 80 | EGF | CHI3L1 | VCAM1 | VEGFA | 0.67 | 0.19 | 0.37 |
| 81 | CHI3L1 | LEP | IL6R | VCAM1 | 0.67 | 0.19 | 0.34 |
| 82 | CHI3L1 | pyridinoline | RETN | VCAM1 | 0.67 | 0.19 | 0.35 |
| 83 | CHI3L1 | RETN | EGF | IL6R | 0.67 | 0.19 | 0.36 |
| 84 | EGF | IL6R | IL8 | pyridinoline | 0.67 | 0.19 | 0.39 |
| 85 | CHI3L1 | LEP | ICAM1 | pyridinoline | 0.67 | 0.19 | 0.36 |
| 86 | EGF | IL6R | IL8 | TNFRSF1A | 0.67 | 0.19 | 0.41 |
| 87 | EGF | ICAM1 | IL6R | IL8 | 0.67 | 0.19 | 0.40 |
| 88 | CCL22 | IL6R | MMP1 | TNFRSF1A | 0.67 | 0.19 | 0.36 |
| 89 | CHI3L1 | IL1RN | EGF | IL6R | 0.67 | 0.19 | 0.37 |
| 90 | IL6R | MMP1 | pyridinoline | TNFRSF1A | 0.67 | 0.19 | 0.35 |
| 91 | CHI3L1 | IL1RN | IL6R | pyridinoline | 0.67 | 0.19 | 0.36 |
| 92 | CHI3L1 | LEP | ICAM1 | VCAM1 | 0.67 | 0.18 | 0.35 |
| 93 | MMP1 | pyridinoline | VCAM1 | VEGFA | 0.67 | 0.18 | 0.35 |
| 94 | CHI3L1 | IL1RN | pyridinoline | VEGFA | 0.67 | 0.18 | 0.35 |
| 95 | CHI3L1 | IL1RN | VCAM1 | VEGFA | 0.67 | 0.18 | 0.35 |
| 96 | EGF | IL8 | LEP | TNFRSF1A | 0.67 | 0.18 | 0.38 |
| 97 | CHI3L1 | IL1RN | LEP | RETN | 0.67 | 0.18 | 0.36 |
| 98 | CCL22 | EGF | MMP1 | VEGFA | 0.67 | 0.18 | 0.37 |
| 99 | CHI3L1 | IL1RN | IL6R | VCAM1 | 0.67 | 0.18 | 0.34 |
| 100 | CHI3L1 | IL1RN | pyridinoline | VCAM1 | 0.67 | 0.18 | 0.35 |
| 101 | EGF | CHI3L1 | ICAM1 | IL6R | 0.67 | 0.18 | 0.37 |
| 102 | CHI3L1 | LEP | EGF | VCAM1 | 0.67 | 0.18 | 0.35 |
| 103 | EGF | IL1B | IL1RN | LEP | 0.67 | 0.18 | 0.33 |
| 104 | IL1B | IL1RN | RETN | TNFRSF1A | 0.67 | 0.18 | 0.39 |
| 105 | CHI3L1 | pyridinoline | EGF | VCAM1 | 0.67 | 0.18 | 0.36 |
| 106 | CHI3L1 | IL1RN | ICAM1 | VEGFA | 0.67 | 0.18 | 0.35 |
| 107 | IL6R | IL8 | IL1RN | VCAM1 | 0.67 | 0.18 | 0.39 |
| 108 | CCL22 | IL6R | RETN | TNFRSF1A | 0.67 | 0.18 | 0.34 |
| 109 | EGF | IL8 | LEP | pyridinoline | 0.67 | 0.18 | 0.38 |
| 110 | EGF | IL6R | MMP1 | TNFRSF1A | 0.67 | 0.18 | 0.40 |
| 111 | CHI3L1 | LEP | IL6R | pyridinoline | 0.67 | 0.18 | 0.35 |
| 112 | CCL22 | ICAM1 | IL6R | TNFRSF1A | 0.67 | 0.17 | 0.31 |
| 113 | CHI3L1 | IL1RN | ICAM1 | RETN | 0.67 | 0.17 | 0.33 |
| 114 | CCL22 | IL6R | pyridinoline | TNFRSF1A | 0.67 | 0.17 | 0.32 |
| 115 | CHI3L1 | LEP | IL6R | RETN | 0.67 | 0.17 | 0.34 |
| 116 | CHI3L1 | LEP | ICAM1 | RETN | 0.67 | 0.17 | 0.34 |
| 117 | EGF | IL8 | pyridinoline | VCAM1 | 0.67 | 0.17 | 0.39 |
| 118 | CHI3L1 | LEP | ICAM1 | IL6R | 0.67 | 0.17 | 0.34 |
| 119 | ICAM1 | IL8 | IL1RN | LEP | 0.67 | 0.17 | 0.39 |
| 120 | ICAM1 | IL6R | TNFRSF1A | VEGFA | 0.67 | 0.17 | 0.32 |

FIG. 18C

| | | | | | | | |
|---|---|---|---|---|---|---|---|
| 121 | CCL22 | IL1RN | TNFRSF1A | VEGFA | 0.67 | 0.17 | 0.30 |
| 122 | IL1B | pyridinoline | RETN | VCAM1 | 0.67 | 0.17 | 0.36 |
| 123 | CHI3L1 | LEP | RETN | VCAM1 | 0.67 | 0.17 | 0.35 |
| 124 | CHI3L1 | IL1RN | IL6R | LEP | 0.67 | 0.17 | 0.35 |
| 125 | IL6R | IL8 | pyridinoline | VCAM1 | 0.67 | 0.17 | 0.39 |
| 126 | CHI3L1 | IL1RN | IL6R | RETN | 0.67 | 0.17 | 0.35 |
| 127 | IL6R | MMP1 | RETN | TNFRSF1A | 0.67 | 0.17 | 0.35 |
| 128 | CCL22 | MMP1 | RETN | VEGFA | 0.67 | 0.17 | 0.33 |
| 129 | IL6R | IL8 | IL1RN | LEP | 0.67 | 0.17 | 0.38 |
| 130 | IL8 | IL1RN | LEP | VCAM1 | 0.67 | 0.17 | 0.39 |
| 131 | ICAM1 | IL6R | MMP1 | TNFRSF1A | 0.67 | 0.17 | 0.35 |
| 132 | CHI3L1 | IL1RN | ICAM1 | VCAM1 | 0.67 | 0.16 | 0.36 |
| 133 | CCL22 | TNFRSF1A | VCAM1 | VEGFA | 0.67 | 0.16 | 0.31 |
| 134 | CHI3L1 | LEP | EGF | IL6R | 0.67 | 0.16 | 0.34 |
| 135 | EGF | IL8 | IL1RN | LEP | 0.67 | 0.16 | 0.39 |
| 136 | CCL22 | IL6R | IL1RN | TNFRSF1A | 0.67 | 0.16 | 0.32 |
| 137 | CHI3L1 | IL1RN | EGF | LEP | 0.67 | 0.16 | 0.34 |
| 138 | CHI3L1 | LEP | VCAM1 | VEGFA | 0.67 | 0.16 | 0.33 |
| 139 | IL6R | TNFRSF1A | VCAM1 | VEGFA | 0.67 | 0.16 | 0.32 |
| 140 | IL1B | IL1RN | pyridinoline | RETN | 0.67 | 0.16 | 0.34 |
| 141 | IL6R | MMP1 | pyridinoline | VEGFA | 0.67 | 0.16 | 0.34 |
| 142 | ICAM1 | MMP1 | TNFRSF1A | VEGFA | 0.67 | 0.16 | 0.33 |
| 143 | MMP1 | IL1RN | TNFRSF1A | VEGFA | 0.67 | 0.16 | 0.33 |
| 144 | EGF | IL8 | IL1RN | pyridinoline | 0.67 | 0.16 | 0.39 |
| 145 | IL1B | IL1RN | pyridinoline | VCAM1 | 0.67 | 0.16 | 0.35 |
| 146 | CHI3L1 | pyridinoline | EGF | RETN | 0.67 | 0.16 | 0.36 |
| 147 | EGF | IL6R | IL8 | VCAM1 | 0.67 | 0.16 | 0.38 |
| 148 | CHI3L1 | IL1RN | ICAM1 | LEP | 0.67 | 0.16 | 0.33 |
| 149 | EGF | IL1B | RETN | VCAM1 | 0.67 | 0.16 | 0.35 |
| 150 | IL6R | RETN | TNFRSF1A | VEGFA | 0.67 | 0.16 | 0.31 |
| 151 | CCL22 | MMP1 | TNFRSF1A | VEGFA | 0.67 | 0.16 | 0.34 |
| 152 | CHI3L1 | IL1RN | EGF | VCAM1 | 0.67 | 0.16 | 0.34 |
| 153 | CCL22 | pyridinoline | TNFRSF1A | VEGFA | 0.67 | 0.16 | 0.32 |
| 154 | CHI3L1 | IL1RN | EGF | ICAM1 | 0.67 | 0.16 | 0.36 |
| 155 | LEP | pyridinoline | MMP1 | VEGFA | 0.67 | 0.16 | 0.32 |
| 156 | CHI3L1 | IL1RN | LEP | pyridinoline | 0.67 | 0.16 | 0.35 |
| 157 | IL1B | LEP | pyridinoline | VCAM1 | 0.67 | 0.16 | 0.33 |
| 158 | CHI3L1 | LEP | pyridinoline | VCAM1 | 0.66 | 0.16 | 0.35 |
| 159 | IL1B | IL1RN | LEP | RETN | 0.66 | 0.15 | 0.33 |
| 160 | IL8 | LEP | pyridinoline | VCAM1 | 0.66 | 0.15 | 0.38 |
| 161 | EGF | IL8 | LEP | VCAM1 | 0.66 | 0.15 | 0.39 |

FIG. 18D

| | | | | | | | |
|---|---|---|---|---|---|---|---|
| 162 | CCL22 | RETN | TNFRSF1A | VEGFA | 0.66 | 0.15 | 0.32 |
| 163 | IL6R | LEP | TNFRSF1A | VEGFA | 0.66 | 0.15 | 0.32 |
| 164 | CHI3L1 | LEP | EGF | VEGFA | 0.66 | 0.15 | 0.36 |
| 165 | CHI3L1 | LEP | EGF | pyridinoline | 0.66 | 0.15 | 0.35 |
| 166 | CHI3L1 | IL1RN | LEP | VEGFA | 0.66 | 0.15 | 0.33 |
| 167 | IL1B | LEP | pyridinoline | RETN | 0.66 | 0.15 | 0.33 |
| 168 | IL1B | LEP | RETN | VCAM1 | 0.66 | 0.15 | 0.33 |
| 169 | CCL22 | IL6R | MMP1 | VEGFA | 0.66 | 0.15 | 0.31 |
| 170 | CCL22 | ICAM1 | MMP1 | VEGFA | 0.66 | 0.15 | 0.31 |
| 171 | ICAM1 | IL6R | pyridinoline | TNFRSF1A | 0.66 | 0.15 | 0.31 |
| 172 | CCL22 | IL6R | LEP | TNFRSF1A | 0.66 | 0.15 | 0.32 |
| 173 | EGF | MMP1 | pyridinoline | VEGFA | 0.66 | 0.15 | 0.36 |
| 174 | EGF | IL8 | IL1RN | VCAM1 | 0.66 | 0.15 | 0.38 |
| 175 | IL1B | IL1RN | LEP | VCAM1 | 0.66 | 0.15 | 0.34 |
| 176 | IL6R | IL8 | LEP | VCAM1 | 0.66 | 0.15 | 0.37 |
| 177 | CCL22 | ICAM1 | MMP1 | TNFRSF1A | 0.66 | 0.15 | 0.34 |
| 178 | MMP1 | RETN | TNFRSF1A | VEGFA | 0.66 | 0.15 | 0.34 |
| 179 | CHI3L1 | LEP | EGF | RETN | 0.66 | 0.15 | 0.34 |
| 180 | IL6R | IL8 | LEP | pyridinoline | 0.66 | 0.15 | 0.37 |
| 181 | IL6R | MMP1 | VCAM1 | VEGFA | 0.66 | 0.15 | 0.31 |
| 182 | IL6R | pyridinoline | RETN | TNFRSF1A | 0.66 | 0.15 | 0.31 |
| 183 | CHI3L1 | RETN | EGF | VCAM1 | 0.66 | 0.15 | 0.36 |
| 184 | IL6R | IL1RN | MMP1 | VEGFA | 0.66 | 0.15 | 0.30 |
| 185 | EGF | MMP1 | pyridinoline | TNFRSF1A | 0.66 | 0.15 | 0.37 |
| 186 | EGF | IL1B | LEP | RETN | 0.66 | 0.15 | 0.34 |
| 187 | EGF | IL6R | TNFRSF1A | VEGFA | 0.66 | 0.14 | 0.31 |
| 188 | CCL22 | IL6R | TNFRSF1A | VCAM1 | 0.66 | 0.14 | 0.32 |
| 189 | CCL22 | LEP | MMP1 | VEGFA | 0.66 | 0.14 | 0.31 |
| 190 | IL6R | IL1RN | MMP1 | TNFRSF1A | 0.66 | 0.14 | 0.34 |
| 191 | EGF | ICAM1 | MMP1 | VEGFA | 0.66 | 0.14 | 0.35 |
| 192 | ICAM1 | MMP1 | VCAM1 | VEGFA | 0.66 | 0.14 | 0.31 |
| 193 | EGF | IL1B | LEP | VCAM1 | 0.66 | 0.14 | 0.32 |
| 194 | TNFRSF1A | pyridinoline | VCAM1 | VEGFA | 0.66 | 0.14 | 0.32 |
| 195 | EGF | IL6R | IL8 | IL1RN | 0.66 | 0.14 | 0.39 |
| 196 | EGF | IL6R | IL8 | LEP | 0.66 | 0.14 | 0.37 |
| 197 | EGF | IL1B | IL1RN | RETN | 0.66 | 0.14 | 0.34 |
| 198 | ICAM1 | IL6R | IL1RN | TNFRSF1A | 0.66 | 0.14 | 0.31 |
| 199 | IL1RN | pyridinoline | MMP1 | VEGFA | 0.66 | 0.14 | 0.33 |
| 200 | IL6R | MMP1 | TNFRSF1A | VCAM1 | 0.66 | 0.14 | 0.35 |
| 201 | MMP1 | RETN | VCAM1 | VEGFA | 0.66 | 0.14 | 0.31 |
| 202 | IL6R | IL1RN | pyridinoline | TNFRSF1A | 0.66 | 0.14 | 0.31 |

FIG. 18E

| 203 | ICAM1 | MMP1 | TNFRSF1A | VCAM1 | 0.66 | 0.14 | 0.35 |
| --- | --- | --- | --- | --- | --- | --- | --- |
| 204 | ICAM1 | IL6R | MMP1 | VEGFA | 0.66 | 0.14 | 0.31 |
| 205 | CCL22 | IL1RN | MMP1 | VEGFA | 0.66 | 0.14 | 0.32 |
| 206 | CHI3L1 | IL1RN | RETN | VCAM1 | 0.66 | 0.14 | 0.33 |
| 207 | MMP1 | pyridinoline | TNFRSF1A | VEGFA | 0.66 | 0.14 | 0.34 |
| 208 | CCL22 | ICAM1 | RETN | VEGFA | 0.66 | 0.14 | 0.26 |
| 209 | MMP1 | LEP | TNFRSF1A | VEGFA | 0.66 | 0.14 | 0.34 |
| 210 | EGF | IL6R | MMP1 | VEGFA | 0.66 | 0.14 | 0.34 |
| 211 | ICAM1 | MMP1 | pyridinoline | VEGFA | 0.66 | 0.14 | 0.32 |
| 212 | CHI3L1 | IL1RN | LEP | VCAM1 | 0.66 | 0.14 | 0.33 |
| 213 | TNFRSF1A | IL1RN | VCAM1 | VEGFA | 0.66 | 0.14 | 0.30 |
| 214 | CCL22 | MMP1 | TNFRSF1A | VCAM1 | 0.66 | 0.14 | 0.33 |
| 215 | CCL22 | EGF | MMP1 | TNFRSF1A | 0.66 | 0.14 | 0.36 |
| 216 | CCL22 | MMP1 | VCAM1 | VEGFA | 0.66 | 0.14 | 0.32 |
| 217 | CHI3L1 | LEP | pyridinoline | RETN | 0.66 | 0.14 | 0.33 |
| 218 | IL6R | IL1RN | TNFRSF1A | VEGFA | 0.66 | 0.14 | 0.31 |
| 219 | CCL22 | MMP1 | RETN | TNFRSF1A | 0.66 | 0.13 | 0.35 |
| 220 | CCL22 | EGF | IL6R | TNFRSF1A | 0.65 | 0.13 | 0.33 |
| 221 | pyridinoline | RETN | TNFRSF1A | VEGFA | 0.65 | 0.13 | 0.31 |
| 222 | CCL22 | ICAM1 | pyridinoline | VEGFA | 0.65 | 0.13 | 0.29 |
| 223 | EGF | LEP | MMP1 | VEGFA | 0.65 | 0.13 | 0.33 |
| 224 | CCL22 | MMP1 | pyridinoline | TNFRSF1A | 0.65 | 0.13 | 0.37 |
| 225 | CCL22 | ICAM1 | TNFRSF1A | VEGFA | 0.65 | 0.13 | 0.32 |
| 226 | EGF | MMP1 | VCAM1 | VEGFA | 0.65 | 0.13 | 0.34 |
| 227 | MMP1 | pyridinoline | RETN | VEGFA | 0.65 | 0.13 | 0.34 |
| 228 | CCL22 | EGF | TNFRSF1A | VEGFA | 0.65 | 0.13 | 0.33 |
| 229 | MMP1 | pyridinoline | TNFRSF1A | VCAM1 | 0.65 | 0.13 | 0.33 |
| 230 | LEP | RETN | MMP1 | VEGFA | 0.65 | 0.13 | 0.30 |
| 231 | IL6R | MMP1 | RETN | VEGFA | 0.65 | 0.13 | 0.30 |
| 232 | CCL22 | pyridinoline | RETN | VEGFA | 0.65 | 0.13 | 0.29 |
| 233 | IL1B | IL1RN | RETN | VCAM1 | 0.65 | 0.13 | 0.33 |
| 234 | IL6R | LEP | MMP1 | TNFRSF1A | 0.65 | 0.13 | 0.33 |
| 235 | EGF | MMP1 | RETN | VEGFA | 0.65 | 0.13 | 0.35 |
| 236 | CCL22 | EGF | MMP1 | RETN | 0.65 | 0.13 | 0.35 |
| 237 | ICAM1 | MMP1 | RETN | TNFRSF1A | 0.65 | 0.13 | 0.32 |
| 238 | ICAM1 | pyridinoline | TNFRSF1A | VEGFA | 0.65 | 0.13 | 0.30 |
| 239 | EGF | MMP1 | TNFRSF1A | VCAM1 | 0.65 | 0.13 | 0.38 |
| 240 | EGF | IL1RN | MMP1 | VEGFA | 0.65 | 0.13 | 0.31 |
| 241 | CCL22 | MMP1 | pyridinoline | RETN | 0.65 | 0.13 | 0.32 |
| 242 | MMP1 | pyridinoline | RETN | TNFRSF1A | 0.65 | 0.13 | 0.34 |
| 243 | CCL22 | pyridinoline | RETN | TNFRSF1A | 0.65 | 0.13 | 0.31 |

FIG. 18F

| 244 | CCL22 | ICAM1 | TNFRSF1A | VCAM1 | 0.65 | 0.13 | 0.30 |
|---|---|---|---|---|---|---|---|
| 245 | CCL22 | IL6R | pyridinoline | VEGFA | 0.65 | 0.13 | 0.26 |
| 246 | MMP1 | LEP | TNFRSF1A | VCAM1 | 0.65 | 0.13 | 0.35 |
| 247 | CCL22 | IL6R | MMP1 | RETN | 0.65 | 0.13 | 0.32 |
| 248 | MMP1 | LEP | VCAM1 | VEGFA | 0.65 | 0.13 | 0.30 |
| 249 | ICAM1 | TNFRSF1A | VCAM1 | VEGFA | 0.65 | 0.13 | 0.31 |
| 250 | IL6R | IL1RN | TNFRSF1A | VCAM1 | 0.65 | 0.12 | 0.27 |
| 251 | ICAM1 | IL1RN | TNFRSF1A | VEGFA | 0.65 | 0.12 | 0.29 |
| 252 | ICAM1 | IL1RN | MMP1 | VEGFA | 0.65 | 0.12 | 0.31 |
| 253 | ICAM1 | MMP1 | RETN | VEGFA | 0.65 | 0.12 | 0.31 |
| 254 | MMP1 | RETN | TNFRSF1A | VCAM1 | 0.65 | 0.12 | 0.33 |
| 255 | IL1RN | pyridinoline | MMP1 | TNFRSF1A | 0.65 | 0.12 | 0.33 |
| 256 | CCL22 | EGF | ICAM1 | TNFRSF1A | 0.65 | 0.12 | 0.33 |
| 257 | EGF | IL1RN | MMP1 | TNFRSF1A | 0.65 | 0.12 | 0.36 |
| 258 | ICAM1 | LEP | MMP1 | VEGFA | 0.65 | 0.12 | 0.30 |
| 259 | CCL22 | LEP | TNFRSF1A | VEGFA | 0.65 | 0.12 | 0.30 |
| 260 | CCL22 | EGF | pyridinoline | VEGFA | 0.65 | 0.12 | 0.28 |
| 261 | EGF | ICAM1 | MMP1 | TNFRSF1A | 0.65 | 0.12 | 0.36 |
| 262 | EGF | MMP1 | TNFRSF1A | VEGFA | 0.65 | 0.12 | 0.35 |
| 263 | IL6R | pyridinoline | TNFRSF1A | VCAM1 | 0.65 | 0.12 | 0.30 |
| 264 | EGF | TNFRSF1A | VCAM1 | VEGFA | 0.65 | 0.12 | 0.31 |
| 265 | IL1RN | RETN | MMP1 | VEGFA | 0.65 | 0.12 | 0.32 |
| 266 | IL6R | LEP | pyridinoline | TNFRSF1A | 0.65 | 0.12 | 0.29 |

| FIVEMRK Set No. | Marker 1 | Marker 2 | Marker 3 | Marker 4 | Marker 5 | AUC | % | r |
|---|---|---|---|---|---|---|---|---|
| 1 | EGF | IL1B | RETN | TNFRSF1A | VCAM1 | 0.70 | 0.29 | 0.38 |
| 2 | CCL22 | IL6R | PYD | TNFRSF1A | VEGFA | 0.69 | 0.26 | 0.33 |
| 3 | IL1B | PYD | RETN | TNFRSF1A | VCAM1 | 0.69 | 0.26 | 0.40 |
| 4 | EGF | IL1B | IL1RN | TNFRSF1A | VCAM1 | 0.69 | 0.26 | 0.40 |
| 5 | CHI3L1 | LEP | ICAM1 | RETN | VEGFA | 0.69 | 0.25 | 0.34 |
| 6 | CHI3L1 | LEP | EGF | RETN | VEGFA | 0.69 | 0.25 | 0.37 |
| 7 | CHI3L1 | PYD | IL6R | RETN | VCAM1 | 0.69 | 0.24 | 0.36 |
| 8 | CHI3L1 | PYD | ICAM1 | RETN | VEGFA | 0.69 | 0.24 | 0.37 |
| 9 | CHI3L1 | PYD | ICAM1 | IL6R | VCAM1 | 0.69 | 0.23 | 0.35 |
| 10 | IL1B | IL1RN | RETN | TNFRSF1A | VCAM1 | 0.68 | 0.22 | 0.38 |
| 11 | CHI3L1 | IL1RN | PYD | RETN | VEGFA | 0.68 | 0.22 | 0.36 |
| 12 | CHI3L1 | IL1RN | EGF | PYD | VEGFA | 0.68 | 0.22 | 0.36 |
| 13 | IL1B | IL1RN | PYD | RETN | TNFRSF1A | 0.68 | 0.21 | 0.40 |
| 14 | ICAM1 | IL6R | IL8 | IL1RN | PYD | 0.68 | 0.21 | 0.39 |
| 15 | CHI3L1 | PYD | RETN | VCAM1 | VEGFA | 0.68 | 0.21 | 0.34 |
| 16 | CHI3L1 | PYD | ICAM1 | RETN | VCAM1 | 0.68 | 0.21 | 0.35 |
| 17 | CHI3L1 | PYD | EGF | ICAM1 | VEGFA | 0.68 | 0.21 | 0.35 |
| 18 | CHI3L1 | LEP | PYD | RETN | VEGFA | 0.68 | 0.21 | 0.35 |
| 19 | EGF | ICAM1 | IL8 | IL1RN | PYD | 0.68 | 0.21 | 0.40 |
| 20 | IL6R | IL8 | IL1RN | TNFRSF1A | VCAM1 | 0.68 | 0.21 | 0.40 |
| 21 | CHI3L1 | PYD | EGF | RETN | VEGFA | 0.68 | 0.20 | 0.37 |
| 22 | ICAM1 | IL8 | IL1RN | PYD | VCAM1 | 0.68 | 0.20 | 0.40 |
| 23 | CHI3L1 | LEP | ICAM1 | IL6R | VCAM1 | 0.68 | 0.20 | 0.36 |
| 24 | ICAM1 | IL6R | IL8 | IL1RN | VCAM1 | 0.68 | 0.20 | 0.39 |
| 25 | CHI3L1 | LEP | EGF | PYD | VEGFA | 0.68 | 0.20 | 0.35 |
| 26 | CHI3L1 | IL1RN | ICAM1 | PYD | VCAM1 | 0.68 | 0.20 | 0.36 |
| 27 | ICAM1 | IL8 | IL1RN | LEP | PYD | 0.68 | 0.20 | 0.39 |
| 28 | CHI3L1 | RETN | EGF | ICAM1 | VCAM1 | 0.68 | 0.19 | 0.36 |
| 29 | IL6R | MMP1 | PYD | TNFRSF1A | VEGFA | 0.68 | 0.19 | 0.36 |
| 30 | IL6R | IL8 | IL1RN | PYD | VCAM1 | 0.68 | 0.19 | 0.38 |
| 31 | ICAM1 | IL6R | IL8 | LEP | PYD | 0.68 | 0.19 | 0.38 |
| 32 | EGF | CHI3L1 | ICAM1 | VCAM1 | VEGFA | 0.68 | 0.19 | 0.35 |
| 33 | CHI3L1 | LEP | ICAM1 | VCAM1 | VEGFA | 0.68 | 0.19 | 0.33 |
| 34 | EGF | IL8 | IL1RN | LEP | VEGFA | 0.68 | 0.19 | 0.40 |
| 35 | CHI3L1 | IL1RN | ICAM1 | LEP | VEGFA | 0.68 | 0.19 | 0.34 |
| 36 | EGF | ICAM1 | IL8 | LEP | PYD | 0.68 | 0.19 | 0.38 |
| 37 | EGF | IL6R | IL8 | IL1RN | TNFRSF1A | 0.68 | 0.19 | 0.41 |
| 38 | CCL22 | IL6R | MMP1 | TNFRSF1A | VEGFA | 0.68 | 0.18 | 0.33 |

| 39 | EGF | IL6R | IL8 | TNFRSF1A | VCAM1 | 0.68 | 0.18 | 0.40 |
|---|---|---|---|---|---|---|---|---|
| 40 | ICAM1 | IL6R | IL8 | PYD | VCAM1 | 0.68 | 0.18 | 0.38 |
| 41 | CHI3L1 | PYD | EGF | VCAM1 | VEGFA | 0.68 | 0.18 | 0.35 |
| 42 | IL6R | IL8 | IL1RN | LEP | TNFRSF1A | 0.68 | 0.18 | 0.40 |
| 43 | CHI3L1 | IL1RN | EGF | ICAM1 | PYD | 0.68 | 0.18 | 0.37 |
| 44 | CHI3L1 | LEP | IL6R | PYD | VCAM1 | 0.68 | 0.18 | 0.36 |
| 45 | CCL22 | ICAM1 | IL6R | TNFRSF1A | VEGFA | 0.68 | 0.18 | 0.31 |
| 46 | CHI3L1 | LEP | ICAM1 | PYD | VEGFA | 0.68 | 0.18 | 0.35 |
| 47 | CHI3L1 | RETN | EGF | ICAM1 | IL6R | 0.68 | 0.18 | 0.38 |
| 48 | CHI3L1 | IL1RN | ICAM1 | IL6R | VCAM1 | 0.68 | 0.17 | 0.36 |
| 49 | CHI3L1 | PYD | EGF | RETN | VCAM1 | 0.68 | 0.17 | 0.36 |
| 50 | IL1B | IL1RN | PYD | TNFRSF1A | VCAM1 | 0.68 | 0.17 | 0.37 |
| 51 | CHI3L1 | LEP | EGF | VCAM1 | VEGFA | 0.68 | 0.17 | 0.35 |
| 52 | ICAM1 | IL8 | LEP | PYD | VCAM1 | 0.67 | 0.17 | 0.38 |
| 53 | IL6R | IL8 | LEP | TNFRSF1A | VCAM1 | 0.67 | 0.17 | 0.37 |
| 54 | CHI3L1 | RETN | ICAM1 | VCAM1 | VEGFA | 0.67 | 0.17 | 0.36 |
| 55 | CHI3L1 | PYD | EGF | ICAM1 | RETN | 0.67 | 0.17 | 0.36 |
| 56 | CHI3L1 | IL1RN | EGF | IL6R | PYD | 0.67 | 0.17 | 0.36 |
| 57 | CHI3L1 | LEP | PYD | VCAM1 | VEGFA | 0.67 | 0.16 | 0.34 |
| 58 | EGF | IL1B | IL1RN | RETN | TNFRSF1A | 0.67 | 0.16 | 0.39 |
| 59 | IL6R | PYD | TNFRSF1A | VCAM1 | VEGFA | 0.67 | 0.16 | 0.32 |
| 60 | CHI3L1 | PYD | ICAM1 | VCAM1 | VEGFA | 0.67 | 0.16 | 0.35 |
| 61 | CHI3L1 | LEP | RETN | VCAM1 | VEGFA | 0.67 | 0.16 | 0.33 |
| 62 | ICAM1 | IL6R | MMP1 | TNFRSF1A | VEGFA | 0.67 | 0.16 | 0.34 |
| 63 | CHI3L1 | IL1RN | ICAM1 | IL6R | PYD | 0.67 | 0.16 | 0.35 |
| 64 | IL8 | IL1RN | LEP | VCAM1 | VEGFA | 0.67 | 0.16 | 0.38 |
| 65 | CHI3L1 | IL1RN | LEP | PYD | VEGFA | 0.67 | 0.16 | 0.35 |
| 66 | EGF | IL8 | IL1RN | VCAM1 | VEGFA | 0.67 | 0.16 | 0.40 |
| 67 | IL6R | IL8 | LEP | PYD | VCAM1 | 0.67 | 0.15 | 0.37 |
| 68 | CHI3L1 | LEP | EGF | ICAM1 | VEGFA | 0.67 | 0.15 | 0.34 |
| 69 | CHI3L1 | IL1RN | PYD | RETN | VCAM1 | 0.67 | 0.15 | 0.34 |
| 70 | EGF | IL6R | MMP1 | TNFRSF1A | VEGFA | 0.67 | 0.15 | 0.37 |
| 71 | CHI3L1 | RETN | ICAM1 | IL6R | VCAM1 | 0.67 | 0.15 | 0.36 |
| 72 | CHI3L1 | IL1RN | ICAM1 | IL6R | RETN | 0.67 | 0.15 | 0.35 |
| 73 | CHI3L1 | IL1RN | EGF | LEP | VEGFA | 0.67 | 0.15 | 0.34 |
| 74 | EGF | IL6R | TNFRSF1A | VCAM1 | VEGFA | 0.67 | 0.15 | 0.33 |
| 75 | CHI3L1 | PYD | EGF | ICAM1 | VCAM1 | 0.67 | 0.15 | 0.36 |
| 76 | CHI3L1 | IL1RN | EGF | VCAM1 | VEGFA | 0.67 | 0.15 | 0.34 |
| 77 | CHI3L1 | IL1RN | RETN | VCAM1 | VEGFA | 0.67 | 0.15 | 0.34 |
| 78 | IL6R | MMP1 | RETN | TNFRSF1A | VEGFA | 0.67 | 0.15 | 0.34 |
| 79 | IL8 | IL1RN | LEP | TNFRSF1A | VCAM1 | 0.67 | 0.15 | 0.39 |

FIG. 19B

| | | | | | | | | |
|---|---|---|---|---|---|---|---|---|
| 80 | CHI3L1 | LEP | EGF | ICAM1 | IL6R | 0.67 | 0.15 | 0.34 |
| 81 | CCL22 | IL6R | MMP1 | RETN | VEGFA | 0.67 | 0.15 | 0.32 |
| 82 | CCL22 | IL6R | MMP1 | TNFRSF1A | VCAM1 | 0.67 | 0.15 | 0.34 |
| 83 | MMP1 | PYD | TNFRSF1A | VCAM1 | VEGFA | 0.67 | 0.15 | 0.34 |
| 84 | CHI3L1 | IL1RN | ICAM1 | PYD | VEGFA | 0.67 | 0.14 | 0.34 |
| 85 | CCL22 | IL6R | IL1RN | TNFRSF1A | VEGFA | 0.67 | 0.14 | 0.30 |
| 86 | CHI3L1 | PYD | EGF | ICAM1 | IL6R | 0.67 | 0.14 | 0.36 |
| 87 | CHI3L1 | IL1RN | EGF | ICAM1 | VCAM1 | 0.67 | 0.14 | 0.34 |
| 88 | EGF | ICAM1 | IL6R | IL8 | IL1RN | 0.67 | 0.14 | 0.40 |
| 89 | CHI3L1 | IL1RN | EGF | ICAM1 | VEGFA | 0.67 | 0.14 | 0.35 |
| 90 | CHI3L1 | LEP | EGF | IL6R | PYD | 0.67 | 0.14 | 0.33 |
| 91 | EGF | ICAM1 | IL8 | LEP | VCAM1 | 0.67 | 0.14 | 0.38 |
| 92 | CHI3L1 | LEP | ICAM1 | PYD | VCAM1 | 0.67 | 0.14 | 0.34 |
| 93 | CCL22 | IL6R | TNFRSF1A | VCAM1 | VEGFA | 0.67 | 0.14 | 0.29 |
| 94 | CCL22 | IL1RN | MMP1 | TNFRSF1A | VEGFA | 0.67 | 0.14 | 0.33 |
| 95 | CCL22 | IL6R | LEP | TNFRSF1A | VEGFA | 0.67 | 0.14 | 0.31 |
| 96 | CCL22 | EGF | MMP1 | PYD | VEGFA | 0.67 | 0.14 | 0.36 |
| 97 | EGF | IL8 | LEP | VCAM1 | VEGFA | 0.67 | 0.14 | 0.38 |
| 98 | EGF | IL8 | LEP | TNFRSF1A | VCAM1 | 0.67 | 0.14 | 0.40 |
| 99 | CCL22 | IL6R | RETN | TNFRSF1A | VEGFA | 0.67 | 0.14 | 0.30 |
| 100 | IL1B | LEP | PYD | RETN | VCAM1 | 0.67 | 0.14 | 0.33 |
| 101 | EGF | IL8 | IL1RN | LEP | TNFRSF1A | 0.67 | 0.14 | 0.39 |
| 102 | CHI3L1 | IL1RN | ICAM1 | VCAM1 | VEGFA | 0.67 | 0.14 | 0.34 |
| 103 | CHI3L1 | RETN | EGF | ICAM1 | VEGFA | 0.67 | 0.14 | 0.34 |
| 104 | CCL22 | ICAM1 | IL6R | MMP1 | TNFRSF1A | 0.67 | 0.14 | 0.35 |
| 105 | CHI3L1 | IL1RN | EGF | IL6R | VCAM1 | 0.67 | 0.14 | 0.34 |
| 106 | CHI3L1 | IL1RN | PYD | VCAM1 | VEGFA | 0.67 | 0.14 | 0.33 |
| 107 | CHI3L1 | LEP | ICAM1 | RETN | VCAM1 | 0.67 | 0.14 | 0.34 |
| 108 | CCL22 | MMP1 | PYD | TNFRSF1A | VEGFA | 0.67 | 0.14 | 0.34 |
| 109 | EGF | ICAM1 | IL6R | IL8 | PYD | 0.67 | 0.14 | 0.38 |
| 110 | CHI3L1 | LEP | IL6R | PYD | RETN | 0.67 | 0.13 | 0.34 |
| 111 | IL6R | IL8 | IL1RN | LEP | PYD | 0.67 | 0.13 | 0.37 |
| 112 | EGF | IL6R | PYD | TNFRSF1A | VEGFA | 0.67 | 0.13 | 0.32 |
| 113 | CHI3L1 | IL1RN | IL6R | PYD | RETN | 0.67 | 0.13 | 0.35 |
| 114 | CHI3L1 | LEP | EGF | RETN | VCAM1 | 0.67 | 0.13 | 0.34 |
| 115 | CCL22 | IL6R | MMP1 | RETN | TNFRSF1A | 0.67 | 0.13 | 0.34 |
| 116 | CCL22 | IL6R | MMP1 | PYD | TNFRSF1A | 0.67 | 0.13 | 0.34 |
| 117 | CHI3L1 | PYD | ICAM1 | IL6R | RETN | 0.67 | 0.13 | 0.34 |
| 118 | CCL22 | MMP1 | PYD | RETN | VEGFA | 0.67 | 0.13 | 0.33 |
| 119 | CHI3L1 | LEP | ICAM1 | IL6R | RETN | 0.67 | 0.13 | 0.34 |
| 120 | CHI3L1 | IL1RN | ICAM1 | RETN | VEGFA | 0.67 | 0.13 | 0.32 |

FIG. 19C

| 121 | ICAM1 | IL6R | IL8 | IL1RN | LEP | 0.67 | 0.13 | 0.39 |
| --- | --- | --- | --- | --- | --- | --- | --- | --- |
| 122 | IL6R | MMP1 | PYD | RETN | TNFRSF1A | 0.67 | 0.13 | 0.35 |
| 123 | IL6R | MMP1 | TNFRSF1A | VCAM1 | VEGFA | 0.67 | 0.13 | 0.33 |
| 124 | CHI3L1 | RETN | EGF | VCAM1 | VEGFA | 0.67 | 0.13 | 0.34 |
| 125 | CHI3L1 | LEP | EGF | IL6R | RETN | 0.67 | 0.13 | 0.36 |
| 126 | EGF | ICAM1 | IL8 | IL1RN | VCAM1 | 0.67 | 0.13 | 0.40 |
| 127 | CHI3L1 | IL1RN | LEP | RETN | VEGFA | 0.67 | 0.13 | 0.34 |
| 128 | CHI3L1 | IL1RN | EGF | ICAM1 | IL6R | 0.66 | 0.13 | 0.34 |
| 129 | CHI3L1 | IL1RN | ICAM1 | RETN | VCAM1 | 0.66 | 0.13 | 0.34 |
| 130 | CCL22 | PYD | TNFRSF1A | VCAM1 | VEGFA | 0.66 | 0.13 | 0.32 |
| 131 | CHI3L1 | IL1RN | EGF | RETN | VCAM1 | 0.66 | 0.13 | 0.35 |
| 132 | CHI3L1 | LEP | ICAM1 | PYD | RETN | 0.66 | 0.13 | 0.34 |
| 133 | CCL22 | IL6R | RETN | TNFRSF1A | VCAM1 | 0.66 | 0.13 | 0.30 |
| 134 | EGF | MMP1 | PYD | VCAM1 | VEGFA | 0.66 | 0.13 | 0.36 |
| 135 | ICAM1 | IL6R | RETN | TNFRSF1A | VEGFA | 0.66 | 0.13 | 0.30 |
| 136 | EGF | MMP1 | TNFRSF1A | VCAM1 | VEGFA | 0.66 | 0.13 | 0.37 |
| 137 | CHI3L1 | IL1RN | EGF | RETN | VEGFA | 0.66 | 0.13 | 0.34 |
| 138 | ICAM1 | IL6R | TNFRSF1A | VCAM1 | VEGFA | 0.66 | 0.13 | 0.30 |
| 139 | CCL22 | MMP1 | TNFRSF1A | VCAM1 | VEGFA | 0.66 | 0.12 | 0.33 |
| 140 | ICAM1 | IL6R | IL1RN | TNFRSF1A | VEGFA | 0.66 | 0.12 | 0.29 |
| 141 | ICAM1 | MMP1 | PYD | TNFRSF1A | VCAM1 | 0.66 | 0.12 | 0.34 |
| 142 | CCL22 | EGF | MMP1 | RETN | VEGFA | 0.66 | 0.12 | 0.35 |
| 143 | ICAM1 | IL6R | LEP | TNFRSF1A | VEGFA | 0.66 | 0.12 | 0.32 |
| 144 | EGF | IL6R | MMP1 | PYD | VEGFA | 0.66 | 0.12 | 0.35 |
| 145 | EGF | IL6R | MMP1 | PYD | TNFRSF1A | 0.66 | 0.12 | 0.37 |
| 146 | CHI3L1 | LEP | EGF | ICAM1 | PYD | 0.66 | 0.12 | 0.35 |
| 147 | ICAM1 | MMP1 | TNFRSF1A | VCAM1 | VEGFA | 0.66 | 0.12 | 0.31 |
| 148 | CHI3L1 | IL1RN | EGF | ICAM1 | RETN | 0.66 | 0.12 | 0.34 |
| 149 | ICAM1 | IL6R | MMP1 | PYD | TNFRSF1A | 0.66 | 0.12 | 0.34 |
| 150 | EGF | ICAM1 | IL6R | IL8 | VCAM1 | 0.66 | 0.12 | 0.37 |
| 151 | CHI3L1 | PYD | EGF | IL6R | VCAM1 | 0.66 | 0.12 | 0.35 |
| 152 | CCL22 | EGF | MMP1 | TNFRSF1A | VEGFA | 0.66 | 0.12 | 0.37 |
| 153 | CHI3L1 | IL1RN | IL6R | LEP | VCAM1 | 0.66 | 0.12 | 0.32 |
| 154 | CHI3L1 | LEP | EGF | PYD | RETN | 0.66 | 0.12 | 0.34 |
| 155 | MMP1 | IL1RN | TNFRSF1A | VCAM1 | VEGFA | 0.66 | 0.12 | 0.33 |
| 156 | EGF | IL6R | IL8 | LEP | TNFRSF1A | 0.66 | 0.12 | 0.39 |
| 157 | EGF | ICAM1 | IL8 | IL1RN | LEP | 0.66 | 0.12 | 0.39 |
| 158 | ICAM1 | IL8 | IL1RN | LEP | VCAM1 | 0.66 | 0.12 | 0.37 |
| 159 | EGF | IL6R | IL8 | IL1RN | PYD | 0.66 | 0.12 | 0.38 |
| 160 | IL6R | IL1RN | PYD | TNFRSF1A | VEGFA | 0.66 | 0.12 | 0.30 |
| 161 | EGF | IL1RN | MMP1 | PYD | VEGFA | 0.66 | 0.12 | 0.34 |

FIG. 19D

| | | | | | | | | |
|---|---|---|---|---|---|---|---|---|
| 162 | CCL22 | ICAM1 | IL6R | PYD | TNFRSF1A | 0.66 | 0.12 | 0.31 |
| 163 | EGF | ICAM1 | IL8 | PYD | VCAM1 | 0.66 | 0.12 | 0.37 |
| 164 | CHI3L1 | RETN | EGF | IL6R | VCAM1 | 0.66 | 0.12 | 0.35 |
| 165 | EGF | IL6R | MMP1 | RETN | VEGFA | 0.66 | 0.12 | 0.34 |
| 166 | EGF | IL8 | IL1RN | TNFRSF1A | VCAM1 | 0.66 | 0.12 | 0.38 |
| 167 | CHI3L1 | LEP | EGF | ICAM1 | RETN | 0.66 | 0.12 | 0.34 |
| 168 | EGF | IL8 | IL1RN | LEP | PYD | 0.66 | 0.12 | 0.37 |
| 169 | CCL22 | ICAM1 | IL6R | RETN | TNFRSF1A | 0.66 | 0.12 | 0.31 |
| 170 | CHI3L1 | IL1RN | ICAM1 | LEP | VCAM1 | 0.66 | 0.12 | 0.34 |
| 171 | IL6R | LEP | PYD | TNFRSF1A | VEGFA | 0.66 | 0.12 | 0.31 |
| 172 | EGF | LEP | MMP1 | TNFRSF1A | VEGFA | 0.66 | 0.12 | 0.35 |
| 173 | EGF | IL6R | MMP1 | RETN | TNFRSF1A | 0.66 | 0.12 | 0.38 |
| 174 | CCL22 | ICAM1 | IL1RN | MMP1 | TNFRSF1A | 0.66 | 0.12 | 0.32 |
| 175 | EGF | IL8 | IL1RN | PYD | VCAM1 | 0.66 | 0.11 | 0.38 |
| 176 | CCL22 | IL6R | MMP1 | PYD | VEGFA | 0.66 | 0.11 | 0.32 |
| 177 | IL6R | PYD | RETN | TNFRSF1A | VEGFA | 0.66 | 0.11 | 0.30 |
| 178 | CHI3L1 | LEP | PYD | RETN | VCAM1 | 0.66 | 0.11 | 0.34 |
| 179 | ICAM1 | IL6R | IL8 | LEP | VCAM1 | 0.66 | 0.11 | 0.36 |
| 180 | CHI3L1 | IL1RN | IL6R | RETN | VCAM1 | 0.66 | 0.11 | 0.32 |
| 181 | CHI3L1 | IL1RN | EGF | LEP | VCAM1 | 0.66 | 0.11 | 0.34 |
| 182 | CHI3L1 | IL1RN | ICAM1 | PYD | RETN | 0.66 | 0.11 | 0.33 |
| 183 | CHI3L1 | IL1RN | ICAM1 | LEP | PYD | 0.66 | 0.11 | 0.33 |
| 184 | CCL22 | IL6R | LEP | MMP1 | TNFRSF1A | 0.66 | 0.11 | 0.34 |
| 185 | CHI3L1 | IL1RN | IL6R | PYD | VCAM1 | 0.66 | 0.11 | 0.34 |
| 186 | CHI3L1 | IL1RN | EGF | LEP | PYD | 0.66 | 0.11 | 0.34 |
| 187 | CCL22 | ICAM1 | MMP1 | TNFRSF1A | VCAM1 | 0.66 | 0.11 | 0.33 |
| 188 | IL6R | MMP1 | PYD | RETN | VEGFA | 0.66 | 0.11 | 0.32 |
| 189 | IL6R | LEP | MMP1 | TNFRSF1A | VEGFA | 0.66 | 0.11 | 0.33 |
| 190 | MMP1 | RETN | TNFRSF1A | VCAM1 | VEGFA | 0.66 | 0.11 | 0.34 |
| 191 | IL6R | MMP1 | PYD | TNFRSF1A | VCAM1 | 0.66 | 0.11 | 0.33 |
| 192 | CHI3L1 | IL1RN | LEP | VCAM1 | VEGFA | 0.66 | 0.11 | 0.32 |
| 193 | CHI3L1 | PYD | EGF | IL6R | RETN | 0.66 | 0.11 | 0.33 |
| 194 | CCL22 | IL6R | LEP | PYD | TNFRSF1A | 0.66 | 0.11 | 0.29 |
| 195 | ICAM1 | IL6R | LEP | MMP1 | VEGFA | 0.66 | 0.11 | 0.29 |
| 196 | ICAM1 | IL6R | MMP1 | RETN | VEGFA | 0.66 | 0.11 | 0.30 |
| 197 | CHI3L1 | IL1RN | IL6R | LEP | PYD | 0.66 | 0.11 | 0.33 |
| 198 | EGF | ICAM1 | MMP1 | PYD | VEGFA | 0.66 | 0.11 | 0.34 |
| 199 | CHI3L1 | IL1RN | EGF | LEP | RETN | 0.66 | 0.11 | 0.34 |
| 200 | EGF | IL8 | LEP | PYD | VCAM1 | 0.66 | 0.11 | 0.37 |
| 201 | CHI3L1 | LEP | ICAM1 | IL6R | PYD | 0.66 | 0.11 | 0.33 |
| 202 | CCL22 | MMP1 | RETN | VCAM1 | VEGFA | 0.66 | 0.11 | 0.30 |

FIG. 19E

| 203 | IL6R | IL1RN | MMP1 | TNFRSF1A | VEGFA | 0.66 | 0.11 | 0.33 |
| --- | --- | --- | --- | --- | --- | --- | --- | --- |
| 204 | CHI3L1 | IL1RN | EGF | IL6R | RETN | 0.66 | 0.11 | 0.33 |
| 205 | IL6R | IL1RN | LEP | TNFRSF1A | VEGFA | 0.66 | 0.11 | 0.28 |
| 206 | IL6R | MMP1 | PYD | VCAM1 | VEGFA | 0.66 | 0.11 | 0.31 |
| 207 | CHI3L1 | LEP | EGF | PYD | VCAM1 | 0.66 | 0.11 | 0.33 |
| 208 | IL1B | IL1RN | LEP | PYD | VCAM1 | 0.66 | 0.11 | 0.35 |
| 209 | CHI3L1 | LEP | IL6R | RETN | VCAM1 | 0.66 | 0.11 | 0.33 |
| 210 | LEP | PYD | MMP1 | RETN | VEGFA | 0.66 | 0.11 | 0.30 |
| 211 | CCL22 | EGF | LEP | MMP1 | VEGFA | 0.66 | 0.11 | 0.34 |
| 212 | CCL22 | IL6R | PYD | TNFRSF1A | VCAM1 | 0.66 | 0.11 | 0.28 |
| 213 | IL6R | IL1RN | MMP1 | PYD | VEGFA | 0.66 | 0.11 | 0.31 |
| 214 | CCL22 | IL6R | LEP | TNFRSF1A | VCAM1 | 0.66 | 0.11 | 0.30 |
| 215 | IL8 | IL1RN | LEP | PYD | VCAM1 | 0.66 | 0.11 | 0.36 |
| 216 | CHI3L1 | IL1RN | ICAM1 | IL6R | LEP | 0.66 | 0.11 | 0.31 |
| 217 | IL6R | IL1RN | MMP1 | TNFRSF1A | VCAM1 | 0.66 | 0.11 | 0.34 |
| 218 | CCL22 | IL6R | MMP1 | PYD | RETN | 0.66 | 0.11 | 0.32 |
| 219 | CHI3L1 | LEP | EGF | ICAM1 | VCAM1 | 0.66 | 0.11 | 0.33 |
| 220 | ICAM1 | IL6R | PYD | TNFRSF1A | VEGFA | 0.66 | 0.11 | 0.29 |
| 221 | EGF | ICAM1 | MMP1 | RETN | VEGFA | 0.66 | 0.11 | 0.34 |
| 222 | EGF | CHI3L1 | ICAM1 | IL6R | VCAM1 | 0.66 | 0.11 | 0.35 |
| 223 | CHI3L1 | IL1RN | EGF | PYD | VCAM1 | 0.66 | 0.11 | 0.33 |
| 224 | MMP1 | PYD | RETN | VCAM1 | VEGFA | 0.66 | 0.11 | 0.31 |
| 225 | ICAM1 | MMP1 | RETN | TNFRSF1A | VEGFA | 0.66 | 0.11 | 0.34 |
| 226 | EGF | IL6R | IL8 | LEP | PYD | 0.66 | 0.11 | 0.36 |
| 227 | ICAM1 | IL6R | MMP1 | PYD | VEGFA | 0.66 | 0.11 | 0.31 |
| 228 | CCL22 | EGF | IL6R | TNFRSF1A | VEGFA | 0.66 | 0.11 | 0.31 |
| 229 | IL1RN | PYD | MMP1 | TNFRSF1A | VEGFA | 0.66 | 0.11 | 0.33 |
| 230 | EGF | MMP1 | RETN | TNFRSF1A | VEGFA | 0.66 | 0.11 | 0.36 |
| 231 | CHI3L1 | IL1RN | LEP | RETN | VCAM1 | 0.66 | 0.10 | 0.32 |
| 232 | EGF | ICAM1 | IL6R | MMP1 | TNFRSF1A | 0.66 | 0.10 | 0.35 |
| 233 | CCL22 | EGF | IL1RN | MMP1 | TNFRSF1A | 0.66 | 0.10 | 0.35 |
| 234 | CHI3L1 | IL1RN | LEP | PYD | RETN | 0.66 | 0.10 | 0.32 |
| 235 | CCL22 | ICAM1 | MMP1 | TNFRSF1A | VEGFA | 0.66 | 0.10 | 0.32 |
| 236 | CCL22 | EGF | ICAM1 | MMP1 | VEGFA | 0.66 | 0.10 | 0.33 |

| SIXMRK Set No. | Marker 1 | Marker 2 | Marker 3 | Marker 4 | Marker 5 | Marker 6 | AUC | % | r |
|---|---|---|---|---|---|---|---|---|---|
| 1 | IL1B | IL1RN | PYD | RETN | TNFRSF1A | VCAM1 | 0.69 | 0.19 | 0.38 |
| 2 | CCL22 | ICAM1 | IL6R | PYD | TNFRSF1A | VEGFA | 0.69 | 0.18 | 0.32 |
| 3 | CHI3L1 | IL1RN | ICAM1 | PYD | RETN | VEGFA | 0.69 | 0.18 | 0.35 |
| 4 | IL6R | MMP1 | PYD | RETN | TNFRSF1A | VEGFA | 0.68 | 0.17 | 0.34 |
| 5 | CHI3L1 | IL1RN | EGF | ICAM1 | VCAM1 | VEGFA | 0.68 | 0.17 | 0.37 |
| 6 | CHI3L1 | IL1RN | EGF | ICAM1 | PYD | VEGFA | 0.68 | 0.16 | 0.34 |
| 7 | CHI3L1 | PYD | EGF | ICAM1 | IL6R | RETN | 0.68 | 0.16 | 0.35 |
| 8 | CCL22 | IL6R | PYD | TNFRSF1A | VCAM1 | VEGFA | 0.68 | 0.16 | 0.32 |
| 9 | CHI3L1 | LEP | ICAM1 | IL6R | PYD | RETN | 0.68 | 0.16 | 0.35 |
| 10 | CHI3L1 | LEP | PYD | RETN | VCAM1 | VEGFA | 0.68 | 0.16 | 0.36 |
| 11 | CCL22 | IL6R | IL1RN | TNFRSF1A | VCAM1 | VEGFA | 0.68 | 0.15 | 0.29 |
| 12 | CHI3L1 | IL1RN | ICAM1 | LEP | RETN | VEGFA | 0.68 | 0.15 | 0.35 |
| 13 | EGF | IL1B | IL1RN | RETN | TNFRSF1A | VCAM1 | 0.68 | 0.15 | 0.37 |
| 14 | CHI3L1 | IL1RN | ICAM1 | PYD | VCAM1 | VEGFA | 0.68 | 0.14 | 0.35 |
| 15 | IL6R | IL1RN | MMP1 | PYD | TNFRSF1A | VEGFA | 0.68 | 0.14 | 0.34 |
| 16 | CCL22 | ICAM1 | IL6R | LEP | TNFRSF1A | VEGFA | 0.68 | 0.14 | 0.31 |
| 17 | CCL22 | IL6R | MMP1 | RETN | TNFRSF1A | VEGFA | 0.68 | 0.14 | 0.33 |
| 18 | ICAM1 | IL8 | IL1RN | LEP | PYD | VCAM1 | 0.68 | 0.13 | 0.38 |
| 19 | CHI3L1 | IL1RN | ICAM1 | IL6R | PYD | VCAM1 | 0.68 | 0.13 | 0.35 |
| 20 | CHI3L1 | LEP | ICAM1 | PYD | VCAM1 | VEGFA | 0.68 | 0.13 | 0.32 |
| 21 | CHI3L1 | PYD | EGF | RETN | VCAM1 | VEGFA | 0.68 | 0.13 | 0.36 |
| 22 | CHI3L1 | IL1RN | ICAM1 | LEP | VCAM1 | VEGFA | 0.68 | 0.13 | 0.33 |
| 23 | CCL22 | IL6R | LEP | MMP1 | TNFRSF1A | VEGFA | 0.68 | 0.13 | 0.31 |
| 24 | CHI3L1 | PYD | EGF | ICAM1 | RETN | VEGFA | 0.68 | 0.13 | 0.34 |
| 25 | CHI3L1 | RETN | EGF | ICAM1 | VCAM1 | VEGFA | 0.68 | 0.13 | 0.34 |
| 26 | CCL22 | IL6R | IL1RN | MMP1 | TNFRSF1A | VEGFA | 0.67 | 0.13 | 0.34 |
| 27 | CHI3L1 | LEP | EGF | ICAM1 | PYD | VEGFA | 0.67 | 0.13 | 0.32 |
| 28 | EGF | IL8 | IL1RN | LEP | VCAM1 | VEGFA | 0.67 | 0.12 | 0.39 |
| 29 | CCL22 | IL6R | MMP1 | TNFRSF1A | VCAM1 | VEGFA | 0.67 | 0.12 | 0.34 |
| 30 | CHI3L1 | PYD | EGF | ICAM1 | VCAM1 | VEGFA | 0.67 | 0.12 | 0.33 |
| 31 | CHI3L1 | PYD | EGF | IL6R | RETN | VCAM1 | 0.67 | 0.12 | 0.34 |
| 32 | ICAM1 | IL6R | MMP1 | PYD | TNFRSF1A | VEGFA | 0.67 | 0.12 | 0.33 |
| 33 | CHI3L1 | IL1RN | LEP | PYD | RETN | VEGFA | 0.67 | 0.12 | 0.32 |
| 34 | CCL22 | MMP1 | PYD | RETN | TNFRSF1A | VEGFA | 0.67 | 0.12 | 0.33 |
| 35 | CCL22 | IL6R | MMP1 | RETN | TNFRSF1A | VCAM1 | 0.67 | 0.12 | 0.34 |
| 36 | CHI3L1 | LEP | EGF | RETN | VCAM1 | VEGFA | 0.67 | 0.12 | 0.34 |
| 37 | CHI3L1 | IL1RN | ICAM1 | IL6R | RETN | VCAM1 | 0.67 | 0.11 | 0.34 |
| 38 | EGF | ICAM1 | IL6R | IL8 | IL1RN | PYD | 0.67 | 0.11 | 0.40 |

| 39 | ICAM1 | IL6R | MMP1 | RETN | TNFRSF1A | VEGFA | 0.67 | 0.11 | 0.33 |
|---|---|---|---|---|---|---|---|---|---|
| 40 | CCL22 | IL6R | MMP1 | PYD | VCAM1 | VEGFA | 0.67 | 0.11 | 0.31 |
| 41 | IL6R | MMP1 | PYD | TNFRSF1A | VCAM1 | VEGFA | 0.67 | 0.11 | 0.33 |
| 42 | CCL22 | ICAM1 | MMP1 | TNFRSF1A | VCAM1 | VEGFA | 0.67 | 0.11 | 0.34 |
| 43 | CCL22 | MMP1 | PYD | TNFRSF1A | VCAM1 | VEGFA | 0.67 | 0.11 | 0.32 |
| 44 | EGF | ICAM1 | MMP1 | TNFRSF1A | VCAM1 | VEGFA | 0.67 | 0.11 | 0.38 |
| 45 | CHI3L1 | PYD | ICAM1 | RETN | VCAM1 | VEGFA | 0.67 | 0.11 | 0.34 |
| 46 | CHI3L1 | PYD | EGF | ICAM1 | IL6R | VCAM1 | 0.67 | 0.10 | 0.35 |
| 47 | CHI3L1 | IL1RN | ICAM1 | IL6R | LEP | PYD | 0.67 | 0.10 | 0.32 |
| 48 | ICAM1 | IL6R | IL1RN | MMP1 | PYD | VEGFA | 0.67 | 0.10 | 0.33 |
| 49 | CCL22 | ICAM1 | IL6R | MMP1 | TNFRSF1A | VEGFA | 0.67 | 0.10 | 0.32 |
| 50 | CHI3L1 | PYD | ICAM1 | IL6R | RETN | VCAM1 | 0.67 | 0.10 | 0.32 |
| 51 | IL6R | LEP | MMP1 | PYD | TNFRSF1A | VEGFA | 0.67 | 0.10 | 0.31 |
| 52 | CHI3L1 | LEP | EGF | PYD | VCAM1 | VEGFA | 0.67 | 0.10 | 0.32 |
| 53 | EGF | IL6R | IL8 | IL1RN | TNFRSF1A | VCAM1 | 0.67 | 0.10 | 0.39 |
| 54 | CHI3L1 | IL1RN | ICAM1 | LEP | RETN | VCAM1 | 0.67 | 0.10 | 0.31 |
| 55 | CHI3L1 | LEP | EGF | PYD | RETN | VEGFA | 0.67 | 0.10 | 0.33 |
| 56 | CCL22 | EGF | IL1RN | MMP1 | TNFRSF1A | VEGFA | 0.67 | 0.10 | 0.35 |
| 57 | CHI3L1 | IL1RN | EGF | PYD | VCAM1 | VEGFA | 0.67 | 0.10 | 0.35 |
| 58 | ICAM1 | IL6R | IL8 | IL1RN | PYD | VCAM1 | 0.67 | 0.10 | 0.37 |
| 59 | CHI3L1 | LEP | ICAM1 | PYD | RETN | VEGFA | 0.67 | 0.10 | 0.33 |
| 60 | EGF | ICAM1 | IL8 | LEP | PYD | VCAM1 | 0.67 | 0.10 | 0.37 |
| 61 | CHI3L1 | IL1RN | EGF | ICAM1 | RETN | VEGFA | 0.67 | 0.10 | 0.33 |
| 62 | EGF | ICAM1 | IL6R | IL8 | PYD | VCAM1 | 0.67 | 0.10 | 0.37 |
| 63 | EGF | IL6R | IL8 | IL1RN | PYD | VCAM1 | 0.67 | 0.10 | 0.39 |
| 64 | CHI3L1 | LEP | EGF | ICAM1 | IL6R | PYD | 0.67 | 0.10 | 0.34 |
| 65 | CCL22 | EGF | MMP1 | RETN | VCAM1 | VEGFA | 0.67 | 0.10 | 0.34 |
| 66 | CCL22 | ICAM1 | IL6R | RETN | TNFRSF1A | VEGFA | 0.67 | 0.10 | 0.29 |
| 67 | CHI3L1 | IL1RN | EGF | ICAM1 | PYD | RETN | 0.67 | 0.10 | 0.35 |
| 68 | CHI3L1 | LEP | EGF | IL6R | PYD | RETN | 0.67 | 0.10 | 0.33 |
| 69 | CHI3L1 | IL1RN | ICAM1 | RETN | VCAM1 | VEGFA | 0.67 | 0.10 | 0.32 |
| 70 | EGF | ICAM1 | IL6R | IL8 | LEP | PYD | 0.67 | 0.09 | 0.38 |
| 71 | EGF | IL6R | MMP1 | PYD | RETN | VEGFA | 0.67 | 0.09 | 0.34 |
| 72 | CCL22 | ICAM1 | MMP1 | PYD | TNFRSF1A | VEGFA | 0.67 | 0.09 | 0.33 |
| 73 | EGF | IL1RN | MMP1 | PYD | TNFRSF1A | VEGFA | 0.67 | 0.09 | 0.37 |
| 74 | CCL22 | EGF | ICAM1 | MMP1 | TNFRSF1A | VEGFA | 0.67 | 0.09 | 0.34 |
| 75 | EGF | IL6R | IL8 | LEP | TNFRSF1A | VCAM1 | 0.67 | 0.09 | 0.40 |
| 76 | IL6R | LEP | MMP1 | PYD | TNFRSF1A | VCAM1 | 0.67 | 0.09 | 0.34 |
| 77 | CHI3L1 | IL1RN | PYD | RETN | VCAM1 | VEGFA | 0.67 | 0.09 | 0.33 |
| 78 | CHI3L1 | IL1RN | EGF | PYD | RETN | VEGFA | 0.67 | 0.09 | 0.33 |
| 79 | CCL22 | ICAM1 | IL6R | MMP1 | PYD | TNFRSF1A | 0.67 | 0.09 | 0.34 |

FIG. 20B

| | | | | | | | | | |
|---|---|---|---|---|---|---|---|---|---|
| 80 | IL6R | IL8 | IL1RN | LEP | TNFRSF1A | VCAM1 | 0.66 | 0.09 | 0.38 |
| 81 | CHI3L1 | LEP | ICAM1 | IL6R | PYD | VCAM1 | 0.66 | 0.09 | 0.33 |
| 82 | CHI3L1 | IL1RN | EGF | RETN | VCAM1 | VEGFA | 0.66 | 0.09 | 0.32 |
| 83 | IL6R | LEP | MMP1 | TNFRSF1A | VCAM1 | VEGFA | 0.66 | 0.09 | 0.32 |
| 84 | CCL22 | IL6R | MMP1 | PYD | TNFRSF1A | VEGFA | 0.66 | 0.09 | 0.32 |
| 85 | CCL22 | IL6R | PYD | RETN | TNFRSF1A | VEGFA | 0.66 | 0.09 | 0.30 |
| 86 | CCL22 | ICAM1 | MMP1 | PYD | RETN | VEGFA | 0.66 | 0.09 | 0.33 |
| 87 | CHI3L1 | LEP | ICAM1 | PYD | RETN | VCAM1 | 0.66 | 0.09 | 0.35 |
| 88 | CCL22 | IL6R | MMP1 | PYD | RETN | TNFRSF1A | 0.66 | 0.09 | 0.34 |
| 89 | CCL22 | ICAM1 | IL6R | IL1RN | PYD | TNFRSF1A | 0.66 | 0.09 | 0.29 |
| 90 | CCL22 | ICAM1 | IL1RN | TNFRSF1A | VCAM1 | VEGFA | 0.66 | 0.09 | 0.29 |
| 91 | CCL22 | EGF | LEP | MMP1 | PYD | VEGFA | 0.66 | 0.09 | 0.35 |
| 92 | CHI3L1 | LEP | ICAM1 | RETN | VCAM1 | VEGFA | 0.66 | 0.09 | 0.32 |
| 93 | CCL22 | ICAM1 | IL6R | IL1RN | TNFRSF1A | VEGFA | 0.66 | 0.09 | 0.28 |
| 94 | CHI3L1 | LEP | EGF | ICAM1 | PYD | RETN | 0.66 | 0.09 | 0.35 |
| 95 | CHI3L1 | LEP | EGF | ICAM1 | IL6R | RETN | 0.66 | 0.09 | 0.32 |
| 96 | CCL22 | IL6R | LEP | MMP1 | PYD | TNFRSF1A | 0.66 | 0.09 | 0.32 |
| 97 | CHI3L1 | LEP | EGF | ICAM1 | VCAM1 | VEGFA | 0.66 | 0.09 | 0.31 |
| 98 | ICAM1 | IL6R | IL8 | IL1RN | LEP | VCAM1 | 0.66 | 0.09 | 0.39 |
| 99 | EGF | MMP1 | PYD | RETN | TNFRSF1A | VEGFA | 0.66 | 0.09 | 0.36 |
| 100 | EGF | MMP1 | PYD | RETN | VCAM1 | VEGFA | 0.66 | 0.08 | 0.35 |
| 101 | CCL22 | IL6R | IL1RN | RETN | TNFRSF1A | VEGFA | 0.66 | 0.08 | 0.28 |
| 102 | CCL22 | ICAM1 | PYD | RETN | TNFRSF1A | VEGFA | 0.66 | 0.08 | 0.31 |
| 103 | ICAM1 | IL6R | PYD | RETN | TNFRSF1A | VEGFA | 0.66 | 0.08 | 0.31 |
| 104 | EGF | ICAM1 | IL6R | IL8 | IL1RN | LEP | 0.66 | 0.08 | 0.38 |
| 105 | CCL22 | ICAM1 | MMP1 | RETN | TNFRSF1A | VEGFA | 0.66 | 0.08 | 0.34 |
| 106 | ICAM1 | IL6R | IL8 | IL1RN | LEP | PYD | 0.66 | 0.08 | 0.37 |
| 107 | IL6R | LEP | MMP1 | RETN | TNFRSF1A | VEGFA | 0.66 | 0.08 | 0.31 |
| 108 | CHI3L1 | IL1RN | ICAM1 | IL6R | LEP | VCAM1 | 0.66 | 0.08 | 0.32 |
| 109 | CHI3L1 | IL1RN | EGF | PYD | RETN | VCAM1 | 0.66 | 0.08 | 0.34 |
| 110 | CCL22 | IL6R | MMP1 | PYD | RETN | VEGFA | 0.66 | 0.08 | 0.31 |
| 111 | LEP | RETN | MMP1 | TNFRSF1A | VCAM1 | VEGFA | 0.66 | 0.08 | 0.31 |
| 112 | CCL22 | ICAM1 | IL6R | TNFRSF1A | VCAM1 | VEGFA | 0.66 | 0.08 | 0.29 |
| 113 | CCL22 | ICAM1 | MMP1 | PYD | VCAM1 | VEGFA | 0.66 | 0.08 | 0.32 |
| 114 | CCL22 | EGF | IL6R | TNFRSF1A | VCAM1 | VEGFA | 0.66 | 0.08 | 0.31 |
| 115 | ICAM1 | IL6R | IL8 | LEP | PYD | VCAM1 | 0.66 | 0.08 | 0.36 |
| 116 | CHI3L1 | IL1RN | EGF | LEP | RETN | VEGFA | 0.66 | 0.08 | 0.31 |
| 117 | CCL22 | EGF | IL6R | MMP1 | TNFRSF1A | VEGFA | 0.66 | 0.08 | 0.35 |
| 118 | EGF | IL6R | IL1RN | TNFRSF1A | VCAM1 | VEGFA | 0.66 | 0.08 | 0.29 |
| 119 | CHI3L1 | IL1RN | EGF | ICAM1 | PYD | VCAM1 | 0.66 | 0.08 | 0.33 |
| 120 | ICAM1 | IL6R | MMP1 | TNFRSF1A | VCAM1 | VEGFA | 0.66 | 0.08 | 0.31 |

FIG. 20C

| | | | | | | | | | |
|---|---|---|---|---|---|---|---|---|---|
| 121 | CHI3L1 | IL1RN | ICAM1 | PYD | RETN | VCAM1 | 0.66 | 0.08 | 0.35 |
| 122 | CHI3L1 | IL1RN | EGF | IL6R | PYD | RETN | 0.66 | 0.08 | 0.36 |
| 123 | CCL22 | LEP | MMP1 | PYD | TNFRSF1A | VEGFA | 0.66 | 0.08 | 0.33 |
| 124 | CCL22 | EGF | IL6R | MMP1 | RETN | TNFRSF1A | 0.66 | 0.08 | 0.35 |
| 125 | EGF | ICAM1 | IL8 | IL1RN | LEP | VCAM1 | 0.66 | 0.08 | 0.37 |
| 126 | CHI3L1 | IL1RN | LEP | PYD | VCAM1 | VEGFA | 0.66 | 0.08 | 0.33 |
| 127 | EGF | IL6R | RETN | TNFRSF1A | VCAM1 | VEGFA | 0.66 | 0.08 | 0.31 |
| 128 | CHI3L1 | RETN | EGF | ICAM1 | IL6R | VCAM1 | 0.66 | 0.08 | 0.33 |
| 129 | CHI3L1 | IL1RN | EGF | LEP | VCAM1 | VEGFA | 0.66 | 0.08 | 0.31 |
| 130 | CCL22 | EGF | ICAM1 | IL6R | MMP1 | VEGFA | 0.66 | 0.08 | 0.34 |
| 131 | CCL22 | PYD | RETN | TNFRSF1A | VCAM1 | VEGFA | 0.66 | 0.08 | 0.30 |
| 132 | CHI3L1 | IL1RN | EGF | ICAM1 | IL6R | PYD | 0.66 | 0.08 | 0.33 |
| 133 | CCL22 | EGF | MMP1 | PYD | RETN | VEGFA | 0.66 | 0.08 | 0.33 |
| 134 | CCL22 | EGF | MMP1 | PYD | VCAM1 | VEGFA | 0.66 | 0.08 | 0.34 |
| 135 | CCL22 | IL6R | LEP | PYD | TNFRSF1A | VEGFA | 0.66 | 0.08 | 0.30 |
| 136 | ICAM1 | IL6R | IL1RN | MMP1 | TNFRSF1A | VCAM1 | 0.66 | 0.08 | 0.33 |
| 137 | CCL22 | IL6R | LEP | PYD | RETN | TNFRSF1A | 0.66 | 0.08 | 0.32 |
| 138 | CCL22 | EGF | IL6R | RETN | TNFRSF1A | VEGFA | 0.66 | 0.08 | 0.31 |
| 139 | CCL22 | EGF | ICAM1 | IL6R | IL1RN | TNFRSF1A | 0.66 | 0.08 | 0.31 |
| 140 | CCL22 | ICAM1 | IL1RN | PYD | TNFRSF1A | VEGFA | 0.66 | 0.08 | 0.31 |
| 141 | ICAM1 | IL6R | MMP1 | PYD | TNFRSF1A | VCAM1 | 0.66 | 0.08 | 0.32 |
| 142 | CCL22 | LEP | MMP1 | PYD | VCAM1 | VEGFA | 0.66 | 0.08 | 0.31 |
| 143 | CCL22 | EGF | MMP1 | PYD | TNFRSF1A | VEGFA | 0.66 | 0.08 | 0.35 |
| 144 | CCL22 | ICAM1 | IL6R | PYD | RETN | VEGFA | 0.66 | 0.08 | 0.27 |
| 145 | EGF | IL8 | IL1RN | LEP | TNFRSF1A | VCAM1 | 0.66 | 0.08 | 0.36 |
| 146 | EGF | IL6R | MMP1 | PYD | TNFRSF1A | VEGFA | 0.66 | 0.08 | 0.36 |
| 147 | EGF | IL1RN | MMP1 | RETN | TNFRSF1A | VEGFA | 0.66 | 0.08 | 0.34 |
| 148 | CHI3L1 | IL1RN | ICAM1 | IL6R | LEP | RETN | 0.66 | 0.08 | 0.31 |
| 149 | CCL22 | MMP1 | RETN | TNFRSF1A | VCAM1 | VEGFA | 0.66 | 0.08 | 0.34 |
| 150 | EGF | IL6R | MMP1 | RETN | TNFRSF1A | VEGFA | 0.66 | 0.07 | 0.35 |
| 151 | EGF | ICAM1 | IL6R | IL8 | LEP | VCAM1 | 0.66 | 0.07 | 0.36 |
| 152 | EGF | IL6R | MMP1 | TNFRSF1A | VCAM1 | VEGFA | 0.66 | 0.07 | 0.35 |
| 153 | CCL22 | IL6R | IL1RN | MMP1 | PYD | TNFRSF1A | 0.66 | 0.07 | 0.33 |
| 154 | EGF | ICAM1 | MMP1 | PYD | TNFRSF1A | VEGFA | 0.66 | 0.07 | 0.36 |
| 155 | CCL22 | ICAM1 | IL6R | LEP | PYD | TNFRSF1A | 0.66 | 0.07 | 0.30 |
| 156 | CHI3L1 | IL1RN | EGF | ICAM1 | LEP | RETN | 0.66 | 0.07 | 0.34 |
| 157 | CHI3L1 | IL1RN | LEP | RETN | VCAM1 | VEGFA | 0.66 | 0.07 | 0.31 |
| 158 | CCL22 | ICAM1 | LEP | MMP1 | PYD | TNFRSF1A | 0.66 | 0.07 | 0.34 |
| 159 | CCL22 | IL6R | MMP1 | RETN | VCAM1 | VEGFA | 0.66 | 0.07 | 0.30 |
| 160 | CHI3L1 | IL1RN | IL6R | LEP | PYD | VCAM1 | 0.66 | 0.07 | 0.32 |
| 161 | CHI3L1 | LEP | EGF | ICAM1 | RETN | VEGFA | 0.66 | 0.07 | 0.32 |

FIG. 20D

| | | | | | | | | | |
|---|---|---|---|---|---|---|---|---|---|
| 162 | CCL22 | LEP | MMP1 | PYD | RETN | VEGFA | 0.66 | 0.07 | 0.30 |
| 163 | ICAM1 | IL6R | LEP | PYD | TNFRSF1A | VEGFA | 0.66 | 0.07 | 0.28 |
| 164 | CHI3L1 | LEP | IL6R | PYD | RETN | VCAM1 | 0.66 | 0.07 | 0.34 |
| 165 | CCL22 | EGF | LEP | MMP1 | TNFRSF1A | VEGFA | 0.66 | 0.07 | 0.35 |
| 166 | CCL22 | EGF | ICAM1 | MMP1 | PYD | VEGFA | 0.66 | 0.07 | 0.34 |
| 167 | ICAM1 | MMP1 | PYD | RETN | VCAM1 | VEGFA | 0.66 | 0.07 | 0.32 |
| 168 | ICAM1 | IL6R | IL1RN | MMP1 | TNFRSF1A | VEGFA | 0.66 | 0.07 | 0.32 |
| 169 | CCL22 | ICAM1 | IL6R | MMP1 | RETN | TNFRSF1A | 0.66 | 0.07 | 0.32 |
| 170 | CCL22 | IL1RN | MMP1 | RETN | VCAM1 | VEGFA | 0.66 | 0.07 | 0.31 |
| 171 | CHI3L1 | IL1RN | ICAM1 | IL6R | PYD | RETN | 0.66 | 0.07 | 0.33 |
| 172 | CHI3L1 | LEP | EGF | ICAM1 | PYD | VCAM1 | 0.66 | 0.07 | 0.34 |
| 173 | CCL22 | EGF | IL1RN | MMP1 | RETN | VEGFA | 0.66 | 0.07 | 0.32 |
| 174 | IL6R | LEP | MMP1 | PYD | RETN | VEGFA | 0.66 | 0.07 | 0.30 |
| 175 | CCL22 | EGF | ICAM1 | IL6R | MMP1 | RETN | 0.66 | 0.07 | 0.31 |
| 176 | CCL22 | EGF | ICAM1 | IL1RN | MMP1 | VEGFA | 0.66 | 0.07 | 0.31 |
| 177 | CCL22 | ICAM1 | IL1RN | MMP1 | TNFRSF1A | VEGFA | 0.66 | 0.07 | 0.30 |
| 178 | CHI3L1 | IL1RN | IL6R | LEP | PYD | RETN | 0.66 | 0.07 | 0.30 |
| 179 | EGF | ICAM1 | IL6R | IL8 | IL1RN | VCAM1 | 0.66 | 0.07 | 0.39 |
| 180 | CCL22 | IL1RN | MMP1 | PYD | RETN | VEGFA | 0.66 | 0.07 | 0.32 |
| 181 | IL6R | MMP1 | PYD | RETN | TNFRSF1A | VCAM1 | 0.66 | 0.07 | 0.33 |
| 182 | ICAM1 | IL6R | MMP1 | PYD | RETN | TNFRSF1A | 0.66 | 0.07 | 0.34 |
| 183 | CCL22 | IL6R | IL1RN | MMP1 | PYD | VEGFA | 0.66 | 0.07 | 0.30 |
| 184 | ICAM1 | IL6R | LEP | MMP1 | RETN | TNFRSF1A | 0.66 | 0.07 | 0.32 |
| 185 | CHI3L1 | IL1RN | EGF | LEP | PYD | VEGFA | 0.66 | 0.07 | 0.34 |
| 186 | EGF | ICAM1 | IL6R | MMP1 | VCAM1 | VEGFA | 0.66 | 0.07 | 0.33 |
| 187 | CCL22 | IL6R | IL1RN | LEP | TNFRSF1A | VEGFA | 0.66 | 0.07 | 0.30 |
| 188 | CCL22 | ICAM1 | IL6R | RETN | TNFRSF1A | VCAM1 | 0.66 | 0.07 | 0.31 |
| 189 | EGF | MMP1 | PYD | TNFRSF1A | VCAM1 | VEGFA | 0.66 | 0.07 | 0.37 |
| 190 | EGF | IL6R | LEP | MMP1 | RETN | VEGFA | 0.66 | 0.07 | 0.33 |
| 191 | CCL22 | ICAM1 | PYD | TNFRSF1A | VCAM1 | VEGFA | 0.66 | 0.07 | 0.28 |
| 192 | CHI3L1 | IL1RN | EGF | ICAM1 | IL6R | RETN | 0.66 | 0.07 | 0.33 |

FIG. 20E

```
                        SEQUENCE LISTING

<160> NUMBER OF SEQ ID NOS: 25

<210> SEQ ID NO 1
<211> LENGTH: 267
<212> TYPE: PRT
<213> ORGANISM: Homo sapiens

<400> SEQUENCE: 1

Met Lys Ala Ala Val Leu Thr Leu Ala Val Leu Phe Leu Thr Gly Ser
1               5                   10                  15

Gln Ala Arg His Phe Trp Gln Gln Asp Glu Pro Pro Gln Ser Pro Trp
            20                  25                  30

Asp Arg Val Lys Asp Leu Ala Thr Val Tyr Val Asp Val Leu Lys Asp
        35                  40                  45

Ser Gly Arg Asp Tyr Val Ser Gln Phe Glu Gly Ser Ala Leu Gly Lys
    50                  55                  60

Gln Leu Asn Leu Lys Leu Leu Asp Asn Trp Asp Ser Val Thr Ser Thr
65                  70                  75                  80

Phe Ser Lys Leu Arg Glu Gln Leu Gly Pro Val Thr Gln Glu Phe Trp
                85                  90                  95

Asp Asn Leu Glu Lys Glu Thr Glu Gly Leu Arg Gln Glu Met Ser Lys
            100                 105                 110

Asp Leu Glu Glu Val Lys Ala Lys Val Gln Pro Tyr Leu Asp Asp Phe
        115                 120                 125

Gln Lys Lys Trp Gln Glu Glu Met Glu Leu Tyr Arg Gln Lys Val Glu
    130                 135                 140

Pro Leu Arg Ala Glu Leu Gln Glu Gly Ala Arg Gln Lys Leu His Glu
145                 150                 155                 160

Leu Gln Glu Lys Leu Ser Pro Leu Gly Glu Glu Met Arg Asp Arg Ala
                165                 170                 175

Arg Ala His Val Asp Ala Leu Arg Thr His Leu Ala Pro Tyr Ser Asp
            180                 185                 190

Glu Leu Arg Gln Arg Leu Ala Ala Arg Leu Glu Ala Leu Lys Glu Asn
        195                 200                 205

Gly Gly Ala Arg Leu Ala Glu Tyr His Ala Lys Ala Thr Glu His Leu
    210                 215                 220

Ser Thr Leu Ser Glu Lys Ala Lys Pro Ala Leu Glu Asp Leu Arg Gln
225                 230                 235                 240

Gly Leu Leu Pro Val Leu Glu Ser Phe Lys Val Ser Phe Leu Ser Ala
                245                 250                 255

Leu Glu Glu Tyr Thr Lys Lys Leu Asn Thr Gln
            260                 265

<210> SEQ ID NO 2
<211> LENGTH: 99
<212> TYPE: PRT
<213> ORGANISM: Homo sapiens

<400> SEQUENCE: 2

Met Gln Pro Arg Val Leu Leu Val Val Ala Leu Leu Ala Leu Leu Ala
1               5                   10                  15
```

```
Ser Ala Arg Ala Ser Glu Ala Glu Asp Ala Ser Leu Leu Ser Phe Met
            20                  25                  30

Gln Gly Tyr Met Lys His Ala Thr Lys Thr Ala Lys Asp Ala Leu Ser
        35                  40                  45

Ser Val Gln Glu Ser Gln Val Ala Gln Ala Arg Gly Trp Val Thr
 50                  55                  60

Asp Gly Phe Ser Ser Leu Lys Asp Tyr Trp Ser Thr Val Lys Asp Lys
 65                  70                  75                  80

Phe Ser Glu Phe Trp Asp Leu Asp Pro Glu Val Arg Pro Thr Ser Ala
                85                  90                  95

Val Ala Ala

<210> SEQ ID NO 3
<211> LENGTH: 93
<212> TYPE: PRT
<213> ORGANISM: Homo sapiens

<400> SEQUENCE: 3

Met Asp Arg Leu Gln Thr Ala Leu Leu Val Val Leu Val Leu Leu Ala
 1               5                  10                  15

Val Ala Leu Gln Ala Thr Glu Ala Gly Pro Tyr Gly Ala Asn Met Glu
            20                  25                  30

Asp Ser Val Cys Cys Arg Asp Tyr Val Arg Tyr Arg Leu Pro Leu Arg
        35                  40                  45

Val Val Lys His Phe Tyr Trp Thr Ser Asp Ser Cys Pro Arg Pro Gly
 50                  55                  60

Val Val Leu Leu Thr Phe Arg Asp Lys Glu Ile Cys Ala Asp Pro Arg
 65                  70                  75                  80

Val Pro Trp Val Lys Met Ile Leu Asn Lys Leu Ser Gln
                85                  90

<210> SEQ ID NO 4
<211> LENGTH: 383
<212> TYPE: PRT
<213> ORGANISM: Homo sapiens

<400> SEQUENCE: 4

Met Gly Val Lys Ala Ser Gln Thr Gly Phe Val Val Leu Val Leu Leu
 1               5                  10                  15

Gln Cys Cys Ser Ala Tyr Lys Leu Val Cys Tyr Tyr Thr Ser Trp Ser
            20                  25                  30

Gln Tyr Arg Glu Gly Asp Gly Ser Cys Phe Pro Asp Ala Leu Asp Arg
        35                  40                  45

Phe Leu Cys Thr His Ile Ile Tyr Ser Phe Ala Asn Ile Ser Asn Asp
 50                  55                  60

His Ile Asp Thr Trp Glu Trp Asn Asp Val Thr Leu Tyr Gly Met Leu
 65                  70                  75                  80

Asn Thr Leu Lys Asn Arg Asn Pro Asn Leu Lys Thr Leu Leu Ser Val
                85                  90                  95

Gly Gly Trp Asn Phe Gly Ser Gln Arg Phe Ser Lys Ile Ala Ser Asn
            100                 105                 110

Thr Gln Ser Arg Arg Thr Phe Ile Lys Ser Val Pro Pro Phe Leu Arg
        115                 120                 125

Thr His Gly Phe Asp Gly Leu Asp Leu Ala Trp Leu Tyr Pro Gly Arg
    130                 135                 140
```

-continued

```
Arg Asp Lys Gln His Phe Thr Thr Leu Ile Lys Glu Met Lys Ala Glu
145                 150                 155                 160

Phe Ile Lys Glu Ala Gln Pro Gly Lys Lys Gln Leu Leu Leu Ser Ala
                165                 170                 175

Ala Leu Ser Ala Gly Lys Val Thr Ile Asp Ser Ser Tyr Asp Ile Ala
            180                 185                 190

Lys Ile Ser Gln His Leu Asp Phe Ile Ser Ile Met Thr Tyr Asp Phe
        195                 200                 205

His Gly Ala Trp Arg Gly Thr Thr Gly His His Ser Pro Leu Phe Arg
    210                 215                 220

Gly Gln Glu Asp Ala Ser Pro Asp Arg Phe Ser Asn Thr Asp Tyr Ala
225                 230                 235                 240

Val Gly Tyr Met Leu Arg Leu Gly Ala Pro Ala Ser Lys Leu Val Met
                245                 250                 255

Gly Ile Pro Thr Phe Gly Arg Ser Phe Thr Leu Ala Ser Ser Glu Thr
            260                 265                 270

Gly Val Gly Ala Pro Ile Ser Gly Pro Gly Ile Pro Gly Arg Phe Thr
        275                 280                 285

Lys Glu Ala Gly Thr Leu Ala Tyr Tyr Glu Ile Cys Asp Phe Leu Arg
    290                 295                 300

Gly Ala Thr Val His Arg Ile Leu Gly Gln Gln Val Pro Tyr Ala Thr
305                 310                 315                 320

Lys Gly Asn Gln Trp Val Gly Tyr Asp Asp Gln Glu Ser Val Lys Ser
                325                 330                 335

Lys Val Gln Tyr Leu Lys Asp Arg Gln Leu Ala Gly Ala Met Val Trp
            340                 345                 350

Ala Leu Asp Leu Asp Asp Phe Gln Gly Ser Phe Cys Gly Gln Asp Leu
        355                 360                 365

Arg Phe Pro Leu Thr Asn Ala Ile Lys Asp Ala Leu Ala Ala Thr
    370                 375                 380

<210> SEQ ID NO 5
<211> LENGTH: 224
<212> TYPE: PRT
<213> ORGANISM: Homo sapiens

<400> SEQUENCE: 5

Met Glu Lys Leu Leu Cys Phe Leu Val Leu Thr Ser Leu Ser His Ala
1               5                   10                  15

Phe Gly Gln Thr Asp Met Ser Arg Lys Ala Phe Val Phe Pro Lys Glu
                20                  25                  30

Ser Asp Thr Ser Tyr Val Ser Leu Lys Ala Pro Leu Thr Lys Pro Leu
            35                  40                  45

Lys Ala Phe Thr Val Cys Leu His Phe Tyr Thr Glu Leu Ser Ser Thr
        50                  55                  60

Arg Gly Tyr Ser Ile Phe Ser Tyr Ala Thr Lys Arg Gln Asp Asn Glu
65                  70                  75                  80

Ile Leu Ile Phe Trp Ser Lys Asp Ile Gly Tyr Ser Phe Thr Val Gly
                85                  90                  95

Gly Ser Glu Ile Leu Phe Glu Val Pro Glu Val Thr Val Ala Pro Val
            100                 105                 110

His Ile Cys Thr Ser Trp Glu Ser Ala Ser Gly Ile Val Glu Phe Trp
        115                 120                 125

Val Asp Gly Lys Pro Arg Val Arg Lys Ser Leu Lys Lys Gly Tyr Thr
    130                 135                 140
```

```
Val Gly Ala Glu Ala Ser Ile Ile Leu Gly Gln Gln Asp Ser Phe
145                 150                 155                 160

Gly Gly Asn Phe Glu Gly Ser Gln Ser Leu Val Gly Asp Ile Gly Asn
            165                 170                 175

Val Asn Met Trp Asp Phe Val Leu Ser Pro Asp Glu Ile Asn Thr Ile
        180                 185                 190

Tyr Leu Gly Gly Pro Phe Ser Pro Asn Val Leu Asn Trp Arg Ala Leu
            195                 200                 205

Lys Tyr Glu Val Gln Gly Glu Val Phe Thr Lys Pro Gln Leu Trp Pro
        210                 215                 220
```

<210> SEQ ID NO 6
<211> LENGTH: 1207
<212> TYPE: PRT
<213> ORGANISM: Homo sapiens

<400> SEQUENCE: 6

```
Met Leu Leu Thr Leu Ile Ile Leu Leu Pro Val Val Ser Lys Phe Ser
1               5                   10                  15

Phe Val Ser Leu Ser Ala Pro Gln His Trp Ser Cys Pro Glu Gly Thr
            20                  25                  30

Leu Ala Gly Asn Gly Asn Ser Thr Cys Val Gly Pro Ala Pro Phe Leu
        35                  40                  45

Ile Phe Ser His Gly Asn Ser Ile Phe Arg Ile Asp Thr Glu Gly Thr
    50                  55                  60

Asn Tyr Glu Gln Leu Val Val Asp Ala Gly Val Ser Val Ile Met Asp
65                  70                  75                  80

Phe His Tyr Asn Glu Lys Arg Ile Tyr Trp Val Asp Leu Glu Arg Gln
                85                  90                  95

Leu Leu Gln Arg Val Phe Leu Asn Gly Ser Arg Gln Glu Arg Val Cys
            100                 105                 110

Asn Ile Glu Lys Asn Val Ser Gly Met Ala Ile Asn Trp Ile Asn Glu
        115                 120                 125

Glu Val Ile Trp Ser Asn Gln Gln Glu Gly Ile Ile Thr Val Thr Asp
    130                 135                 140

Met Lys Gly Asn Asn Ser His Ile Leu Leu Ser Ala Leu Lys Tyr Pro
145                 150                 155                 160

Ala Asn Val Ala Val Asp Pro Val Glu Arg Phe Ile Phe Trp Ser Ser
                165                 170                 175

Glu Val Ala Gly Ser Leu Tyr Arg Ala Asp Leu Asp Gly Val Gly Val
            180                 185                 190

Lys Ala Leu Leu Glu Thr Ser Glu Lys Ile Thr Ala Val Ser Leu Asp
        195                 200                 205

Val Leu Asp Lys Arg Leu Phe Trp Ile Gln Tyr Asn Arg Glu Gly Ser
    210                 215                 220

Asn Ser Leu Ile Cys Ser Cys Asp Tyr Asp Gly Gly Ser Val His Ile
225                 230                 235                 240

Ser Lys His Pro Thr Gln His Asn Leu Phe Ala Met Ser Leu Phe Gly
                245                 250                 255

Asp Arg Ile Phe Tyr Ser Thr Trp Lys Met Lys Thr Ile Trp Ile Ala
            260                 265                 270

Asn Lys His Thr Gly Lys Asp Met Val Arg Ile Asn Leu His Ser Ser
        275                 280                 285

Phe Val Pro Leu Gly Glu Leu Lys Val Val His Pro Leu Ala Gln Pro
```

-continued

```
                290                 295                 300
Lys Ala Glu Asp Asp Thr Trp Glu Pro Glu Gln Lys Leu Cys Lys Leu
305                 310                 315                 320

Arg Lys Gly Asn Cys Ser Ser Thr Val Cys Gly Gln Asp Leu Gln Ser
                325                 330                 335

His Leu Cys Met Cys Ala Glu Gly Tyr Ala Leu Ser Arg Asp Arg Lys
                340                 345                 350

Tyr Cys Glu Asp Val Asn Glu Cys Ala Phe Trp Asn His Gly Cys Thr
                355                 360                 365

Leu Gly Cys Lys Asn Thr Pro Gly Ser Tyr Tyr Cys Thr Cys Pro Val
                370                 375                 380

Gly Phe Val Leu Leu Pro Asp Gly Lys Arg Cys His Gln Leu Val Ser
385                 390                 395                 400

Cys Pro Arg Asn Val Ser Glu Cys Ser His Asp Cys Val Leu Thr Ser
                405                 410                 415

Glu Gly Pro Leu Cys Phe Cys Pro Glu Gly Ser Val Leu Glu Arg Asp
                420                 425                 430

Gly Lys Thr Cys Ser Gly Cys Ser Ser Pro Asp Asn Gly Gly Cys Ser
                435                 440                 445

Gln Leu Cys Val Pro Leu Ser Pro Val Ser Trp Glu Cys Asp Cys Phe
                450                 455                 460

Pro Gly Tyr Asp Leu Gln Leu Asp Glu Lys Ser Cys Ala Ala Ser Gly
465                 470                 475                 480

Pro Gln Pro Phe Leu Leu Phe Ala Asn Ser Gln Asp Ile Arg His Met
                485                 490                 495

His Phe Asp Gly Thr Asp Tyr Gly Thr Leu Leu Ser Gln Gln Met Gly
                500                 505                 510

Met Val Tyr Ala Leu Asp His Asp Pro Val Glu Asn Lys Ile Tyr Phe
                515                 520                 525

Ala His Thr Ala Leu Lys Trp Ile Glu Arg Ala Asn Met Asp Gly Ser
                530                 535                 540

Gln Arg Glu Arg Leu Ile Glu Glu Gly Val Asp Val Pro Glu Gly Leu
545                 550                 555                 560

Ala Val Asp Trp Ile Gly Arg Arg Phe Tyr Trp Thr Asp Arg Gly Lys
                565                 570                 575

Ser Leu Ile Gly Arg Ser Asp Leu Asn Gly Lys Arg Ser Lys Ile Ile
                580                 585                 590

Thr Lys Glu Asn Ile Ser Gln Pro Arg Gly Ile Ala Val His Pro Met
                595                 600                 605

Ala Lys Arg Leu Phe Trp Thr Asp Thr Gly Ile Asn Pro Arg Ile Glu
                610                 615                 620

Ser Ser Ser Leu Gln Gly Leu Gly Arg Leu Val Ile Ala Ser Ser Asp
625                 630                 635                 640

Leu Ile Trp Pro Ser Gly Ile Thr Ile Asp Phe Leu Thr Asp Lys Leu
                645                 650                 655

Tyr Trp Cys Asp Ala Lys Gln Ser Val Ile Glu Met Ala Asn Leu Asp
                660                 665                 670

Gly Ser Lys Arg Arg Arg Leu Thr Gln Asn Asp Val Gly His Pro Phe
                675                 680                 685

Ala Val Ala Val Phe Glu Asp Tyr Val Trp Phe Ser Asp Trp Ala Met
                690                 695                 700

Pro Ser Val Met Arg Val Asn Lys Arg Thr Gly Lys Asp Arg Val Arg
705                 710                 715                 720
```

```
Leu Gln Gly Ser Met Leu Lys Pro Ser Ser Leu Val Val His Pro
            725                 730                 735

Leu Ala Lys Pro Gly Ala Asp Pro Cys Leu Tyr Gln Asn Gly Cys
            740                 745                 750

Glu His Ile Cys Lys Lys Arg Leu Gly Thr Ala Trp Cys Ser Cys
            755                 760                 765

Glu Gly Phe Met Lys Ala Ser Asp Gly Lys Thr Cys Leu Ala Leu Asp
            770                 775                 780

Gly His Gln Leu Leu Ala Gly Gly Glu Val Asp Leu Lys Asn Gln Val
785                 790                 795                 800

Thr Pro Leu Asp Ile Leu Ser Lys Thr Arg Val Ser Glu Asp Asn Ile
            805                 810                 815

Thr Glu Ser Gln His Met Leu Val Ala Glu Ile Met Val Ser Asp Gln
            820                 825                 830

Asp Asp Cys Ala Pro Val Gly Cys Ser Met Tyr Ala Arg Cys Ile Ser
            835                 840                 845

Glu Gly Glu Asp Ala Thr Cys Gln Cys Leu Lys Gly Phe Ala Gly Asp
            850                 855                 860

Gly Lys Leu Cys Ser Asp Ile Asp Glu Cys Glu Met Gly Val Pro Val
865                 870                 875                 880

Cys Pro Pro Ala Ser Ser Lys Cys Ile Asn Thr Glu Gly Gly Tyr Val
                    885                 890                 895

Cys Arg Cys Ser Glu Gly Tyr Gln Gly Asp Gly Ile His Cys Leu Asp
                    900                 905                 910

Ile Asp Glu Cys Gln Leu Gly Glu His Ser Cys Gly Glu Asn Ala Ser
            915                 920                 925

Cys Thr Asn Thr Glu Gly Gly Tyr Thr Cys Met Cys Ala Gly Arg Leu
            930                 935                 940

Ser Glu Pro Gly Leu Ile Cys Pro Asp Ser Thr Pro Pro His Leu
945                 950                 955                 960

Arg Glu Asp Asp His His Tyr Ser Val Arg Asn Ser Asp Ser Glu Cys
                    965                 970                 975

Pro Leu Ser His Asp Gly Tyr Cys Leu His Asp Gly Val Cys Met Tyr
                    980                 985                 990

Ile Glu Ala Leu Asp Lys Tyr Ala  Cys Asn Cys Val Val  Gly Tyr Ile
            995                 1000                1005

Gly Glu  Arg Cys Gln Tyr Arg  Asp Leu Lys Trp Trp  Glu Leu Arg
    1010                1015                1020

His Ala  Gly His Gly Gln Gln  Gln Lys Val Ile Val  Val Ala Val
    1025                1030                1035

Cys Val  Val Val Leu Val Met  Leu Leu Leu Leu Ser  Leu Trp Gly
    1040                1045                1050

Ala His  Tyr Tyr Arg Thr Gln  Lys Leu Leu Ser Lys  Asn Pro Lys
    1055                1060                1065

Asn Pro  Tyr Glu Glu Ser Ser  Arg Asp Val Arg Ser  Arg Arg Pro
    1070                1075                1080

Ala Asp  Thr Glu Asp Gly Met  Ser Ser Cys Pro Gln  Pro Trp Phe
    1085                1090                1095

Val Val  Ile Lys Glu His Gln  Asp Leu Lys Asn Gly  Gly Gln Pro
    1100                1105                1110

Val Ala  Gly Glu Asp Gly Gln  Ala Ala Asp Gly Ser  Met Gln Pro
    1115                1120                1125
```

```
Thr Ser Trp Arg Gln Glu Pro Gln Leu Cys Gly Met Gly Thr Glu
    1130                1135                1140

Gln Gly Cys Trp Ile Pro Val Ser Ser Asp Lys Gly Ser Cys Pro
    1145                1150                1155

Gln Val Met Glu Arg Ser Phe His Met Pro Ser Tyr Gly Thr Gln
    1160                1165                1170

Thr Leu Glu Gly Gly Val Glu Lys Pro His Ser Leu Leu Ser Ala
    1175                1180                1185

Asn Pro Leu Trp Gln Gln Arg Ala Leu Asp Pro Pro His Gln Met
    1190                1195                1200

Glu Leu Thr Gln
    1205

<210> SEQ ID NO 7
<211> LENGTH: 532
<212> TYPE: PRT
<213> ORGANISM: Homo sapiens

<400> SEQUENCE: 7

Met Ala Pro Ser Ser Pro Arg Pro Ala Leu Pro Ala Leu Leu Val Leu
1               5                   10                  15

Leu Gly Ala Leu Phe Pro Gly Pro Gly Asn Ala Gln Thr Ser Val Ser
                20                  25                  30

Pro Ser Lys Val Ile Leu Pro Arg Gly Gly Ser Val Leu Val Thr Cys
            35                  40                  45

Ser Thr Ser Cys Asp Gln Pro Lys Leu Leu Gly Ile Glu Thr Pro Leu
        50                  55                  60

Pro Lys Lys Glu Leu Leu Leu Pro Gly Asn Asn Arg Lys Val Tyr Glu
65                  70                  75                  80

Leu Ser Asn Val Gln Glu Asp Ser Gln Pro Met Cys Tyr Ser Asn Cys
                85                  90                  95

Pro Asp Gly Gln Ser Thr Ala Lys Thr Phe Leu Thr Val Tyr Trp Thr
            100                 105                 110

Pro Glu Arg Val Glu Leu Ala Pro Leu Pro Ser Trp Gln Pro Val Gly
        115                 120                 125

Lys Asn Leu Thr Leu Arg Cys Gln Val Glu Gly Gly Ala Pro Arg Ala
    130                 135                 140

Asn Leu Thr Val Val Leu Leu Arg Gly Glu Lys Glu Leu Lys Arg Glu
145                 150                 155                 160

Pro Ala Val Gly Glu Pro Ala Glu Val Thr Thr Thr Val Leu Val Arg
                165                 170                 175

Arg Asp His His Gly Ala Asn Phe Ser Cys Arg Thr Glu Leu Asp Leu
            180                 185                 190

Arg Pro Gln Gly Leu Glu Leu Phe Glu Asn Thr Ser Ala Pro Tyr Gln
        195                 200                 205

Leu Gln Thr Phe Val Leu Pro Ala Thr Pro Pro Gln Leu Val Ser Pro
    210                 215                 220

Arg Val Leu Glu Val Asp Thr Gln Gly Thr Val Val Cys Ser Leu Asp
225                 230                 235                 240

Gly Leu Phe Pro Val Ser Glu Ala Gln Val His Leu Ala Leu Gly Asp
                245                 250                 255

Gln Arg Leu Asn Pro Thr Val Thr Tyr Gly Asn Asp Ser Phe Ser Ala
            260                 265                 270

Lys Ala Ser Val Ser Val Thr Ala Glu Asp Glu Gly Thr Gln Arg Leu
        275                 280                 285
```

```
Thr Cys Ala Val Ile Leu Gly Asn Gln Ser Gln Glu Thr Leu Gln Thr
        290                 295                 300
Val Thr Ile Tyr Ser Phe Pro Ala Pro Asn Val Ile Leu Thr Lys Pro
305                 310                 315                 320
Glu Val Ser Glu Gly Thr Glu Val Thr Val Lys Cys Glu Ala His Pro
                325                 330                 335
Arg Ala Lys Val Thr Leu Asn Gly Val Pro Ala Gln Pro Leu Gly Pro
            340                 345                 350
Arg Ala Gln Leu Leu Leu Lys Ala Thr Pro Glu Asp Asn Gly Arg Ser
        355                 360                 365
Phe Ser Cys Ser Ala Thr Leu Glu Val Ala Gly Gln Leu Ile His Lys
370                 375                 380
Asn Gln Thr Arg Glu Leu Arg Val Leu Tyr Gly Pro Arg Leu Asp Glu
385                 390                 395                 400
Arg Asp Cys Pro Gly Asn Trp Thr Trp Pro Glu Asn Ser Gln Gln Thr
                405                 410                 415
Pro Met Cys Gln Ala Trp Gly Asn Pro Leu Pro Glu Leu Lys Cys Leu
            420                 425                 430
Lys Asp Gly Thr Phe Pro Leu Pro Ile Gly Glu Ser Val Thr Val Thr
        435                 440                 445
Arg Asp Leu Glu Gly Thr Tyr Leu Cys Arg Ala Arg Ser Thr Gln Gly
450                 455                 460
Glu Val Thr Arg Lys Val Thr Val Asn Val Leu Ser Pro Arg Tyr Glu
465                 470                 475                 480
Ile Val Ile Ile Thr Val Ala Ala Val Ile Met Gly Thr Ala
                485                 490                 495
Gly Leu Ser Thr Tyr Leu Tyr Asn Arg Gln Arg Lys Ile Lys Lys Tyr
            500                 505                 510
Arg Leu Gln Gln Ala Gln Lys Gly Thr Pro Met Lys Pro Asn Thr Gln
        515                 520                 525
Ala Thr Pro Pro
    530

<210> SEQ ID NO 8
<211> LENGTH: 193
<212> TYPE: PRT
<213> ORGANISM: Homo sapiens

<400> SEQUENCE: 8

Met Ala Ala Glu Pro Val Glu Asp Asn Cys Ile Asn Phe Val Ala Met
1               5                   10                  15
Lys Phe Ile Asp Asn Thr Leu Tyr Phe Ile Ala Glu Asp Asp Glu Asn
            20                  25                  30
Leu Glu Ser Asp Tyr Phe Gly Lys Leu Glu Ser Lys Leu Ser Val Ile
        35                  40                  45
Arg Asn Leu Asn Asp Gln Val Leu Phe Ile Asp Gln Gly Asn Arg Pro
    50                  55                  60
Leu Phe Glu Asp Met Thr Asp Ser Asp Cys Arg Pro Arg Thr Pro Arg
65                  70                  75                  80
Thr Ile Phe Ile Ile Ser Met Tyr Lys Asp Ser Gln Pro Arg Gly Met
                85                  90                  95
Ala Val Thr Ile Ser Val Lys Cys Glu Lys Ile Ser Thr Leu Ser Cys
            100                 105                 110
Glu Asn Lys Ile Ile Ser Phe Lys Glu Met Asn Pro Pro Asp Asn Ile
```

```
            115                 120                 125
Lys Asp Thr Lys Ser Asp Ile Ile Phe Phe Gln Arg Ser Val Pro Gly
130                 135                 140

His Asp Asn Lys Met Gln Phe Glu Ser Ser Tyr Glu Gly Tyr Phe
145                 150                 155                 160

Leu Ala Cys Glu Lys Glu Arg Asp Leu Phe Lys Leu Ile Leu Lys Lys
                165                 170                 175

Glu Asp Glu Leu Gly Asp Arg Ser Ile Met Phe Thr Val Gln Asn Glu
                180                 185                 190

Asp

<210> SEQ ID NO 9
<211> LENGTH: 269
<212> TYPE: PRT
<213> ORGANISM: Homo sapiens

<400> SEQUENCE: 9

Met Ala Glu Val Pro Glu Leu Ala Ser Glu Met Met Ala Tyr Tyr Ser
1               5                   10                  15

Gly Asn Glu Asp Asp Leu Phe Phe Glu Ala Asp Gly Pro Lys Gln Met
                20                  25                  30

Lys Cys Ser Phe Gln Asp Leu Asp Leu Cys Pro Leu Asp Gly Gly Ile
            35                  40                  45

Gln Leu Arg Ile Ser Asp His His Tyr Ser Lys Gly Phe Arg Gln Ala
        50                  55                  60

Ala Ser Val Val Val Ala Met Asp Lys Leu Arg Lys Met Leu Val Pro
65                  70                  75                  80

Cys Pro Gln Thr Phe Gln Glu Asn Asp Leu Ser Thr Phe Phe Pro Phe
                85                  90                  95

Ile Phe Glu Glu Glu Pro Ile Phe Phe Asp Thr Trp Asp Asn Glu Ala
                100                 105                 110

Tyr Val His Asp Ala Pro Val Arg Ser Leu Asn Cys Thr Leu Arg Asp
            115                 120                 125

Ser Gln Gln Lys Ser Leu Val Met Ser Gly Pro Tyr Glu Leu Lys Ala
130                 135                 140

Leu His Leu Gln Gly Gln Asp Met Glu Gln Gln Val Val Phe Ser Met
145                 150                 155                 160

Ser Phe Val Gln Gly Glu Glu Ser Asn Asp Lys Ile Pro Val Ala Leu
                165                 170                 175

Gly Leu Lys Glu Lys Asn Leu Tyr Leu Ser Cys Val Leu Lys Asp Asp
                180                 185                 190

Lys Pro Thr Leu Gln Leu Glu Ser Val Asp Pro Lys Asn Tyr Pro Lys
            195                 200                 205

Lys Lys Met Glu Lys Arg Phe Val Phe Asn Lys Ile Glu Ile Asn Asn
210                 215                 220

Lys Leu Glu Phe Glu Ser Ala Gln Phe Pro Asn Trp Tyr Ile Ser Thr
225                 230                 235                 240

Ser Gln Ala Glu Asn Met Pro Val Phe Leu Gly Gly Thr Lys Gly Gly
                245                 250                 255

Gln Asp Ile Thr Asp Phe Thr Met Gln Phe Val Ser Ser
            260                 265

<210> SEQ ID NO 10
<211> LENGTH: 159
<212> TYPE: PRT
```

<213> ORGANISM: Homo sapiens

<400> SEQUENCE: 10

```
Met Ala Leu Glu Thr Ile Cys Arg Pro Ser Gly Arg Lys Ser Lys
1               5                   10                  15

Met Gln Ala Phe Arg Ile Trp Asp Val Asn Gln Lys Thr Phe Tyr Leu
            20                  25                  30

Arg Asn Asn Gln Leu Val Ala Gly Tyr Leu Gln Gly Pro Asn Val Asn
        35                  40                  45

Leu Glu Glu Lys Ile Asp Val Val Pro Ile Glu Pro His Ala Leu Phe
    50                  55                  60

Leu Gly Ile His Gly Gly Lys Met Cys Leu Ser Cys Val Lys Ser Gly
65                  70                  75                  80

Asp Glu Thr Arg Leu Gln Leu Glu Ala Val Asn Ile Thr Asp Leu Ser
                85                  90                  95

Glu Asn Arg Lys Gln Asp Lys Arg Phe Ala Phe Ile Arg Ser Asp Ser
            100                 105                 110

Gly Pro Thr Thr Ser Phe Glu Ser Ala Ala Cys Pro Gly Trp Phe Leu
        115                 120                 125

Cys Thr Ala Met Glu Ala Asp Gln Pro Val Ser Leu Thr Asn Met Pro
130                 135                 140

Asp Glu Gly Val Met Val Thr Lys Phe Tyr Phe Gln Glu Asp Glu
145                 150                 155
```

<210> SEQ ID NO 11
<211> LENGTH: 212
<212> TYPE: PRT
<213> ORGANISM: Homo sapiens

<400> SEQUENCE: 11

```
Met Asn Ser Phe Ser Thr Ser Ala Phe Gly Pro Val Ala Phe Ser Leu
1               5                   10                  15

Gly Leu Leu Leu Val Leu Pro Ala Ala Phe Pro Ala Pro Val Pro Pro
            20                  25                  30

Gly Glu Asp Ser Lys Asp Val Ala Ala Pro His Arg Gln Pro Leu Thr
        35                  40                  45

Ser Ser Glu Arg Ile Asp Lys Gln Ile Arg Tyr Ile Leu Asp Gly Ile
    50                  55                  60

Ser Ala Leu Arg Lys Glu Thr Cys Asn Lys Ser Asn Met Cys Glu Ser
65                  70                  75                  80

Ser Lys Glu Ala Leu Ala Glu Asn Asn Leu Asn Leu Pro Lys Met Ala
                85                  90                  95

Glu Lys Asp Gly Cys Phe Gln Ser Gly Phe Asn Glu Glu Thr Cys Leu
            100                 105                 110

Val Lys Ile Ile Thr Gly Leu Leu Glu Phe Glu Val Tyr Leu Glu Tyr
        115                 120                 125

Leu Gln Asn Arg Phe Glu Ser Ser Glu Glu Gln Ala Arg Ala Val Gln
    130                 135                 140

Met Ser Thr Lys Val Leu Ile Gln Phe Leu Gln Lys Lys Ala Lys Asn
145                 150                 155                 160

Leu Asp Ala Ile Thr Thr Pro Asp Pro Thr Thr Asn Ala Ser Leu Leu
                165                 170                 175

Thr Lys Leu Gln Ala Gln Asn Gln Trp Leu Gln Asp Met Thr Thr His
            180                 185                 190

Leu Ile Leu Arg Ser Phe Lys Glu Phe Leu Gln Ser Ser Leu Arg Ala
```

```
            195                 200                 205
Leu Arg Gln Met
    210

<210> SEQ ID NO 12
<211> LENGTH: 468
<212> TYPE: PRT
<213> ORGANISM: Homo sapiens

<400> SEQUENCE: 12

Met Leu Ala Val Gly Cys Ala Leu Leu Ala Leu Leu Ala Ala Pro
1               5                   10                  15

Gly Ala Ala Leu Ala Pro Arg Arg Cys Pro Ala Gln Glu Val Ala Arg
                20                  25                  30

Gly Val Leu Thr Ser Leu Pro Gly Asp Ser Val Thr Leu Thr Cys Pro
                35                  40                  45

Gly Val Glu Pro Glu Pro Arg Thr Thr Val His Trp Val Leu Arg Lys
50                  55                  60

Pro Ala Ala Gly Ser His Pro Ser Arg Trp Ala Gly Met Gly Arg Arg
65                  70                  75                  80

Leu Leu Leu Arg Ser Val Gln Leu His Asp Ser Gly Asn Tyr Ser Cys
                85                  90                  95

Tyr Arg Ala Gly Arg Pro Ala Gly Thr Val His Leu Leu Val Asp Val
                100                 105                 110

Pro Pro Glu Glu Pro Gln Leu Ser Cys Phe Arg Lys Ser Pro Leu Ser
            115                 120                 125

Asn Val Val Cys Glu Trp Gly Pro Arg Ser Thr Pro Ser Leu Thr Thr
130                 135                 140

Lys Ala Val Leu Leu Val Arg Lys Phe Gln Asn Ser Pro Ala Glu Asp
145                 150                 155                 160

Phe Gln Glu Pro Cys Gln Tyr Ser Gln Glu Ser Gln Lys Phe Ser Cys
                165                 170                 175

Gln Leu Ala Val Pro Glu Gly Asp Ser Ser Phe Tyr Ile Val Ser Met
                180                 185                 190

Cys Val Ala Ser Ser Val Gly Ser Lys Phe Ser Lys Thr Gln Thr Phe
                195                 200                 205

Gln Gly Cys Gly Ile Leu Gln Pro Asp Pro Pro Ala Asn Ile Thr Val
            210                 215                 220

Thr Ala Val Ala Arg Asn Pro Arg Trp Leu Ser Val Thr Trp Gln Asp
225                 230                 235                 240

Pro His Ser Trp Asn Ser Ser Phe Tyr Arg Leu Arg Phe Glu Leu Arg
                245                 250                 255

Tyr Arg Ala Glu Arg Ser Lys Thr Phe Thr Thr Trp Met Val Lys Asp
                260                 265                 270

Leu Gln His His Cys Val Ile His Asp Ala Trp Ser Gly Leu Arg His
                275                 280                 285

Val Val Gln Leu Arg Ala Gln Glu Glu Phe Gly Gln Gly Glu Trp Ser
            290                 295                 300

Glu Trp Ser Pro Glu Ala Met Gly Thr Pro Trp Thr Glu Ser Arg Ser
305                 310                 315                 320

Pro Pro Ala Glu Asn Glu Val Ser Thr Pro Met Gln Ala Leu Thr Thr
                325                 330                 335

Asn Lys Asp Asp Asp Asn Ile Leu Phe Arg Asp Ser Ala Asn Ala Thr
                340                 345                 350
```

```
Ser Leu Pro Val Gln Asp Ser Ser Val Pro Leu Pro Thr Phe Leu
        355                 360                 365

Val Ala Gly Gly Ser Leu Ala Phe Gly Thr Leu Leu Cys Ile Ala Ile
370                 375                 380

Val Leu Arg Phe Lys Lys Thr Trp Lys Leu Arg Ala Leu Lys Glu Gly
385                 390                 395                 400

Lys Thr Ser Met His Pro Pro Tyr Ser Leu Gly Gln Leu Val Pro Glu
                405                 410                 415

Arg Pro Arg Pro Thr Pro Val Leu Val Pro Leu Ile Ser Pro Pro Val
                420                 425                 430

Ser Pro Ser Ser Leu Gly Ser Asp Asn Thr Ser Ser His Asn Arg Pro
                435                 440                 445

Asp Ala Arg Asp Pro Arg Ser Pro Tyr Asp Ile Ser Asn Thr Asp Tyr
        450                 455                 460

Phe Phe Pro Arg
465

<210> SEQ ID NO 13
<211> LENGTH: 99
<212> TYPE: PRT
<213> ORGANISM: Homo sapiens

<400> SEQUENCE: 13

Met Thr Ser Lys Leu Ala Val Ala Leu Leu Ala Ala Phe Leu Ile Ser
1               5                   10                  15

Ala Ala Leu Cys Glu Gly Ala Val Leu Pro Arg Ser Ala Lys Glu Leu
                20                  25                  30

Arg Cys Gln Cys Ile Lys Thr Tyr Ser Lys Pro Phe His Pro Lys Phe
            35                  40                  45

Ile Lys Glu Leu Arg Val Ile Glu Ser Gly Pro His Cys Ala Asn Thr
        50                  55                  60

Glu Ile Ile Val Lys Leu Ser Asp Gly Arg Glu Leu Cys Leu Asp Pro
65                  70                  75                  80

Lys Glu Asn Trp Val Gln Arg Val Val Glu Lys Phe Leu Lys Arg Ala
                85                  90                  95

Glu Asn Ser

<210> SEQ ID NO 14
<211> LENGTH: 167
<212> TYPE: PRT
<213> ORGANISM: Homo sapiens

<400> SEQUENCE: 14

Met His Trp Gly Thr Leu Cys Gly Phe Leu Trp Leu Trp Pro Tyr Leu
1               5                   10                  15

Phe Tyr Val Gln Ala Val Pro Ile Gln Lys Val Gln Asp Asp Thr Lys
                20                  25                  30

Thr Leu Ile Lys Thr Ile Val Thr Arg Ile Asn Asp Ile Ser His Thr
            35                  40                  45

Gln Ser Val Ser Ser Lys Gln Lys Val Thr Gly Leu Asp Phe Ile Pro
        50                  55                  60

Gly Leu His Pro Ile Leu Thr Leu Ser Lys Met Asp Gln Thr Leu Ala
65                  70                  75                  80

Val Tyr Gln Gln Ile Leu Thr Ser Met Pro Ser Arg Asn Val Ile Gln
                85                  90                  95

Ile Ser Asn Asp Leu Glu Asn Leu Arg Asp Leu Leu His Val Leu Ala
```

```
                100               105               110
Phe Ser Lys Ser Cys His Leu Pro Trp Ala Ser Gly Leu Glu Thr Leu
        115                 120                 125

Asp Ser Leu Gly Gly Val Leu Glu Ala Ser Gly Tyr Ser Thr Glu Val
        130                 135                 140

Val Ala Leu Ser Arg Leu Gln Gly Ser Leu Gln Asp Met Leu Trp Gln
145                 150                 155                 160

Leu Asp Leu Ser Pro Gly Cys
                165

<210> SEQ ID NO 15
<211> LENGTH: 469
<212> TYPE: PRT
<213> ORGANISM: Homo sapiens

<400> SEQUENCE: 15

Met His Ser Phe Pro Pro Leu Leu Leu Leu Phe Trp Gly Val Val
1               5                   10                  15

Ser His Ser Phe Pro Ala Thr Leu Glu Thr Gln Glu Gln Asp Val Asp
                20                  25                  30

Leu Val Gln Lys Tyr Leu Glu Lys Tyr Tyr Asn Leu Lys Asn Asp Gly
        35                  40                  45

Arg Gln Val Glu Lys Arg Arg Asn Ser Gly Pro Val Val Glu Lys Leu
50                  55                  60

Lys Gln Met Gln Glu Phe Phe Gly Leu Lys Val Thr Gly Lys Pro Asp
65                  70                  75                  80

Ala Glu Thr Leu Lys Val Met Lys Gln Pro Arg Cys Gly Val Pro Asp
                85                  90                  95

Val Ala Gln Phe Val Leu Thr Glu Gly Asn Pro Arg Trp Glu Gln Thr
                100                 105                 110

His Leu Thr Tyr Arg Ile Glu Asn Tyr Thr Pro Asp Leu Pro Arg Ala
        115                 120                 125

Asp Val Asp His Ala Ile Glu Lys Ala Phe Gln Leu Trp Ser Asn Val
        130                 135                 140

Thr Pro Leu Thr Phe Thr Lys Val Ser Glu Gly Gln Ala Asp Ile Met
145                 150                 155                 160

Ile Ser Phe Val Arg Gly Asp His Arg Asp Asn Ser Pro Phe Asp Gly
                165                 170                 175

Pro Gly Gly Asn Leu Ala His Ala Phe Gln Pro Gly Pro Gly Ile Gly
                180                 185                 190

Gly Asp Ala His Phe Asp Glu Asp Glu Arg Trp Thr Asn Asn Phe Arg
        195                 200                 205

Glu Tyr Asn Leu His Arg Val Ala Ala His Glu Leu Gly His Ser Leu
210                 215                 220

Gly Leu Ser His Ser Thr Asp Ile Gly Ala Leu Met Tyr Pro Ser Tyr
225                 230                 235                 240

Thr Phe Ser Gly Asp Val Gln Leu Ala Gln Asp Asp Ile Asp Gly Ile
                245                 250                 255

Gln Ala Ile Tyr Gly Arg Ser Gln Asn Pro Val Gln Pro Ile Gly Pro
                260                 265                 270

Gln Thr Pro Lys Ala Cys Asp Ser Lys Leu Thr Phe Asp Ala Ile Thr
        275                 280                 285

Thr Ile Arg Gly Glu Val Met Phe Phe Lys Asp Arg Phe Tyr Met Arg
        290                 295                 300
```

```
Thr Asn Pro Phe Tyr Pro Glu Val Glu Leu Asn Phe Ile Ser Val Phe
305                 310                 315                 320

Trp Pro Gln Leu Pro Asn Gly Leu Glu Ala Ala Tyr Glu Phe Ala Asp
                325                 330                 335

Arg Asp Glu Val Arg Phe Phe Lys Gly Asn Lys Tyr Trp Ala Val Gln
            340                 345                 350

Gly Gln Asn Val Leu His Gly Tyr Pro Lys Asp Ile Tyr Ser Ser Phe
        355                 360                 365

Gly Phe Pro Arg Thr Val Lys His Ile Asp Ala Ala Leu Ser Glu Glu
    370                 375                 380

Asn Thr Gly Lys Thr Tyr Phe Val Ala Asn Lys Tyr Trp Arg Tyr
385                 390                 395                 400

Asp Glu Tyr Lys Arg Ser Met Asp Pro Gly Tyr Pro Lys Met Ile Ala
            405                 410                 415

His Asp Phe Pro Gly Ile Gly His Lys Val Asp Ala Val Phe Met Lys
        420                 425                 430

Asp Gly Phe Phe Tyr Phe Phe His Gly Thr Arg Gln Tyr Lys Phe Asp
    435                 440                 445

Pro Lys Thr Lys Arg Ile Leu Thr Leu Gln Lys Ala Asn Ser Trp Phe
450                 455                 460

Asn Cys Arg Lys Asn
465

<210> SEQ ID NO 16
<211> LENGTH: 477
<212> TYPE: PRT
<213> ORGANISM: Homo sapiens

<400> SEQUENCE: 16

Met Lys Ser Leu Pro Ile Leu Leu Leu Leu Cys Val Ala Val Cys Ser
1               5                   10                  15

Ala Tyr Pro Leu Asp Gly Ala Ala Arg Gly Glu Asp Thr Ser Met Asn
            20                  25                  30

Leu Val Gln Lys Tyr Leu Glu Asn Tyr Tyr Asp Leu Lys Lys Asp Val
        35                  40                  45

Lys Gln Phe Val Arg Arg Lys Asp Ser Gly Pro Val Val Lys Lys Ile
50                  55                  60

Arg Glu Met Gln Lys Phe Leu Gly Leu Glu Val Thr Gly Lys Leu Asp
65                  70                  75                  80

Ser Asp Thr Leu Glu Val Met Arg Lys Pro Arg Cys Gly Val Pro Asp
                85                  90                  95

Val Gly His Phe Arg Thr Phe Pro Gly Ile Pro Lys Trp Arg Lys Thr
            100                 105                 110

His Leu Thr Tyr Arg Ile Val Asn Tyr Thr Pro Asp Leu Pro Lys Asp
        115                 120                 125

Ala Val Asp Ser Ala Val Glu Lys Ala Leu Lys Val Trp Glu Glu Val
    130                 135                 140

Thr Pro Leu Thr Phe Ser Arg Leu Tyr Glu Gly Glu Ala Asp Ile Met
145                 150                 155                 160

Ile Ser Phe Ala Val Arg Glu His Gly Asp Phe Tyr Pro Phe Asp Gly
                165                 170                 175

Pro Gly Asn Val Leu Ala His Ala Tyr Ala Pro Gly Pro Gly Ile Asn
            180                 185                 190

Gly Asp Ala His Phe Asp Asp Asp Glu Gln Trp Thr Lys Asp Thr Thr
        195                 200                 205
```

Gly Thr Asn Leu Phe Leu Val Ala Ala His Glu Ile Gly His Ser Leu
210                 215                 220

Gly Leu Phe His Ser Ala Asn Thr Glu Ala Leu Met Tyr Pro Leu Tyr
225                 230                 235                 240

His Ser Leu Thr Asp Leu Thr Arg Phe Arg Leu Ser Gln Asp Asp Ile
            245                 250                 255

Asn Gly Ile Gln Ser Leu Tyr Gly Pro Pro Asp Ser Pro Glu Thr
            260                 265                 270

Pro Leu Val Pro Thr Glu Pro Val Pro Glu Pro Gly Thr Pro Ala
            275                 280                 285

Asn Cys Asp Pro Ala Leu Ser Phe Asp Ala Val Ser Thr Leu Arg Gly
290                 295                 300

Glu Ile Leu Ile Phe Lys Asp Arg His Phe Trp Arg Lys Ser Leu Arg
305                 310                 315                 320

Lys Leu Glu Pro Glu Leu His Leu Ile Ser Ser Phe Trp Pro Ser Leu
                325                 330                 335

Pro Ser Gly Val Asp Ala Ala Tyr Glu Val Thr Ser Lys Asp Leu Val
                340                 345                 350

Phe Ile Phe Lys Gly Asn Gln Phe Trp Ala Ile Arg Gly Asn Glu Val
                355                 360                 365

Arg Ala Gly Tyr Pro Arg Gly Ile His Thr Leu Gly Phe Pro Pro Thr
370                 375                 380

Val Arg Lys Ile Asp Ala Ala Ile Ser Asp Lys Glu Lys Asn Lys Thr
385                 390                 395                 400

Tyr Phe Phe Val Glu Asp Lys Tyr Trp Arg Phe Asp Glu Lys Arg Asn
                405                 410                 415

Ser Met Glu Pro Gly Phe Pro Lys Gln Ile Ala Glu Asp Phe Pro Gly
                420                 425                 430

Ile Asp Ser Lys Ile Asp Ala Val Phe Glu Glu Phe Gly Phe Phe Tyr
            435                 440                 445

Phe Phe Thr Gly Ser Ser Gln Leu Glu Phe Asp Pro Asn Ala Lys Lys
450                 455                 460

Val Thr His Thr Leu Lys Ser Asn Ser Trp Leu Asn Cys
465                 470                 475

<210> SEQ ID NO 17
<211> LENGTH: 108
<212> TYPE: PRT
<213> ORGANISM: Homo sapiens

<400> SEQUENCE: 17

Met Lys Ala Leu Cys Leu Leu Leu Leu Pro Val Leu Gly Leu Leu Val
1               5                   10                  15

Ser Ser Lys Thr Leu Cys Ser Met Glu Glu Ala Ile Asn Glu Arg Ile
                20                  25                  30

Gln Glu Val Ala Gly Ser Leu Ile Phe Arg Ala Ile Ser Ser Ile Gly
            35                  40                  45

Leu Glu Cys Gln Ser Val Thr Ser Arg Gly Asp Leu Ala Thr Cys Pro
50                  55                  60

Arg Gly Phe Ala Val Thr Gly Cys Thr Cys Gly Ser Ala Cys Gly Ser
65                  70                  75                  80

Trp Asp Val Arg Ala Glu Thr Thr Cys His Cys Gln Cys Ala Gly Met
                85                  90                  95

Asp Trp Thr Gly Ala Arg Cys Cys Arg Val Gln Pro

<210> SEQ ID NO 18
<211> LENGTH: 93
<212> TYPE: PRT
<213> ORGANISM: Homo sapiens

<400> SEQUENCE: 18

Met Leu Thr Glu Leu Glu Lys Ala Leu Asn Ser Ile Ile Asp Val Tyr
1               5                   10                  15

His Lys Tyr Ser Leu Ile Lys Gly Asn Phe His Ala Val Tyr Arg Asp
                20                  25                  30

Asp Leu Lys Lys Leu Leu Glu Thr Glu Cys Pro Gln Tyr Ile Arg Lys
            35                  40                  45

Lys Gly Ala Asp Val Trp Phe Lys Glu Leu Asp Ile Asn Thr Asp Gly
        50                  55                  60

Ala Val Asn Phe Gln Glu Phe Leu Ile Leu Val Ile Lys Met Gly Val
65                  70                  75                  80

Ala Ala His Lys Lys Ser His Glu Glu Ser His Lys Glu
                85                  90

<210> SEQ ID NO 19
<211> LENGTH: 114
<212> TYPE: PRT
<213> ORGANISM: Homo sapiens

<400> SEQUENCE: 19

Met Thr Cys Lys Met Ser Gln Leu Glu Arg Asn Ile Glu Thr Ile Ile
1               5                   10                  15

Asn Thr Phe His Gln Tyr Ser Val Lys Leu Gly His Pro Asp Thr Leu
                20                  25                  30

Asn Gln Gly Glu Phe Lys Glu Leu Val Arg Lys Asp Leu Gln Asn Phe
            35                  40                  45

Leu Lys Lys Glu Asn Lys Asn Glu Lys Val Ile Glu His Ile Met Glu
        50                  55                  60

Asp Leu Asp Thr Asn Ala Asp Lys Gln Leu Ser Phe Glu Glu Phe Ile
65                  70                  75                  80

Met Leu Met Ala Arg Leu Thr Trp Ala Ser His Glu Lys Met His Glu
                85                  90                  95

Gly Asp Glu Gly Pro Gly His His Lys Pro Gly Leu Gly Glu Gly
                100                 105                 110

Thr Pro

<210> SEQ ID NO 20
<211> LENGTH: 122
<212> TYPE: PRT
<213> ORGANISM: Homo sapiens

<400> SEQUENCE: 20

Met Lys Leu Leu Thr Gly Leu Val Phe Cys Ser Leu Val Leu Gly Val
1               5                   10                  15

Ser Ser Arg Ser Phe Phe Ser Phe Leu Gly Glu Ala Phe Asp Gly Ala
                20                  25                  30

Arg Asp Met Trp Arg Ala Tyr Ser Asp Met Arg Glu Ala Asn Tyr Ile
            35                  40                  45

Gly Ser Asp Lys Tyr Phe His Ala Arg Gly Asn Tyr Asp Ala Ala Lys
        50                  55                  60

-continued

```
Arg Gly Pro Gly Gly Ala Trp Ala Ala Glu Val Ile Ser Asp Ala Arg
 65                  70                  75                  80

Glu Asn Ile Gln Arg Phe Phe Gly His Gly Ala Glu Asp Ser Leu Ala
                 85                  90                  95

Asp Gln Ala Ala Asn Glu Trp Gly Arg Ser Gly Lys Asp Pro Asn His
            100                 105                 110

Phe Arg Pro Ala Gly Leu Pro Glu Lys Tyr
        115                 120

<210> SEQ ID NO 21
<211> LENGTH: 455
<212> TYPE: PRT
<213> ORGANISM: Homo sapiens

<400> SEQUENCE: 21

Met Gly Leu Ser Thr Val Pro Asp Leu Leu Leu Pro Leu Val Leu Leu
 1               5                  10                  15

Glu Leu Leu Val Gly Ile Tyr Pro Ser Gly Val Ile Gly Leu Val Pro
            20                  25                  30

His Leu Gly Asp Arg Glu Lys Arg Asp Ser Val Cys Pro Gln Gly Lys
        35                  40                  45

Tyr Ile His Pro Gln Asn Asn Ser Ile Cys Cys Thr Lys Cys His Lys
    50                  55                  60

Gly Thr Tyr Leu Tyr Asn Asp Cys Pro Gly Pro Gly Gln Asp Thr Asp
 65                  70                  75                  80

Cys Arg Glu Cys Glu Ser Gly Ser Phe Thr Ala Ser Glu Asn His Leu
                 85                  90                  95

Arg His Cys Leu Ser Cys Ser Lys Cys Arg Lys Glu Met Gly Gln Val
            100                 105                 110

Glu Ile Ser Ser Cys Thr Val Asp Arg Asp Thr Val Cys Gly Cys Arg
        115                 120                 125

Lys Asn Gln Tyr Arg His Tyr Trp Ser Glu Asn Leu Phe Gln Cys Phe
    130                 135                 140

Asn Cys Ser Leu Cys Leu Asn Gly Thr Val His Leu Ser Cys Gln Glu
145                 150                 155                 160

Lys Gln Asn Thr Val Cys Thr Cys His Ala Gly Phe Phe Leu Arg Glu
                165                 170                 175

Asn Glu Cys Val Ser Cys Ser Asn Cys Lys Lys Ser Leu Glu Cys Thr
            180                 185                 190

Lys Leu Cys Leu Pro Gln Ile Glu Asn Val Lys Gly Thr Glu Asp Ser
        195                 200                 205

Gly Thr Thr Val Leu Leu Pro Leu Val Ile Phe Phe Gly Leu Cys Leu
    210                 215                 220

Leu Ser Leu Leu Phe Ile Gly Leu Met Tyr Arg Tyr Gln Arg Trp Lys
225                 230                 235                 240

Ser Lys Leu Tyr Ser Ile Val Cys Gly Lys Ser Thr Pro Glu Lys Glu
                245                 250                 255

Gly Glu Leu Glu Gly Thr Thr Thr Lys Pro Leu Ala Pro Asn Pro Ser
            260                 265                 270

Phe Ser Pro Thr Pro Gly Phe Thr Pro Thr Leu Gly Phe Ser Pro Val
        275                 280                 285

Pro Ser Ser Thr Phe Thr Ser Ser Ser Thr Tyr Thr Pro Gly Asp Cys
    290                 295                 300

Pro Asn Phe Ala Ala Pro Arg Arg Glu Val Ala Pro Pro Tyr Gln Gly
305                 310                 315                 320
```

```
Ala Asp Pro Ile Leu Ala Thr Ala Leu Ala Ser Asp Pro Ile Pro Asn
            325                 330                 335

Pro Leu Gln Lys Trp Glu Asp Ser Ala His Lys Pro Gln Ser Leu Asp
            340                 345                 350

Thr Asp Asp Pro Ala Thr Leu Tyr Ala Val Val Glu Asn Val Pro Pro
            355                 360                 365

Leu Arg Trp Lys Glu Phe Val Arg Arg Leu Gly Leu Ser Asp His Glu
            370                 375                 380

Ile Asp Arg Leu Glu Leu Gln Asn Gly Arg Cys Leu Arg Glu Ala Gln
385                 390                 395                 400

Tyr Ser Met Leu Ala Thr Trp Arg Arg Thr Pro Arg Arg Glu Ala
            405                 410                 415

Thr Leu Glu Leu Leu Gly Arg Val Leu Arg Asp Met Asp Leu Leu Gly
            420                 425                 430

Cys Leu Glu Asp Ile Glu Glu Ala Leu Cys Gly Pro Ala Ala Leu Pro
            435                 440                 445

Pro Ala Pro Ser Leu Leu Arg
            450                 455

<210> SEQ ID NO 22
<211> LENGTH: 266
<212> TYPE: PRT
<213> ORGANISM: Homo sapiens

<400> SEQUENCE: 22

Met Asp Asp Ser Thr Glu Arg Glu Gln Ser Arg Leu Thr Ser Cys Leu
1               5                   10                  15

Lys Lys Arg Glu Glu Met Lys Leu Lys Glu Cys Val Ser Ile Leu Pro
            20                  25                  30

Arg Lys Glu Ser Pro Ser Val Arg Ser Ser Lys Asp Gly Lys Leu Leu
            35                  40                  45

Ala Ala Thr Leu Leu Ala Leu Leu Ser Cys Cys Leu Thr Val Val
            50                  55                  60

Ser Phe Tyr Gln Val Ala Ala Leu Gln Gly Asp Leu Ala Ser Leu Arg
65                  70                  75                  80

Ala Glu Leu Gln Gly His His Ala Glu Lys Leu Pro Ala Gly Ala Gly
            85                  90                  95

Ala Pro Lys Ala Gly Leu Glu Glu Ala Pro Ala Val Thr Ala Gly Leu
            100                 105                 110

Lys Ile Phe Glu Pro Pro Ala Pro Gly Glu Gly Asn Ser Ser Gln Asn
            115                 120                 125

Ser Arg Asn Lys Arg Ala Val Gln Gly Pro Glu Glu Thr Gly Ser Tyr
            130                 135                 140

Thr Phe Val Pro Trp Leu Leu Ser Phe Lys Arg Gly Ser Ala Leu Glu
145                 150                 155                 160

Glu Lys Glu Asn Lys Ile Leu Val Lys Glu Thr Gly Tyr Phe Phe Ile
            165                 170                 175

Tyr Gly Gln Val Leu Tyr Thr Asp Lys Thr Tyr Ala Met Gly His Leu
            180                 185                 190

Ile Gln Arg Lys Lys Val His Val Phe Gly Asp Glu Leu Ser Leu Val
            195                 200                 205

Thr Leu Phe Arg Cys Ile Gln Asn Met Pro Glu Thr Leu Pro Asn Asn
            210                 215                 220

Ser Cys Tyr Ser Ala Gly Ile Ala Lys Leu Glu Glu Gly Asp Glu Leu
```

```
                225                 230                 235                 240
        Gln Leu Ala Ile Pro Arg Glu Asn Ala Gln Ile Ser Leu Asp Gly Asp
                        245                 250                 255

Val Thr Phe Phe Gly Ala Leu Lys Leu Leu
                        260                 265

<210> SEQ ID NO 23
<211> LENGTH: 285
<212> TYPE: PRT
<213> ORGANISM: Homo sapiens

<400> SEQUENCE: 23

Met Asp Asp Ser Thr Glu Arg Glu Gln Ser Arg Leu Thr Ser Cys Leu
1               5                   10                  15

Lys Lys Arg Glu Glu Met Lys Leu Lys Glu Cys Val Ser Ile Leu Pro
            20                  25                  30

Arg Lys Glu Ser Pro Ser Val Arg Ser Ser Lys Asp Gly Lys Leu Leu
        35                  40                  45

Ala Ala Thr Leu Leu Leu Ala Leu Leu Ser Cys Cys Leu Thr Val Val
    50                  55                  60

Ser Phe Tyr Gln Val Ala Ala Leu Gln Gly Asp Leu Ala Ser Leu Arg
65                  70                  75                  80

Ala Glu Leu Gln Gly His His Ala Glu Lys Leu Pro Ala Gly Ala Gly
                85                  90                  95

Ala Pro Lys Ala Gly Leu Glu Glu Ala Pro Ala Val Thr Ala Gly Leu
            100                 105                 110

Lys Ile Phe Glu Pro Pro Ala Pro Gly Glu Gly Asn Ser Ser Gln Asn
        115                 120                 125

Ser Arg Asn Lys Arg Ala Val Gln Gly Pro Glu Glu Thr Val Thr Gln
    130                 135                 140

Asp Cys Leu Gln Leu Ile Ala Asp Ser Glu Thr Pro Thr Ile Gln Lys
145                 150                 155                 160

Gly Ser Tyr Thr Phe Val Pro Trp Leu Leu Ser Phe Lys Arg Gly Ser
                165                 170                 175

Ala Leu Glu Glu Lys Glu Asn Lys Ile Leu Val Lys Glu Thr Gly Tyr
            180                 185                 190

Phe Phe Ile Tyr Gly Gln Val Leu Tyr Thr Asp Lys Thr Tyr Ala Met
        195                 200                 205

Gly His Leu Ile Gln Arg Lys Lys Val His Val Phe Gly Asp Glu Leu
    210                 215                 220

Ser Leu Val Thr Leu Phe Arg Cys Ile Gln Asn Met Pro Glu Thr Leu
225                 230                 235                 240

Pro Asn Asn Ser Cys Tyr Ser Ala Gly Ile Ala Lys Leu Glu Glu Gly
                245                 250                 255

Asp Glu Leu Gln Leu Ala Ile Pro Arg Glu Asn Ala Gln Ile Ser Leu
            260                 265                 270

Asp Gly Asp Val Thr Phe Phe Gly Ala Leu Lys Leu Leu
        275                 280                 285

<210> SEQ ID NO 24
<211> LENGTH: 739
<212> TYPE: PRT
<213> ORGANISM: Homo sapiens

<400> SEQUENCE: 24

Met Pro Gly Lys Met Val Val Ile Leu Gly Ala Ser Asn Ile Leu Trp
```

-continued

```
1               5                   10                  15
Ile Met Phe Ala Ala Ser Gln Ala Phe Lys Ile Glu Thr Thr Pro Glu
                20                  25                  30
Ser Arg Tyr Leu Ala Gln Ile Gly Asp Ser Val Ser Leu Thr Cys Ser
                35                  40                  45
Thr Thr Gly Cys Glu Ser Pro Phe Phe Ser Trp Arg Thr Gln Ile Asp
 50                  55                  60
Ser Pro Leu Asn Gly Lys Val Thr Asn Glu Gly Thr Thr Ser Thr Leu
 65                  70                  75                  80
Thr Met Asn Pro Val Ser Phe Gly Asn Glu His Ser Tyr Leu Cys Thr
                85                  90                  95
Ala Thr Cys Glu Ser Arg Lys Leu Glu Lys Gly Ile Gln Val Glu Ile
                100                 105                 110
Tyr Ser Phe Pro Lys Asp Pro Glu Ile His Leu Ser Gly Pro Leu Glu
                115                 120                 125
Ala Gly Lys Pro Ile Thr Val Lys Cys Ser Val Ala Asp Val Tyr Pro
                130                 135                 140
Phe Asp Arg Leu Glu Ile Asp Leu Leu Lys Gly Asp His Leu Met Lys
145                 150                 155                 160
Ser Gln Glu Phe Leu Glu Asp Ala Asp Arg Lys Ser Leu Glu Thr Lys
                165                 170                 175
Ser Leu Glu Val Thr Phe Thr Pro Val Ile Glu Asp Ile Gly Lys Val
                180                 185                 190
Leu Val Cys Arg Ala Lys Leu His Ile Asp Glu Met Asp Ser Val Pro
                195                 200                 205
Thr Val Arg Gln Ala Val Lys Glu Leu Gln Val Tyr Ile Ser Pro Lys
                210                 215                 220
Asn Thr Val Ile Ser Val Asn Pro Ser Thr Lys Leu Gln Glu Gly Gly
225                 230                 235                 240
Ser Val Thr Met Thr Cys Ser Ser Glu Gly Leu Pro Ala Pro Glu Ile
                245                 250                 255
Phe Trp Ser Lys Lys Leu Asp Asn Gly Asn Leu Gln His Leu Ser Gly
                260                 265                 270
Asn Ala Thr Leu Thr Leu Ile Ala Met Arg Met Glu Asp Ser Gly Ile
                275                 280                 285
Tyr Val Cys Glu Gly Val Asn Leu Ile Gly Lys Asn Arg Lys Glu Val
                290                 295                 300
Glu Leu Ile Val Gln Glu Lys Pro Phe Thr Val Glu Ile Ser Pro Gly
305                 310                 315                 320
Pro Arg Ile Ala Ala Gln Ile Gly Asp Ser Val Met Leu Thr Cys Ser
                325                 330                 335
Val Met Gly Cys Glu Ser Pro Ser Phe Ser Trp Arg Thr Gln Ile Asp
                340                 345                 350
Ser Pro Leu Ser Gly Lys Val Arg Ser Glu Gly Thr Asn Ser Thr Leu
                355                 360                 365
Thr Leu Ser Pro Val Ser Phe Glu Asn Glu His Ser Tyr Leu Cys Thr
                370                 375                 380
Val Thr Cys Gly His Lys Lys Leu Glu Lys Gly Ile Gln Val Glu Leu
385                 390                 395                 400
Tyr Ser Phe Pro Arg Asp Pro Glu Ile Glu Met Ser Gly Gly Leu Val
                405                 410                 415
Asn Gly Ser Ser Val Thr Val Ser Cys Lys Val Pro Ser Val Tyr Pro
                420                 425                 430
```

```
Leu Asp Arg Leu Glu Ile Glu Leu Lys Gly Glu Thr Ile Leu Glu
            435                 440                 445

Asn Ile Glu Phe Leu Glu Asp Thr Asp Met Lys Ser Leu Glu Asn Lys
450                 455                 460

Ser Leu Glu Met Thr Phe Ile Pro Thr Ile Glu Asp Thr Gly Lys Ala
465                 470                 475                 480

Leu Val Cys Gln Ala Lys Leu His Ile Asp Asp Met Glu Phe Glu Pro
                485                 490                 495

Lys Gln Arg Gln Ser Thr Gln Thr Leu Tyr Val Asn Val Ala Pro Arg
            500                 505                 510

Asp Thr Thr Val Leu Val Ser Pro Ser Ile Leu Glu Glu Gly Ser
            515                 520                 525

Ser Val Asn Met Thr Cys Leu Ser Gln Gly Phe Pro Ala Pro Lys Ile
530                 535                 540

Leu Trp Ser Arg Gln Leu Pro Asn Gly Glu Leu Gln Pro Leu Ser Glu
545                 550                 555                 560

Asn Ala Thr Leu Thr Leu Ile Ser Thr Lys Met Glu Asp Ser Gly Val
                565                 570                 575

Tyr Leu Cys Glu Gly Ile Asn Gln Ala Gly Arg Ser Arg Lys Glu Val
            580                 585                 590

Glu Leu Ile Ile Gln Val Thr Pro Lys Asp Ile Lys Leu Thr Ala Phe
            595                 600                 605

Pro Ser Glu Ser Val Lys Glu Gly Asp Thr Val Ile Ile Ser Cys Thr
610                 615                 620

Cys Gly Asn Val Pro Glu Thr Trp Ile Ile Leu Lys Lys Lys Ala Glu
625                 630                 635                 640

Thr Gly Asp Thr Val Leu Lys Ser Ile Asp Gly Ala Tyr Thr Ile Arg
                645                 650                 655

Lys Ala Gln Leu Lys Asp Ala Gly Val Tyr Glu Cys Glu Ser Lys Asn
            660                 665                 670

Lys Val Gly Ser Gln Leu Arg Ser Leu Thr Leu Asp Val Gln Gly Arg
            675                 680                 685

Glu Asn Asn Lys Asp Tyr Phe Ser Pro Glu Leu Leu Val Leu Tyr Phe
            690                 695                 700

Ala Ser Ser Leu Ile Ile Pro Ala Ile Gly Met Ile Ile Tyr Phe Ala
705                 710                 715                 720

Arg Lys Ala Asn Met Lys Gly Ser Tyr Ser Leu Val Glu Ala Gln Lys
                725                 730                 735

Ser Lys Val

<210> SEQ ID NO 25
<211> LENGTH: 371
<212> TYPE: PRT
<213> ORGANISM: Homo sapiens

<400> SEQUENCE: 25

Met Thr Asp Arg Gln Thr Asp Thr Ala Pro Ser Pro Ser Tyr His Leu
1               5                   10                  15

Leu Pro Gly Arg Arg Arg Thr Val Asp Ala Ala Ala Ser Arg Gly Gln
            20                  25                  30

Gly Pro Glu Pro Ala Pro Gly Gly Val Glu Gly Val Gly Ala Arg
            35                  40                  45

Gly Val Ala Leu Lys Leu Phe Val Gln Leu Leu Gly Cys Ser Arg Phe
50                  55                  60
```

```
Gly Gly Ala Val Val Arg Ala Gly Glu Ala Glu Pro Ser Gly Ala Ala
 65              70              75              80

Arg Ser Ala Ser Ser Gly Arg Glu Glu Pro Gln Pro Glu Glu Gly Glu
             85              90              95

Glu Glu Glu Glu Lys Glu Glu Glu Arg Gly Pro Gln Trp Arg Leu Gly
            100             105             110

Ala Arg Lys Pro Gly Ser Trp Thr Gly Glu Ala Ala Val Cys Ala Asp
            115             120             125

Ser Ala Pro Ala Ala Arg Ala Pro Gln Ala Leu Ala Arg Ala Ser Gly
            130             135             140

Arg Gly Gly Arg Val Ala Arg Arg Gly Ala Glu Glu Ser Gly Pro Pro
145             150             155             160

His Ser Pro Ser Arg Arg Gly Ser Ala Ser Arg Ala Gly Pro Gly Arg
            165             170             175

Ala Ser Glu Thr Met Asn Phe Leu Leu Ser Trp Val His Trp Ser Leu
            180             185             190

Ala Leu Leu Leu Tyr Leu His His Ala Lys Trp Ser Gln Ala Ala Pro
            195             200             205

Met Ala Glu Gly Gly Gly Gln Asn His His Glu Val Val Lys Phe Met
210             215             220

Asp Val Tyr Gln Arg Ser Tyr Cys His Pro Ile Glu Thr Leu Val Asp
225             230             235             240

Ile Phe Gln Glu Tyr Pro Asp Glu Ile Glu Tyr Ile Phe Lys Pro Ser
            245             250             255

Cys Val Pro Leu Met Arg Cys Gly Gly Cys Cys Asn Asp Glu Gly Leu
            260             265             270

Glu Cys Val Pro Thr Glu Glu Ser Asn Ile Thr Met Gln Ile Met Arg
            275             280             285

Ile Lys Pro His Gln Gly Gln His Ile Gly Glu Met Ser Phe Leu Gln
            290             295             300

His Asn Lys Cys Glu Cys Arg Pro Lys Lys Asp Arg Ala Arg Gln Glu
305             310             315             320

Asn Pro Cys Gly Pro Cys Ser Glu Arg Arg Lys His Leu Phe Val Gln
            325             330             335

Asp Pro Gln Thr Cys Lys Cys Ser Cys Lys Asn Thr Asp Ser Arg Cys
            340             345             350

Lys Ala Arg Gln Leu Glu Leu Asn Glu Arg Thr Cys Arg Cys Asp Lys
            355             360             365

Pro Arg Arg
            370
```

BIOMARKERS AND METHODS FOR MEASURING AND MONITORING INFLAMMATORY DISEASE ACTIVITY

CROSS-REFERENCE TO RELATED APPLICATIONS

This application is related to and claims the benefit of U.S. Provisional Application No. 61/252,110, filed on Oct. 15, 2009, U.S. Provisional Application No. 61/304,317 filed on Feb. 12, 2010 and U.S. Provisional Application 61/355,087, filed on Jun. 15, 2010, all of which are herein incorporated by reference in their entirety for all purposes.

SEQUENCE LISTING

The instant application contains a Sequence Listing which has been submitted in ASCII format via EFS-Web on Feb. 14, 2011 and is hereby incorporated by reference in its entirety. Said ASCII copy, created on Jan. 19, 2011, is named 17543US CRF sequencelisting.txt and is 69,138 bytes in size.

INTRODUCTION

The present teachings are generally directed to biomarkers associated with inflammatory disease, and methods of characterizing biological conditions by scoring quantitative datasets derived from a subject sample, as well as various other embodiments as described herein.

The section headings used herein are for convenience and organizational purposes only, and are not to be construed as limiting the subject matter described in any way. All literature and similar materials cited in this application, including but not limited to scientific publications, articles, books, treatises, published patent applications, issued patents, and internet web pages, regardless the format of such literature and similar materials, are expressly incorporated by reference in their entirety for any purpose.

BACKGROUND

This application is directed to the fields of bioinformatics and inflammatory and autoimmune diseases, with rheumatoid arthritis (RA) as an example of these diseases. The present teachings relate to methods and compositions for assessing, diagnosing, monitoring, and selecting treatment for inflammatory disease and autoimmune disease; e.g., RA.

RA is an example of an inflammatory disease, and is a chronic, systemic autoimmune disorder. It is one of the most common systemic autoimmune diseases worldwide. The immune system of the RA subject targets his/her own joints as well as other organs including the lung, blood vessels and pericardium, leading to inflammation of the joints (arthritis), widespread endothelial inflammation, and even destruction of joint tissue. Erosions and joint space narrowing are largely irreversible and result in cumulative disability.

The precise etiology of RA has not been established, but underlying disease pathogenesis is complex and includes inflammation and immune dysregulation. The precise mechanisms involved are different in individual subjects, and can change in those subjects over time. Variables such as race, sex, genetics, hormones, and environmental factors can impact the development and severity of RA disease. Emerging data are also beginning to reveal the characteristics of new RA subject subgroups and complex overlapping relationships with other autoimmune disorders. Disease duration and level of inflammatory activity is also associated with other comorbidities such as risk of lymphoma, extra-articular manifestations, and cardiovascular disease. See, e.g., S. Banerjee et al., Am. J. Cardiol. 2008, 101(8):1201-1205; E. Baecklund et al., Arth. Rheum. 2006, 54(3):692-701; and, N. Goodson et al., Ann. Rheum. Dis. 2005, 64(11):1595-1601. Because of the complexity of RA, it is difficult to develop a single test that can accurately and consistently assess, quantify, and monitor RA disease activity in every subject.

Traditional models for treating RA are based on the expectation that controlling disease activity (i.e., inflammation) in an RA subject should slow or prevent disease progression, in terms of tissue destruction, cartilage loss and joint erosion. There is evidence, however, that disease activity and disease progression can be uncoupled, and may not always function completely in tandem. Indeed, different cell signaling pathways and mediators are involved in these two processes. See W. van den Berg et al., Arth. Rheum. 2005, 52:995-999. The uncoupling of disease progression and disease activity is described in a number of RA clinical trials and animal studies. See, e.g., P E Lipsky et al., N. Engl. J. Med. 2003, 343:1594-602; AK Brown et al., Arth. Rheum. 2006, 54:3761-3773; and, AR Pettit et al., Am. J. Pathol. 2001, 159:1689-99. Studies of RA subjects indicate limited association between clinical and radiographic responses. See E. Zatarain and V. Strand, Nat. Clin. Pract. Rheum. 2006, 2(11):611-618 (Review). RA subjects have been described who demonstrated radiographic benefits from combination treatment with infliximab and methotrexate (MTX), yet did not demonstrate any clinical improvement, as measured by DAS (Disease Activity Score) and CRP (C-reactive protein). See J S Smolen et al., Arth. Rheum. 2005, 52(4):1020-30. To best study the uncoupling of disease progression and activity (erosion and inflammation, respectively), and to analyze the relationship between disease activity and progression, RA subjects should be assessed frequently for both disease activity and progression.

An increasing number of studies have demonstrated that frequent monitoring of disease activity (known as "tight control") results in quicker improvement in and better subject outcomes. The underlying reason for regularly monitoring an RA subject's disease activity, using appropriate and validated assessment tools, is because RA disease in general displays a highly variable and unpredictable course of progression. In chronic inflammatory diseases, and RA in particular, treatment is ultimately aimed at remission. It has been shown that a greater proportion of subjects with monthly disease activity assessments were in remission at one year compared to those receiving standard of care (standard of care being no assessment of disease activity, or assessments made less frequently than monthly); and further, that subjects with monthly disease activity assessments had better radiographic outcomes and physical function compared to those with standard of care. See Y P M Goekoop-Ruiterman et al., Ann. Rheum. Dis. 2009 (Epublication Jan. 20, 2009); C. Grigor et al., Lancet 2004, 364:263-269; W. Kievit et al., Ann. Rheum. Dis. 2008, 67(9): 1229-1234; T. Mottonen et al., Arth. Rheum. 2002, 46(4):894-898; V K Ranganath et al., J. Rheum. 2008, 35:1966-1971; T. Sokka et al., Clin. Exp. Rheum. 2006, 24(Suppl. 43):S74-76; LHD van Tuyl et al., Ann. Rheum. Dis. 2008, 67:1574-1577; and, SMM Verstappen et al., Ann. Rheum. Dis. 2007, 66:1443-1449. The ability to effectively monitor disease activity would allow for tight control of subjects, thus leading to better subject outcomes.

There is a need to classify subjects by disease activity in order to ensure that each receives treatment that is appropriate and optimized for that patient. In treatment for RA, for example, the use of disease-modifying anti-rheumatic drug (DMARD) combinations has become accepted for subjects who fail to respond to a single DMARD. Studies analyzing treatment with MTX alone and treatment with MTX in combination with other DMARDs demonstrate that in DMARD-naive subjects, the balance of efficacy versus toxicity favors MTX monotherapy, while in DMARD-inadequate responders, the evidence is inconclusive. In regards to biologics (e.g., anti-TNFα), studies support the use of biologics in combination with MTX in subjects with early RA, or in subjects with established RA who have not yet been treated with MTX. The number of drugs available for treating RA is increasing; from this it follows that the number of possible combinations of these drugs is increasing as well. In addition, the chronological order in which each drug in a combination is administered can be varied depending on the needs of the subject. For the clinician to apply a simple trial-and-error process to find the optimum treatment for the RA subject from among the myriad of possible combinations, the clinician runs the risk of under- or over treating the subject. Irreversible joint damage for the subject could be the result. See, e.g., AK Brown et al., *Arth. Rheum.* 2008, 58(10):2958-2967, and G. Cohen et al., *Ann. Rheum. Dis.* 2007, 66:358-363. Clearly there exists a need to accurately classify subjects by disease activity, in order to establish their optimal treatment regimen.

Current clinical management and treatment goals, in the case of RA, focus on the suppression of disease activity with the goal of improving the subject's functional ability and slowing the progression of joint damage. Clinical assessments of RA disease activity include measuring the subject's difficulty in performing activities, morning stiffness, pain, inflammation, and number of tender and swollen joints, an overall assessment of the subject by the physician, an assessment by the subject of how good s/he feels in general, and measuring the subject's erythrocyte sedimentation rate (ESR) and levels of acute phase reactants, such as CRP. Composite indices comprising multiple variables, such as those just described, have been developed as clinical assessment tools to monitor disease activity. The most commonly used are: American College of Rheumatology (ACR) criteria (DT Felson et al., *Arth. Rheum.* 1993, 36(6):729-740 and DT Felson et al., *Arth. Rheum.* 1995, 38(6):727-735); Clinical Disease Activity Index (CDAI) (D. Aletaha et al., *Arth. Rheum.* 2005, 52(9):2625-2636); the DAS (MLL Prevoo et al., *Arth. Rheum.* 1995, 38(1):44-48 and AM van Gestel et al., *Arth. Rheum.* 1998, 41(10):1845-1850); Rheumatoid Arthritis Disease Activity Index (RADAI) (G. Stucki et al., *Arth. Rheum.* 1995, 38(6):795-798); and, Simplified Disease Activity Index (SDAI) (JS Smolen et al., *Rheumatology* (Oxford) 2003, 42:244-257).

Current laboratory tests routinely used to monitor disease activity in RA subjects, such as CRP and ESR, are relatively non-specific (e.g., are not RA-specific and cannot be used to diagnose RA), and cannot be used to determine response to treatment or predict future outcomes. See, e.g., L. Gossec et al., *Ann. Rheum. Dis.* 2004, 63(6):675-680; EJA Kroot et al., *Arth. Rheum.* 2000, 43(8):1831-1835; H. Mäkinen et al., *Ann. Rheum. Dis.* 2005, 64(10):1410-1413; Z. Nadareishvili et al., *Arth. Rheum.* 2008, 59(8):1090-1096; N A Khan et al., Abstract, *ACR/ARHP Scientific Meeting* 2008; TA Pearson et al., *Circulation* 2003, 107(3):499-511; MJ Plant et al., *Arth. Rheum.* 2000, 43(7):1473-1477; T. Pincus et al., *Clin. Exp. Rheum.* 2004, 22(Suppl. 35):550-556; and, PM Ridker et al., *NEJM* 2000, 342(12):836-843. In the case of ESR and CRP, RA subjects may continue to have elevated ESR or CRP levels despite being in clinical remission (and non-RA subjects may display elevated ESR or CRP levels). Some subjects in clinical remission, as determined by DAS, continue to demonstrate continued disease progression radiographically, by erosion. Furthermore, some subjects who do not demonstrate clinical benefits still demonstrate radiographic benefits from treatment. See, e.g., FC Breedveld et al., *Arth. Rheum.* 2006, 54(1):26-37. Clearly, in order to predict future outcome and treat the RA subject accordingly, there is a need for clinical assessment tools that accurately assess an RA subject's disease activity level and that act as predictors of future course of disease.

Clinical assessments of disease activity contain subjective measurements of RA, such as signs and symptoms, and subject-reported outcomes, all difficult to quantify consistently. In clinical trials, the DAS is generally used for assessing RA disease activity. The DAS is an index score of disease activity based in part on these subjective parameters. Besides its subjectivity component, another drawback to use of the DAS as a clinical assessment of RA disease activity is its invasiveness. The physical examination required to derive a subject's DAS can be painful, because it requires assessing the amount of tenderness and swelling in the subject's joints, as measured by the level of discomfort felt by the subject when pressure is applied to the joints. Assessing the factors involved in DAS scoring is also time-consuming. Furthermore, to accurately determine a subject's DAS requires a skilled assessor so as to minimize wide inter- and intra-operator variability. A method of clinically assessing disease activity is needed that is less invasive and time-consuming than DAS, and more consistent, objective and quantitative, while being specific to the disease assessed (such as RA).

Developing biomarker-based tests (e.g., measuring cytokines), e.g. specific to the clinical assessment of RA, has proved difficult in practice because of the complexity of RA biology—the various molecular pathways involved and the intersection of autoimmune dysregulation and inflammatory response. Adding to the difficulty of developing RA-specific biomarker-based tests are the technical challenges involved; e.g., the need to block non-specific matrix binding in serum or plasma samples, such as rheumatoid factor (RF) in the case of RA. The detection of cytokines using bead-based immunoassays, for example, is not reliable because of interference by RF; hence, RF-positive subjects cannot be tested for RA-related cytokines using this technology (and RF removal methods attempted did not significantly improve results). See S. Churchman et al., *Ann. Rheum. Dis.* 2009, 68:A1-A56, Abstract A77. Approximately 70% of RA subjects are RF-positive, so any biomarker-based test that cannot assess RF-positive patients is obviously of limited use.

To achieve the maximum therapeutic benefits for individual subjects, it is important to be able to specifically quantify and assess the subject's disease activity at any particular time, determine the effects of treatment on disease activity, and predict future outcomes. No existing single biomarker or multi-biomarker test produces results demonstrating a high association with level of RA disease activity. The embodiments of the present teachings identify multiple serum biomarkers for the accurate clinical assessment of disease activity in subjects with chronic inflammatory disease, such as RA, along with methods of their use.

SUMMARY

The present teachings relate to biomarkers associated with inflammatory disease, and with autoimmune disease, including RA, and methods of using the biomarkers to measure disease activity in a subject.

One embodiment provides a method for scoring a sample, said method comprising: receiving a first dataset associated with a first sample obtained from a first subject, wherein said first dataset comprises quantitative data for at least two markers selected from the group consisting of: apolipoprotein A-I (APOA1); apolipoprotein C-III (APOC3); calprotectin (heteropolymer of protein subunits S100A8 and S100A9); chemokine (C-C motif) ligand 22 (CCL22); chitinase 3-like 1 (cartilage glycoprotein-39) (CHI3L1); C-reactive protein, pentraxin-related (CRP); epidermal growth factor (beta-urogastrone) (EGF); intercellular adhesion molecule 1 (ICAM1); ICTP; interleukin 18 (interferon-gamma-inducing factor) (IL18); interleukin 1, beta (IL1B); interleukin 1 receptor antagonist (IL1RN); interleukin 6 (interferon, beta 2) (IL6); interleukin 6 receptor (IL6R); interleukin 8 (IL8); keratan sulfate; leptin (LEP); matrix metallopeptidase 1 (interstitial collagenase) (MMP1); matrix metallopeptidase 3 (stromelysin 1, progelatinase) (MMP3); pyridinoline (PYD); resistin (RETN); serum amyloid A1 (SAA1); tumor necrosis factor receptor superfamily, member 1A (TNFRSF1A); tumor necrosis factor (ligand) superfamily, member 13b (TNFSF13B, or BAFF); vascular cell adhesion molecule 1 (VCAM1); and, vascular endothelial growth factor A (VEGFA); and determining, a first DAI score from said first dataset using an interpretation function, wherein said first DAI score provides a quantitative measure of inflammatory disease activity in said first subject.

In one embodiment first dataset is obtained by a method comprising obtaining said first sample from said first subject, wherein said first sample comprises a plurality of analytes; contacting said first sample with a reagent; generating a plurality of complexes between said reagent and said plurality of analytes; and detecting said plurality of complexes to obtain said first dataset associated with said first sample, wherein said first dataset comprises quantitative data for said least two markers.

In one embodiment said at least two markers are selected from the group consisting of: chitinase 3-like 1 (cartilage glycoprotein-39) (CHI3L1); C-reactive protein, pentraxin-related (CRP); epidermal growth factor (beta-urogastrone) (EGF); interleukin 6 (interferon, beta 2) (IL6); leptin (LEP); matrix metallopeptidase 1 (interstitial collagenase) (MMP1); matrix metallopeptidase 3 (stromelysin 1, progelatinase) (MMP3); resistin (RETN); serum amyloid A1 (SAA1); tumor necrosis factor receptor superfamily, member 1A (TNFRSF1A); vascular cell adhesion molecule 1 (VCAM1) and vascular endothelial growth factor A (VEGFA).

In one embodiment said at least two markers are selected from the group consisting of IL6, EGF, VEGFA, LEP, SAA1, VCAM1, CRP, MMP1, MMP3, TNFRSF1A, RETN, and CHI3L1.

In one embodiment the method further comprises reporting said DAI score to said first subject.

In one embodiment said inflammatory disease activity is rheumatoid arthritis disease activity and further comprising predicting a Sharp score change for said first subject, based on said DAI score.

In one embodiment said interpretation function is based on a predictive model.

In one embodiment said predictive model is developed using an algorithm comprising a forward linear stepwise regression algorithm; a Lasso shrinkage and selection method for linear regression; or an Elastic Net for regularization and variable selection for linear regression.

In one embodiment said algorithm is DAI score=(0.56*sqrt(IPTJC))+(0.28*sqrt(IPSJC))+(0.14*(PPGA))+(0.36*ln(CRP/$10^6$+1))+0.96; wherein IPTJC=Improved PTJC=max(0.1739*PTJC+0.7865*PSJC,0); IPSJC=Improved PSJC=max(0.1734*PTJC+0.7839*PSJC,0); PTJC=Prediction of Tender Joint Count=−38.564+3.997* (SAA1)$^{1/10}$+17.331*(IL6)$^{1/10}$+4.665*(CHI3L1)$^{1/10}$− 15.236*(EGF)$^{1/10}$+2.651*(TNFRSF1A)$^{1/10}$+2.641* (LEP)$^{1/10}$+4.026*(VEGFA)$^{1/10}$−1.47*(VCAM1)$^{1/10}$; PSJC=Prediction of Swollen Joint Count=−25.444+4.051* (SAA1)$^{1/10}$+16.154*(IL6)$^{1/10}$−11.847*(EGF)$^{1/10}$+3.091* (CHI3L1)$^{1/10}$+0.353*(TNFRSF1A)$^{1/10}$; PPGA=Prediction of Patient Global Assessment=−13.489+5.474*(IL6)$^{1/10}$+ 0.486*(SAA1)$^{1/10}$+2.246*(MMP1)$^{1/10}$+1.684*(leptin)$^{1/10}$+ 4.14*(TNFRSF1A)$^{1/10}$+2.292*(VEGFA)$^{1/10}$−1.898* (EGF)$^{1/10}$+0.028*(MMP3)$^{1/10}$−2.892*(VCAM1)$^{1/10}$− 0.506*(RETN)$^{1/10}$ wherein units for all biomarkers are pg/mL.

In one embodiment said algorithm is DAI score=(0.56*sqrt(IPTJC))+(0.28*sqrt(IPSJC))+(0.14*(PPGA))+(0.36*ln(CRP+1))+0.96; wherein IPTJC=Improved PTJC=max(0.1739*PTJC+0.7865*PSJC,0); IPSJC=Improved PSJC=max(0.1734*PTJC+0.7839*PSJC,0); PTJC=Prediction of Tender Joint Count=−38.564+3.997* (SAA1)$^{1/10}$+17.331*(IL6)$^{1/10}$+4.665*(CHI3L1)$^{1/10}$− 15.236*(EGF)$^{1/10}$+2.651*(TNFRSF1A)$^{1/10}$+2.641* (LEP)$^{1/10}$+4.026*(VEGFA)$^{1/10}$−1.47*(VCAM1)$^{1/10}$; PSJC=Prediction of Swollen Joint Count=−25.444+4.051* (SAA1)$^{1/10}$+16.154*(IL6)$^{1/10}$−11.847*(EGF)$^{1/10}$+3.091* (CHI3L1)$^{1/10}$+0.353*(TNFRSF1A)$^{1/10}$; PPGA=Prediction of Patient Global Assessment=−13.489+5.474*(IL6)$^{1/10}$+ 0.486*(SAA1)$^{1/10}$+2.246*(MMP1)$^{1/10}$+1.684*(leptin)$^{1/10}$+ 4.14*(TNFRSF1A)$^{1/10}$+2.292*(VEGFA)$^{1/10}$−1.898* (EGF)$^{1/10}$+0.028*(MMP3)$^{1/10}$−2.892*(VCAM1)$^{1/10}$− 0.506*(RETN)$^{1/10}$ wherein units for CRP are mg/L and for other biomarkers are pg/mL.

In one embodiment, the method further comprises determining a scaled DAI score wherein said scaled DAI score=round(max(min((DAI score)*10.53+1, 100),1)).

In one embodiment said first DAI score is predictive of a clinical assessment.

In one embodiment said clinical assessment is selected from the group consisting of: a DAS, a DAS28, a Sharp score, a tender joint count (TJC), and a swollen joint count (SJC).

In one embodiment said clinical assessment is a DAS.

In one embodiment said clinical assessment is a DAS28.

In one embodiment said DAS28 comprises a component selected from the group consisting of tender joint count (TJC), the swollen joint count (SJC), and the patient global health assessment.

In one embodiment said clinical assessment is TJC and said first dataset comprises quantitative data for at least one marker selected from the group consisting of CHI3L1, EGF, IL6, LEP, SAA1, TNFRSF1A, VCAM1, and VEGFA.

In one embodiment said clinical assessment is SJC and said first dataset comprises quantitative data for at least one marker selected from the group consisting of CHI3L1, EGF, IL6, SAA1, and TNFRSF1A.

In one embodiment said clinical assessment is patient global health assessment and said first dataset comprises quantitative data for at least one marker selected from the group consisting of EGF, IL6, LEP, MMP1, MMP3, RETN, SAA1, TNFRSF1A, VCAM1, and VEGFA.

In one embodiment, the method further comprises receiving a second dataset associated with a second sample obtained from said first subject, wherein said first sample and said second sample are obtained from said first subject at different times; determining a second DAI score from said second dataset using said interpretation function; and comparing said first DAI score and said second DAI score to determine a change in said DAI scores, wherein said change indicates a change in said inflammatory disease activity in said first subject.

In one embodiment said inflammatory disease activity is rheumatoid arthritis activity and said indicated change in rheumatoid arthritis disease activity indicates the presence, absence or extent of the subject's response to a therapeutic regimen.

In one embodiment, the method further comprises determining a rate of said change in DAI scores, wherein said rate indicates the extent of said first subject's response to a therapeutic regimen.

In one embodiment said inflammatory disease activity is rheumatoid arthritis disease activity and further comprising predicting a Sharp score change rate for said first subject, based on said indicated change in rheumatoid arthritis disease activity.

In one embodiment the method further comprises determining a prognosis for rheumatoid arthritis progression in said first subject based on said predicted Sharp score change rate.

In one embodiment said inflammatory disease is rheumatoid arthritis.

In one embodiment said inflammatory disease is undifferentiated arthritis.

In one embodiment one of said at least two markers is CRP or SAA1.

In one embodiment said DAI score is used as an inflammatory disease surrogate endpoint, the inflammatory disease may be rheumatoid arthritis.

In one embodiment a method for determining a presence or absence of rheumatoid arthritis in a subject is provided, the method comprising determining DAI scores according the disclosed methods for subjects in a population wherein said subjects are negative for rheumatoid arthritis; deriving an aggregate DAI value for said population based on said determined DAI scores; determining a second DAI score for a second subject; comparing the aggregate DAI value to the second DAI score; and determining a presence or absence of rheumatoid arthritis in said second subject based on said comparison.

In one embodiment said first subject has received a treatment for rheumatoid arthritis, and the method further comprises the steps of determining a second DAI score according to the disclosed method for a second subject wherein said second subject is of the same species as said first subject and wherein said second subject has received treatment for rheumatoid arthritis; comparing said first DAI score to said second DAI score; and determining a treatment efficacy for said first subject based on said score comparison.

In one embodiment the method further comprises determining a response to rheumatoid arthritis therapy based on said DAI score.

In one embodiment the method further comprises selecting a rheumatoid arthritis therapeutic regimen based on said DAI score.

In one embodiment the method further comprises determining a rheumatoid arthritis treatment course based on said DAI score.

In one embodiment the method further comprises rating a rheumatoid arthritis disease activity as low or high based on said DAI score.

In one embodiment said predictive model performance is characterized by an AUC ranging from 0.60 to 0.99.

In one embodiment said predictive model performance is characterized by an AUC ranging from 0.70 to 0.79.

In one embodiment said predictive model performance is characterized by an AUC ranging from 0.80 to 0.89.

In one embodiment said at least two markers comprise (APOA1 and IL8), (Calprotectin and CRP), (Calprotectin and EGF), (Calprotectin and IL8), (CRP and APOA1), (CRP and APOC3), (CRP and CCL22), (CRP and CHI3L1), (CRP and EGF), (CRP and ICAM1), (CRP and IL1B), (CRP and IL6), (CRP and IL6R), (CRP and IL8), (CRP and LEP), (CRP and MMP1), (CRP and MMP3), (CRP and RETN), (CRP and SAA1), (CRP and TNFRSF1A), (CRP and VCAM1), (CRP and VEGF), (EGF and APOA1), (EGF and CHI3L1), (EGF and ICAM1), (EGF and IL8), (EGF and LEP), (EGF and MMP1), (EGF and TNFRSF1A), (EGF and VCAM1), (ICAM1 and IL8), (IL1RN and CRP), (IL1RN and EGF), (IL1RN and IL8), (IL8 and APOC3), (IL8 and CCL22), (IL8 and CHI3L1), (IL8 and IL6), (IL8 and IL6R), (IL8 and TNFRSF1A), (LEP and IL8), (MMP3 and IL8), (RETN and IL8), (SAA1 and EGF), (SAA1 and IL8), (SAA1 and LEP), (SAA1 and RETN), or (VCAM1 and IL8).

In one embodiment said at least two markers comprise (calprotectin and CHI3L1), (calprotectin and interleukin), (calprotectin and LEP), (calprotectin and pyridinoline), (calprotectin and RETN), (CCL22 and calprotectin), (CCL22 and CRP), (CCL22 and IL6), (CCL22 and SAA1), (CRP and calprotectin), (CRP and CHI3L1), (CRP and EGF), (CRP and ICAM1), (CRP and IL1B), (CRP and IL1RN), (CRP and IL6), (CRP and IL6R), (CRP and IL8), (CRP and LEP), (CRP and MMP1), (CRP and MMP3), (CRP and pyridinoline), (CRP and RETN), (CRP and SAA1), (CRP and TNFRSF1A), (CRP and VCAM1), (CRP and VEGFA), (EGF and calprotectin), (EGF and IL6), (EGF and SAA1), (ICAM1 and calprotectin), (ICAM1 and IL6), (ICAM1 and SAA1), (IL1B and calprotectin), (IL1B and IL6), (IL1B and MMP3), (IL1B and SAA1), (IL6 and calprotectin), (IL6 and CHI3L1), (IL6 and IL1RN), (IL6 and IL8), (IL6 and LEP), (IL6 and MMP1), (IL6 and MMP3), (IL6 and pyridinoline), (IL6 and RETN), (IL6 and SAA1), (IL6 and TNFRSF1A), (IL6 and VCAM1), (IL6 and VEGFA), (IL6R and calprotectin), (IL6R and IL6), (IL6R and SAA1), (IL8 and calprotectin), (IL8 and MMP3), (IL8 and SAA1), (MMP1 and calprotectin), (MMP1 and SAA1), (MMP3 and calprotectin), (MMP3 and CHI3L1), (MMP3 and SAA1), (SAA1 and calprotectin), (SAA1 and CHI3L1), (SAA1 and IL1RN), (SAA1 and LEP), (SAA1 and pyridinoline), (SAA1 and RETN), (SAA1 and TNFRSF1A), (SAA1 and VCAM1), (SAA1 and VEGFA), (TNFRSF1A and calprotectin), (VCAM1 and calprotectin); or, (VEGFA and calprotectin)

In one embodiment said at least two markers comprise one set of markers selected from the group consisting of TWOMRK Set Nos. 1 through 208 of FIG. 1.

In one embodiment said at least two markers comprise one set of markers selected from the group consisting of TWOMRK Set Nos. 1 through 157 of FIG. 17.

In one embodiment said at least two markers comprises at least three markers selected from the group consisting of: apolipoprotein A-I (APOA1); apolipoprotein C-III (APOC3); chemokine (C-C motif) ligand 22 (CCL22); chitinase 3-like 1 (cartilage glycoprotein-39) (CHI3L1); ICTP; C-reactive protein, pentraxin-related (CRP); epidermal growth factor (beta-urogastrone) (EGF); intercellular adhesion molecule 1 (ICAM1); interleukin 18 (interferon-gamma-inducing factor) (IL18); interleukin 1, beta (IL1B); interleukin 1 receptor antagonist (IL1RN); interleukin 6 (interferon, beta 2) (IL6); interleukin 6 receptor (IL6R); interleukin 8 (IL8); keratan sulfate; leptin (LEP); matrix metallopeptidase 1 (interstitial collagenase) (MMP1); matrix metallopeptidase 3 (stromelysin 1, progelatinase) (MMP3); resistin (RETN); calprotectin (heteropolymer of protein subunits S100A8 and S100A9); serum amyloid A1 (SAA1); tumor necrosis factor receptor superfamily, member 1A (TNFRSF1A); vascular cell adhesion molecule 1 (VCAM1); vascular endothelial growth factor A (VEGFA); and, pyridinoline (PYD).

In one embodiment said at least two markers comprises one set of three markers selected from the group consisting of THREEMRK Set Nos. 1 through 378 of FIG. 2 and THREEMRK Set Nos. 1 through 236 of FIG. 18.

In one embodiment said at least two markers comprises one set of three markers selected from the group consisting of THREEMRK Set Nos. 1 through 236 of FIG. 18.

In one embodiment said at least two markers comprises at least four markers selected from the group consisting of: apolipoprotein A-I (APOA1); apolipoprotein C-III (APOC3); chemokine (C-C motif) ligand 22 (CCL22); chitinase 3-like 1 (cartilage glycoprotein-39) (CHI3L1); ICTP; C-reactive protein, pentraxin-related (CRP); epidermal growth factor (beta-urogastrone) (EGF); intercellular adhesion molecule 1 (ICAM1); interleukin 18 (interferon-gamma-inducing factor) (IL18); interleukin 1, beta (IL1B); interleukin 1 receptor antagonist (IL1RN); interleukin 6 (interferon, beta 2) (IL6); interleukin 6 receptor (IL6R); interleukin 8 (IL8); keratan sulfate; leptin (LEP); matrix metallopeptidase 1 (interstitial collagenase) (MMP1); matrix metallopeptidase 3 (stromelysin 1, progelatinase) (MMP3); resistin (RETN); calprotectin (heteropolymer of protein subunits S100A8 and S100A9); serum amyloid A1 (SAA1); tumor necrosis factor receptor superfamily, member 1A (TNFRSF1A); vascular cell adhesion molecule 1 (VCAM1); vascular endothelial growth factor A (VEGFA); and, pyridinoline (PYD).

In one embodiment said at least two markers comprises one set of four markers selected from the group consisting of FOURMRK Set Nos. 1 through 54 of FIG. 3.

In one embodiment said at least two markers comprises one set of four markers selected from the group consisting of FOURMRK Set Nos. 1 through 266 of FIG. 19.

In one embodiment said at least two markers comprises at least five markers selected from the group consisting of: apolipoprotein A-I (APOA1); apolipoprotein C-III (APOC3); chemokine (C-C motif) ligand 22 (CCL22); chitinase 3-like 1 (cartilage glycoprotein-39) (CHI3L1); ICTP; C-reactive protein, pentraxin-related (CRP); epidermal growth factor (beta-urogastrone) (EGF); intercellular adhesion molecule 1 (ICAM1); interleukin 18 (interferon-gamma-inducing factor) (IL18); interleukin 1, beta (IL1B); interleukin 1 receptor antagonist (IL1RN); interleukin 6 (interferon, beta 2) (IL6); interleukin 6 receptor (IL6R); interleukin 8 (IL8); keratan sulfate; leptin (LEP); matrix metallopeptidase 1 (interstitial collagenase) (MMP1); matrix metallopeptidase 3 (stromelysin 1, progelatinase) (MMP3); resistin (RETN); calprotectin (heteropolymer of protein subunits S100A8 and S100A9); serum amyloid A1 (SAA1); tumor necrosis factor receptor superfamily, member 1A (TNFRSF1A); vascular cell adhesion molecule 1 (VCAM1); vascular endothelial growth factor A (VEGFA); and, pyridinoline (PYD).

In one embodiment said at least two markers comprises one set of five markers selected from the group consisting of FIVEMRK Set Nos. 1 through 44 of FIG. 4.

In one embodiment said at least two markers comprises one set of five markers selected from the group consisting of FIVEMRK Set Nos. 1 through 236 of FIG. 20.

In one embodiment said at least two markers comprises at least six markers selected from the group consisting of: apolipoprotein A-I (APOA1); apolipoprotein C-III (APOC3); chemokine (C-C motif) ligand 22 (CCL22); chitinase 3-like 1 (cartilage glycoprotein-39) (CHI3L1); ICTP; C-reactive protein, pentraxin-related (CRP); epidermal growth factor (beta-urogastrone) (EGF); intercellular adhesion molecule 1 (ICAM1); interleukin 18 (interferon-gamma-inducing factor) (IL18); interleukin 1, beta (IL1B); interleukin 1 receptor antagonist (IL1RN); interleukin 6 (interferon, beta 2) (IL6); interleukin 6 receptor (IL6R); interleukin 8 (IL8); keratan sulfate; leptin (LEP); matrix metallopeptidase 1 (interstitial collagenase) (MMP1); matrix metallopeptidase 3 (stromelysin 1, progelatinase) (MMP3); resistin (RETN); calprotectin (heteropolymer of protein subunits S100A8 and S100A9); serum amyloid A1 (SAA1); tumor necrosis factor receptor superfamily, member 1A (TNFRSF1A); vascular cell adhesion molecule 1 (VCAM1); vascular endothelial growth factor A (VEGFA); and, pyridinoline (PYD).

In one embodiment said at least two markers comprises one set of six markers selected from the group consisting of SIXMRK Set Nos. 1 through 84 of FIG. 5.

In one embodiment said at least two markers comprises one set of six markers selected from the group consisting of SIXMRK Set Nos. 1 through 192 of FIG. 21.

In one embodiment said at least two markers comprises calprotectin, CCL22, CRP, EGF, ICAM1, CHI3L1, ICTP, IL1B, IL1RA, IL6, IL6R, IL8, LEP, MMP1, MMP3, pyridinoline, RETN, SAA1, TNFRSF1A, VCAM1 and VEGFA.

In one embodiment said at least two markers comprises IL6, EGF, VEGFA, LEP, SAA1, VCAM1, CRP, MMP1, MMP3, TNFRSF1A, RETN, and CHI3L1.

Also provided are computer-implemented methods, systems and computer-readable storage mediums with program code for carrying out the disclosed methods.

BRIEF DESCRIPTION OF THE DRAWINGS

The skilled artisan will understand that the drawings, described below, are for illustration purposes only. The drawings are not intended to limit the scope of the present teachings in any way.

FIG. 1 depicts a list of two-biomarker (TWOMRK) sets or panels, as described in certain embodiments of the present teachings, and according to Example 1. FIG. 1A depicts set numbers 1-38, FIG. 1B depicts set numbers 39-77, FIG. 1C depicts set numbers 78-116, FIG. 1D depicts set numbers 117-155, FIG. 1E depicts set numbers 156-194, and FIG. 1F depicts set numbers 195-208. Models were run for all possible two-biomarker combinations of the DAIMRK biomarkers analyzed in Example 1. DAI scores derived from the levels of a set of biomarkers comprising the TWOMRK sets of biomarkers in FIG. 1 demonstrated a strong predictive ability to classify subject disease activity, as evidenced by the AUC values shown (greater than or equal to 0.60). In this and following figures, correlations of the DAI scores with DAS28 are shown by r, as estimated using 100 test set cross-validation.

FIG. 2 depicts a list of three-biomarker (THREEMRK) sets or panels, as described in certain embodiments of the present teachings, and according to the methods of Example 1. FIG. 2A depicts set numbers 1-38, FIG. 2B depicts set numbers 39-77, FIG. 2C depicts set numbers 78-116, FIG. 2D depicts set numbers 117-155, FIG. 2E depicts set numbers 156-194, FIG. 2F depicts set numbers 195-233, FIG. 2G depicts set numbers 234-272, FIG. 2H depicts set numbers 273-311, FIG. 2I depicts set numbers 312-350, and FIG. 2J depicts set numbers 351-378. DAI scores derived from the levels of a set of biomarkers comprising the THREEMRK sets of biomarkers in FIG. 2 demonstrated a strong association with DAS28-CRP, as evidenced by the AUC values shown (greater than or equal to 0.65). Note that the list of THREEMRK sets in FIG. 2 does not contain any panels comprising the two biomarkers of FIG. 1, as this would be redundant (FIG. 1 describes biomarker sets comprising the TWOMRK sets, not consisting of the TWOMRK sets).

FIG. 3 depicts a list of four-biomarker (FOURMRK) sets or panels, as described in certain embodiments of the present teachings, and according to Example 1. 3A depicts set numbers 1-38 and FIG. 3B depicts set numbers 39-54. DAI scores derived from the levels of a set of biomarkers comprising the FOURMRK sets of biomarkers in FIG. 3 demonstrated a strong association with DAS28-CRP, as evidenced by the AUC values shown (greater than or equal to 0.70). Note that the list of FOURMRK sets in FIG. 3 does not contain any panels comprising the three biomarkers of FIG. 2, as this would be redundant (FIG. 2 describes biomarker sets comprising the THREEMRK sets, not consisting of the THREEMRK sets).

FIG. 4 depicts a list of five-biomarker (FIVEMRK) sets or panels, as described in certain embodiments of the present teachings, and according to Example 1. FIG. 4A depicts set numbers 1-38 and FIG. 4B depicts set numbers 39-44. DAI scores derived from the levels of a set of biomarkers comprising the FIVEMRK sets of biomarkers in FIG. 4 demonstrated a strong association with DAS28-CRP, as evidenced by the AUC values shown (greater than or equal to 0.70). Note that the list of FIVEMRK sets in FIG. 4 does not contain any panels comprising the four biomarkers of FIG. 3, as this would be redundant (FIG. 3 describes biomarker sets comprising the FOURMRK sets, not consisting of the FOURMRK sets).

FIG. 5 depicts a list of six-biomarker (SIXMRK) sets or panels, as described in certain embodiments of the present teachings, and according to Example 1. FIG. 5A depicts set numbers 1-26, FIG. 5B depicts set numbers 27-54, FIG. 5C depicts set numbers 55-82, and FIG. 5D depicts set number 83-84. DAI scores derived from the levels of a set of biomarkers comprising the SIXMRK sets of biomarkers in FIG. 5 demonstrated a strong association with DAS28-CRP, as evidenced by the AUC values shown (greater than or equal to 0.70). Note that the list of SIXMRK sets in FIG. 5 does not contain any panels comprising the five biomarkers of FIG. 4, as this would be redundant (FIG. 4 describes biomarker sets comprising the FIVEMRK sets, not consisting of the FIVEMRK sets).

FIG. 9 depicts a correlation matrix between the continuous clinical variables and biomarkers of Example 1.

FIG. 16 depicts another list of two-biomarker (TWOMRK) sets or panels, as described in certain embodiments of the present teachings, and according to Example 7. FIG. 16A depicts set numbers 1-38, FIG. 16B depicts set numbers 39-79, FIG. 16C depicts set numbers 80-120, and FIG. 16D depicts set numbers 121-157. Models were run for all possible two-biomarker combinations of the DAIMRK biomarkers analyzed in Example 7. DAI scores derived from the levels of a set of biomarkers comprising the TWOMRK sets of biomarkers in FIG. 17 demonstrated a strong predictive ability to classify subject disease activity, as evidenced by the AUC values shown (greater than or equal to 0.60).

FIG. 17 depicts another list of three-biomarker (THREEMRK) sets or panels, as described in certain embodiments of the present teachings, and according to the methods of Example 7. FIG. 17A depicts set numbers 1-38, FIG. 17B depicts set numbers 39-79, FIG. 17C depicts set numbers 80-120, FIG. 17D depicts set numbers 121-161, FIG. 17E depicts set numbers 162-202, and FIG. 17F depicts set numbers 203-236. DAI scores derived from the levels of a set of biomarkers comprising the THREEMRK sets of biomarkers in FIG. 18 demonstrated a strong association with DAS28-CRP, as evidenced by the AUC values shown (greater than or equal to 0.60). Note that the list of THREEMRK sets in FIG. 2 does not contain any panels comprising the two biomarkers of FIG. 17, as this would be redundant (FIG. 17 describes biomarker sets comprising the TWOMRK sets, not consisting of the TWOMRK sets).

FIG. 18 depicts another list of four-biomarker (FOURMRK) sets or panels, as described in certain embodiments of the present teachings, and according to Example 7. FIG. 18A depicts set numbers 1-38, FIG. 18B depicts set numbers 39-79, FIG. 18C depicts set numbers 80-120, FIG. 18D depicts set numbers 121-161, FIG. 18E depicts set numbers 162-202, FIG. 18F depicts set numbers 203-243, and FIG. 18G depicts set numbers 244-266. DAI scores derived from the levels of a set of biomarkers comprising the FOURMRK sets of biomarkers in FIG. 19 demonstrated a strong association with DAS28-CRP, as evidenced by the AUC values shown (greater than or equal to 0.65). Note that the list of FOURMRK sets in FIG. 19 does not contain any panels comprising the three biomarkers of FIG. 18, as this would be redundant (FIG. 18 describes biomarker sets comprising the THREEMRK sets, not consisting of the THREEMRK sets).

FIG. 19 depicts another list of five-biomarker (FIVEMRK) sets or panels, as described in certain embodiments of the present teachings, and according to Example 7. FIG. 19A depicts set numbers 1-38, FIG. 19B depicts set numbers 39-79, FIG. 19C depicts set numbers 80-120, FIG. 19D depicts set numbers 121-161, FIG. 19E depicts set numbers 162-202, and FIG. 19F depicts set numbers 203-236. DAI scores derived from the levels of a set of biomarkers comprising the FIVEMRK sets of biomarkers in FIG. 20 demonstrated a strong association with DAS28-CRP, as evidenced by the AUC values shown (greater than 0.65). Note that the list of FIVEMRK sets in FIG. 20 does not contain any panels comprising the four biomarkers of FIG. 19, as this would be redundant (FIG. 19 describes biomarker sets comprising the FOURMRK sets, not consisting of the FOURMRK sets).

FIG. 20 depicts another list of six-biomarker (SIXMRK) sets or panels, as described in certain embodiments of the present teachings, and according to Example 7. FIG. 20A depicts set numbers 1-38, FIG. 20B depicts set numbers 39-79, FIG. 20C depicts set numbers 80-120, FIG. 20D depicts set numbers 121-161, and FIG. 20E depicts set numbers 162-192. DAI scores derived from the levels of a set of biomarkers comprising the SIXMRK sets of biomarkers in FIG. 21 demonstrated a strong association with DAS28-CRP, as evidenced by the AUC values shown (greater than 0.65). Note that the list of SIXMRK sets in FIG. 21 does not contain any panels comprising the five biomarkers of FIG. 20, as this would be redundant (FIG. 20 describes biomarker sets comprising the FIVEMRK sets, not consisting of the FIVEMRK sets).

DESCRIPTION OF VARIOUS EMBODIMENTS

Figure 6:
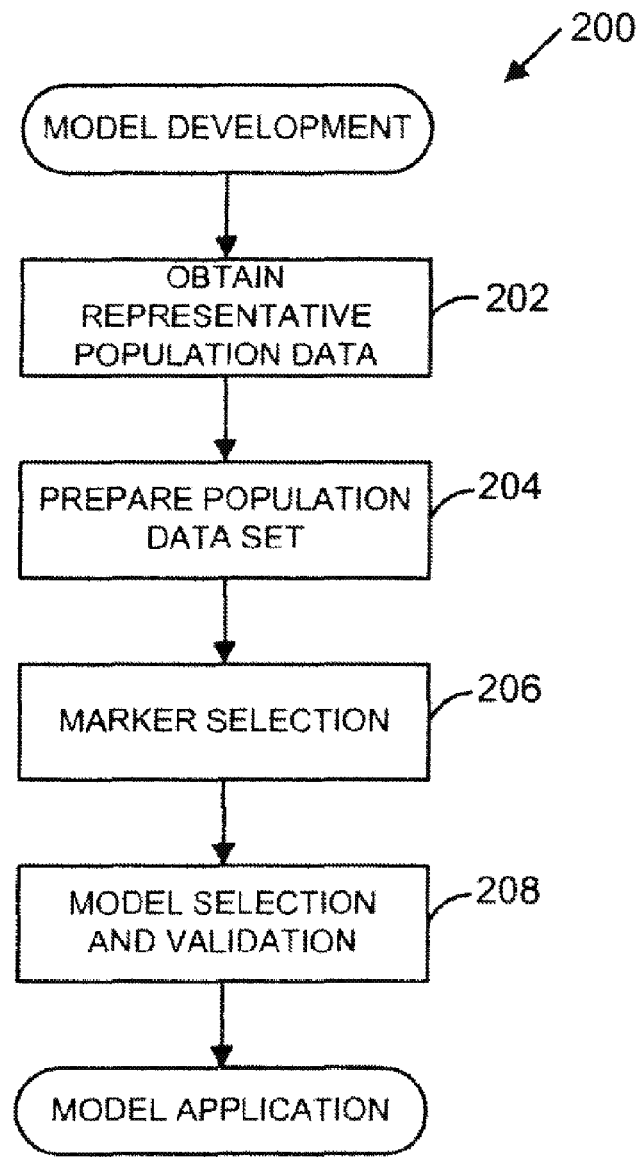
FIG. 6 is a flow diagram, which describes an example of a method for developing a model that can be used to determine the inflammatory disease activity of a person or population.

These and other features of the present teachings will become more apparent from the description herein. While the present teachings are described in conjunction with various embodiments, it is not intended that the present teachings be limited to such embodiments. On the contrary, the present teachings encompass various alternatives, modifications, and equivalents, as will be appreciated by those of skill in the art.

The present teachings relate generally to the identification of biomarkers associated with subjects having inflammatory and/or autoimmune diseases, such as for example RA, and that are useful in determining or assessing disease activity.

Most of the words used in this specification have the meaning that would be attributed to those words by one skilled in the art. Words specifically defined in the specification have the meaning provided in the context of the present teachings as a whole, and as are typically understood by those skilled in the art. In the event that a conflict arises between an art-understood definition of a word or phrase and a definition of the word or phrase as specifically taught in this specification, the specification shall control. It must be noted that, as used in the specification and the appended claims, the singular forms "a," "an," and "the" include plural referents unless the context clearly dictates otherwise.

Definitions

"Accuracy" refers to the degree that a measured or calculated value conforms to its actual value. "Accuracy" in clinical testing relates to the proportion of actual outcomes (true positives or true negatives, wherein a subject is correctly classified as having disease or as healthy/normal, respectively) versus incorrectly classified outcomes (false positives or false negatives, wherein a subject is incorrectly classified as having disease or as healthy/normal, respectively). Other and/or equivalent terms for "accuracy" can include, for example, "sensitivity," "specificity," "positive predictive value (PPV)," "the AUC," "negative predictive value (NPV)," "likelihood," and "odds ratio." "Analytical accuracy," in the context of the present teachings, refers to the repeatability and predictability of the measurement process. Analytical accuracy can be summarized in such measurements as, e.g., coefficients of variation (CV), and tests of concordance and calibration of the same samples or controls at different times or with different assessors, users, equipment, and/or reagents. See, e.g., R. Vasan, *Circulation* 2006, 113(19):2335-2362 for a summary of considerations in evaluating new biomarkers.

The term "algorithm" encompasses any formula, model, mathematical equation, algorithmic, analytical or programmed process, or statistical technique or classification analysis that takes one or more inputs or parameters, whether continuous or categorical, and calculates an output value, index, index value or score. Examples of algorithms include but are not limited to ratios, sums, regression operators such as exponents or coefficients, biomarker value transformations and normalizations (including, without limitation, normalization schemes that are based on clinical parameters such as age, gender, ethnicity, etc.), rules and guidelines, statistical classification models, and neural networks trained on populations. Also of use in the context of biomarkers are linear and non-linear equations and statistical classification analyses to determine the relationship between (a) levels of biomarkers detected in a subject sample and (b) the level of the respective subject's disease activity.

"ALLMRK" in the present teachings refers to a specific group, panel or set of biomarkers, as the term "biomarkers" is defined herein. Where the biomarkers of certain embodiments of the present teachings are proteins, the gene symbols and names used herein are to be understood to refer to the protein products of these genes, and the protein products of these genes are intended to include any protein isoforms of these genes, whether or not such isoform sequences are specifically described herein. Where the biomarkers are nucleic acids, the gene symbols and names used herein are to refer to the nucleic acids (DNA or RNA) of these genes, and the nucleic acids of these genes are intended to include any transcript variants of these genes, whether or not such transcript variants are specifically described herein. The ALLMRK group of the present teachings is the group of markers consisting of the following, where the name(s) or symbols in parentheses at the end of the marker name generally refers to the gene name, if known, or an alias: adiponectin, C1Q and collagen domain containing (ADIPOQ); adrenomedullin (ADM); alkaline phosphatase, liver/bone/kidney (ALPL); amyloid P component, serum (APCS); advanced glycosylation end product-specific receptor (AGER); apolipoprotein A-I (APOA1); apolipoprotein A-II (APOA2); apolipoprotein B (including Ag(x) antigen) (APOB); apolipoprotein C-II (APOC2); apolipoprotein C-III (APOC3); apolipoprotein E (APOE); bone gamma-carboxyglutamate (gla) protein (BGLAP, or osteocalcin); bone morphogenetic protein 6 (BMP6); calcitonin-related polypeptide beta (CALCB); calprotectin (dimer of S100A8 and S100A9 protein subunits); chemokine (C-C motif) ligand 22 (CCL22); CD40 ligand (CD40LG); chitinase 3-like 1 (cartilage glycoprotein-39) (CHI3L1, or YKL-40); cartilage oligomeric matrix protein (COMP); C-reactive protein, pentraxin-related (CRP); CS3B3 epitope, a cartilage fragment; colony stimulating factor 1 (macrophage) (CSF1, or MCSF); colony stimulating factor 2 (granulocyte-macrophage) (CSF2); colony stimulating factor 3 (granulocyte) (CSF3); cystatin C (CST3); epidermal growth factor (beta-urogastrone) (EGF); epidermal growth factor receptor (erythroblastic leukemia viral (v-erb-b) oncogene homolog, avian) (EGFR); erythropoietin (EPO); Fas (TNF receptor superfamily, member 6) (FAS); fibrinogen alpha chain (FGA); fibroblast growth factor 2 (basic) (FGF2); fibrinogen; fms-related tyrosine kinase 1 (vascular endothelial growth factor/vascular permeability factor receptor) (FLT1); fms-related tyrosine kinase 3 ligand (FLT3LG); fms-related tyrosine kinase 4 (FLT4); follicle stimulating hormone; follicle stimulating hormone, beta polypeptide (FSHB); gastric inhibitory polypeptide (GIP); ghrelin; ghrelin/obestatin prepropeptide (GHRL); growth hormone 1 (GH1); GLP1; hepatocyte growth factor (HGF); haptoglobin (HP); intercellular adhesion molecule 1 (ICAM1); intercellular adhesion molecule 3 (ICAM3); ICTP; interferon, alpha 1 (IFNA1); interferon, alpha 2 (IFNA2); glial cell derived neurotrophic factor (GDNF); interferon, gamma (IFNG); insulin-like growth factor binding protein 1 (IGFBP1); interleukin 10 (IL10); interleukin 12; interleukin 12A (natural killer cell stimulatory factor 1, cytotoxic lymphocyte maturation factor 1, p35) (IL12A); interleukin 12B (natural killer cell stimulatory factor 2, cytotoxic lymphocyte maturation factor 2, p40) (IL12B); interleukin 13 (IL13); interleukin 15 (IL15); interleukin 17A (IL17A); interleukin 18 (interferon-gamma-inducing factor) (IL18); interleukin 1, alpha (IL1A); interleukin 1, beta (IL1B); interleukin 1 receptor, type I (IL1R1); interleukin 1 receptor, type II (IL1R2); interleukin 1 receptor antagonist (IL1RN, or IL1RA); interleukin 2 (IL2); interleukin 2 receptor; interleukin 2 receptor, alpha (IL2RA); interleukin 3 (colony-stimulating factor, multiple) (IL3); interleukin 4 (IL4); interleukin 4 receptor (IL4R); interleukin 5 (colony-stimulating factor, eosinophil) (IL5); interleukin 6 (interferon, beta 2) (IL6); interleukin 6 receptor (IL6R); interleukin 6 signal transducer (gp130, oncostatin M receptor) (IL6ST); interleukin 7 (IL7); interleukin 8 (IL8); insulin (INS); interleukin 9 (IL9); kinase insert domain receptor (a type III receptor tyrosine kinase) (KDR); v-kit Hardy-Zuckerman 4 feline sarcoma viral oncogene homolog (KIT); keratan sulfate, or KS; leptin (LEP); leukemia inhibitory factor (cholinergic differentiation factor) (LIF); lymphotoxin alpha (TNF superfamily, member 1) (LTA); lysozyme (renal amyloidosis) (LYZ); matrix metallopeptidase 1 (interstitial collagenase) (MMP1); matrix metallopeptidase 10 (stromelysin 2) (MMP10); matrix metallopeptidase 2 (gelatinase A, 72 kDa gelatinase, 72 kDa type IV collagenase) (MMP2); matrix metallopeptidase 3 (stromelysin 1, progelatinase) (MMP3); matrix metallopeptidase 9 (gelatinase B, 92 kDa gelatinase, 92 kDa type IV collagenase) (MMP9); myeloperoxidase (MPO); nerve growth factor (beta polypeptide) (NGF); natriuretic peptide precursor B (NPPB, or NT-proBNP); neurotrophin 4 (NTF4); platelet-derived growth factor alpha polypeptide (PDGFA); the dimer of two PDGFA subunits (or PDGF-AA); the dimer of one PDGFA subunit and one PDGFB subunit (or PDGF-AB); platelet-derived growth factor beta polypeptide (PDGFB); prostaglandin E2 (PGE2); phosphatidylinositol glycan anchor biosynthesis, class F (P1GF); proopiomelanocortin (POMC); pancreatic polypeptide (PPY); prolactin (PRL); pentraxin-related gene, rapidly induced by IL-1 beta (PTX3, or pentraxin 3); pyridinoline (PYD); peptide YY (PYY); resistin (RETN); serum amyloid A1 (SAA1); selectin E (SELE); selectin L (SELL); selectin P (granule membrane protein 140 kDa, antigen CD62) (SELP); serpin peptidase inhibitor, Glade E (nexin, plasminogen activator inhibitor type 1), member 1 (SERPINE1); secretory leukocyte peptidase inhibitor (SLPI); sclerostin (SOST); secreted protein, acidic, cysteine-rich (SPARC, or osteonectin); secreted phosphoprotein 1 (SPP1, or osteopontin); transforming growth factor, alpha (TGFA); thrombomodulin (THBD); tumor necrosis factor (TNF superfamily, member 2; or TNF-alpha) (TNF); tumor necrosis factor receptor superfamily, member 11b (TNFRSF11B, or osteoprotegerin); tumor necrosis factor receptor superfamily, member 1A (TNFRSF1A); tumor necrosis factor receptor superfamily, member 1B (TNFRSF1B); tumor necrosis factor receptor superfamily, member 8 (TNFRSF8); tumor necrosis factor receptor superfamily, member 9 (TNFRSF9); tumor necrosis factor (ligand) superfamily, member 11 (TNFSF11, or RANKL); tumor necrosis factor (ligand) superfamily, member 12 (TNFSF12, or TWEAK); tumor necrosis factor (ligand) superfamily, member 13 (TNFSF13, or APRIL); tumor necrosis factor (ligand) superfamily, member 13b (TNFSF13B, or BAFF); tumor necrosis factor (ligand) superfamily, member 14 (TNFSF14, or LIGHT); tumor necrosis factor (ligand) superfamily, member 18 (TNFSF18); thyroid peroxidase (TPO); vascular cell adhesion molecule 1 (VCAM1); and, vascular endothelial growth factor A (VEGFA).

The term "analyte" in the context of the present teachings can mean any substance to be measured, and can encompass biomarkers, markers, nucleic acids, electrolytes, metabolites, proteins, sugars, carbohydrates, fats, lipids, cytokines, chemokines, growth factors, proteins, peptides, nucleic acids, oligonucleotides, metabolites, mutations, variants, polymorphisms, modifications, fragments, subunits, degradation products and other elements. For simplicity, standard gene symbols may be used throughout to refer not only to genes but also gene products/proteins, rather than using the standard protein symbol; e.g., APOA1 as used herein can refer to the gene APOA1 and also the protein ApoAI. In general, hyphens are dropped from analyte names and symbols herein (IL-6=IL6).

To "analyze" includes determining a value or set of values associated with a sample by measurement of analyte levels in the sample. "Analyze" may further comprise and comparing the levels against constituent levels in a sample or set of samples from the same subject or other subject(s). The biomarkers of the present teachings can be analyzed by any of various conventional methods known in the art. Some such methods include but are not limited to: measuring serum protein or sugar or metabolite or other analyte level, measuring enzymatic activity, and measuring gene expression.

The term "antibody" refers to any immunoglobulin-like molecule that reversibly binds to another with the required selectivity. Thus, the term includes any such molecule that is capable of selectively binding to a biomarker of the present teachings. The term includes an immunoglobulin molecule capable of binding an epitope present on an antigen. The term is intended to encompass not only intact immunoglobulin molecules, such as monoclonal and polyclonal antibodies, but also antibody isotypes, recombinant antibodies, bi-specific antibodies, humanized antibodies, chimeric antibodies, anti-idiopathic (anti-ID) antibodies, single-chain antibodies, Fab fragments, F(ab') fragments, fusion protein antibody fragments, immunoglobulin fragments, $F_v$ fragments, single chain $F_v$ fragments, and chimeras comprising an immunoglobulin sequence and any modifications of the foregoing that comprise an antigen recognition site of the required selectivity.

"Autoimmune disease" encompasses any disease, as defined herein, resulting from an immune response against substances and tissues normally present in the body. Examples of suspected or known autoimmune diseases include rheumatoid arthritis, juvenile idiopathic arthritis, seronegative spondyloarthropathies, ankylosing spondylitis, psoriatic arthritis, antiphospholipid antibody syndrome, autoimmune hepatitis, Behçet's disease, bullous pemphigoid, coeliac disease, Crohn's disease, dermatomyositis, Goodpasture's syndrome, Graves' disease, Hashimoto's disease, idiopathic thrombocytopenic purpura, IgA nephropathy, Kawasaki disease, systemic lupus erythematosus, mixed connective tissue disease, multiple sclerosis, myasthenia gravis, polymyositis, primary biliary cirrhosis, psoriasis, scleroderma, Sjögren's syndrome, ulcerative colitis, vasculitis, Wegener's granulomatosis, temporal arteritis, Takayasu's arteritis, Henoch-Schonlein purpura, leucocytoclastic vasculitis, polyarteritis nodosa, Churg-Strauss Syndrome, and mixed cryoglobulinemic vasculitis.

"Biomarker," "biomarkers," "marker" or "markers" in the context of the present teachings encompasses, without limitation, cytokines, chemokines, growth factors, proteins, peptides, nucleic acids, oligonucleotides, and metabolites, together with their related metabolites, mutations, isoforms, variants, polymorphisms, modifications, fragments, subunits, degradation products, elements, and other analytes or sample-derived measures. Biomarkers can also include mutated proteins, mutated nucleic acids, variations in copy numbers and/or transcript variants. Biomarkers also encompass non-blood borne factors and non-analyte physiological markers of health status, and/or other factors or markers not measured from samples (e.g., biological samples such as bodily fluids), such as clinical parameters and traditional factors for clinical assessments. Biomarkers can also include any indices that are calculated and/or created mathematically. Biomarkers can also include combinations of any one or more of the foregoing measurements, including temporal trends and differences.

A "clinical assessment," or "clinical datapoint" or "clinical endpoint," in the context of the present teachings can refer to a measure of disease activity or severity. A clinical assessment can include a score, a value, or a set of values that can be obtained from evaluation of a sample (or population of samples) from a subject or subjects under determined conditions. A clinical assessment can also be a questionnaire completed by a subject. A clinical assessment can also be predicted by biomarkers and/or other parameters. One of skill in the art will recognize that the clinical assessment for RA, as an example, can comprise, without limitation, one or more of the following: DAS, DAS28, DAS28-ESR, DAS28-CRP, HAQ, mHAQ, MDHAQ, physician global assessment VAS, patient global assessment VAS, pain VAS, fatigue VAS, overall VAS, sleep VAS, SDAI, CDAI, RAPID3, RAPID4, RAPID5, ACR20, ACR50, ACR70, SF-36 (a well-validated measure of general health status), RAMRI score (RAMRIS; or RAMRI scoring system), total Sharp score (TSS), van der Heijde-modified TSS, van der Heijde-modified Sharp score (or Sharp-van der Heijde score (SHS)), Larsen score, TJC, swollen joint count (SJC), CRP titer (or level), and ESR.

The term "clinical parameters" in the context of the present teachings encompasses all measures of the health status of a subject. A clinical parameter can be used to derive a clinical assessment of the subject's disease activity. Clinical parameters can include, without limitation: therapeutic regimen (including but not limited to DMARDs, whether conventional or biologics, steroids, etc.), TJC, SJC, morning stiffness, arthritis of three or more joint areas, arthritis of hand joints, symmetric arthritis, rheumatoid nodules, radiographic changes and other imaging, gender/sex, age, race/ethnicity, disease duration, diastolic and systolic blood pressure, resting heart rate, height, weight, body-mass index, family history, CCP status (i.e., whether subject is positive or negative for anti-CCP antibody), CCP titer, RF status, RF titer, ESR, CRP titer, menopausal status, and whether a smoker/non-smoker.

"Clinical assessment" and "clinical parameter" are not mutually exclusive terms. There may be overlap in members of the two categories. For example, CRP titer can be used as a clinical assessment of disease activity; or, it can be used as a measure of the health status of a subject, and thus serve as a clinical parameter.

The term "computer" carries the meaning that is generally known in the art; that is, a machine for manipulating data according to a set of instructions. For illustration purposes only, FIG. 16 is a high-level block diagram of a computer (1600). As is known in the art, a "computer" can have different and/or other components than those shown in FIG. 16. In addition, the computer 1600 can lack certain illustrated components. Moreover, the storage device (1608) can be local and/or remote from the computer (1600) (such as embodied within a storage area network (SAN)). As is known in the art, the computer (1600) is adapted to execute computer program modules for providing functionality described herein. As used herein, the term "module" refers to computer program logic utilized to provide the specified functionality. Thus, a module can be implemented in hardware, firmware, and/or software. In one embodiment, program modules are stored on the storage device (1608), loaded into the memory (1606), and executed by the processor (1602). Embodiments of the entities described herein can include other and/or different modules than the ones described here. In addition, the functionality attributed to the modules can be performed by other or different modules in other embodiments. Moreover, this description occasionally omits the term "module" for purposes of clarity and convenience.

The term "cytokine" in the present teachings refers to any substance secreted by specific cells of the immune system that carries signals locally between cells and thus has an effect on other cells. The term "cytokines" encompasses "growth factors." "Chemokines" are also cytokines. They are a subset of cytokines that are able to induce chemotaxis in cells; thus, they are also known as "chemotactic cytokines."

"DAIMRK" in the present teachings refers to a specific group, set or panel of biomarkers, as the term "biomarkers" is defined herein. Where the biomarkers of certain embodiments of the present teachings are proteins, the gene symbols and names used herein are to be understood to refer to the protein products of these genes, and the protein products of these genes are intended to include any protein isoforms of these genes, whether or not such isoform sequences are specifically described herein. Where the biomarkers are nucleic acids, the gene symbols and names used herein are to refer to the nucleic acids (DNA or RNA) of these genes, and the nucleic acids of these genes are intended to include any transcript variants of these genes, whether or not such transcript variants are specifically described herein. The DAIMRK group of the present teachings is the group consisting of: apolipoprotein A-I (APOA1); apolipoprotein C-III (APOC3); calprotectin; chemokine (C-C motif) ligand 22 (CCL22); chitinase 3-like 1 (cartilage glycoprotein-39) (CHI3L1, or YKL-40); C-reactive protein, pentraxin-related (CRP); epidermal growth factor (beta-urogastrone) (EGF); intercellular adhesion molecule 1 (ICAM1); ICTP; interleukin 18 (interferon-gamma-inducing factor) (IL18); interleukin 1, beta (IL1B); interleukin 1 receptor antagonist (IL1RN); interleukin 6 (interferon, beta 2) (IL6); interleukin 6 receptor (IL6R); interleukin 8 (IL8); keratan sulfate, or KS; leptin (LEP); matrix metallopeptidase 1 (interstitial collagenase) (MMP1); matrix metallopeptidase 3 (stromelysin 1, progelatinase) (MMP3); pyridinoline (cross-links formed in collagen, derived from three lysine residues), which may be referred to herein as PYD; resistin (RETN); serum amyloid A1 (SAA1); tumor necrosis factor receptor superfamily, member 1A (TNFRSF1A); tumor necrosis factor (ligand) superfamily, member 13b (TNFSF13B, or BAFF); vascular cell adhesion molecule 1 (VCAM1); and, vascular endothelial growth factor A (VEGFA).

Calprotectin is a heteropolymer, comprising two protein subunits of gene symbols S100A8 and S100A9. ICTP is the carboxyterminal telopeptide region of type I collagen, and is liberated during the degradation of mature type I collagen. Type I collagen is present as fibers in tissue; in bone, the type I collagen molecules are crosslinked. The ICTP peptide is immunochemically intact in blood. (For the type I collagen gene, see official symbol COL1A1, HUGO Gene Nomenclature Committee; also known as O14; alpha 1 type I collagen; collagen alpha 1 chain type I; collagen of skin, tendon and bone, alpha-1 chain; and, pro-alpha-1 collagen type 1). Keratan sulfate (KS, or keratosulfate) is not the product of a discrete gene, but refers to any of several sulfated glycosaminoglycans. They are synthesized in the central nervous system, and are found especially in cartilage and bone. Keratan sulfates are large, highly hydrated molecules, which in joints can act as a cushion to absorb mechanical shock.

"DAS" refers to the Disease Activity Score, a measure of the activity of RA in a subject, well-known to those of skill in the art. See D. van der Heijde et al., *Ann. Rheum. Dis.* 1990, 49(11):916-920. "DAS" as used herein refers to this particular Disease Activity Score. The "DAS28" involves the evaluation of 28 specific joints. It is a current standard well-recognized in research and clinical practice. Because the DAS28 is a well-recognized standard, it is often simply referred to as "DAS." Unless otherwise specified, "DAS" herein will encompass the DAS28. A DAS28 can be calculated for an RA subject according to the standard as outlined at the das-score.nl website, maintained by the Department of Rheumatology of the University Medical Centre in Nijmegen, the Netherlands. The number of swollen joints, or swollen joint count out of a total of 28 (SJC28), and tender joints, or tender joint count out of a total of 28 (TJC28) in each subject is assessed. In some DAS28 calculations the subject's general health (GH) is also a factor, and can be measured on a 100 mm Visual Analogue Scale (VAS). GH may also be referred to herein as PG or PGA, for "patient global health assessment" (or merely "patient global assessment"). A "patient global health assessment VAS," then, is GH measured on a Visual Analogue Scale.

"DAS28-CRP" (or "DAS28CRP") is a DAS28 assessment calculated using CRP in place of ESR (see below). CRP is produced in the liver. Normally there is little or no CRP circulating in an individual's blood serum—CRP is generally present in the body during episodes of acute inflammation or infection, so that a high or increasing amount of CRP in blood serum can be associated with acute infection or inflammation. A blood serum level of CRP greater than 1 mg/dL is usually considered high. Most inflammation and infections result in CRP levels greater than 10 mg/dL. The amount of CRP in subject sera can be quantified using, for example, the DSL-10-42100 ACTIVE® US C-Reactive Protein Enzyme-Linked Immunosorbent Assay (ELISA), developed by Diagnostics Systems Laboratories, Inc. (Webster, Tex.). CRP production is associated with radiological progression in RA. See M. Van Leeuwen et al., *Br. J. Rheum.* 1993, 32(suppl.):9-13). CRP is thus considered an appropriate alternative to ESR in measuring RA disease activity. See R. Mallya et al., *J. Rheum.* 1982, 9(2):224-228, and F. Wolfe, *J. Rheum.* 1997, 24:1477-1485.

The DAS28-CRP can be calculated according to either of the formulas below, with or without the GH factor, where "CRP" represents the amount of this protein present in a subject's blood serum in mg/L, "sqrt" represents the square root, and "ln" represents the natural logarithm:

DAS28-CRP with GH (or DAS28-CRP4)=(0.56*sqrt (TJC28)+0.28*sqrt(SJC28)+0.36*ln(CRP+1))+ (0.014*GH)+0.96; (a)

or,

DAS28-CRP without GH (or DAS28-CRP3)= (0.56*sqrt(TJC28)+0.28*sqrt(SJC28)+0.36*ln (CRP+1))*1.10+1.15. (b)

The "DAS28-ESR" is a DAS28 assessment wherein the ESR for each subject is also measured (in mm/hour). The DAS28-ESR can be calculated according to the formula:

DAS28-ESR with GH (or DAS28-ESR4)=0.56*sqrt (TJC28)+0.28*sqrt(SJC28)+0.70*ln(ESR)+ 0.014*GH; (a)

or,

DAS28-ESR without GH=0.56*sqrt(TJC28)+ 0.28*sqrt(SJC28)+0.70*ln(ESR)*1.08+0.16. (b)

Unless otherwise specified herein, the term "DAS28," as used in the present teachings, can refer to a DAS28-ESR or DAS28-CRP, as obtained by any of the four formulas described above; or, DAS28 can refer to another reliable DAS28 formula as may be known in the art.

A "dataset" is a set of numerical values resulting from evaluation of a sample (or population of samples) under a desired condition. The values of the dataset can be obtained, for example, by experimentally obtaining measures from a sample and constructing a dataset from these measurements; or alternatively, by obtaining a dataset from a service provider such as a laboratory, or from a database or a server on which the dataset has been stored.

In certain embodiments of the present teachings, a dataset of values is determined by measuring at least two biomarkers from the DAIMRK group. This dataset is used by an interpretation function according to the present teachings to derive a DAI score (see definition, "DAI score," below), which provides a quantitative measure of inflammatory disease activity in a subject. In the context of RA, the DAI score thus derived from this dataset is also useful in predicting a DAS28 score, with a high degree of association, as is shown in the Examples below. The at least two markers can comprise: (APOA1 and IL8), (Calprotectin and CRP), (Calprotectin and EGF), (Calprotectin and IL8), (CRP and APOA1), (CRP and APOC3), (CRP and CCL22), (CRP and CHI3L1), (CRP and EGF), (CRP and ICAM1), (CRP and IL1B), (CRP and IL6), (CRP and IL6R), (CRP and IL8), (CRP and LEP), (CRP and MMP1), (CRP and MMP3), (CRP and RETN), (CRP and SAA1), (CRP and TNFRSF1A), (CRP and VCAM1), (CRP and VEGF), (EGF and APOA1), (EGF and CHI3L1), (EGF and ICAM1), (EGF and IL8), (EGF and LEP), (EGF and MMP1), (EGF and TNFRSF1A), (EGF and VCAM1), (ICAM1 and IL8), (IL1RN and CRP), (IL1RN and EGF), (IL1RN and IL8), (IL8 and APOC3), (IL8 and CCL22), (IL8 and CHI3L1), (IL8 and IL6), (IL8 and IL6R), (IL8 and TNFRSF1A), (LEP and IL8), (MMP3 and IL8), (RETN and IL8), (SAA1 and EGF), (SAA1 and IL8), (SAA1 and LEP), (SAA1 and RETN), or (VCAM1 and IL8). The at least two markers can also comprise (calprotectin and CHI3L1), (calprotectin and interleukin), (calprotectin and LEP), (calprotectin and pyridinoline), (calprotectin and RETN), (CCL22 and calprotectin), (CCL22 and CRP), (CCL22 and IL6), (CCL22 and SAA1), (CRP and calprotectin), (CRP and CHI3L1), (CRP and EGF), (CRP and ICAM1), (CRP and IL1B), (CRP and IL1RN), (CRP and IL6), (CRP and IL6R), (CRP and IL8), (CRP and LEP), (CRP and MMP1), (CRP and MMP3), (CRP and pyridinoline), (CRP and RETN), (CRP and SAA1), (CRP and TNFRSF1A), (CRP and VCAM1), (CRP and VEGFA), (EGF and calprotectin), (EGF and IL6), (EGF and SAA1), (ICAM1 and calprotectin), (ICAM1 and IL6), (ICAM1 and SAA1), (IL1B and calprotectin), (IL1B and IL6), (IL1B and MMP3), (IL1B and SAA1), (IL6 and calprotectin), (IL6 and CHI3L1), (IL6 and IL1RN), (IL6 and IL8), (IL6 and LEP), (IL6 and MMP1), (IL6 and MMP3), (IL6 and pyridinoline), (IL6 and RETN), (IL6 and SAA1), (IL6 and TNFRSF1A), (IL6 and VCAM1), (IL6 and VEGFA), (IL6R and calprotectin), (IL6R and IL6), (IL6R and SAA1), (IL8 and calprotectin), (IL8 and MMP3), (IL8 and SAA1), (MMP1 and calprotectin), (MMP1 and SAA1), (MMP3 and calprotectin), (MMP3 and CHI3L1), (MMP3 and SAA1), (SAA1 and calprotectin), (SAA1 and CHI3L1), (SAA1 and IL1RN), (SAA1 and LEP), (SAA1 and pyridinoline), (SAA1 and RETN), (SAA1 and TNFRSF1A), (SAA1 and VCAM1), (SAA1 and VEGFA), (TNFRSF1A and calprotectin), (VCAM1 and calprotectin); or, (VEGFA and calprotectin).

The term "disease" in the context of the present teachings encompasses any disorder, condition, sickness, ailment, etc. that manifests in, e.g., a disordered or incorrectly functioning organ, part, structure, or system of the body, and results from, e.g., genetic or developmental errors, infection, poisons, nutritional deficiency or imbalance, toxicity, or unfavorable environmental factors.

A "disease activity index score," "DAI score," or simply "DAI," in the context of the present teachings, is a score that provides a quantitative measure of inflammatory disease activity or the state of inflammatory disease in a subject. A set of data from particularly selected biomarkers, such as markers from the DAIMRK or ALLMRK set, is input into an interpretation function according to the present teachings to derive the DAI score. The interpretation function, in some embodiments, can be created from predictive or multivariate modeling based on statistical algorithms. Input to the interpretation function can comprise the results of testing two or more of the DAIMRK or ALLMRK set of biomarkers, alone or in combination with clinical parameters and/or clinical assessments, also described herein. In some embodiments of the present teachings, the DAI score is a quantitative measure of autoimmune disease activity. In some embodiments, the DAI score is a quantitative measure of RA disease activity.

A DMARD can be conventional or biologic. Examples of DMARDs that are generally considered conventional include, but are not limited to, MTX, azathioprine (AZA), bucillamine (BUC), chloroquine (CQ), ciclosporin (CSA, or cyclosporine, or cyclosporin), doxycycline (DOXY), hydroxychloroquine (HCQ), intramuscular gold (IM gold), leflunomide (LEF), levofloxacin (LEV), and sulfasalazine (SSZ). Examples of other conventional DMARDs include, but are not limited to, folinic acid, D-pencillamine, gold auranofin, gold aurothioglucose, gold thiomalate, cyclophosphamide, and chlorambucil. Examples of biologic DMARDs (or biologic drugs) include but are not limited to biological agents that target the tumor necrosis factor (TNF)-alpha molecules and the TNF inhibitors, such as infliximab, adalimumab, etanercept and golimumab. Other classes of biologic DMARDs include IL1 inhibitors such as anakinra, T-cell modulators such as abatacept, B-cell modulators such as rituximab, and IL6 inhibitors such as tocilizumab.

"Inflammatory disease" in the context of the present teachings encompasses, without limitation, any disease, as defined herein, resulting from the biological response of vascular tissues to harmful stimuli, including but not limited to such stimuli as pathogens, damaged cells, irritants, antigens and, in the case of autoimmune disease, substances and tissues normally present in the body. Examples of inflammatory disease include RA, atherosclerosis, asthma, autoimmune diseases, chronic inflammation, chronic prostatitis, glomerulonephritis, hypersensitivities, inflammatory bowel diseases, pelvic inflammatory disease, reperfusion injury, transplant rejection, and vasculitis.

"Interpretation function," as used herein, means the transformation of a set of observed data into a meaningful determination of particular interest; e.g., an interpretation function may be a predictive model that is created by utilizing one or more statistical algorithms to transform a dataset of observed biomarker data into a meaningful determination of disease activity or the disease state of a subject.

"Measuring" or "measurement" in the context of the present teachings refers to determining the presence, absence, quantity, amount, or effective amount of a substance in a clinical or subject-derived sample, including the concentration levels of such substances, or evaluating the values or categorization of a subject's clinical parameters.

"Performance" in the context of the present teachings relates to the quality and overall usefulness of, e.g., a model, algorithm, or diagnostic or prognostic test. Factors to be considered in model or test performance include, but are not limited to, the clinical and analytical accuracy of the test, use characteristics such as stability of reagents and various components, ease of use of the model or test, health or economic value, and relative costs of various reagents and components of the test.

A "population" is any grouping of subjects of like specified characteristics. The grouping could be according to, for example but without limitation, clinical parameters, clinical assessments, therapeutic regimen, disease status (e.g. with disease or healthy), level of disease activity, etc. In the context of using the DAI score in comparing disease activity between populations, an aggregate value can be determined based on the observed DAI scores of the subjects of a population; e.g., at particular timepoints in a longitudinal study. The aggregate value can be based on, e.g., any mathematical or statistical formula useful and known in the art for arriving at a meaningful aggregate value from a collection of individual datapoints; e.g., mean, median, median of the mean, etc.

A "predictive model," which term may be used synonymously herein with "multivariate model" or simply a "model," is a mathematical construct developed using a statistical algorithm or algorithms for classifying sets of data. The term "predicting" refers to generating a value for a datapoint without actually performing the clinical diagnostic procedures normally or otherwise required to produce that datapoint; "predicting" as used in this modeling context should not be understood solely to refer to the power of a model to predict a particular outcome. Predictive models can provide an interpretation function; e.g., a predictive model can be created by utilizing one or more statistical algorithms or methods to transform a dataset of observed data into a meaningful determination of disease activity or the disease state of a subject. See Calculation of the DAI score for some examples of statistical tools useful in model development.

A "prognosis" is a prediction as to the likely outcome of a disease. Prognostic estimates are useful in, e.g., determining an appropriate therapeutic regimen for a subject.

A "quantitative dataset," as used in the present teachings, refers to the data derived from, e.g., detection and composite measurements of a plurality of biomarkers (i.e., two or more) in a subject sample. The quantitative dataset can be used in the identification, monitoring and treatment of disease states, and in characterizing the biological condition of a subject. It is possible that different biomarkers will be detected depending on the disease state or physiological condition of interest.

A "sample" in the context of the present teachings refers to any biological sample that is isolated from a subject. A sample can include, without limitation, a single cell or multiple cells, fragments of cells, an aliquot of body fluid, whole blood, platelets, serum, plasma, red blood cells, white blood cells or leucocytes, endothelial cells, tissue biopsies, synovial fluid, lymphatic fluid, ascites fluid, and interstitial or extracellular fluid. The term "sample" also encompasses the fluid in spaces between cells, including gingival crevicular fluid, bone marrow, cerebrospinal fluid (CSF), saliva, mucous, sputum, semen, sweat, urine, or any other bodily fluids. "Blood sample" can refer to whole blood or any fraction thereof, including blood cells, red blood cells, white blood cells or leucocytes, platelets, serum and plasma. Samples can be obtained from a subject by means including but not limited to venipuncture, excretion, ejaculation, massage, biopsy, needle aspirate, lavage, scraping, surgical incision, or intervention or other means known in the art.

A "score" is a value or set of values selected so as to provide a quantitative measure of a variable or characteristic of a subject's condition, and/or to discriminate, differentiate or otherwise characterize a subject's condition. The value(s) comprising the score can be based on, for example, a measured amount of one or more sample constituents obtained from the subject, or from clinical parameters, or from clinical assessments, or any combination thereof. In certain embodiments the score can be derived from a single constituent, parameter or assessment, while in other embodiments the score is derived from multiple constituents, parameters and/or assessments. The score can be based upon or derived from an interpretation function; e.g., an interpretation function derived from a particular predictive model using any of various statistical algorithms known in the art. A "change in score" can refer to the absolute change in score, e.g. from one timepoint to the next, or the percent change in score, or the change in the score per unit time (i.e., the rate of score change).

"Statistically significant" in the context of the present teachings means an observed alteration is greater than what would be expected to occur by chance alone (e.g., a "false positive"). Statistical significance can be determined by any of various methods well-known in the art. An example of a commonly used measure of statistical significance is the p-value. The p-value represents the probability of obtaining a given result equivalent to a particular datapoint, where the datapoint is the result of random chance alone. A result is often considered highly significant (not random chance) at a p-value less than or equal to 0.05.

A "subject" in the context of the present teachings is generally a mammal. The subject can be a patient. The term "mammal" as used herein includes but is not limited to a human, non-human primate, dog, cat, mouse, rat, cow, horse, and pig. Mammals other than humans can be advantageously used as subjects that represent animal models of inflammation. A subject can be male or female. A subject can be one who has been previously diagnosed or identified as having an inflammatory disease. A subject can be one who has already undergone, or is undergoing, a therapeutic intervention for an inflammatory disease. A subject can also be one who has not been previously diagnosed as having an inflammatory disease; e.g., a subject can be one who exhibits one or more symptoms or risk factors for an inflammatory condition, or a subject who does not exhibit symptoms or risk factors for an inflammatory condition, or a subject who is asymptomatic for inflammatory disease.

A "therapeutic regimen," "therapy" or "treatment(s)," as described herein, includes all clinical management of a subject and interventions, whether biological, chemical, physical, or a combination thereof, intended to sustain, ameliorate, improve, or otherwise alter the condition of a subject. These terms may be used synonymously herein. Treatments include but are not limited to administration of prophylactics or therapeutic compounds (including conventional DMARDs, biologic DMARDs, non-steroidal anti-inflammatory drugs (NSAID's) such as COX-2 selective inhibitors, and corticosteroids), exercise regimens, physical therapy, dietary modification and/or supplementation, bariatric surgical intervention, administration of pharmaceuticals and/or anti-inflammatories (prescription or over-the-counter), and any other treatments known in the art as efficacious in preventing, delaying the onset of, or ameliorating disease. A "response to treatment" includes a subject's response to any of the above-described treatments, whether biological, chemical, physical, or a combination of the foregoing. A "treatment course" relates to the dosage, duration, extent, etc. of a particular treatment or therapeutic regimen.

Use of the Present Teachings in the Diagnosis and Prognosis of Disease

In some embodiments of the present teachings, biomarkers selected from the DAIMARK or ALLMRK group can be used in the derivation of a DAI score, as described herein, which DAI score can be used to provide diagnosis, prognosis and monitoring of disease state and/or disease activity in inflammatory disease and in autoimmune disease. In certain embodiments, the DAI score can be used to provide diagnosis, prognosis and monitoring of disease state and/or disease activity of RA.

Identifying the state of inflammatory disease in a subject allows for a prognosis of the disease, and thus for the informed selection of, initiation of, adjustment of or increasing or decreasing various therapeutic regimens in order to delay, reduce or prevent that subject's progression to a more advanced disease state. In some embodiments, therefore, subjects can be identified as having a particular level of inflammatory disease activity and/or as being at a particular state of disease, based on the determination of their DAI scores, and so can be selected to begin or accelerate treatment, as treatment is defined herein, to prevent or delay the further progression of inflammatory disease. In other embodiments, subjects that are identified via their DAI scores as having a particular level of inflammatory disease activity, and/or as being at a particular state of inflammatory disease, can be selected to have their treatment decreased or discontinued, where improvement or remission in the subject is seen.

Blood-based biomarkers that report on the current rate of joint destructive processes could also present a powerful prognostic approach to identifying subjects at highest risk of accelerated bone and cartilage damage. In some embodiments of the present teachings, biomarkers from the DAIMRK or ALLMRK group can be measured from subjects' or a subject's samples obtained at various time points (e.g., longitudinally), to obtain a series of DAI scores, and the scores can then be associated with radiological results (such as, e.g., those obtained by TSS) at various time points and so provide a measurement of disease progression. See Example 2. The association of the DAI scores with, e.g., change of TSS results can be analyzed statistically for correlation (e.g., Spearman correlation) using multivariate analysis to create single time point or longitudinal hierarchical linear models and ensure accuracy. Serum biomarkers of the DAIMRK or ALLMRK group can thus be used as an alternative to US/radiological results in estimating rates of progression of disease, and predicting joint damage in RA. Predictive models using biomarkers can thus identify subjects who need more aggressive treatment, and earlier, and can thereby improve subject outcomes. In other embodiments, the DAI scores from one subject can be compared with each other, for observations of longitudinal trending as an effect of, e.g., choice or effectiveness of therapeutic regimen, or as a result of the subject's response to treatment regimens, or a comparison of the subject's responses to different regimens.

The present teachings indicate that DAIMRK- or ALLMRK-derived formulas developed in cross-sectional analysis are a strong predictor of disease activity over time; e.g., longitudinally. See Example 2. This is a significant finding from a clinical care perspective. Currently no tests are available to accurately measure and track RA disease activity over time in the clinic. Several recent studies have demonstrated that optimal treatment intervention can dramatically improve clinical outcomes. See Y P M Goekoop-Ruiterman et al., *Ann. Rheum. Dis.* 2009 (Epublication Jan. 20, 2009); C. Grigor et al., *Lancet* 2004, 364:263-269; SMM Verstappen et al., *Ann. Rheum. Dis.* 2007, 66:1443-1449. In these studies disease activity levels are frequently monitored and treatment is increased in nonremission subjects. This concept of treating to remission has been denoted, "Tight Control." Numbers of subjects achieving low disease activity and remission in Tight Control trials is high. In addition, Tight Control cohorts achieve dramatically improved outcomes relative to cohorts receiving standard of care in clinical practice, where remission is less achievable. This is in part due to a lack of easy and sensitive tools to quantitatively monitor disease activity in a real-world clinical practice. Monitoring in these controlled trials is via clinical trial measures, such as DAS and Sharp Scores changes, which are not widely practiced in the real-world clinical setting. The tests developed from various embodiments of the present teachings will facilitate the monitoring of disease activity and Tight Control practices, and result in improved control of disease activity and improved clinical outcomes.

In regards to the need for early and accurate diagnosis of RA, recent advances in RA treatment provide a means for more profound disease management and optimal treatment of RA within the first months of symptom onset, which in turn result in significantly improved outcomes. See F. Wolfe, *Arth. Rheum.* 2000, 43(12):2751-2761; M. Matucci-Cerinic, *Clin. Exp. Rheum.* 2002, 20(4):443-444; and, V. Nell et. al., *Lancet* 2005, 365(9455):199-200. Unfortunately, most subjects do not receive optimal treatment within this narrow window of opportunity, resulting in poorer outcomes and irreversible joint damage, in part because of the limits of current diagnostic laboratory tests. Numerous difficulties exist in diagnosing RA subject. This is in part because at their early stages, symptoms may not be fully differentiated. It is also because diagnostic tests for RA were developed based on phenomenological findings, not the biological basis of disease. In various embodiments of the present teachings, multi-biomarker algorithms can be derived from biomarkers of the DAIMRK set, which have diagnostic potential. See Example 4. This aspect of the present teachings has the potential to improve both the accuracy of RA diagnosis, and the speed of detection of RA.

Rating Disease Activity

In some embodiments of the present teachings, the DAI score, derived as described herein, can be used to rate inflammatory disease activity; e.g., as high, medium or low. In some embodiments of the present teachings, autoimmune disease activity can be so rated. In other embodiments, RA disease activity can be so rated. Using RA disease as an example, because the DAI score correlates well and with high accuracy with clinical assessments of RA (e.g., with the DAS28 score), DAI cut-off scores can be set at predetermined levels to indicate levels of RA disease activity, and to correlate with the cut-offs traditionally established for rating RA activity via DAS28 scores. See Example 3. Because the DAI score correlates well with traditional clinical assessments of inflammatory disease activity, e.g. in RA, in other embodiments of the present teachings bone damage itself in a subject or population, and thus disease progression, can be tracked via the use and application of the DAI score.

These properties of the DAIMRK set of biomarkers can be used for several purposes. On a subject-specific basis, they provide a context for understanding the relative level of disease activity. The DAIMRK-based rating of disease activity can be used, e.g., to guide the clinician in determining treatment, in setting a treatment course, and/or to inform the clinician that the subject is in remission. Moreover, it provides a means to more accurately assess and document the qualitative level of disease activity in a subject. It is also useful from the perspective of assessing clinical differences among populations of subjects within a practice. For example, this tool can be used to assess the relative efficacy of different treatment modalities. Moreover, it is also useful from the perspective of assessing clinical differences among different practices. This would allow physicians to determine what global level of disease control is achieved by their colleagues, and/or for healthcare management groups to compare their results among different practices for both cost and comparative effectiveness.

Subject Screening

Certain embodiments of the present teachings can also be used to screen subject populations in any number of settings. For example, a health maintenance organization, public health entity or school health program can screen a group of subjects to identify those requiring interventions, as described above. Other embodiments of these teachings can be used to collect disease activity data on one or more populations of subjects, to identify subject disease status in the aggregate, in order to, e.g., determine the effectiveness of the clinical management of a population, or determine gaps in clinical management. Insurance companies (e.g., health, life, or disability) may request the screening of applicants in the process of determining coverage for possible intervention. Data collected in such population screens, particularly when tied to any clinical progression to conditions such as inflammatory disease and RA, will be of value in the operations of, for example, health maintenance organizations, public health programs and insurance companies.

Such data arrays or collections can be stored in machine-readable media and used in any number of health-related data management systems to provide improved healthcare services, cost-effective healthcare, and improved insurance operation, among other things. See, e.g., U.S. Patent Application No. 2002/0038227; U.S. Patent Application No. 2004/0122296; U.S. Patent Application No. 2004/0122297; and U.S. Pat. No. 5,018,067. Such systems can access the data directly from internal data storage or remotely from one or more data storage sites as further detailed herein. Thus, in a health-related data management system, wherein it is important to manage inflammatory disease progression for a population in order to reduce disease-related employment productivity loss, disability and surgery, and thus reduce healthcare costs in the aggregate, various embodiments of the present teachings provide an improvement comprising the use of a data array encompassing the biomarker measurements as defined herein, and/or the resulting evaluation of disease status and activity from those biomarker measurements.

Measuring Accuracy and Performance of the Present Teachings

The performance of the present teachings can be assessed in any of various ways. Assessing the performance of an embodiment of the present teachings can provide a measurement of the accuracy of that embodiment, where, e.g., that embodiment is a predictive model, or a test, assay, method or procedure, whether diagnostic or prognostic. This accuracy assessment can relate to the ability of the predictive model or the test to determine the inflammatory disease activity status of a subject or population. In other embodiments, the performance assessment relates to the accuracy of the predictive model or test in distinguishing between subjects with or without inflammatory disease. In other embodiments, the assessment relates to the accuracy of the predictive model or test in distinguishing between states of inflammatory disease in one subject at different time points.

The distinguishing ability of the predictive model or test can be based on whether the subject or subjects have a significant alteration in the levels of one or more biomarkers. In some embodiments a significant alteration, in the context of the present teachings, can mean that the measurement of the biomarkers, as represented by the DAI score computed by the DAI formula as generated by the predictive model, is different than some predetermined DAI cut-off point (or threshold value) for those biomarkers when input to the DAI formula as described herein. This significant alteration in biomarker levels as reflected in differing DAI scores can therefore indicate that the subject has inflammatory disease, or is at a particular state or severity of inflammatory disease. The difference in the levels of biomarkers between the subject and normal, in those embodiments where such comparisons are done, is preferably statistically significant, and can be an increase in biomarker level or levels, or a decrease in biomarker level or levels. In some embodiments of the present teachings, a significant alteration can mean that a DAI score is derived from measuring the levels of one or more biomarkers, and this score alone, without comparison to some predetermined cut-off point (or threshold value) for those biomarkers, indicates that the subject has inflammatory disease or has a particular state of inflammatory disease. Further, achieving increased analytical and clinical accuracy may require that combinations of two or more biomarkers be used together in panels, and combined with mathematical algorithms derived from predictive models to obtain the DAI score.

Use of statistical values such as the AUC, and specifically the AUC as it relates to the ROC curve, encompassing all potential threshold or cut-off point values is generally used to quantify predictive model performance. Acceptable degrees of accuracy can be defined. In certain embodiments of the present teachings, an acceptable degree of accuracy can be one in which the AUC for the ROC curve is 0.60 or higher.

In general, defining the degree of accuracy for the relevant predictive model or test (e.g., cut-off points on a ROC curve), defining an acceptable AUC value, and determining the acceptable ranges in relative concentration of what constitutes an effective amount of the biomarkers of the present teachings, allows one of skill in the art to use the biomarkers of the present teachings to identify inflammatory disease activity in subjects or populations with a pre-determined level of predictability and performance.

In various embodiments of the present teachings, measurements from multiple biomarkers, such as those of the DAIMRK set, can be combined into a single value, the DAI score, using various statistical analyses and modeling techniques as described herein. Because the DAI score demonstrates strong association with established disease activity assessments, such as the DAS28, the DAI score can provide a quantitative measure for monitoring the extent of subject disease activity, and response to treatment. Example 1 below, e.g., demonstrates that DAI scores are strongly associated with DAS28; thus, DAI provides an accurate quantitative measure of subject disease activity. See also FIG. 1 et seq., in which are shown DAI scores based on sets of biomarkers, which scores demonstrate a strong association with DAS28-CRP, as evidenced by the AUC values shown (e.g., greater than or equal to 0.65).

Calculation of the DAI Score

In some embodiments of the present teachings, inflammatory disease activity in a subject is measured by: determining the levels in inflammatory disease subject serum of two or more biomarkers selected from the DAIMRK set, then applying an interpretation function to transform the biomarker levels into a single DAI score, which provides a quantitative measure of inflammatory disease activity in the subject, correlating well with traditional clinical assessments of inflammatory disease activity (e.g., a DAS28 or CDAI score in RA), as is demonstrated in the Examples below. In some embodiments, the disease activity so measured relates to an autoimmune disease. In some embodiments, the disease activity so measured relates to RA.

In some embodiments, the interpretation function is based on a predictive model. Established statistical algorithms and methods well-known in the art, useful as models or useful in designing predictive models, can include but are not limited to: analysis of variants (ANOVA); Bayesian networks; boosting and Ada-boosting; bootstrap aggregating (or bagging) algorithms; decision trees classification techniques, such as Classification and Regression Trees (CART), boosted CART, Random Forest (RF), Recursive Partitioning Trees (RPART), and others; Curds and Whey (CW); Curds and Whey-Lasso; dimension reduction methods, such as principal component analysis (PCA) and factor rotation or factor analysis; discriminant analysis, including Linear Discriminant Analysis (LDA), Eigengene Linear Discriminant Analysis (ELDA), and quadratic discriminant analysis; Discriminant Function Analysis (DFA); factor rotation or factor analysis; genetic algorithms; Hidden Markov Models; kernel based machine algorithms such as kernel density estimation, kernel partial least squares algorithms, kernel matching pursuit algorithms, kernel Fisher's discriminate analysis algorithms, and kernel principal components analysis algorithms; linear regression and generalized linear models, including or utilizing Forward Linear Stepwise Regression, Lasso (or LASSO) shrinkage and selection method, and Elastic Net regularization and selection method; glmnet (Lasso and Elastic Net-regularized generalized linear model); Logistic Regression (LogReg); meta-learner algorithms; nearest neighbor methods for classification or regression, e.g. Kth-nearest neighbor (KNN); non-linear regression or classification algorithms; neural networks; partial least square; rules based classifiers; shrunken centroids (SC); sliced inverse regression; Standard for the Exchange of Product model data, Application Interpreted Constructs (StepAIC); super principal component (SPC) regression; and, Support Vector Machines (SVM) and Recursive Support Vector Machines (RSVM), among others. Additionally, clustering algorithms as are known in the art can be useful in determining subject sub-groups.

Logistic Regression is the traditional predictive modeling method of choice for dichotomous response variables; e.g., treatment 1 versus treatment 2. It can be used to model both linear and non-linear aspects of the data variables and provides easily interpretable odds ratios.

Discriminant Function Analysis (DFA) uses a set of analytes as variables (roots) to discriminate between two or more naturally occurring groups. DFA is used to test analytes that are significantly different between groups. A forward stepwise DFA can be used to select a set of analytes that maximally discriminate among the groups studied. Specifically, at each step all variables can be reviewed to determine which will maximally discriminate among groups. This information is then included in a discriminative function, denoted a root, which is an equation consisting of linear combinations of analyte concentrations for the prediction of group membership. The discriminatory potential of the final equation can be observed as a line plot of the root values obtained for each group. This approach identifies groups of analytes whose changes in concentration levels can be used to delineate profiles, diagnose and assess therapeutic efficacy. The DFA model can also create an arbitrary score by which new subjects can be classified as either "healthy" or "diseased." To facilitate the use of this score for the medical community the score can be rescaled so a value of 0 indicates a healthy individual and scores greater than 0 indicate increasing disease activity.

Classification and regression trees (CART) perform logical splits (if/then) of data to create a decision tree. All observations that fall in a given node are classified according to the most common outcome in that node. CART results are easily interpretable—one follows a series of if/then tree branches until a classification results.

Support vector machines (SVM) classify objects into two or more classes. Examples of classes include sets of treatment alternatives, sets of diagnostic alternatives, or sets of prognostic alternatives. Each object is assigned to a class based on its similarity to (or distance from) objects in the training data set in which the correct class assignment of each object is known. The measure of similarity of a new object to the known objects is determined using support vectors, which define a region in a potentially high dimensional space (>R6).

The process of bootstrap aggregating, or "bagging," is computationally simple. In the first step, a given dataset is randomly resampled a specified number of times (e.g., thousands), effectively providing that number of new datasets, which are referred to as "bootstrapped resamples" of data, each of which can then be used to build a model. Then, in the example of classification models, the class of every new observation is predicted by the number of classification models created in the first step. The final class decision is based upon a "majority vote" of the classification models; i.e., a final classification call is determined by counting the number of times a new observation is classified into a given group, and taking the majority classification (33%+for a three-class system). In the example of logistical regression models, if a logistical regression is bagged 1000 times, there will be 1000 logistical models, and each will provide the probability of a sample belonging to class 1 or 2.

Curds and Whey (CW) using ordinary least squares (OLS) is another predictive modeling method. See L. Breiman and JH Friedman, *J. Royal. Stat. Soc. B* 1997, 59(1):3-54. This method takes advantage of the correlations between response variables to improve predictive accuracy, compared with the usual procedure of performing an individual regression of each response variable on the common set of predictor variables X. In CW, $Y=XB*S$, where $Y=(y_{kj})$ with k for the $k^{th}$ patient and j for $j^{th}$ response (j=1 for TJC, j=2 for SJC, etc.), B is obtained using OLS, and S is the shrinkage matrix computed from the canonical coordinate system. Another method is Curds and Whey and Lasso in combination (CW-Lasso). Instead of using OLS to obtain B, as in CW, here Lasso is used, and parameters are adjusted accordingly for the Lasso approach.

Many of these techniques are useful either combined with a biomarker selection technique (such as, for example, forward selection, backwards selection, or stepwise selection), or for complete enumeration of all potential panels of a given size, or genetic algorithms, or they can themselves include biomarker selection methodologies in their own techniques. These techniques can be coupled with information criteria, such as Akaike's Information Criterion (AIC), Bayes Information Criterion (BIC), or cross-validation, to quantify the tradeoff between the inclusion of additional biomarkers and model improvement, and to minimize overfit. The resulting predictive models can be validated in other studies, or cross-validated in the study they were originally trained in, using such techniques as, for example, Leave-One-Out (LOO) and 10-Fold cross-validation (10-Fold CV).

One example of an interpretation function that provides a DAI score, derived from a statistical modeling method as described above, is given by the following function:

$$DAI = b_0 + b_1 * DAIMRK_1^x - b_2 * DAIMRK_2^x - b_3 * DAIMRK_3^x \ldots - b_n * DAIMRK_n^x;$$

where DAI is the DAI score, $b_0$, are constants, and $DAIMRK_{1-n}^x$ are the serum concentrations to the $x^{th}$ power of n different biomarkers selected from the DAIMRK panel. DAI scores thus obtained for RA subjects with known clinical assessments (e.g., DAS28 scores) can then be compared to those known assessments to determine the level of correlation between the two assessments, and hence determine the accuracy of the DAI score and its underlying predictive model. See Examples below for specific formulas and constants.

More generally, the function can be described as:

$$DAI = F(DAIMRK_1^x, DAIMRK_2^x, \ldots, DAIMRK^{-x})$$

where DAI is the DAI score, F is the function, and $DAIMRK_{1-n}^x$ are the serum concentrations to the $x^{th}$ power of n different biomarkers selected from the DAIMRK panel. The function is described in the following paragraph.

An interpretation function for providing a DAI score can also be derived based on models built to predict components of a disease activity assessment, such as DAS28-CRP, rather than predicting disease activity entirely. See Example 11. An example of such a function is given by the following, wherein biomarkers are used to provide improved predicted components of the DAS score:

$$\text{DAI score} = ((0.56*\text{sqrt}(IPTJC))+(0.28*\text{sqrt}(IPSJC))+\\(0.14*PPGA)+(0.36*\ln(CRP/10^6+1))+\\0.96)*10.53+1;$$

$$IPTJC = \text{Improved PTJC} = \max(0.1739*PTJC+\\0.7865*PSJC,0);$$

$$IPSJC = \text{Improved PSJC} = \max(0.1734*PTJC+\\0.7839*PSJC,0);$$

$$PTJC = \text{Prediction of Tender Joint Count} = -38.564+\\3.997*(SAA1)^{1/10}+17.331*(IL6)^{1/10}+4.665*\\(CHI3L1)^{1/10}-15.236*(EGF)^{1/10}+2.651*\\(TNFRSF1A)^{1/10}+2.641*(LEP)^{1/10}+4.026*\\(VEGFA)^{1/10}-1.47*(VCAM1)^{1/10};$$

$$PSJC = \text{Prediction of Swollen Joint Count} = -25.444+\\4.051*(SAA1)^{1/10}+16.154*(IL6)^{1/10}-11.847*\\(EGF)^{1/10}+3.091*(CHI3L1)^{1/10}+0.353*\\(TNFRSF1A)^{1/10};$$

$$PPGA = \text{Prediction of Patient Global Assessment} =\\-13.489+5.474*(IL6)^{1/10}+0.486*(SAA1)^{1/10}+\\2.246*(MMP1)^{1/10}+1.684*(\text{leptin})^{1/10}+4.14*\\(TNFRSF1A)^{1/10}+2.292*(VEGFA)^{1/10}-1.898*\\(EGF)^{1/10}+0.028*(MMP3)^{1/10}-2.892*\\(VCAM1)^{1/10}-0.506*(RETN)^{1/10}$$

in which serum levels x for all biomarkers but CRP are transformed as $x^{1/10}$, units for all biomarkers are in pg/mL, and ln is natural log, or $\log_e$.

Where CRP units are obtained in mg/L and other markers are pg/mL, DAI score=$((0.56*\text{sqrt}(IPTJC))+(0.28*\text{sqrt}(IPSJC))+(0.14*(PPGA))+(0.36*\ln(CRP+1))+0.96)*10.53+1$.

It is understood that if biomarkers are measured in other units, appropriate conversion can be applied to use those measurements in the above interpretation function.

The DAI score can be further rounded and capped, in order to provide a whole number between 1 and 100, the scaled DAI score. To accomplish this, the immediately preceding function can be re-written:

$$\text{scaled DAI score} = \text{round}(\max(\min((0.56*\text{sqrt}(IP\text{-}\\TJC))+(0.28*\text{sqrt}(IPSJC))+(0.14*(PPGA))+\\(0.36*\ln(CRP+1)+0.96)*10.53+1,100),1)).$$

Biomarker gene names provided in the above formulas represent the concentrations of those markers, and will depend on the types of assays used.

In some embodiments of the present teachings, it is not required that the DAI score be compared to any pre-determined "reference," "normal," "control," "standard," "healthy," "pre-disease" or other like index, in order for the DAI score to provide a quantitative measure of inflammatory disease activity in the subject.

In other embodiments of the present teachings, the amount of the biomarker(s) can be measured in a sample and used to derive a DAI score, which DAI score is then compared to a "normal" or "control" level or value, utilizing techniques such as, e.g., reference or discrimination limits or risk defining thresholds, in order to define cut-off points and/or abnormal values for inflammatory disease. The normal level then is the level of one or more biomarkers or combined biomarker indices typically found in a subject who is not suffering from the inflammatory disease under evaluation. Other terms for "normal" or "control" are, e.g., "reference," "index," "baseline," "standard," "healthy," "pre-disease," etc. Such normal levels can vary, based on whether a biomarker is used alone or in a formula combined with other biomarkers to output a score. Alternatively, the normal level can be a database of biomarker patterns from previously tested subjects who did not convert to the inflammatory disease under evaluation over a clinically relevant time period. Reference (normal, control) values can also be derived from, e.g., a control subject or population whose inflammatory disease activity level or state is known. In some embodiments of the present teachings, the reference value can be derived from one or more subjects who have been exposed to treatment for inflammatory disease, or from one or more subjects who are at low risk of developing inflammatory disease, or from subjects who have shown improvements in inflammatory disease activity factors (such as, e.g., clinical parameters as defined herein) as a result of exposure to treatment. In some embodiments the reference value can be derived from one or more subjects who have not been exposed to treatment; for example, samples can be collected from (a) subjects who have received initial treatment for inflammatory disease, and (b) subjects who have received subsequent treatment for inflammatory disease, to monitor the progress of the treatment. A reference value can also be derived from disease activity algorithms or computed indices from population studies.

Systems for Implementing Disease Activity Tests

Tests for measuring disease activity according to various embodiments of the present teachings can be implemented on a variety of systems typically used for obtaining test results, such as results from immunological or nucleic acid detection assays. Such systems may comprise modules that automate sample preparation, that automate testing such as measuring biomarker levels, that facilitate testing of multiple samples, and/or are programmed to assay the same test or different tests on each sample. In some embodiments, the testing system comprises one or more of a sample preparation module, a clinical chemistry module, and an immunoassay module on one platform. Testing systems are typically designed such that they also comprise modules to collect, store, and track results, such as by connecting to and utilizing a database residing on hardware. Examples of these modules include physical and electronic data storage devices as are well-known in the art, such as a hard drive, flash memory, and magnetic tape. Test systems also generally comprise a module for reporting and/or visualizing results. Some examples of reporting modules include a visible display or graphical user interface, links to a database, a printer, etc. See section Machine-readable storage medium, below.

One embodiment of the present invention comprises a system for determining the inflammatory disease activity of a subject. In some embodiments, the system employs a module for applying a DAIMRK or ALLMRK formula to an input comprising the measured levels of biomarkers in a panel, as described herein, and outputting a disease activity index score. In some embodiments, the measured biomarker levels are test results, which serve as inputs to a computer that is programmed to apply the DAIMRK or ALLMRK formula. The system may comprise other inputs in addition to or in combination with biomarker results in order to derive an output disease activity index; e.g., one or more clinical parameters such as therapeutic regimen, TJC, SJC, morning stiffness, arthritis of three or more joint areas, arthritis of hand joints, symmetric arthritis, rheumatoid nodules, radiographic changes and other imaging, gender/sex, age, race/ethnicity, disease duration, height, weight, body-mass index, family history, CCP status, RF status, ESR, smoker/non-smoker, etc. In some embodiments the system can apply the DAIMRK/ALLMRK formula to biomarker level inputs, and then output a disease activity score that can then be analyzed in conjunction with other inputs such as other clinical parameters. In other embodiments, the system is designed to apply the DAIMRK/ALLMRK formula to the biomarker and non-biomarker inputs (such as clinical parameters) together, and then report a composite output disease activity index.

A number of testing systems are presently available that could be used to implement various embodiments of the present teachings. See, for example, the ARCHITECT series of integrated immunochemistry systems—high-throughput, automated, clinical chemistry analyzers (ARCHITECT is a registered trademark of Abbott Laboratories, Abbott Park, Ill. 60064). See C. Wilson et al., "Clinical Chemistry Analyzer Sub-System Level Performance," American Association for Clinical Chemistry Annual Meeting, Chicago, Ill., Jul. 23-27, 2006; and, HJ Kisner, "Product development: the making of the Abbott ARCHITECT," Clin. Lab. Manage. Rev. 1997 November-December, 11(6):419-21; A. Ognibene et al., "A new modular chemiluminescence immunoassay analyser evaluated," Clin. Chem. Lab. Med. 2000 March, 38(3):251-60; JW Park et al., "Three-year experience in using total laboratory automation system," Southeast Asian J. Trop. Med. Public Health 2002, 33 Suppl 2:68-73; D. Pauli et al., "The Abbott Architect c8000: analytical performance and productivity characteristics of a new analyzer applied to general chemistry testing," Clin. Lab. 2005, 51(1-2):31-41.

Another testing system useful for embodiments of the present teachings is the VITROS system (VITROS is a registered trademark of Johnson & Johnson Corp., New Brunswick, N.J.)—an apparatus for chemistry analysis that is used to generate test results from blood and other body fluids for laboratories and clinics. Another testing system is the DIMENSION system (DIMENSION is a registered trademark of Dade Behring Inc., Deerfield Ill.)—a system for the analysis of body fluids, comprising computer software and hardware for operating the analyzers, and analyzing the data generated by the analyzers.

The testing required for various embodiments of the present teachings, e.g. measuring biomarker levels, can be performed by laboratories such as those certified under the Clinical Laboratory Improvement Amendments (42 U.S.C. Section 263(a)), or by laboratories certified under any other federal or state law, or the law of any other country, state or province that governs the operation of laboratories that analyze samples for clinical purposes. Such laboratories include, for example, Laboratory Corporation of America, 358 South Main Street, Burlington, N.C. 27215 (corporate headquarters); Quest Diagnostics, 3 Giralda Farms, Madison, N.J. 07940 (corporate headquarters); and other reference and clinical chemistry laboratories.

Biomarker Selection

The biomarkers and methods of the present teachings allow one of skill in the art to monitor or assess a subject's inflammatory and/or autoimmune disease activity, such as for RA, with a high degree of accuracy. Over 100 markers were initially identified as having increased or decreased concentration levels in subjects or populations with RA relative to subjects without disease, or at different states of disease, or to the subject himself at other timepoints in the evolution or activity of the disease. For the initial comparison of observed biomarker with RA disease activity, the disease activity for each subject was based upon traditional clinical parameters, such as the DAS28 score.

DAIMRK Group of Markers

Analyte biomarkers can be selected for use in the present teachings to form a panel or group of markers. Table 1 describes several specific biomarkers, collectively referred to as the DAIMRK group of biomarkers. The present teachings describe the DAIMRK set of biomarkers as one set or panel of markers that is strongly associated with inflammatory disease, and especially RA, when used in particular combinations to derive a DAI score, based on their correlation with traditional clinical assessments of disease; in the example of RA, by their correlation with DAS28. See Example 1. As an example, one embodiment of the present teachings comprises a method of determining RA disease activity in a subject comprising measuring the levels of at least two biomarkers from Table 1, wherein the at least two biomarkers are selected from the group consisting of apolipoprotein A-I (APOA1); apolipoprotein C-III (APOC3); chemokine (C-C motif) ligand 22 (CCL22); chitinase 3-like 1 (cartilage glycoprotein-39) (CHI3L1); ICTP; C-reactive protein, pentraxin-related (CRP); epidermal growth factor (beta-urogastrone) (EGF); intercellular adhesion molecule 1 (ICAM1); interleukin 18 (interferon-gamma-inducing factor) (IL18); interleukin 1, beta (IL1B); interleukin 1 receptor antagonist (IL1RN); interleukin 6 (interferon, beta 2) (IL6); interleukin 6 receptor (IL6R); interleukin 8 (IL8); keratan sulfate; leptin (LEP); matrix metallopeptidase 1 (interstitial collagenase) (MMP1); matrix metallopeptidase 3 (stromelysin 1, progelatinase) (MMP3); resistin (RETN); calprotectin (heteropolymer of protein subunits S100A8 and S100A9); serum amyloid A1 (SAA1); tumor necrosis factor receptor superfamily, member 1A (TNFRSF1A); vascular cell adhesion molecule 1 (VCAM1); vascular endothelial growth factor A (VEGFA); and, pyridinoline (PYD); then, using these observed biomarker levels to derive a disease activity index score for the subject via an interpretation function, which score provides a quantitative measure of RA disease activity in that subject.

One skilled in the art will recognize that the DAIMRK biomarkers presented herein encompass all forms and variants of these biomarkers, including but not limited to polymorphisms, isoforms, mutants, derivatives, transcript variants, precursors (including nucleic acids and pre- or pro-proteins), cleavage products, receptors (including soluble and transmembrane receptors), ligands, protein-ligand complexes, protein-protein homo- or heteropolymers, post-translationally modified variants (such as, e.g., via cross-linking or glycosylation), fragments, and degradation products, as well as any multi-unit nucleic acid, protein, and glycoprotein structures comprising any of the DAIMRK biomarkers as constituent subunits of the fully assembled structure.

TABLE 1

| DAIMRK No. | Official Symbol* | Official Name* | Other Name(s) | NCBI RefSeq | Entrez Gene ID |
|---|---|---|---|---|---|
| 1 | APOA1 | Apolipoprotein A-I | MGC117399; ApoAI | NP_000030.1 (SEQ ID NO: 1) | 335 |
| 2 | APOC3 | Apolipoprotein C-III | ApoCIII; MGC150353 | NP_000031.1 (SEQ ID NO: 2) | 345 |

TABLE 1-continued

| DAIMRK No. | Official Symbol* | Official Name* | Other Name(s) | NCBI RefSeq | Entrez Gene ID |
|---|---|---|---|---|---|
| 3 | CCL22 | Chemokine (C-C motif) ligand 22 | MDC; A-152E5.1; ABCD-1; DC/B-CK; MGC34554; SCYA22; STCP-1; CC chemokine STCP-1; macrophage-derived chemokine; small inducible cytokine A22; small inducible cytokine subfamily A (Cys-Cys), member 22; stimulated T cell chemotactic protein 1 | NP_002981.2 (SEQ ID NO: 3) | 6367 |
| 4 | CHI3L1 | Chitinase 3-like 1 (cartilage glycoprotein-39) | YKL-40; ASRT7; DKFZp686N19119; FLJ38139; GP39; HC-gp39; HCGP-3P; YYL-40; cartilage glycoprotein-39; chitinase 3-like 1 | NP_001267.2 (SEQ ID NO: 4) | 1116 |
| 5 | CRP | C-reactive protein, pentraxin-related | MGC149895; MGC88244; PTX1 | NP_000558.2 (SEQ ID NO: 5) | 1401 |
| 6 | EGF | Epidermal growth factor (beta-urogastrone) | HOMG4; URG; beta-urogastrone; epidermal growth factor | NP_001954.2 (SEQ ID NO: 6) | 1950 |
| 7 | ICAM1 | Intercellular adhesion molecule 1 | intercellular adhesion molecule 1 (CD54); human rhinovirus receptor; ICAM-1 | NP_000192.2 (SEQ ID NO: 7) | 3383 |
| 8 | N/A | N/A | ICTP | N/A | N/A |
| 9 | IL18 | Interleukin 18 (interferon-gamma-inducing factor) | IGIF; IL-1g; IL1F4; IL-18; MGC12320; IL-1 gamma; interferon-gamma-inducing factor; interleukin-1 gamma | NP_001553.1 (SEQ ID NO: 8) | 3606 |
| 10 | IL1B | Interleukin 1, Beta | IL-1; IL1-BETA; IL1β; IL1F2; catabolin; preinterleukin 1 beta; pro-interleukin-1-beta | NP_000567.1 (SEQ ID NO: 9) | 3553 |
| 11 | IL1RN | Interleukin 1 receptor antagonist | DIRA; ICIL-1RA; IL-1ra3; IL1F3; IL1RA; IRAP; MGC10430; MVCD4; IL1RN (IL1F3); OTTHUMP00000203730; intracellular IL-1 receptor antagonist type II; intracellular interleukin-1 receptor antagonist (icIL-1ra); type II interleukin-1 | NP_000568.1 (SEQ ID NO: 10) | 3557 |

TABLE 1-continued

| DAIMRK No. | Official Symbol* | Official Name* | Other Name(s) | NCBI RefSeq | Entrez Gene ID |
|---|---|---|---|---|---|
| 12 | IL6 | Interleukin 6 (interferon, beta 2) | receptor antagonist IL-6; BSF2; HGF; HSF; IFNB2; B cell stimulatory factor-2; B-cell differentiation factor; CTL differentiation factor; OTTHUMP00000158544; hybridoma growth factor; interleukin BSF-2 | NP_000591.1 (SEQ ID NO: 11) | 3569 |
| 13 | IL6R | Interleukin 6 receptor | IL-6R; CD126; IL-6R-alpha; IL6RA; MGC104991; CD126 antigen; interleukin 6 receptor alpha subunit | NP_000556.1 (SEQ ID NO: 12) | 3570 |
| 14 | IL8 | Interleukin 8 | IL-8; CXCL8; GCP1; LECT; LUCT; LYNAP; MDNCF; MONAP; NAF; NAP-1; T cell chemotactic factor; beta-thromboglobulin-like protein; chemokine (C—X—C motif) ligand 8; emoctakin; granulocyte chemotactic protein 1; lymphocyte-derived neutrophil-activating factor; monocyte-derived neutrophil chemotactic factor; neutrophil-activating peptide 1; small inducible cytokine subfamily B, member 8 | NP_000575.1 (SEQ ID NO: 13) | 3576 |
| 15† | N/A | N/A | keratan sulfate; KS | N/A | N/A |
| 16 | LEP | Leptin | FLJ94114; OB; OBS; leptin (murine obesity homolog); leptin (obesity homolog, mouse); obese, mouse, homolog of; obesity factor | NP_000221.1 (SEQ ID NO: 14) | 3952 |
| 17 | MMP1 | Matrix metallopeptidase 1 (interstitial collagenase) | MMP-1; CLG; CLGN; fibroblast collagenase; matrix metalloprotease 1 | NP_002412.1 (SEQ ID NO: 15) | 4312 |
| 18 | MMP3 | Matrix metallopeptidase 3 (stromelysin 1, progelatinase) | MMP-3; CHDS6; MGC126102; MGC126103; MGC126104; | NP_002413.1 (SEQ ID NO: 16) | 4314 |

TABLE 1-continued

| DAIMRK No. | Official Symbol* | Official Name* | Other Name(s) | NCBI RefSeq | Entrez Gene ID |
|---|---|---|---|---|---|
| 19 | RETN | Resistin | SL-1; STMY; STMY1; STR1; proteoglycanase; transin-1 ADSF; FIZZ3; MGC126603; MGC126609; RETN1; RSTN; XCP1; C/EBP-epsilon regulated myeloid-specific secreted cysteine-rich protein precursor 1; found in inflammatory zone 3 | NP_065148.1 (SEQ ID NO: 17) | 56729 |
| 20‡ | S100A8 | S100 calcium binding protein A8 | Calprotectin; 60B8AG; CAGA; CFAG; CGLA; CP-10; L1Ag; MA387; MIF; MRP8; NIF; P8; myeloid related protein 8; OTTHUMP00000015330; S100 calcium-binding protein A8; S100 calcium-binding protein A8 (calgranulin A); calgranulin A; cystic fibrosis antigen | NP_002955.2 (SEQ ID NO: 18) | 6279 |
|  | S100A9 | S100 calcium binding protein A9 | Calprotectin; 60B8AG; CAGB; CFAG; CGLB; L1AG; L1AG; MAC387; MIF; MRP14; NIF; P14; myeloid related protein 9; S100 calcium-binding protein A9; S100 calcium-binding protein A9 (calgranulin B); calgranulin B | NP_002956.1 (SEQ ID NO: 19) | 6280 |
| 21 | SAA1 | Serum amyloid A1 | MGC111216; PIG4; SAA; TP53I4; tumor protein p53 inducible protein 4 | NP_000322.2 (SEQ ID NO: 20) | 6288 |
| 22 | TNFRSF1A | Tumor necrosis factor receptor superfamily, member 1A | TNFR1; CD120a; FPF; MGC19588; TBP1; TNF-R; TNF-R55; TNFAR; TNFR55; TNFR60; p55; p55-R; p60; tumor necrosis factor binding protein 1; tumor necrosis factor receptor 1; tumor necrosis factor receptor type 1; tumor necrosis factor-alpha receptor | NP_001056.1 (SEQ ID NO: 21) | 7132 |

TABLE 1-continued

| DAIMRK No. | Official Symbol* | Official Name* | Other Name(s) | NCBI RefSeq | Entrez Gene ID |
|---|---|---|---|---|---|
| 23 | TNFSF13B | Tumor necrosis factor (ligand) superfamily, member 13b | BAFF; BLYS; CD257; DTL; TALL1; THANK; TNFSF20; ZTNF4; B cell activation factor | NP_001139117.1; (SEQ ID NO: 22) NP_006564.1 (SEQ ID NO: 23) | 10673 |
| 24 | VCAM1 | Vascular cell adhesion molecule 1 | VCAM-1; CD106; DKFZp779G2333; INCAM-100; MGC99561; CD106 antigen | NP_001069.1 (SEQ ID NO: 24) | 7412 |
| 25 | VEGFA | Vascular endothelial growth factor A | RP1-261G23.1; MGC70609; MVCD1; VEGF; VPF; vascular endothelial growth factor isoform VEGF165; vascular permeability factor | NP_001020539.2 (SEQ ID NO: 25) | 7422 |
| 26 | N/A | N/A | PYD, pyridinoline | N/A | N/A |

*HUGO Gene Nomenclature Committee, as of Sep. 25, 2009; accession numbers refer to sequence versions in NCBI database as of Sep. 25, 2009.
†Keratan sulfate; not a discrete gene
‡Calprotectin heteropolymer
N/A = Not applicable to this analyte Biological Significance of the DAIMRK Group of Markers The present teachings describe a robust, stepwise development process for identifying a panel or panels of biomarkers that are strongly predictive of autoimmune disease activity. Multivariate algorithmic combinations of specific biomarkers as described herein exceed the prognostic and predictive power of individual biomarkers known in the art, because the combinations comprise biomarkers that represent a broad range of disease mechanisms, which no individual biomarker does. As a consequence of the diversity of pathways represented by the combinations as taught herein, the methods of the present teachings are useful in the clinical assessment of individual subjects, despite the heterogeneity of the pathology of the disease assessed.

The group of biomarkers comprising the DAIMRK set, as an example, was identified through a selection process comprising rigorous correlation studies of an initial large, comprehensive set of candidate protein biomarkers, the ALL-MRK set (also described herein). See, e.g., Example 1. All of the biomarkers that resulted from these correlation studies, and that make up the DAIMRK set, are known in the art to play key roles in the pathology of the autoimmune disease, RA. The methodology employed in selecting the DAIMRK biomarkers thus resulted in a set of markers especially useful in quantifying RA disease activity, by providing the clinician with a unique and broad look at RA disease biology. The DAIMRK set of biomarkers of the present teachings are thus more effective in quantifying disease activity than single biomarkers or randomly selected groupings of biomarkers.

By demonstration of the key roles of the resulting DAIMRK markers in RA pathology, the DAIMRK set comprises: the endogenous form of the recombinant molecule anakinra, an FDA-approved biologic therapy for RA (IL1RN); the target of anakinra, IL1B, an inflammatory mediator and key pathologic regulator in RA; key mediators of the IL6 pathway (IL6 and IL6R) and the TNF pathway (TNFRSF1A), which are also targets of biologic therapies in RA; IL8, which modulates neutrophil migration and activation, neutrophils having a key role in RA disease, as they comprise the majority of infiltrating inflammatory cells in RA synovial fluid and release a variety of disease mediators; calprotectin, which has a role in modulating neutrophil activation, in addition to its role in TLR4 inflammatory signaling; CCL22, a key modulator of humoral immunity and B cell activation, and which recruits T cells to the rheumatoid synovium; the pro-angiogenic proteins VEGFA and IL8, which also attract leukocytes to the RA joint; the endothelial adhesion and activation biomarkers ICAM1 and VCAM1; markers derived in large part from fibroblasts, including IL6, IL8, VEGFA, EGF, MMP1 and MMP3; CHI3L1, which is highly elevated in RA joints and thought to modulate intra-articular matrix; bone and cartilage matrix breakdown products of RA joints, including ICTP, keratan sulfate, and PYD; lipid-associated proteins LEP, RETN, APOA1 and APOC3; and, two key acute phase proteins, CRP and SAA1, which reflect the role of RA inflammation in inducing the hepatic acute phase response.

Additionally, because the serum levels of certain protein biomarkers of the DAIMRK set are known to fluctuate in an individual, depending on disease activity, in some embodiments of the present teachings the clinician could select those biomarkers for generating a DAI score, and thus obtain a more concise overview of the subject's present disease activity status.

Moreover, the process of comprehensive candidate biomarker identification and subsequent staged correlation-based analyses in a series of independent cohorts, as described in the Examples that follow, results in the identification of a panel or panels of biomarkers that have significant correlation to disease activity.

Model Development Process

An exemplary method for developing predictive models to determine the inflammatory disease activity of a subject or population is shown by the flow diagram of FIG. 6 (200). Biomarker data from a representative population, as described herein, is obtained (202). This biomarker data can be derived through a variety of methods, including prospective, retrospective, cross-sectional, or longitudinal studies, that involve interventions or observations of the representative subjects or populations from one or more timepoints. The biomarker data can be obtained from a single study or multiple studies. Subject and population data can generally include data pertaining to the subjects' disease status and/or clinical assessments, which can be used for training and validating the algorithms for use in the present teachings, wherein the values of the biomarkers described herein are correlated to the desired clinical measurements.

Data within the representative population dataset is then prepared (204) so as to fit the requirements of the model that will be used for biomarker selection, described below. A variety of methods of data preparation can be used, such as transformations, normalizations, and gap-fill techniques including nearest neighbor interpolation or other pattern recognition techniques. The data preparation techniques that are useful for different model types are well-known in the art. See Examples, below.

Biomarkers are then selected for use in the training of the model to determine inflammatory disease activity (206). Various models can be used to inform this selection, and biomarker data are chosen from the dataset providing the most reproducible results. Methods to evaluate biomarker performance can include, e.g., bootstrapping and cross-validation.

After the biomarkers are selected, the model to be used to determine inflammatory disease activity can be selected. For specific examples of statistical methods useful in designing predictive models, see Calculation of the DAI score.

For the particular selection model used with a dataset, biomarkers can be selected based on such criteria as the biomarker's ranking among all candidate markers, the biomarker's statistical significance in the model, and any improvement in model performance when the biomarker is added to the model. Tests for statistical significance can include, for example, correlation tests, t-tests, and analysis of variance (ANOVA). Models can include, for example, regression models such as regression trees and linear models, and classification models such as logistic regression, Random Forest, SVM, tree models, and LDA. Examples of these are described herein.

In those cases where individual biomarkers are not alone indicative of inflammatory disease activity, biomarker combinations can be applied to the selection model. Instead of univariate biomarker selection, for example, multivariate biomarker selection can be used. One example of an algorithm useful in multivariate biomarker selection is a recursive feature selection algorithm. Biomarkers that are not alone good indicators of inflammatory disease activity may still be useful as indicators when in combination with other biomarkers, in a multivariate input to the model, because each biomarker may bring additional information to the combination that would not be informative where taken alone.

Next, selection, training and validation is performed on the model for assessing disease activity (208). Models can be selected based on various performance and/or accuracy criteria, such as are described herein. By applying datasets to different models, the results can be used to select the best models, while at the same time the models can be used to determine which biomarkers are statistically significant for inflammatory disease activity. Combinations of models and biomarkers can be compared and validated in different datasets. The comparisons and validations can be repeated in order to train and/or choose a particular model.

Figure 7:
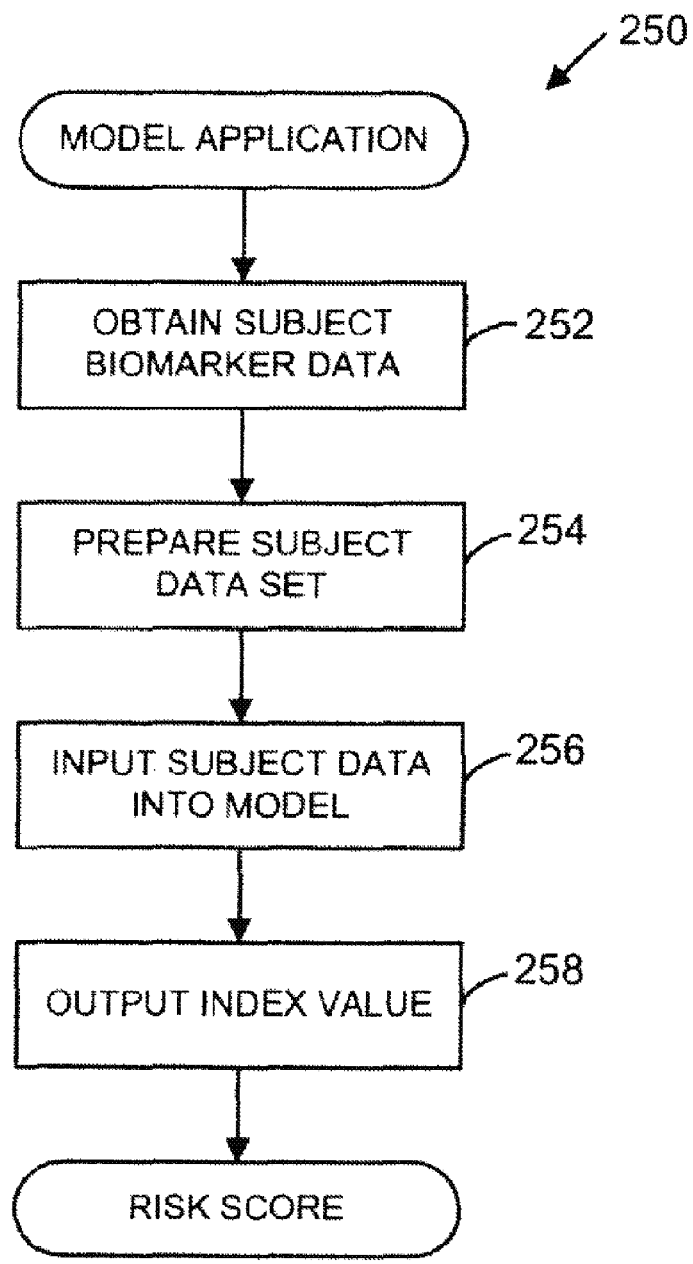
FIG. 7 is a flow diagram, which describes an example of a method for using the model of FIG. 6 to determine the inflammatory disease activity of a subject or population.

FIG. 7 is a flow diagram of an exemplary method (250) of using a model as developed above to determine the inflammatory disease activity of a subject or a population. Biomarker data is obtained from the subject at (252). This data can be obtained by a variety of means, including but not limited to physical examinations, self-reports by the subject, laboratory testing, medical records and charts. Subject data can then be prepared (254) via transformations, logs, normalizations, and so forth, based on the particular model selected and trained in FIG. 6. The data is then input into the model for evaluation (256), which outputs an index value (258); e.g., a DAI score. Examples as to how a model can be used to evaluate a subject's biomarkers and output a DAI value are provided herein.

Modifications for Response to Treatment In certain embodiments of the present teachings, biomarkers from the DAIMRK group can be used to determine a subject's response to treatment for inflammatory disease. Measuring levels of an effective amount of biomarkers also allows for the course of treatment of inflammatory disease to be monitored. In these embodiments, a biological sample can be provided from a subject undergoing therapeutic regimens for inflammatory disease. If desired, biological samples are obtained from the subject at various time points before, during, or after treatment.

Various embodiments of the present teachings can be used to provide a guide to the selection of a therapeutic regimen for a subject; meaning, e.g., that treatment may need to be more or less aggressive, or a subject may need a different therapeutic regimen, or the subject's current therapeutic regimen may need to be changed or stopped, or a new therapeutic regimen may need to be adopted, etc.

Treatment strategies are confounded by the fact that RA is a classification given to a group of subjects with a diverse array of related symptoms. This suggests that certain subtypes of RA are driven by specific cell type or cytokine. As a likely consequence, no single therapy has proven optimal for treatment. Given the increasing numbers of therapeutic options available for RA, the need for an individually tailored treatment directed by immunological prognostic factors of treatment outcome is imperative. In various embodiments of the present teachings, a DAIMRK biomarker-derived algorithm can be used to quantify therapy response in RA subjects. See Example 5. Measuring DAIMRK biomarker levels over a period time can provide the clinician with a dynamic picture of the subject's biological state, and the DAI scores are highly correlated to DAS28. Overlaying the DAS28 score with the DAI score can provide a deeper understanding of how a subject is responding to therapy. These embodiments of the present teachings thus will provide subject-specific biological information, which will be informative for therapy decision and will facilitate therapy response monitoring, and should result in more rapid and more optimized treatment, better control of disease activity, and an increase in the proportion of subjects achieving remission.

Differences in the genetic makeup of subjects can result in differences in their relative abilities to metabolize various drugs, which may modulate the symptoms or state of inflammatory disease. Subjects that have inflammatory disease can vary in age, ethnicity, body mass index (BMI), total cholesterol levels, blood glucose levels, blood pressure, LDL and HDL levels, and other parameters. Accordingly, use of the biomarkers disclosed herein, both alone and together in combination with known genetic factors for drug metabolism, allow for a pre-determined level of predictability that a putative therapeutic or prophylactic to be tested in a selected subject will be suitable for treating or preventing inflammatory disease in the subject.

To identify therapeutics or drugs that are appropriate for a specific subject, a test sample from the subject can also be exposed to a therapeutic agent or a drug, and the level of one or more biomarkers can be determined. The level of one or more biomarkers can be compared to sample derived from the subject before and after treatment or exposure to a therapeutic agent or a drug, or can be compared to samples derived from one or more subjects who have shown improvements in inflammatory disease state or activity (e.g., clinical parameters or traditional laboratory risk factors) as a result of such treatment or exposure.

Combination with Clinical Parameters

Any of the aforementioned clinical parameters can also be used in the practice of the present teachings, as input to the DAIMRK formula or as a pre-selection criteria defining a relevant population to be measured using a particular DAIMRK panel and formula. As noted above, clinical parameters can also be useful in the biomarker normalization and pre-processing, or in selecting particular biomarkers from DAIMRK, panel construction, formula type selection and derivation, and formula result post-processing.

Clinical Assessments of the Present Teachings

In some embodiments of the present teachings, panels of DAIMRK biomarkers and formulas are tailored to the population, endpoints or clinical assessment, and/or use that is intended. For example, the DAIMRK panels and formulas can be used to assess subjects for primary prevention and diagnosis, and for secondary prevention and management. For the primary assessment, the DAIMRK panels and formulas can be used for prediction and risk stratification for future conditions or disease sequelae, for the diagnosis of inflammatory disease, for the prognosis of disease activity and rate of change, and for indications for future diagnosis and therapeutic regimens. For secondary prevention and clinical management, the DAIMRK panels and formulas can be used for prognosis and risk stratification. The DAIMRK panels and formulas can be used for clinical decision support, such as determining whether to defer intervention or treatment, to recommend preventive check-ups for at-risk patients, to recommend increased visit frequency, to recommend increased testing, and to recommend intervention. The DAIMRK panels and formulas can also be useful for therapeutic selection, determining response to treatment, adjustment and dosing of treatment, monitoring ongoing therapeutic efficiency, and indication for change in therapeutic regimen.

In some embodiments of the present teachings, the DAIMRK panels and formulas can be used to aid in the diagnosis of inflammatory disease, and in the determination of the severity of inflammatory disease. The DAIMRK panels and formulas can also be used for determining the future status of intervention such as, for example in RA, determining the prognosis of future joint erosion with or without treatment. Certain embodiments of the present teachings can be tailored to a specific treatment or a combination of treatments. X-ray is currently considered the gold standard for assessment of disease progression, but it has limited capabilities since subjects may have long periods of active symptomatic disease while radiographs remain normal or show only non-specific changes. Conversely, subjects who seem to have quiescent disease (subclinical disease) may slowly progress over time, undetected clinically until significant radiographic progression has occurred. If subjects with a high likelihood of disease progression could be identified in advance, the opportunity for early aggressive treatment could result in much more effective disease outcomes. See, e.g., M. Weinblatt et al., *N. Engl. J. Med.* 1999, 340:253-259. In certain embodiments of the present teachings, an algorithm developed from the DAIMRK set of biomarkers can be used, with significant power, to characterize the level of bone or cartilage damage activity in RA subjects. See Example 6. In other embodiments, an algorithm developed from the DAIMRK set of biomarkers can be used, with significant power, to prognose joint destruction over time. See Example 6. In other embodiments, the DAI score can be used as a strong predictor of radiographic progression, giving the clinician a novel way to identify subjects at risk of RA-induced joint damage and allowing for early prescription of joint-sparing agents, prophylactically.

In some embodiments of the present teachings, the DAIMRK panels and formulas can be used as surrogate markers of clinical events necessary for the development of inflammatory disease-specific agents; e.g., pharmaceutical agents. That is, the DAI surrogate marker, derived from a DAIMRK panel, can be used in the place of clinical events in a clinical trial for an experimental RA treatment. DAIMRK panels and formulas can thus be used to derive an inflammatory disease surrogate endpoint to assist in the design of experimental treatments for RA.

Measurement of Biomarkers

The quantity of one or more biomarkers of the present teachings can be indicated as a value. The value can be one or more numerical values resulting from the evaluation of a sample, and can be derived, e.g., by measuring level(s) of the biomarker(s) in a sample by an assay performed in a laboratory, or from dataset obtained from a provider such as a laboratory, or from a dataset stored on a server. Biomarker levels can be measured using any of several techniques known in the art. The present teachings encompass such techniques, and further include all subject fasting and/or temporal-based sampling procedures for measuring biomarkers.

The actual measurement of levels of the biomarkers can be determined at the protein or nucleic acid level using any method known in the art. "Protein" detection comprises detection of full-length proteins, mature proteins, pre-proteins, polypeptides, isoforms, mutations, variants, post-translationally modified proteins and variants thereof, and can be detected in any suitable manner. Levels of biomarkers can be determined at the protein level, e.g., by measuring the serum levels of peptides encoded by the gene products described herein, or by measuring the enzymatic activities of these protein biomarkers. Such methods are well-known in the art and include, e.g., immunoassays based on antibodies to proteins encoded by the genes, aptamers or molecular imprints. Any biological material can be used for the detection/quantification of the protein or its activity. Alternatively, a suitable method can be selected to determine the activity of proteins encoded by the biomarker genes according to the activity of each protein analyzed. For biomarker proteins, polypeptides, isoforms, mutations, and variants thereof known to have enzymatic activity, the activities can be determined in vitro using enzyme assays known in the art. Such assays include, without limitation, protease assays, kinase assays, phosphatase assays, reductase assays, among many others. Modulation of the kinetics of enzyme activities can be determined by measuring the rate constant KM using known algorithms, such as the Hill plot, Michaelis-Menten equation, linear regression plots such as Lineweaver-Burk analysis, and Scatchard plot.

Using sequence information provided by the public database entries for the biomarker, expression of the biomarker can be detected and measured using techniques well-known to those of skill in the art. For example, nucleic acid sequences in the sequence databases that correspond to nucleic acids of biomarkers can be used to construct primers and probes for detecting and/or measuring biomarker nucleic acids. These probes can be used in, e.g., Northern or Southern blot hybridization analyses, ribonuclease protection assays, and/or methods that quantitatively amplify specific nucleic acid sequences. As another example, sequences from sequence databases can be used to construct primers for specifically amplifying biomarker sequences in, e.g., amplification-based detection and quantitation methods such as reverse-transcription based polymerase chain reaction (RT-PCR) and PCR. When alterations in gene expression are associated with gene amplification, nucleotide deletions, polymorphisms, post-translational modifications and/or mutations, sequence comparisons in test and reference populations can be made by comparing relative amounts of the examined DNA sequences in the test and reference populations.

As an example, Northern hybridization analysis using probes which specifically recognize one or more of these sequences can be used to determine gene expression. Alternatively, expression can be measured using RT-PCR; e.g., polynucleotide primers specific for the differentially expressed biomarker mRNA sequences reverse-transcribe the mRNA into DNA, which is then amplified in PCR and can be visualized and quantified. Biomarker RNA can also be quantified using, for example, other target amplification methods, such as TMA, SDA, and NASBA, or signal amplification methods (e.g., bDNA), and the like. Ribonuclease protection assays can also be used, using probes that specifically recognize one or more biomarker mRNA sequences, to determine gene expression.

Alternatively, biomarker protein and nucleic acid metabolites can be measured. The term "metabolite" includes any chemical or biochemical product of a metabolic process, such as any compound produced by the processing, cleavage or consumption of a biological molecule (e.g., a protein, nucleic acid, carbohydrate, or lipid). Metabolites can be detected in a variety of ways known to one of skill in the art, including the refractive index spectroscopy (RI), ultra-violet spectroscopy (UV), fluorescence analysis, radiochemical analysis, near-infrared spectroscopy (near-IR), nuclear magnetic resonance spectroscopy (NMR), light scattering analysis (LS), mass spectrometry, pyrolysis mass spectrometry, nephelometry, dispersive Raman spectroscopy, gas chromatography combined with mass spectrometry, liquid chromatography combined with mass spectrometry, matrix-assisted laser desorption ionization-time of flight (MALDI-TOF) combined with mass spectrometry, ion spray spectroscopy combined with mass spectrometry, capillary electrophoresis, NMR and IR detection. See WO 04/056456 and WO 04/088309, each of which is hereby incorporated by reference in its entirety. In this regard, other biomarker analytes can be measured using the above-mentioned detection methods, or other methods known to the skilled artisan. For example, circulating calcium ions ($Ca^{2+}$) can be detected in a sample using fluorescent dyes such as the Fluo series, Fura-2A, Rhod-2, among others. Other biomarker metabolites can be similarly detected using reagents that are specifically designed or tailored to detect such metabolites.

In some embodiments, a biomarker is detected by contacting a subject sample with reagents, generating complexes of reagent and analyte, and detecting the complexes. Examples of "reagents" include but are not limited to nucleic acid primers and antibodies.

In some embodiments of the present teachings an antibody binding assay is used to detect a biomarker; e.g., a sample from the subject is contacted with an antibody reagent that binds the biomarker analyte, a reaction product (or complex) comprising the antibody reagent and analyte is generated, and the presence (or absence) or amount of the complex is determined. The antibody reagent useful in detecting biomarker analytes can be monoclonal, polyclonal, chimeric, recombinant, or a fragment of the foregoing, as discussed in detail above, and the step of detecting the reaction product can be carried out with any suitable immunoassay. The sample from the subject is typically a biological fluid as described above, and can be the same sample of biological fluid as is used to conduct the method described above.

Immunoassays carried out in accordance with the present teachings can be homogeneous assays or heterogeneous assays. In a homogeneous assay the immunological reaction can involve the specific antibody (e.g., anti-biomarker protein antibody), a labeled analyte, and the sample of interest. The label produces a signal, and the signal arising from the label becomes modified, directly or indirectly, upon binding of the labeled analyte to the antibody. Both the immunological reaction of binding, and detection of the extent of binding, can be carried out in a homogeneous solution. Immunochemical labels which can be employed include but are not limited to free radicals, radioisotopes, fluorescent dyes, enzymes, bacteriophages, and coenzymes. Immunoassays include competition assays.

In a heterogeneous assay approach, the reagents can be the sample of interest, an antibody, and a reagent for producing a detectable signal. Samples as described above can be used. The antibody can be immobilized on a support, such as a bead (such as protein A and protein G agarose beads), plate or slide, and contacted with the sample suspected of containing the biomarker in liquid phase. The support is separated from the liquid phase, and either the support phase or the liquid phase is examined using methods known in the art for detecting signal. The signal is related to the presence of the analyte in the sample. Methods for producing a detectable signal include but are not limited to the use of radioactive labels, fluorescent labels, or enzyme labels. For example, if the antigen to be detected contains a second binding site, an antibody which binds to that site can be conjugated to a detectable (signal-generating) group and added to the liquid phase reaction solution before the separation step. The presence of the detectable group on the solid support indicates the presence of the biomarker in the test sample. Examples of suitable immunoassays include but are not limited to oligonucleotides, immunoblotting, immunoprecipitation, immunofluorescence methods, chemiluminescence methods, electrochemiluminescence (ECL), and/or enzyme-linked immunoassays (ELISA).

Those skilled in the art will be familiar with numerous specific immunoassay formats and variations thereof which can be useful for carrying out the method disclosed herein. See, e.g., E. Maggio, *Enzyme-Immunoassay* (1980), CRC Press, Inc., Boca Raton, Fla. See also U.S. Pat. No. 4,727,022 to C. Skold et al., titled "Novel Methods for Modulating Ligand-Receptor Interactions and their Application"; U.S. Pat. No. 4,659,678 to GC Forrest et al., titled "Immunoassay of Antigens"; U.S. Pat. No. 4,376,110 to GS David et al., titled "Immunometric Assays Using Monoclonal Antibodies"; U.S. Pat. No. 4,275,149 to D. Litman et al., titled "Macromolecular Environment Control in Specific Receptor Assays"; U.S. Pat. No. 4,233,402 to E. Maggio et al., titled "Reagents and Method Employing Channeling"; and, U.S. Pat. No. 4,230, 797 to R. Boguslaski et al., titled "Heterogenous Specific Binding Assay Employing a Coenzyme as Label."

Antibodies can be conjugated to a solid support suitable for a diagnostic assay (e.g., beads such as protein A or protein G agarose, microspheres, plates, slides or wells formed from materials such as latex or polystyrene) in accordance with known techniques, such as passive binding. Antibodies as described herein can likewise be conjugated to detectable labels or groups such as radiolabels (e.g., $^{35}$S, $^{125}$I, $^{131}$I), enzyme labels (e.g., horseradish peroxidase, alkaline phosphatase), and fluorescent labels (e.g., fluorescein, Alexa, green fluorescent protein, rhodamine) in accordance with known techniques.

Antibodies may also be useful for detecting post-translational modifications of biomarkers. Examples of post-translational modifications include, but are not limited to tyrosine phosphorylation, threonine phosphorylation, serine phosphorylation, citrullination and glycosylation (e.g., O-GlcNAc). Such antibodies specifically detect the phosphorylated amino acids in a protein or proteins of interest, and can be used in the immunoblotting, immunofluorescence, and ELISA assays described herein. These antibodies are well-known to those skilled in the art, and commercially available. Post-translational modifications can also be determined using metastable ions in reflector matrix-assisted laser desorption ionization-time of flight mass spectrometry (MALDI-TOF). See U. Wirth et al., *Proteomics* 2002, 2(10):1445-1451.

Kits

Other embodiments of the present teachings comprise biomarker detection reagents packaged together in the form of a kit for conducting any of the assays of the present teachings. In certain embodiments, the kits comprise oligonucleotides that specifically identify one or more biomarker nucleic acids based on homology and/or complementarity with biomarker nucleic acids. The oligonucleotide sequences may correspond to fragments of the biomarker nucleic acids. For example, the oligonucleotides can be more than 200, 200, 150, 100, 50, 25, 10, or fewer than 10 nucleotides in length. In other embodiments, the kits comprise antibodies to proteins encoded by the biomarker nucleic acids. The kits of the present teachings can also comprise aptamers. The kit can contain in separate containers a nucleic acid or antibody (the antibody either bound to a solid matrix, or packaged separately with reagents for binding to a matrix), control formulations (positive and/or negative), and/or a detectable label, such as but not limited to fluorescein, green fluorescent protein, rhodamine, cyanine dyes, Alexa dyes, luciferase, and radiolabels, among others. Instructions for carrying out the assay, including, optionally, instructions for generating a DAI score, can be included in the kit; e.g., written, tape, VCR, or CD-ROM. The assay can for example be in the form of a Northern hybridization or a sandwich ELISA as known in the art.

In some embodiments of the present teachings, biomarker detection reagents can be immobilized on a solid matrix, such as a porous strip, to form at least one biomarker detection site. In some embodiments, the measurement or detection region of the porous strip can include a plurality of sites containing a nucleic acid. In some embodiments, the test strip can also contain sites for negative and/or positive controls. Alternatively, control sites can be located on a separate strip from the test strip. Optionally, the different detection sites can contain different amounts of immobilized nucleic acids, e.g., a higher amount in the first detection site and lesser amounts in subsequent sites. Upon the addition of test sample, the number of sites displaying a detectable signal provides a quantitative indication of the amount of biomarker present in the sample.

The detection sites can be configured in any suitably detectable shape and can be, e.g., in the shape of a bar or dot spanning the width of a test strip.

In other embodiments of the present teachings, the kit can contain a nucleic acid substrate array comprising one or more nucleic acid sequences. The nucleic acids on the array specifically identify one or more nucleic acid sequences represented by DAIMRK biomarker Nos. 1-25. In various embodiments, the expression of one or more of the sequences represented by DAIMRK Nos. 1-25 can be identified by virtue of binding to the array. In some embodiments the substrate array can be on a solid substrate, such as what is known as a "chip." See, e.g., U.S. Pat. No. 5,744,305. In some embodiments the substrate array can be a solution array; e.g., xMAP (Luminex, Austin, Tex.), Cyvera (Illumina, San Diego, Calif.), RayBio Antibody Arrays (RayBiotech, Inc., Norcross, Ga.), CellCard (Vitra Bioscience, Mountain View, Calif.) and Quantum Dots' Mosaic (Invitrogen, Carlsbad, Calif.).

Machine-readable Storage Medium

A machine-readable storage medium can comprise, for example, a data storage material that is encoded with machine-readable data or data arrays. The data and machine-readable storage medium are capable of being used for a variety of purposes, when using a machine programmed with instructions for using said data. Such purposes include, without limitation, storing, accessing and manipulating information relating to the inflammatory disease activity of a subject or population over time, or disease activity in response to inflammatory disease treatment, or for drug discovery for inflammatory disease, etc. Data comprising measurements of the biomarkers of the present teachings, and/or the evaluation of disease activity or disease state from these biomarkers, can be implemented in computer programs that are executing on programmable computers, which comprise a processor, a data storage system, one or more input devices, one or more output devices, etc. Program code can be applied to the input data to perform the functions described herein, and to generate output information. This output information can then be applied to one or more output devices, according to methods well-known in the art. The computer can be, for example, a personal computer, a microcomputer, or a workstation of conventional design.

The computer programs can be implemented in a high-level procedural or object-oriented programming language, to communicate with a computer system such as for example, the computer system illustrated in FIG. 16. The programs can also be implemented in machine or assembly language. The programming language can also be a compiled or interpreted language. Each computer program can be stored on storage media or a device such as ROM, magnetic diskette, etc., and can be readable by a programmable computer for configuring and operating the computer when the storage media or device is read by the computer to perform the described procedures. Any health-related data management systems of the present teachings can be considered to be implemented as a computer-readable storage medium, configured with a computer program, where the storage medium causes a computer to operate in a specific manner to perform various functions, as described herein.

The biomarkers disclosed herein can be used to generate a "subject biomarker profile" taken from subjects who have inflammatory disease. The subject biomarker profiles can then be compared to a reference biomarker profile, in order to diagnose or identify subjects with inflammatory disease, to monitor the progression or rate of progression of inflammatory disease, or to monitor the effectiveness of treatment for inflammatory disease. The biomarker profiles, reference and subject, of embodiments of the present teachings can be contained in a machine-readable medium, such as analog tapes like those readable by a CD-ROM or USB flash media, among others. Such machine-readable media can also contain additional test results, such as measurements of clinical parameters and clinical assessments. The machine-readable media can also comprise subject information; e.g., the subject's medical or family history. The machine-readable media can also contain information relating to other disease activity algorithms and computed scores or indices, such as those described herein.

EXAMPLES

Aspects of the present teachings can be further understood in light of the following examples, which should not be construed as limiting the scope of the present teachings in any way.

The practice of the present teachings employ, unless otherwise indicated, conventional methods of protein chemistry, biochemistry, recombinant DNA techniques and pharmacology, within the skill of the art. Such techniques are explained fully in the literature. See, e.g., T. Creighton, *Proteins: Structures and Molecular Properties,* 1993, W. Freeman and Co.; A. Lehninger, *Biochemistry*, Worth Publishers, Inc. (current addition); J. Sambrook et al., *Molecular Cloning: A Laboratory Manual,* 2nd Edition, 1989; *Methods In Enzymology*, S. Colowick and N. Kaplan, eds., Academic Press, Inc.; *Remington's Pharmaceutical Sciences,* 18th Edition, 1990, Mack Publishing Company, Easton, Pa.; Carey and Sundberg, *Advanced Organic Chemistry*, Vols. A and B, 3rd Edition, 1992, Plenum Press.

The practice of the present teachings also employ, unless otherwise indicated, conventional methods of statistical analysis, within the skill of the art. Such techniques are explained fully in the literature. See, e.g., J. Little and D. Rubin, *Statistical Analysis with Missing Data,* 2nd Edition 2002, John Wiley and Sons, Inc., NJ; M. Pepe, *The Statistical Evaluation of Medical Tests for Classification and Prediction* (*Oxford Statistical Science Series*) 2003, Oxford University Press, Oxford, UK; X. Zhoue et al., *Statistical Methods in Diagnostic Medicine* 2002, John Wiley and Sons, Inc., NJ; T. Hastie et. al, *The Elements of Statistical Learning: Data Mining, Inference, and Prediction*, Second Edition 2009, Springer, N.Y.; W. Cooley and P. Lohnes, *Multivariate procedures for the behavioral science* 1962, John Wiley and Sons, Inc. NY; E. Jackson, *A User's Guide to Principal Components* 2003, John Wiley and Sons, Inc., NY.

Example 1

Association of DAI with DAS28 Scores in a Large Clinical Cohort

Example 1 demonstrates the transformation of observed biomarker levels into a DAI score by various statistical modeling methodologies, which DAI score serves as a quantitative measurement of disease activity that correlates well with observed DAS28, as for measuring the extent of subject inflammation status and disease activity at any single timepoint. Certain embodiments of the present teachings comprise utilizing the DAIMRK set of biomarkers for determining a DAI score with high correlation with disease activity status.

Samples were obtained from the Brigham and Women's Hospital Rheumatoid Arthritis Sequential Study (BRASS). The appropriate Research Ethics Committee approval was obtained for the study, and all subjects gave informed consent. Since 2003, 1,000 subjects with confirmed RA under the care of the Brigham and Women's hospital have been enrolled in BRASS. The cohort for this study had the following characteristics: 80% female, 62% CCP positive, 83% RF positive, 13% smokers, 61% on MTX, 76% on non-biologic DMARDs, 53% on biologic DMARDs, and 27% on steroids. Additionally, the mean age of the cohort was 59 years (standard deviation (SD)+/−13.1), with a minimum age of 22 and a maximum age of 94. The mean DAS28-CRP for this cohort was 4.1 (SD+/−1.7), with a minimum of 1.2 and a maximum of 8.2.

All subjects fulfilled the American College of Rheumatology criteria for RA, and every subject in the study will be followed for five years. At six-month intervals throughout the study, data are collected from all subjects, comprising medical or clinical information such as disease activity scores, radiological results, subject health status and other clinical assessments. Blood samples are collected at twelve-month intervals from each subject for five years. A subpopulation of one hundred and eighty subjects was selected from the BRASS cohort. Within the subjects selected, a wide distribution of DAS28-CRP scores was represented (DAS28 range=1.19-8.2).

Assays were designed, in multiplex or ELISA format, for measuring multiple disease-related protein biomarkers selected from the ALLMRK set, as that set is described herein. These assays were identified through a screening and optimization process, prior to assaying the BRASS samples. The respective biomarker assays, vendors, and platforms used were as follows: APOA1, Millipore, LUMINEX®; APOC3, Millipore, LUMINEX®; calprotectin, Alpco, ELISA; CCL22, Meso Scale Discovery, MSD®; CHI3L1 (YKL-40), Quidel, ELISA; CRP, Meso Scale Discovery, MSD®; EGF, R&D Systems, LUMINEX®; ICAM1, Meso Scale Discovery, MSD®; ICTP, IDS (Immunodiagnostic Systems), ELISA; IL18, R&D Systems, ELISA; IL1B, Meso Scale Discovery, MSD®; IL1RN, R&D Systems, LUMINEX®; IL6, R&D Systems, LUMINEX®; IL6R, Millipore, LUMINEX®; IL8, R&D Systems, LUMINEX®; keratan sulfate, Cape Cod, Inc., ELISA; LEP, R&D Systems, LUMINEX®; MMP1, R&D Systems, LUMINEX®; MMP3, R&D Systems, LUMINEX®; RETN, R&D Systems, LUMINEX®; SAA1, Meso Scale Discovery, MSD®; TNFRSF1A, Meso Scale Delivery, MSD®; TNFSF13B, R&D Systems, ELISA; VCAM1, Meso Scale Discovery, MSD®; and, VEGFA, R&D Systems, LUMINEX®.

All assays were performed following the manufacturer's instructions, with cohort samples randomly assigned to the sample positions on the plate layouts. Four pooled sera, from healthy, RA, SLE and osteoarthritis (OA) subjects, were included in each assay plate as process controls. All samples were assayed at least in duplicate. Seven-point calibration curves were constructed for each biomarker for an accurate determination of the measureable range of test sera.

Prior to statistical analyses, all assay data were reviewed for pass/fail criteria as predefined by standard operating procedures, including inter-assay CV, intra-assay CV, percent number of samples within the measureable range of the calibration curve, and four serum process controls within the range of the calibration curve. The biomarker values that were not in the measureable range of the calibration curves were marked as missing data, and imputed by the lowest/highest detected value across all the samples within a given biomarker assay. No imputation was performed for the univariate analyses. For multivariate analysis, missing data imputation methods commonly used in microarray expression data and well-known in the art were used. See, e.g., R. Little and D. Rubin, *Statistical Analysis with Missing Data*, 2nd Edition 2002, John Wiley and Sons, Inc., NJ. Biomarkers were excluded from analysis where more than 20% of the data were missing, and the remaining data were imputed by the KNN algorithm (where k=5 nearest neighbors). KNN functions on the intuitive idea that close objects are more likely to be in the same category. Thus, in KNN, predictions are based on a set of prototype examples that are used to predict new (i.e., unseen) data based on the majority vote (for classification tasks) over a set of k-nearest prototypes. Given a new case of dependent values (query point), we would like to estimate the outcome based on the KNN examples. KNN achieves this by finding k examples that are closest in Euclidian distance to the query point.

Univariate Analysis

Biomarker assay data were normalized by plate before correlations were calculated between individual proteins and measurements were transformed into DAI scores. Associations were calculated between the DAI scores and DAS28-CRP scores, SJC, TJC, or CDAI. The correlation results were then compared using univariate analysis. See Table 10.

TABLE 10

| Biomarker | Correlation coefficient | Nominal p-value |
|---|---|---|
| APOA1 | −0.177 | <0.0001 |
| calprotectin | 0.42 | <0.0001 |
| CHI3L1 | 0.178 | <0.0001 |
| CRP | 0.476 | <0.0001 |
| EGF | −0.358 | <0.0001 |
| ICAM1 | 0.242 | <0.0001 |
| IL1B | −0.282 | <0.0001 |
| IL6 | 0.289 | <0.0001 |
| IL6R | 0.082 | <0.0001 |
| IL8 | −0.393 | <0.0001 |
| IL1RN | 0.211 | <0.0001 |
| LEP | 0.21 | <0.0001 |
| RETN | 0.256 | <0.0001 |
| SAA1 | 0.386 | <0.0001 |
| TNFRSF1A | 0.176 | <0.0001 |
| VCAM1 | 0.323 | <0.0001 |
| VEGFA | 0.198 | <0.0001 |
| keratan sulfate | −0.258 | 0.002 |
| TNFSF13B | 0.271 | 0.007 |
| ICTP | 0.266 | 0.014 |
| APOC3 | −0.118 | 0.255 |
| MMP3 | 0.34 | <0.0001 |
| CCL22 | 0.116 | 0.2 |
| MMP1 | 0.261 | 0.006 |

Figure 8:
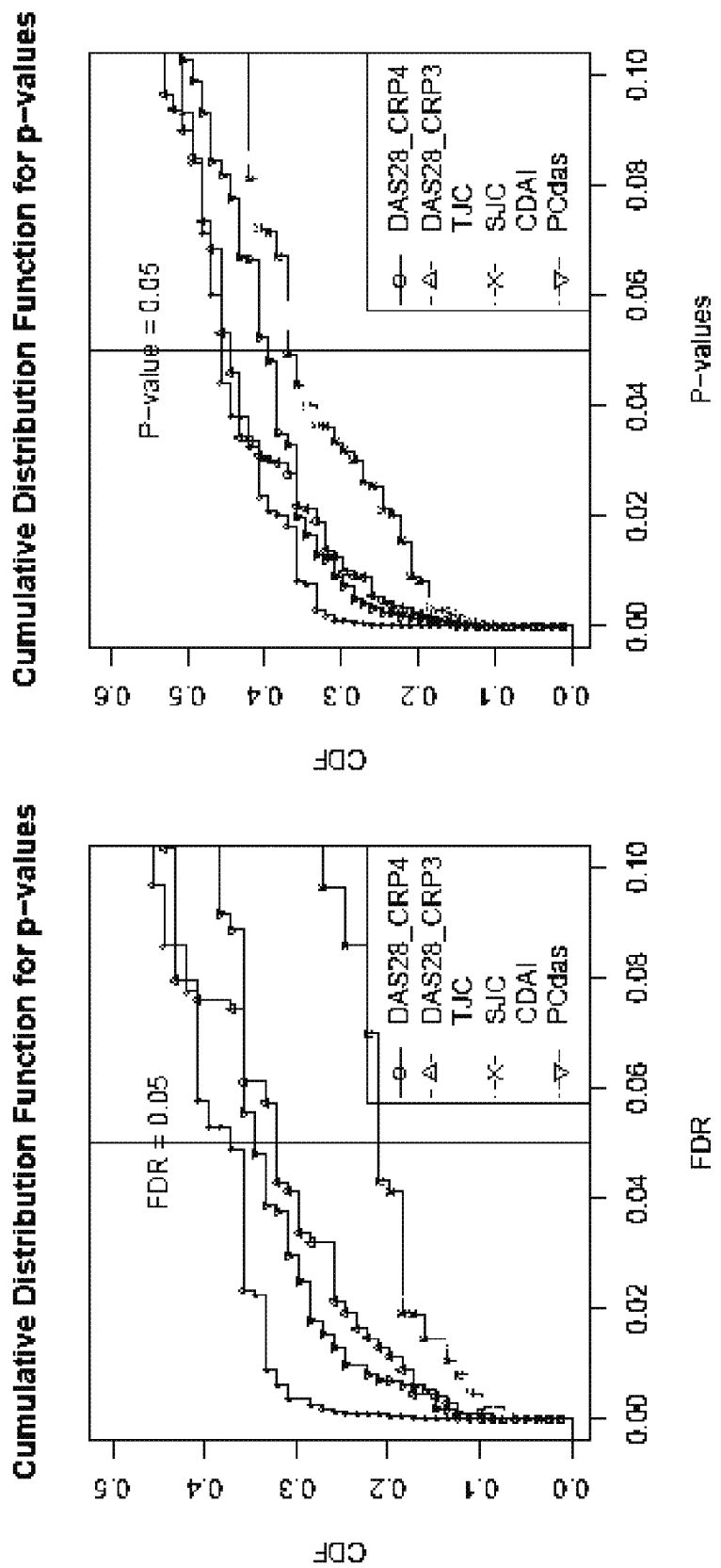
FIG. 8 depicts the cumulative distribution function for p-values and False Discovery Rate, "FDR," as related to the output of the DAS28 and other response variables of Example 1, where the FDR was used as multiple testing correction, according to the following: let k be the largest i for which $p_i \le i/m^*\alpha$; reject all $H_i$, i=1, . . . m. In this equation the variable $\alpha$ is a pre-specified probability of a false-positive (Type I) error, typically 0.05, and H is a hypothesis.
Figure 9A:
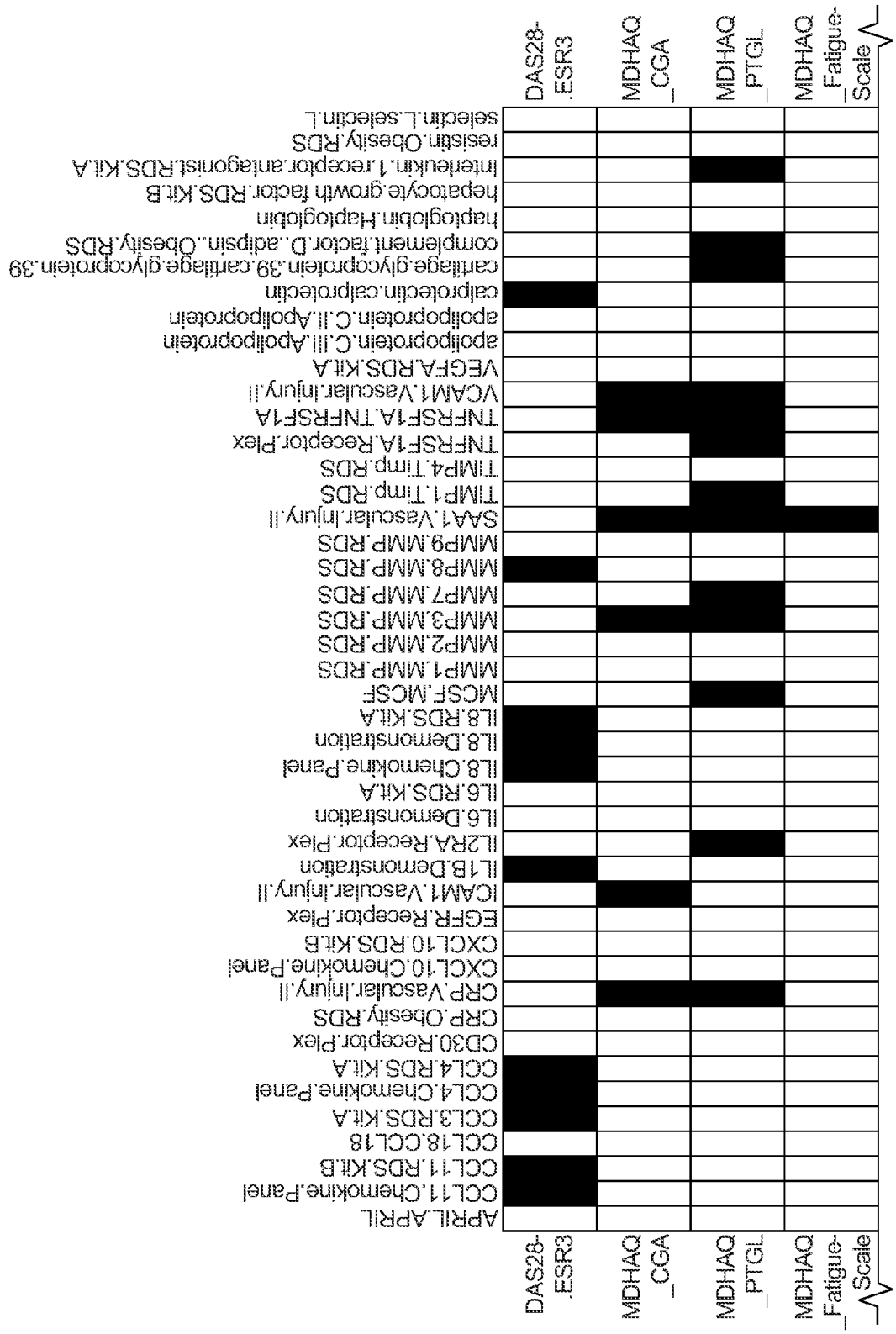
FIG. 9A and FIG. 9B depict the correlation matrix for each respective biomarker listed. Darker gray indicates positive correlation, and lighter gray indicates negative correlation.
Figure 9B:
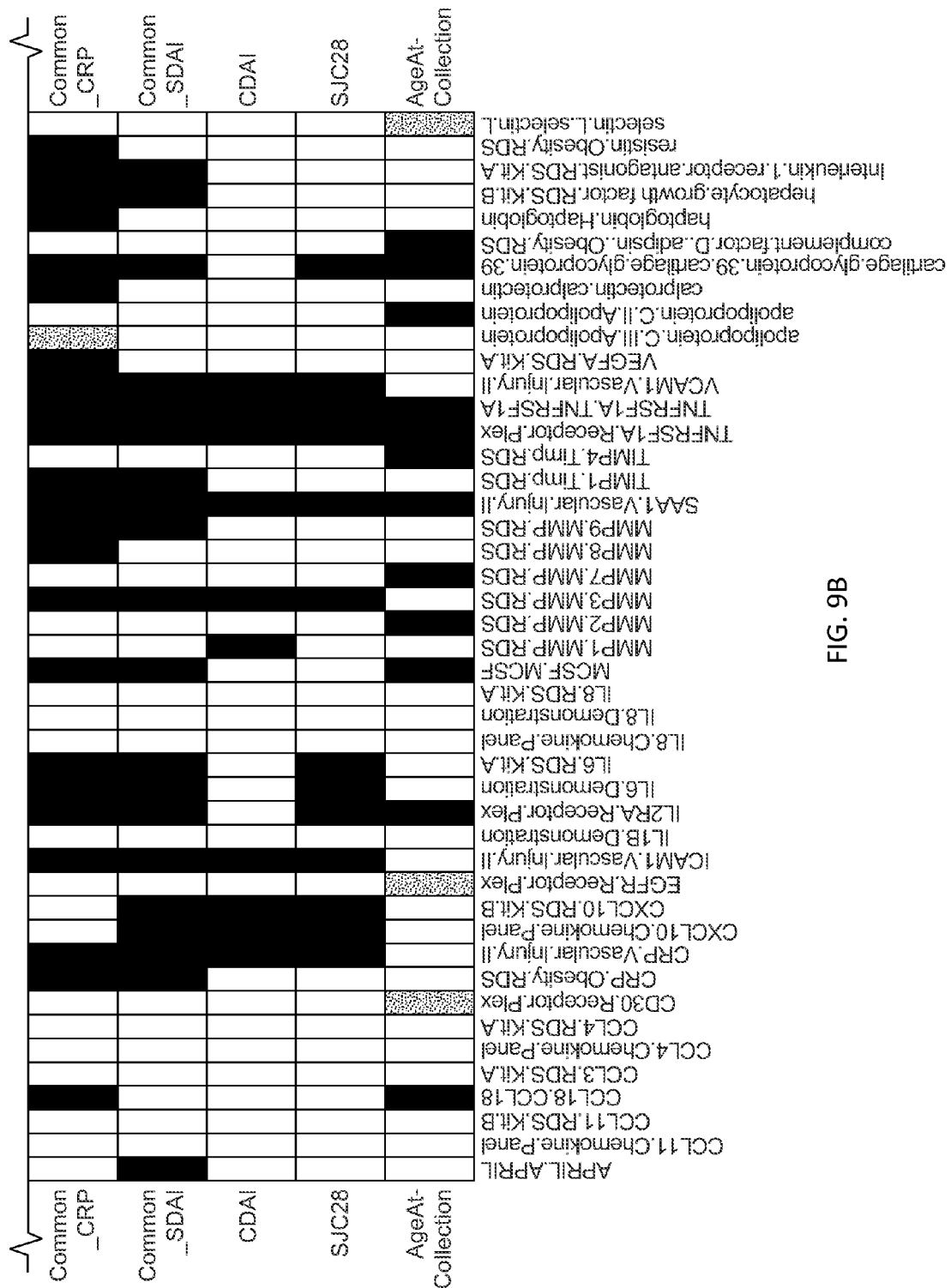
Figure 10:
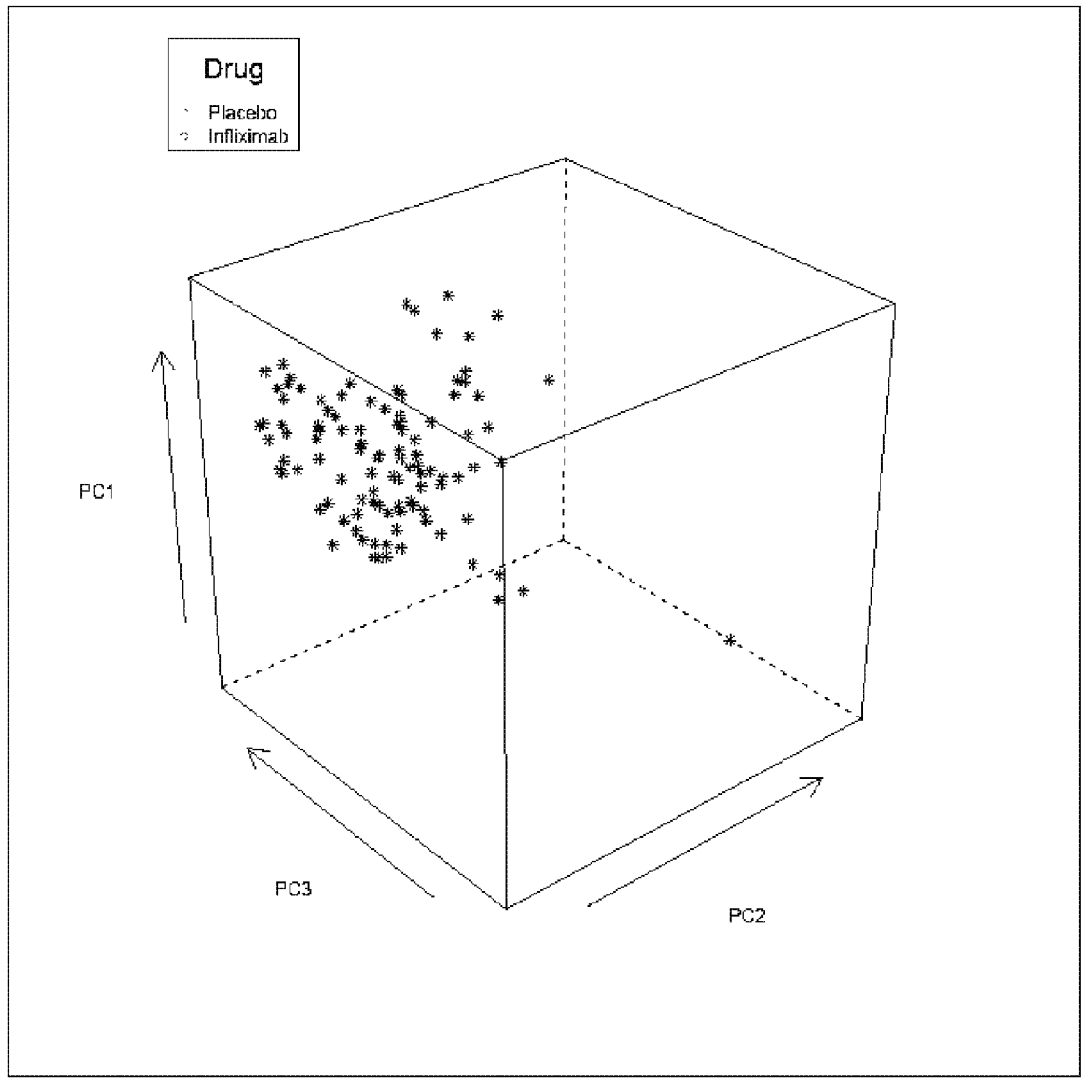
FIG. 10 depicts the three-dimensional PCA plot of Example 1. Each point represents a subject.

See FIG. 8 for a cumulative distribution function (CDF) plot of transformation comparisons, wherein the CDF of p-values is the cumulative distribution function of all the p-values obtained (i.e., one p-value per DAIMRK biomarker), and thus shows the distribution of all p-values. See FIG. 9 for a correlation matrix between 21 DAIMRK biomarkers and continuous clinical variables.

The False Discovery Rate (FDR) was used as a multiple testing correction, according to the following: let k be the largest i for which $p_i \leq i/m^*\alpha$; reject all $H_i$, where i=1, ..., m. In this equation the variable $\alpha$ is a pre-specified probability of a false-positive (Type I) error, typically 0.05, and H is a hypothesis. As will be clear to one of skill in the art, where the DAIMRK biomarker is significantly associated with the DAS score, the q-value (the false discovery rate) is small. FIG. 8 shows the different results obtained from different normalizations. A parametric correlation test was also performed, using the parametric test $H_i: \rho_i = 0$, and the statistic given by $$t = \frac{r(n-2)^{1/2}}{(1-r^2)^{1/2}}.$$

For this analysis, i represents the test statistics (for which p-value can be calculated using the T distribution), r is the correlation coefficient, and n is the sample size.

Figure 11:
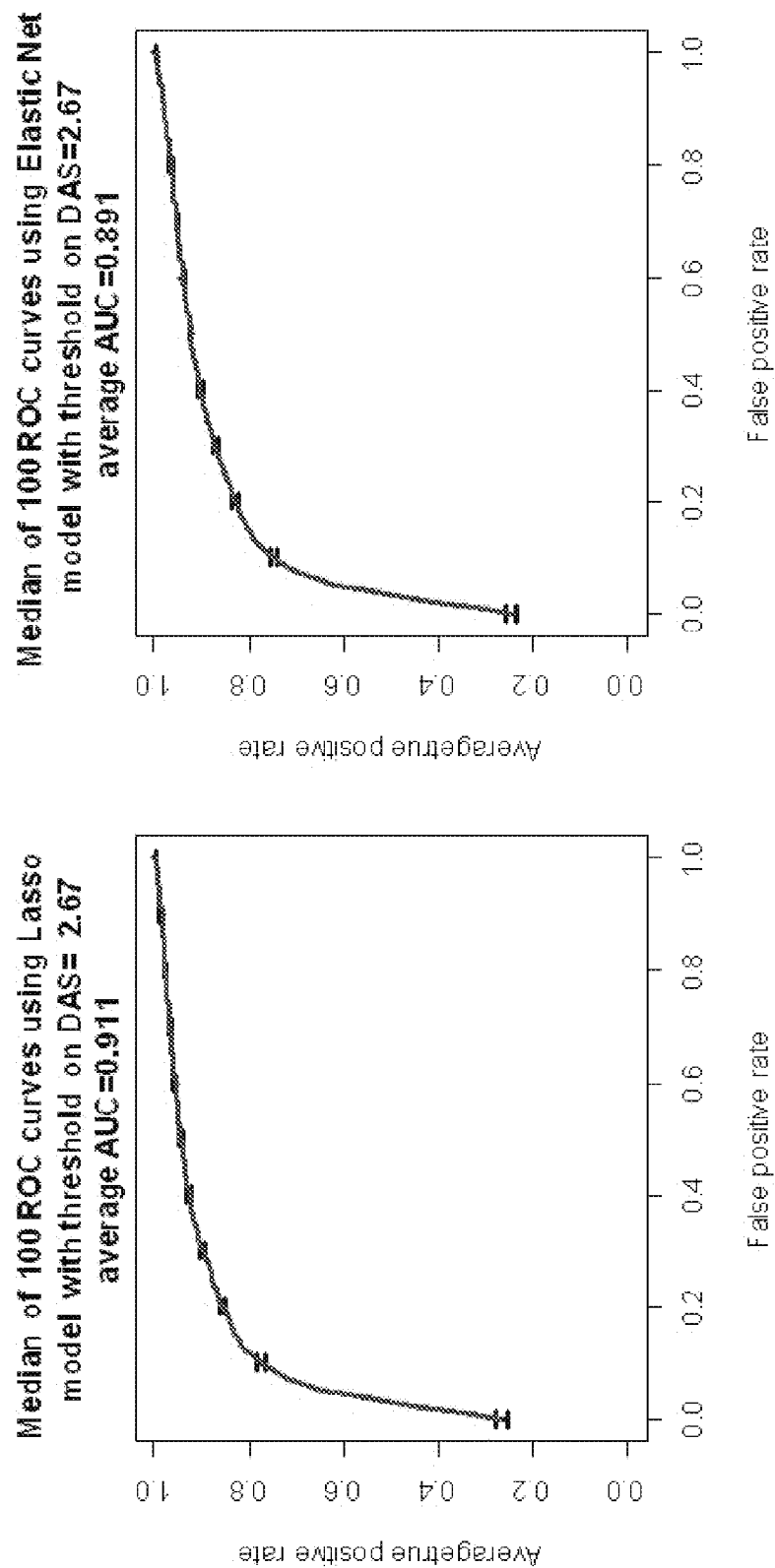
FIG. 11 depicts the use of ROC and AUC to show the ability of DAI scores to classify subjects into high/low disease groups (dichotomized on a DAS of 2.67, where DAS<2.67 is remission) across all DAI cut-off points in 100 cross-validations. The curve represents the average ROC curves across 100 cross-validations. See Example 1.

Covariation and multicolinearity between all variables were evaluated; i.e., for both clinical data and biomarkers. Heatmap, PCA, and correlation matrices were generated. See FIGS. 11 and 9 for PCA and correlation matrices, respectively (heatmap not shown). If a strong correlation was shown to exist between biomarkers, it indicated that multicolinearity should be taken into account during the model building process. If a strong association was detected between baseline clinical variables and biomarkers, it was determined that further evaluation was needed. ANOVA and Spearman correlations, along with p-values and FDR, were used to examine associations between all clinical variables (without DAS28 scores) and biomarkers. See FIG. 9.

Multivariate Analysis

Several multivariate modeling methods were considered. In general, the linear penalized regression methods were determined to perform the best.

Model 1: Forward Stepwise Ordinary Least Square Regression

For this modeling method, the equation $Y=X\beta+\epsilon$ applies, where Y is the column vector with observed values, $\beta$ is a matrix of coefficients for the predictor variables $X_i$, and $\epsilon$ is the random error. The forward selection begins with no variables in the model. Then, given a collection of predictors X, the predictor having the largest absolute correlation with the response Y is selected and a simple linear regression of Y on $X_1$ is performed, where $X_1$ is the first predictor variable. The residual vector is now orthogonal to $X_1$, and is taken to be the new response variable. The other predictors are then projected orthogonally to $X_1$ and the forward selection process is repeated. The DAIMRK biomarker selected at each step is recorded, along with the correlation $R^2$.

Model 2: Penalized Regressions

Penalized regression model methods are a set of statistical techniques that select subsets of variables to include in a model and determine stable coefficients for the variables. These methods are particularly useful when variables are correlated, and include ridge regression, Lasso, Elastic Net, and other methods. All of these methods have the characteristic that they shrink (penalize) the coefficients in the regression model.

In the first penalized regression model, Least Absolute Shrinkage and Selection Operator (LASSO or Lasso) is used to prioritize biomarkers (based on $R^2$ values) and to obtain a Lasso model. The "lasso" in this model minimizes the residual sum of the square, subject to the sum of the absolute value of the coefficients being less than a constant. See R. Tibshirani, *J. Royal Stat. Soc.*, series B 1996, 58(1):267-288. The Lasso method produces interpretable models, such as subset selection, and exhibits the stability of ridge regression (a statistical method that shrinks and stabilizes coefficients in regression models with multicolinearity). See W. Mendenhall and T. Sincich, *A Second Course in Statistics: Regression Analysis*, 6th edition 2003, Pearson Prentice Hall, Inc., Upper Saddle River, N.J.

In the second penalized regression model, linear regression is used with Elastic Net and mixtures of Lasso and ridge penalties to prioritize biomarkers (based on $R^2$ values) and obtain a final Elastic Net model. Elastic Net is a relatively new regularization and variable selection method. It encourages a grouping effect, where strongly correlated predictors segregate together, tending to be either in or out of the model together. See T. Zou, *J. Royal Stat. Soc.*, series B 2005, 67(2): 301-320.

In the third model, the forward variable selection method is a method of finding the "best" combination of variables by starting with a single variable, that which results in the best fit for the dependent variable Y, and increasing the number of variables used, step by step, testing all combinations of the original variable with the remaining variables in order to find the "best" pair of variables, continuing until either all variables are used up or some stopping criterion is met.

Model 3: Random Forest

Random Forest models are based upon the idea of creating hundreds of regression trees as models. See L. Breiman, *Machine Learning* 2001, 45(1):5-32. Each regression tree model is created with a uniform number of terminal nodes ("leaves") at the end of the branches of the tree. To estimate the regression value of a new subject, or to assign the subject to a class, the subject's data is evaluated within each of the regression tree models. The output prediction (i.e., regression value if continuous data, classification if binary data) from all trees is then averaged to create the final regression value or class prediction. In the case of regression values, averaging may be obtained by a weighted average; in class prediction, simply by voting.

The Random Forest methodology is as follows. First, a bootstrap sample (i.e., a sample with replacement) is drawn from the original data. Then a regression tree is "grown" from each bootstrap sample; i.e., at each node one randomly samples p of the n biomarkers measured, and selects the best biomarker and the best value of that biomarker to split the data into pure subsets from those biomarkers. Data from "training" subjects are used to build the tree models. Then, new data is predicted by aggregating the predictions of the various regression trees thus derived. For each subject sample k, where the k subject samples are different from those used in training the model (i.e., all k samples are "out of the bag"), the response estimates are averaged over the trees, given as $\hat{y}_k$. The random forest prediction algorithm is then given by the equation:

$$P\hat{E}_f = E_{XY}(Y - \bar{h}(X))^2 = \frac{1}{K}\sum (y_k - \hat{y}_k)^2,$$

where $P\hat{E}_f$ is a test set estimate of the generalization error of $PE_f$, and $\bar{h}(X)=(1/L)\Sigma h(x;\theta_l)$ is the random forest prediction. The collection of tree predictors is given by $h(x,\theta_l)$, $l=1\ldots$, L, where $\theta_l$ is a random vector. Y represents the actual response variables; e.g., a DAS score. Y represents the predictor; e.g., biomarker levels.

The variable importance is then estimated. In every regression tree thus grown in the random forest, one calculates the prediction error for that tree, $$PE_l = \frac{1}{K}\sum (y_k - \hat{y}_k)^2,$$

as predicted by the lth tree predictor, $h(x,\theta_l)$. One then randomly permutes the values of a biomarker variable i in the "out of bag" cases, and computes the prediction error $$PE_{li} = \frac{1}{K}\sum (y_k - \hat{y}_{ki})^2$$

as predicted by the lth tree predictor. Importance (Imp) is given as the variable i for $Imp_i=PE_li-PE_l$ for the ith biomarker for lth tree. The variable importance of the ith variable is computed $$I_i = \frac{\overline{I_{mp_i}}}{SE(I_{mp_i})}$$

where $\overline{Imp}_i$ is the average and standard area of importance of ith variable over all L trees.

Coefficients Representative of a DAI Model

The following coefficients represent the terms of the respective DAI models:

$DAI_k=\Sigma\beta_i x_{ik}$, where $DAI_{ik}$ is the calculated DAI for the kth subject, $x_{ik}$ represents the transformed ith biomarker concentration for the kth subject, and $\beta_i$ is the coefficient for the ith biomarker.

Cross-validation

A random subset of 70% of the total study population was selected without replacement. The model was fitted using this subset, then evaluated as to AUC for classification of subjects, and correlation (r), against the remaining 30% of the study population. Cross-validation was repeated 100 times, and the resulting accuracy estimates were averaged to predict future performance.

Results

The analyses demonstrated that the DAI scores associate well with DAS28 scores, and also discriminate between subjects with high and low DAS28 scores. Correlations of the DAI scores with DAS28 were r=0.57 to r=0.6, as estimated using 100 test set cross-validations. Specifically, the DAS28 correlation of the DAI score derived using the Lasso method was r=0.5909, the DAS28 correlation of the DAI score derived using the Elastic Net method was r=0.5974, and the DAS28 correlation of the DAI score derived using the forward variable selection method was r=0.5692. These results show that the DAI score derived from each of these methods, and using different subsets of the protein biomarkers, all yield good correlation with DAS28.

Figure 12:
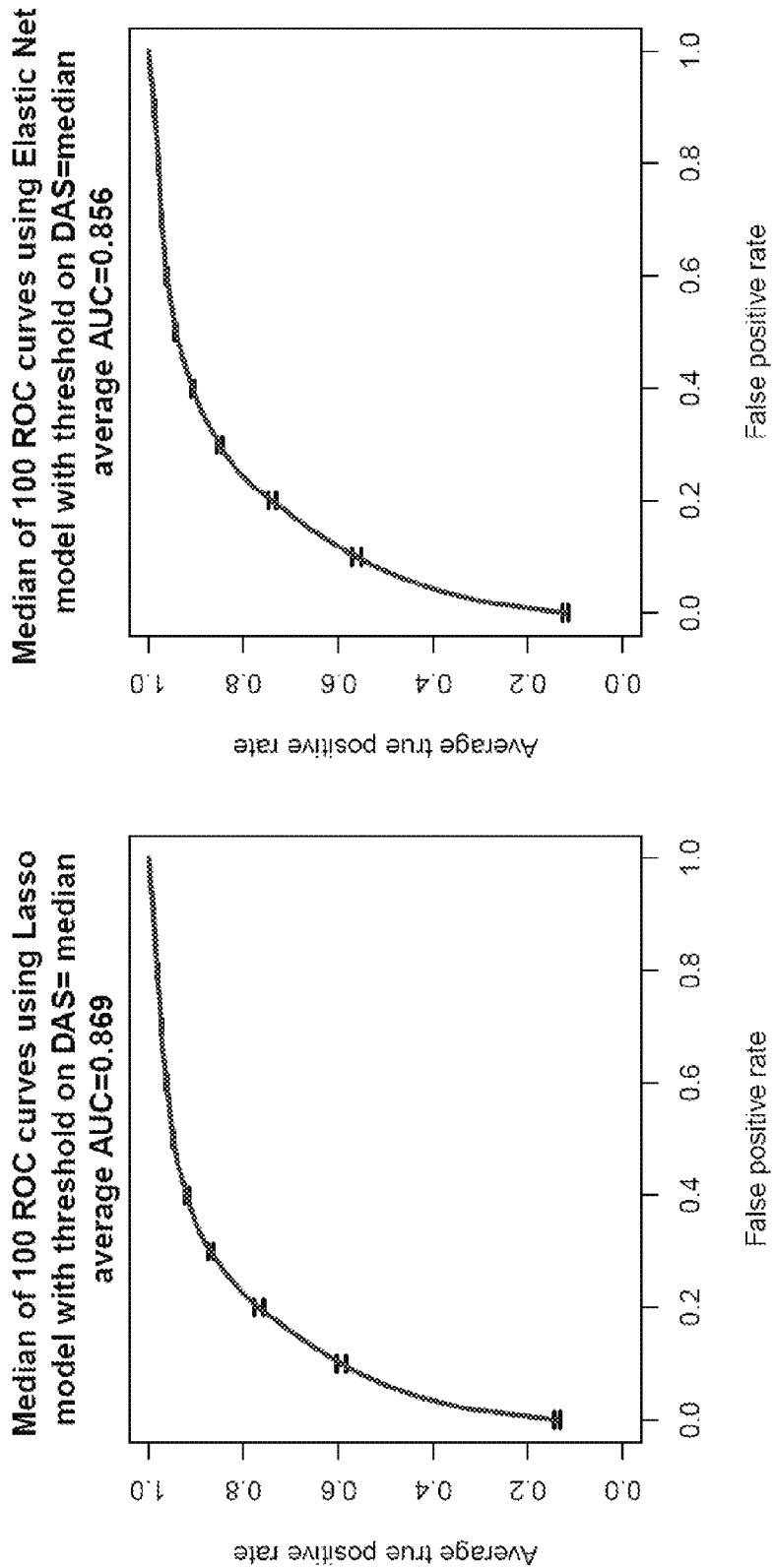
FIG. 12 depicts the use of ROC and AUC to show the ability of the DAI score to classify subjects into high/low disease groups (dichotomized on a DAS of 3.9, the median of the DAS values in the data) across all DAI cut-off points in 100 cross-validations. The curve represents the average ROC curves across 100 cross-validations.
Figure 13:
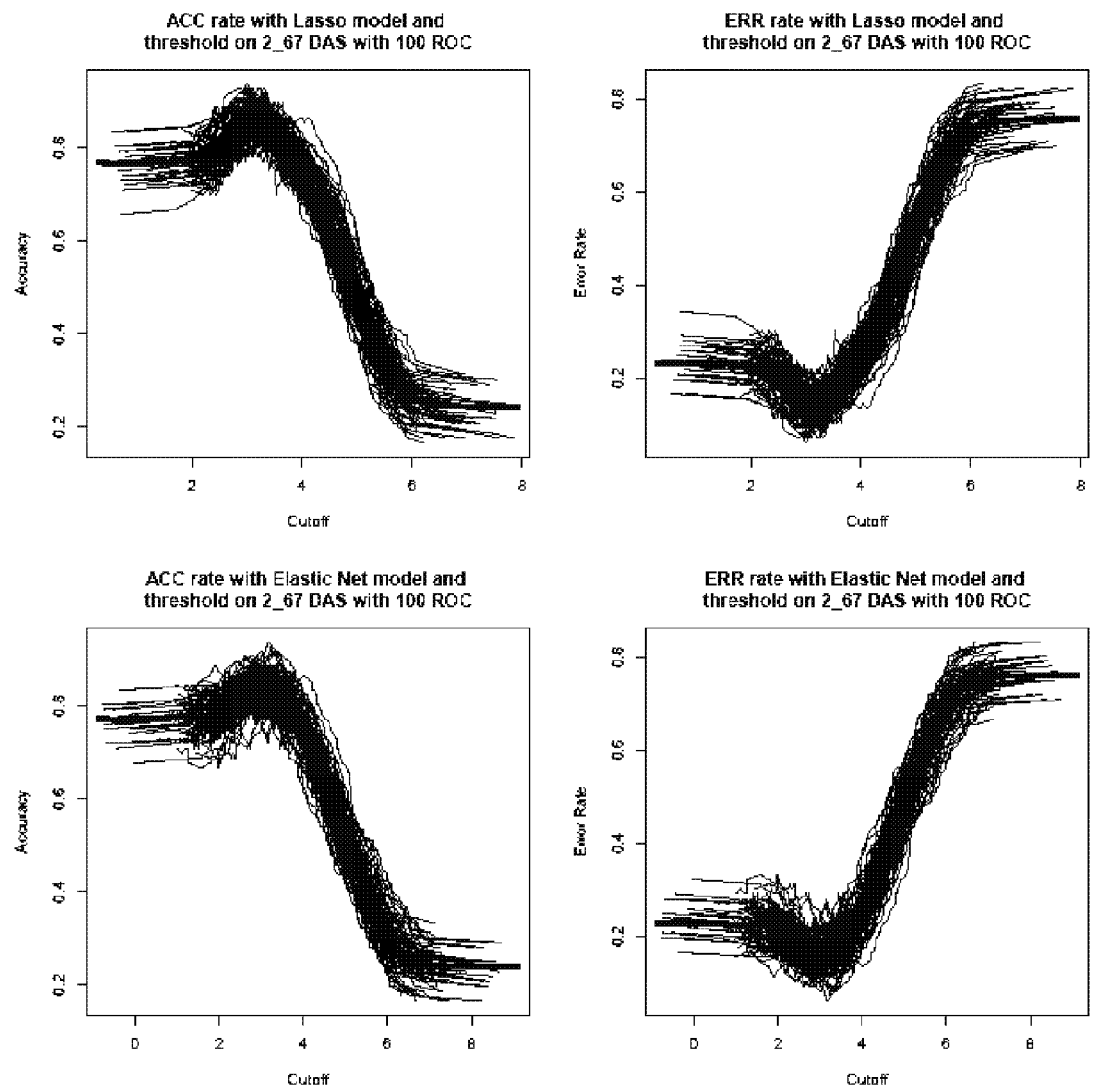
FIG. 13 depicts the accuracy (ACC) and error rates (ERR) of the 100 cross-validation iterations of Example 2, where a DAS28-CRP cut-off of 2.67 was used. Shown are the results of applying the Lasso and Elastic Net models.

The DAI scores can also be used to discriminate between subjects with high and low DAS28 scores, and thus classify subjects by level of disease activity, as shown by the area under the ROC curve (FIGS. 12 and 13), estimated using 100 cross-validation test sets. See also Example 3. Specifically, for subjects dichotomized at a DAS of 2.67, where DAS<2.67 is considered remission, the area under the ROC curve for the DAI score derived using the Lasso method was 0.911. The area under the ROC curve for the DAI score derived using the Elastic Net method was 0.891. For subjects dichotomized on a DAS of 3.9, which is the median DAS value of this study, the area under the ROC curve for the DAI score derived using the Lasso method was 0.869. The area under the ROC curve for the DAI score derived using the Elastic Net method was 0.856. These results show that the DAI scores derived using each of these methods all yield good areas under the ROC curves, and thus good discrimination between subjects with high and low DAS28 scores.

The results further show that by specifically selecting biomarkers from the DAIMRK set, all the DAI scores derived therefrom, according to each of the above-described methods, yield good areas under the ROC curves for discriminating subjects with high and low DAS28 scores.

A specific instance of a formula for calculating a DAI score was developed using seven biomarker proteins selected from the DAIMRK set of biomarkers, according to the methods described above (starting with an ALLMRK biomarker dataset, using data collected from 322 RA samples obtained from the BRASS and OMRF cohorts; see below for a discussion of the OMRF cohort).

The DAI score in this Example was computed using the following formula: DAI=4.49+0.36*CRP−0.29*EGF−0.22*IL8+0.045*LEP+0.21*IL1RN−0.25*APOA1+0.10*CCL22. This formula exhibited a correlation of 0.5801 and AUC of 0.7772 in predicting DAS28.

Example 2

Correlation of DAI to DAS28 Scores Over Multiple Timepoints in a Longitudinal Cohort Example 2 demonstrates the practice of the present teachings in a longitudinal study of RA, and the predictive power of DAI scores to track changes in a subject's DAS28 scores over time. The DAI score thus provides a quantitative measure to monitor changes in subject disease activity and response to treatment.

Experimental Design, Biomarker Selection and Quality Control of Assay Data

Analyzing data obtained from multiple time points for a subject is not only useful in monitoring changes in that subject's disease activity, but can also be useful in increasing the prediction accuracy of a DAI formula. The objective of this study was to develop, validate, and compare biomarker-based models (single time point and longitudinal) that measure disease activity in RA subjects over time, in order to demonstrate that the performance of the longitudinal model is better than cross-sectional.

For the purpose of the longitudinal study described herein, a subject group was selected from the BRASS cohort. See Example 1 for a general description of the BRASS cohort. Note that the specific subject samples used in this study were different from those analyzed in Example 1. (Therefore, this longitudinal study can also serve as an independent cohort validation for the study described in Example 1.) A total of 255 samples were obtained from the annual physician visits of 85 RA subjects (at years 1, 2 and 4), and were used for this study. The cohort for this study had the following characteristics: 91% female, 62% CCP positive, 64% RF positive, 4% smokers, 48% on MTX, 64% on non-biologic DMARDs, 43% on biologic DMARDs, and 27% on steroids. Additionally, the mean age of the cohort was 59 years (SD+/−12.7), with a minimum age of 29 and a maximum age of 85. The mean DAS28-CRP for this cohort was 4.1 (SD+/−1.7), with a wide distribution of DAS28-CRP scores (minimum of 1.2 and a maximum of 8.2).

Twenty-one biomarkers selected from the DAIMRK set were assayed in a multiplex format or an ELISA format. (Various suppliers were identified through a screening and optimization process prior to the study; e.g., Millipore, R & D Systems, Meso Scale Discoveries, and various ELISA assay suppliers.) All assays were performed following the manufacturer's instructions with cohort samples randomly assigned (or the equivalent) to the sample positions on the plate layouts. Four pooled sera (Normal, RA, SLE and OA) were included in each 96-well plate as process controls. All samples were assayed at least in duplicate. Seven-point calibration curves were constructed for each biomarker, to accurately determine the measureable range of test sera. See Example 3 for a discussion of how study assay data were qualified.

Performance of the DAI Model in Tracking Longitudinal Changes in DAS28

See Example 1 for an explanation of selected statistical models used to construct the relationship between DAI and DAS28 scores. In addition, DAI models were also built based on longitudinal hierarchical linear methods (HLM), which incorporated all timepoint information. The HLM include both time-variant and time-invariant variables.

Results

The correlation between change of DAI and change of DAS28 between two time points was r=0.56 in the dataset described in this example, where the DAI model was built from a single-timepoint penalized regression model with cross-sectional data from the BRASS cohort described in Example 1. The correlation increased to 0.69 when a longitudinal HLM was built from the data described in this example and tested on the Taylor cohort described in Example 5.

This study demonstrates that a DAIMRK-derived algorithm developed in both cross-sectional and longitudinal analyses was a strong predictor of disease activity over time. These results further demonstrate that the biomarker algorithm utilized in this study has a high level of accuracy and is robust with respect to sampling over time.

Example 3

Classification of Subjects by DAI Score

Example 3 demonstrates the use of a DAI score to classify subjects according to disease activity. The study was conducted with 182 samples from the BRASS cohort (see Example 1), and 140 samples from a cohort established by the Oklahoma Medical Research Foundation (the OMRF cohort). The appropriate Ethics Committee approval was obtained for the study, and all subjects gave informed consent. Since 2007, more than 800 subjects with confirmed RA have been enrolled in OMRF cohort. All subjects fulfilled the American College of Rheumatology criteria for RA. The cross-sectional study collected medical or clinical information from all subjects, comprising disease activity scores, radiological results, subject health status and other clinical assessments. Blood samples were collected during office visits. The subjects from the BRASS cohort for this study had the following characteristics: 86% female, 65% CCP positive, 70% RF positive, 5% smokers, 60% on MTX, 72% on non-biologic DMARDs, 55% on biologic DMARDs, and 23% on steroids. Additionally, the mean age of the subjects of the BRASS cohort was 58 years (SD+/−14.3), with a minimum age of 22 and a maximum age of 94. The mean DAS28-CRP for the subjects of this cohort was 3.2 (SD+/−1.2), with a minimum of 1.2 and a maximum of 7.5. The subjects from the OMRF cohort for this study had the following characteristics: 75% female, 60% CCP positive, 98% RF positive, 22% smokers, 63% on MTX, 81% on non-biologic DMARDs, 49% on biologic DMARDs, and 32% on steroids. Additionally, the mean age of the subjects of this cohort was 60 years (SD+/−13.1), with a minimum age of 26 and a maximum age of 84. The mean DAS28-CRP for the subjects of this cohort was 5.2 (SD+/−1.5), with a minimum of 2.2 and a maximum of 8.2.

DAIMRK biomarker assays and assay data quality control were performed as described in Example 1.

Figure 14:
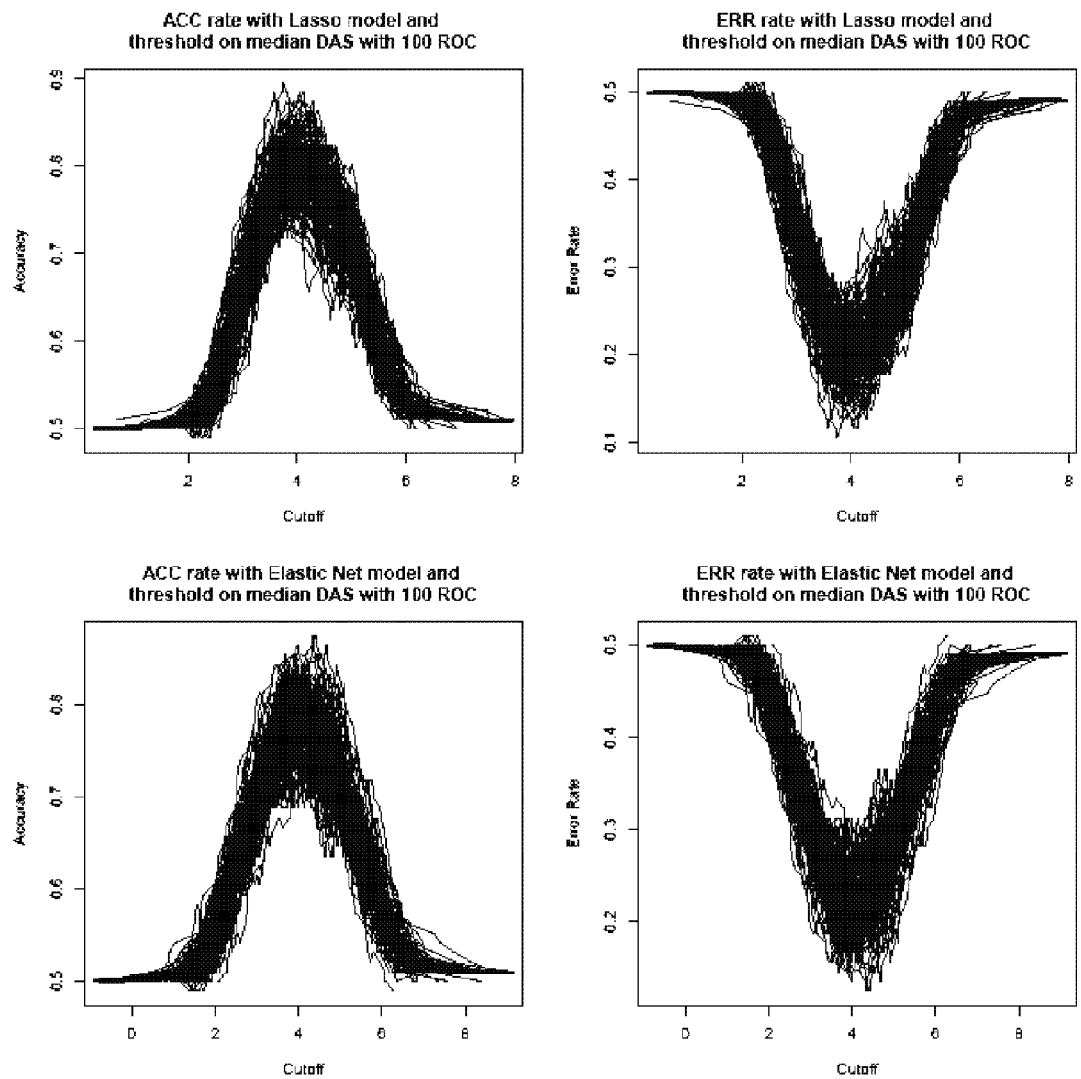
FIG. 14 depicts the accuracy and error rates of the 100 cross-validation iterations of Example 2, where a DAS28-CRP cut-off of 3.94 was used. Shown are the results of applying the Lasso and Elastic Net models.
Figure 15:
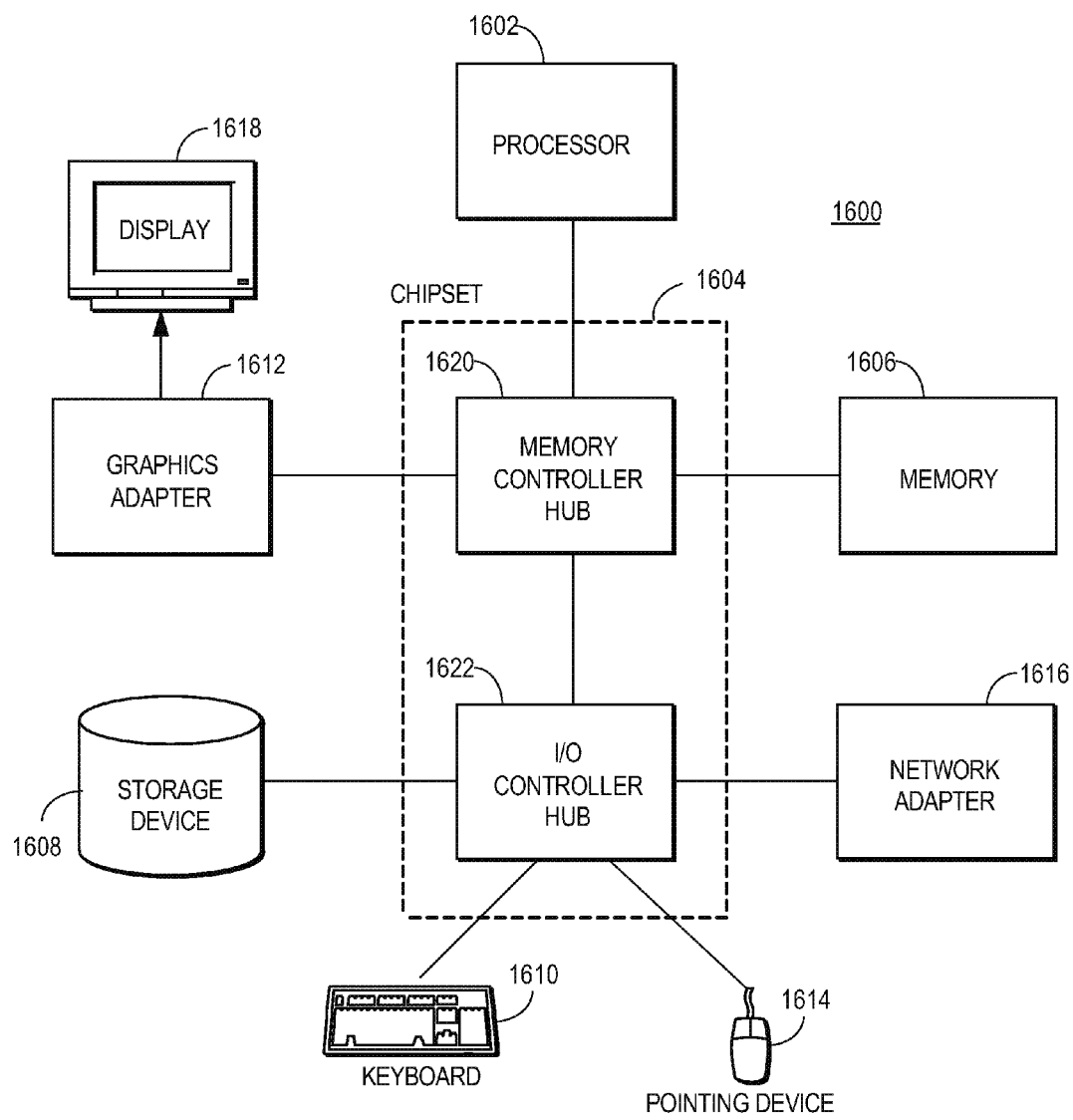
FIG. 15 is a high-level block diagram of a computer (1600). Illustrated are at least one processor (1602) coupled to a chipset (1604). Also coupled to the chipset (1604) are a memory (1606), a storage device (1608), a keyboard (1610), a graphics adapter (1612), a pointing device (1614), and a network adapter (1616). A display (1618) is coupled to the graphics adapter (1612). In one embodiment, the functionality of the chipset (1604) is provided by a memory controller hub 1620) and an I/O controller hub (1622). In another embodiment, the memory (1606) is coupled directly to the processor (1602) instead of the chipset (1604). The storage device 1608 is any device capable of holding data, like a hard drive, compact disk read-only memory (CD-ROM), DVD, or a solid-state memory device. The memory (1606) holds instructions and data used by the processor (1602). The pointing device (1614) may be a mouse, track ball, or other type of pointing device, and is used in combination with the keyboard (1610) to input data into the computer system (1600). The graphics adapter (1612) displays images and other information on the display (1618). The network adapter (1616) couples the computer system (1600) to a local or wide area network.
Figure 21:
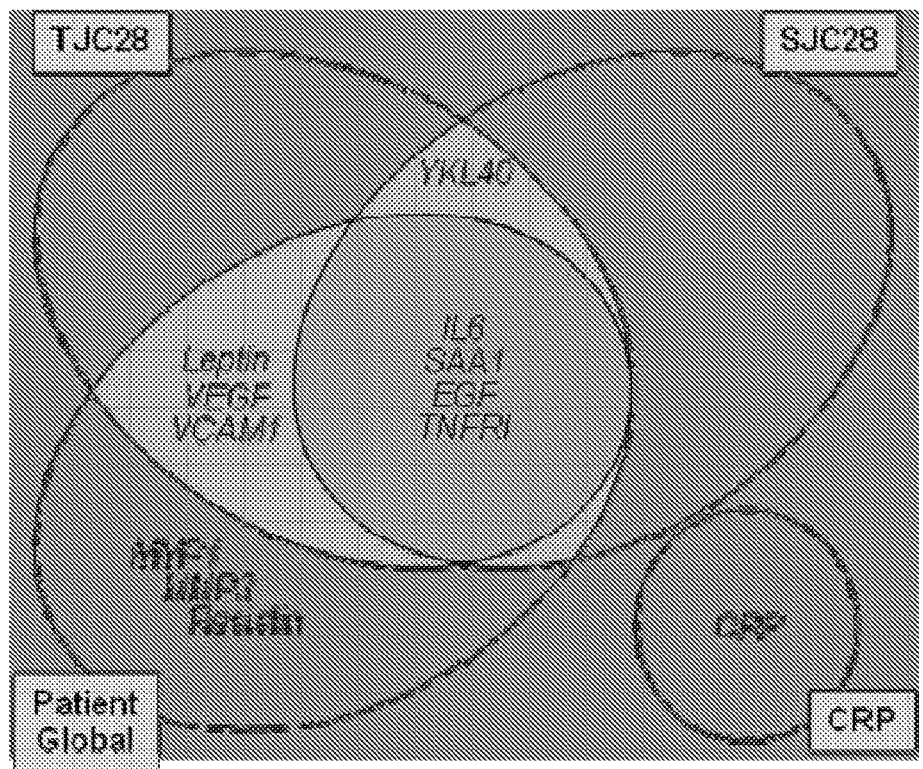
FIG. 21 depicts a Venn diagram indicating biomarkers that were used to predict various DAS components in deriving a DAI score, as described in Example 11.

A cut-off of DAI=3 best separates the low DAS (DAS<2.67) and high DAS (DAS>2.67) subjects, at an accuracy rate of >0.8. See FIG. 14. When the DAS threshold is set to 4.0 instead of 2.67, DAI also reached the accuracy rate of 0.8. See FIG. 15.

This study demonstrates that a DAI algorithm derived from the DAIMRK set of biomarkers can be used to classify subjects into well-established levels of disease activity, relative to the gold-standard clinically-based measure, the DAS28.

Example 4

Use of DAI to Distinguish Subjects with Ra from Unaffected, Healthy Controls

Example 4 demonstrates the use of the DAI score in the diagnosis of RA, by discriminating subjects with RA from unaffected, healthy controls.

Data from 24 healthy control subjects and 31 subjects diagnosed with RA were examined to determine whether mean DAIMRK biomarker levels were different between the two groups. Twenty-one biomarkers selected from the DAIMRK set were assayed in a multiplex format or an ELISA format. Assay suppliers were previously identified through a screening and optimization process (e.g., Millipore, R & D Systems, Meso Scale Discoveries, and various ELISA assay suppliers). All assays were performed following the manufacturer's instructions, with cohort samples randomly assigned (or the equivalent) to the sample positions on the plate layouts. Four pooled sera (normal, RA, SLE and OA) were included in each 96-well plate as process controls. All samples were assayed at least in duplicate. Seven-point calibration curves were constructed for each biomarker protein, for accurate determination of the measureable range of test sera. See Example 3 for a discussion of how study assay data were qualified.

Statistical Analysis

Statistical analyses of data included the t-test, random forests, boosted trees, and KNN. Boosted Trees models are based upon the idea of computing a sequence of trees, where each successive tree is built by predicting the residuals of the preceding tree. Put another way, boosting will generate a sequence of classifiers, where each consecutive classifier in the sequence is an "expert" in classifying observations that were not well-classified by those preceding it.

The univariate statistical analysis in this Example was performed using a two-sample t-test with Satterthwaite adjustment. The resulting data showed a right-skewed distribution, so a logarithmic transformation was used to correct for the skew, and a numeric value of 1 was added to avoid the asymptotic tail of the resulting logarithmic function between the numeric values of 0 and 1. The univariate analyses indicated that the relative levels of CCL22, CRP, IL6, IL8, keratan sulfate, and TNFSF1A were significantly different between healthy (Control) individuals and RA subjects. See Table 2.

TABLE 2

| DAIMARK variable | RA | Control | p-value |
|---|---|---|---|
| CCL22 | 3.71 (0.19) | 3.47 (0.15) | 1.14E−06 |
| CRP | 4.55 (0.61) | 4.22 (0.47) | 0.027294 |
| IL6 | 0.98 (0.37) | 0.82 (0.2) | 0.049 |
| IL6R | 4.23 (0.18) | 4.3 (0.09) | 0.053 |
| IL8 | 1.18 (0.26) | 1.04 (0.15) | 0.015925 |
| keratan sulfate | 2.28 (0.08) | 2.44 (0.08) | 2.21E−09 |
| TNFRSF1A | 2.9 (0.19) | 3.03 (0.15) | 0.007447 |

Multivariate Analysis

The Random Forest algorithm was provided with the DMARK variables from Table 2 and samples were split, 43% into the Test set and 56% into the Training set. The Training set variables were ranked based upon their relative importance in the model. Relative importance is based on the degree to which each variable contributes to improving the model fit. See R A Berk, "Statistical Learning from a Regression Perspective," Springer, 2008, p. 213. See Table 3.

TABLE 3

| Variable | Importance |
|---|---|
| CCL22 | 1 |
| keratan sulfate | 0.748 |
| IL6R | 0.707 |
| TNFRSF1A | 0.452 |
| IL8 | 0.438 |
| IL6R | 0.41 |
| CRP | 0.24 |

The Training set data showed 96.8% accuracy and the Test set data showed 87.5% accuracy, as measured by ability to discriminate subjects with RA from unaffected healthy controls. The test confusion matrix specifies the error (confusion) in the actual versus predicted classification. See Table 4.

TABLE 4

| | Test confusion* matrix | | Training confusion* matrix | |
|---|---|---|---|---|
| | Actual | Predicted | Actual | Predicted |
| RA | 14 | 11 | 17 | 17 |
| Control | 10 | 10 | 14 | 13 |
| Total | 24 | | 31 | |
| Accuracy | | 87.5% | | 96.8% |

Here "Predicted RA" refers to samples from subjects that were predicted to have RA and actually did, while "Predicted Control" refers to samples from subjects that were predicted to be healthy and actually were. Thus in the Test confusion matrix shown in Table 4, of the 24 samples tested, 14 of the RA samples were correctly predicted to be RA positive and three were incorrectly predicted to be healthy, while all 10 control samples were correctly predicted to be healthy. The accuracy then is calculated as: (number Predicted RA that is Actual RA)+(number Predicted Control that is Actual Control)÷total number samples; or, for the Test confusion matrix, (11+10)÷24=0.875, and for the Training confusion matrix, (17+13)÷31=0.968.

The boosted tree algorithm was given the DAIMRK variables in Table 2 and the samples split 33% into the Test set, and 64% into the Training sets. The Training set variables were ranked based upon their relative importance in the model. See Table 5.

TABLE 5

| Variable | Importance |
|---|---|
| keratan sulfate | 1 |
| CCL22 | 0.95 |
| CRP | 0.91 |
| TNFRSF1A | 0.84 |
| IL6R | 0.77 |
| IL6R | 0.72 |
| IL8 | 0.59 |

The Training set data showed 100% accuracy and the Test set data showed 83.3% accuracy. See Table 6.

TABLE 6

|  | Test confusion matrix | | Training confusion matrix | |
| --- | --- | --- | --- | --- |
|  | Actual | Predicted | Actual | Predicted |
| RA | 9 | 7 | 22 | 22 |
| Control | 9 | 8 | 15 | 15 |
| Total | 18 | | 37 | |
| Accuracy | | 83.3% | | 100% |

Results

Using stored blood samples from RA and healthy subjects, relationships were examined between the protein serum levels of different DAIMRK biomarkers related to immune activation and inflammatory response. The mean DAIMRK biomarker levels were different between the two groups of subject. Additionally, the levels of CCL22, CRP, IL6, IL8, keratan sulfate, and TNFSF1A were significantly different between healthy subjects and RA subjects. These results would indicate that as RA disease progresses, additional pathological mechanisms are activated to trigger the onset of clinical symptoms.

Example 5

Assessment of Response to Therapy Using DAI Scores

This example demonstrates that the DAI score is useful in assessing a subject's response to a single therapy, and in comparing subjects' responses to two therapies. The hypothesis that the DAI score is significantly associated with a subject's response to infliximab treatment was tested, as was the hypothesis that the DAI score is associated with differences in response to two therapies.

Serum samples and clinical and imaging data were examined from 24 subjects (the Taylor cohort), who were followed in a two-year blinded study to compare a therapeutic regimen of MTX and infliximab against a therapeutic regimen of MTX alone, in aggressive early RA. Placebo arm subjects were switched to methotrexate and infliximab after one year. Subjects were evaluated by ultrasound at 0, 18, 54 and 110 weeks, and scored for synovial thickening and vascularity by power Doppler area (PDA). Radiographic examination to determine van der Heijde modified Sharp (vdH-Sharp) scores was carried out at 0, 30, 54 and 110 weeks. DAS28 scores were obtained at office examinations carried out every three to five weeks over the two-year study period. DAIMRK biomarker levels were determined in blood samples from all 24 subjects collected at 0, 6, 18, 54 and 110 weeks.

Characteristics of the subjects of the Taylor cohort were as follows: the mean age of the placebo+MTX subgroup was 51 years (SD+/−14.0), the inf+MTX subgroup was 55 years (SD+/−11.8); the mean weight in kg of the placebo+MTX subgroup was 71.1 (SD+/−13.2), the inf+MTX subgroup was 67.9 (SD+/−16.1); the mean disease duration of the placebo+MTX subgroup was 1.64 years (SD+/−0.63), the inf+MTX subgroup was 1.33 (SD+/−0.64).

To show that DAI score is significantly associated with a subject's response to infliximab treatment, each subject's DAI score before infliximab treatment (year 0, week 0) was compared to his/her score after one year of infliximab treatment (year 1, week 52). Row A of Table 7 shows the results of a test (paired t-test) of the difference between the DAI scores at year 0 and year 1 for 12 subjects receiving infliximab (inf). The DAI scores were computed from the model built from BRASS subjects, described elsewhere herein. The t-stat is the value of the test statistic, t, for which a p-value can be calculated using the T distribution.

TABLE 7

|  |  | t-stat | p-value |
| --- | --- | --- | --- |
| A | Change in inf, year 0 to 1 | −2.69981 | 0.007764 |
| B | Difference MTX and difference MTX, year 0 to 1 | −1.41064 | 0.093483 |

As Table 7 shows, the paired t-test is significant (p=0.007764), thus demonstrating that the DAI score changes significantly following infliximab treatment.

To show that the DAI score is useful in assessing differences in subjects' response to two therapies, the DAI scores of subjects receiving infliximab treatment were compared to the DAI scores of subjects receiving MTX treatment. The DAI scores of weeks 0 to 52 were subtracted within both MTX and infliximab subjects. Twelve datapoints (or DAI score differences) were obtained for each treatment group. Then a non-paired t-test (n=12 for each group) was used. Row B of Table 7 shows the results of the t-test for the difference in DAI scores of infliximab subjects and DAI scores of MTX subjects. The t-test shows a trend to significance (p=0.09). A sample size of greater than twelve observations would be expected to yield a significant p-value for this difference.

This example demonstrates that the DAI score is useful in assessing a subject's response to a single therapy, and that the DAI score is useful in comparing subjects' response to two therapies.

Example 6

Correlation of DAI Scores with Clinical Measures of Erosion

This example demonstrates that DAI scores track joint erosion, with a strong correlation between DAI scores and radiographic changes in subjects, based on changes in Sharp scores from X-ray imaging and changes in measures of joint damage (i.e., synovial thickening, vascularity, and intra-articular blood flow) assessed by power Doppler (PD) ultrasonography. Synovial vascularization and mononuclear cell infiltration are known to be characteristics of RA synovitis. See P. Taylor et al., *Arth. Rheum.* 2004, 50(4):1107-1116. This example demonstrates that DAI scores can provide the current rate of joint destructive processes in subjects, and correlate with ultrasound observations of subclinical synovitis. Thus, DAI scores are a powerful complementary approach to identify subjects at highest risk of accelerated bone and cartilage damage.

The samples used in this example were the Taylor cohort, described above. See Example 5. Clinical measures of erosion were assessed using two radiographic modalities: X-ray and ultrasound. X-rays of hands and feet taken at 0, 30, 54 and 110 weeks provided van der Heijde modified Sharp scores. All subjects had erosions at baseline (week 0), but experienced a wide range of changes in total Sharp scores (TSS) over the course of the study (median change 6.25, interquartile range 4-14.5). Ultrasound studies provided three measures of joint damage: color Doppler area (CDA), synovial thickening (SYN), and erosion score (ES). Blood samples from all 24 subjects were collected at 0, 6, 18, 54 and 110 weeks, and were used to measure the levels of protein biomarkers selected from the ALLMRK set, described above.

Correlation coefficients between the DAI scores and the three ultrasound measures observed were calculated. The DAI score was calculated for each subject at each given timepoint, and those DAI score values were then paired with the ultrasound scores for that subject at same timepoints. The 24 subjects had ultrasound scores at timepoint 0, 18, 54, and 110 weeks. The correlation (Cor) was computed as Cor (DAI_kt, ultrasound_kt), where k is 1, ..., 24 and t=0, 18, 54, 110. Thus, 24 subjects*4 timepoints per subject=96 datapoints total were used in computing the Cor. The DAI score was correlated to all three ultrasound measures ($p<0.05$).

Table 8 shows the correlation between DAI scores and Sharp scores. The DAI model was built from a separate cohort of subjects (BRASS) to prevent over-fitting. The DAI scores were computed across all 24 subjects at week 6, when therapeutic effect was observable. The results in Table 8 were computed as follows: (a) build DAI model from BRASS cohort of subjects; (b) calculate the DAI score in Taylor cohort of subjects (all 24) using week 6 data; (c) use leave-one-out cross-validation procedure, and for each 23 subjects (i) build a longitudinal model using the week 6 DAI score to predict rate of change in total Sharp score (TSS) (i.e., change of TSS/week), (ii) calculate three Sharp score rates of change (i.e., 0-54 weeks, 0-110 weeks, and 54-110 weeks) for the left-out subject, (iii) calculate three estimated TSS rates of change (0-54 weeks, 0-110 weeks, and 54-110 weeks) for the left-out subject, from (i); (d) after obtaining all the estimated TSS changes for each subject, calculate the correlation between the actual TSS rate of change and the estimated one based on the DAI scores for all 24 subjects. The correlations were calculated for each interval (e.g., 0-54 weeks) separately.

TABLE 8

| Interval | Correlation |
| --- | --- |
| Week 0-54 | 0.769 |
| Week 0-110 | 0.737 |
| Week 54-110 | 0.567 |

These results demonstrate that DAI scores are correlated with clinical measures of erosion, as determined by X-ray (i.e., Sharp scores) and ultrasound observations of subclinical synovitis in subjects' joints.

Example 7

Association of DAI with DAS28 Scores in Another Large Clinical Cohort

Example 7 demonstrates the transformation of observed biomarker levels into a DAI score by various statistical modeling methodologies, which DAI score serves as a quantitative measurement of disease activity that correlates well with observed DAS28, as for measuring the extent of subject inflammation status and disease activity at any single timepoint. This example also demonstrates the selection of a particular set of 23 biomarkers, all members of the DAIMRK set; namely, SAA1, IL6, TNFRSF1A, VEGFA, PYD, MMP1, ICAM1, calprotectin, CHI3L1, MMP3, EGF, IL1RN, VCAM1, LEP, RETN, CRP, IL8, APOAI, APOC3, CCL22, IL1B, IL6R and IL18. Certain embodiments of the present teachings comprise utilizing these biomarkers from the DAIMRK set of biomarkers for determining a DAI score with significant correlation with disease activity status.

Samples were obtained from the Computer Assisted Management in Early Rheumatoid Arthritis Study (CAMERA). From 1999-2003, all early rheumatoid arthritis patients (i.e., disease duration of one year or less) who fulfilled the 1987 revised American College of Rheumatology (ACR) criteria for rheumatoid arthritis were asked to participate in this two-year randomized, open-label prospective multicentre strategy trial. As a result, 299 patients were studied. Patients visited the outpatient clinic of one of the six rheumatology departments in the region of Utrecht, the Netherlands, collaborating in the Utrecht Rheumatoid Arthritis Cohort study group. Inclusion criteria were that patients must have exhibited symptoms for less than one year, with age greater than 16 years. Exclusion criteria were the previous use of glucocorticoids or any DMARD, use of cytotoxic or immunosuppressive drugs within a period of three months before inclusion, alcohol abuse, defined as more than two units per day, and psychological problems, which would make adherence to the study protocol impossible. At baseline all patients were monitored for medical conditions that would interfere with MTX usage. This screening included a chest X-ray, liver enzymes, albumin, hepatitis serology, serum creatinine and complete blood count. An independent person performed randomization in blocks of nine per hospital. The medical ethics committees of all participating hospitals approved this study, and all patients gave written informed consent before entering the study.

The cohort for this study had the following characteristics: 69% female, 68% CCP positive, 74% RF positive, 100% on MTX, 100% on non-biologic DMARDs, and 0% on biologic DMARDs. Additionally, the mean age of the cohort was 52 years (standard deviation (SD)+/−14.7), with a minimum age of 17 and a maximum age of 78. The mean DAS28-CRP for this cohort was 5.0 (SD+/−1.9), with a minimum of 0.9 and a maximum of 8.4.

A subpopulation of 72 subjects was selected from the CAMERA cohort for this Example. All 72 patients were represented by baseline (time 0) visits and samples, and 48 were also represented by six-month visits and samples. Within the visits selected, a wide distribution of DAS28-CRP scores were represented, ranging from a minimum of 0.96 to a maximum of 8.4.

Assays were designed, in multiplex or ELISA format, for measuring multiple disease-related protein biomarkers selected from the ALLMRK set, as that set is described herein. These assays were identified through a screening process and were extensively optimized prior to assaying the CAMERA samples. SAA1, IL6, TNFRSF1A, VEGFA, MMP1, ICAM1, calprotectin, CHI3L1, MMP3, EGF, VCAM1, LEP, RETN, CRP, IL8, APOAI, APOC3, CCL22, IL1B and IL6R were measured using the MESO SCALE DISCOVERY® (MSD) platform. IL18 and IL1RN were measured with ELISA technology from R&D Systems, and PYD was measured with ELISA from Quidel.

All assays were performed following the manufacturer's instructions, with cohort samples randomly assigned (or the equivalent) to the sample positions on the plate layouts. Four pooled sera (from normal, RA, SLE and osteoarthritis (OA) subjects) were included in each assay plate as process controls. All samples were run at least in duplicate. Seven-point calibration curves were constructed for each biomarker for accurate determination of the measureable range of test sera.

Prior to statistical analyses, all assay data were reviewed for pass/fail criteria as predefined by standard operating procedures on parameters, including inter-assay CV, intra-assay CV, percent of samples within the measureable range of the calibration curve, and four serum process controls within the range of the calibration curve. The biomarker values that were not in the measureable range of the calibration curves were marked as missing data, and imputed by the lowest/highest detected value across all the samples within a given biomarker assay. No imputation was performed for the univariate analyses. For multivariate analysis, missing data imputation methods commonly used in microarray expression data and well known in the art were used. See, e.g., R. Little and D. Rubin, *Statistical Analysis with Missing Data*, 2nd Edition 2002, John Wiley and Sons, Inc., NJ. Biomarkers were excluded from analysis where more than 20% of the data were missing, and the remaining data were imputed by the KNN algorithm (with k=5 nearest neighbors).

Univariate Analysis

Biomarker assay data were normalized across each plate before correlations were calculated between individual proteins and measurements were transformed into DAI scores. Associations were calculated between the DAI scores and DAS28-CRP scores, swollen joint counts, TJCs, or CDAI. The correlation results were then compared using univariate analysis. See Table 9, results of univariate analyses for several DAIMRK biomarkers in the CAMERA training set.

The False Discovery Rate (FDR) was used as multiple testing correction, according to the following: let k be the largest i for which pi≤i/m*α; reject all Hi, i=1, . . . , m. As will be clear to one of skill in the art, where the DAIMRK biomarker is significantly associated with the DAS score, then the q-value is small. A parametric correlation test was also performed, using the parametric test $H_i:\rho_i=0$, and the statistic given by $$t = \frac{r(n-2)^{1/2}}{(1-r^2)^{1/2}}.$$

Covariation and multicolinearity between all variables were evaluated; i.e., for both clinical data and biomarkers. If a strong correlation was seen to exist between biomarkers, it indicated that multicolinearity should be taken into account during the model building process. If a strong association was detected between baseline clinical variables and biomarkers, it was determined that further evaluation was needed. ANOVA and Spearman correlations, along with p-values and FDR, were used to examine associations between all continuous clinical variables (without DAS28 scores) and biomarkers.

TABLE 9

| DAIMRK | Correlation coefficient | Nominal p-value |
| --- | --- | --- |
| IL6 | 0.693 | 0 |
| CRP | 0.685 | 0 |
| SAA1 | 0.658 | 0 |
| calprotectin | 0.557 | 0 |
| MMP3 | 0.509 | 0 |
| IL8 | 0.466 | 0 |
| IL1B | 0.454 | 0 |
| CHI3L1 | 0.423 | 0 |
| MMP1 | 0.364 | 0 |
| TNFRSF1A | 0.363 | 0 |
| VEGFA | 0.293 | 0.001 |
| ICAM1 | 0.23 | 0.012 |

TABLE 9-continued

| DAIMRK | Correlation coefficient | Nominal p-value |
| --- | --- | --- |
| pyridinoline | 0.228 | 0.013 |
| RETN | 0.219 | 0.016 |

Multivariate Analysis

Several multivariate modeling methods were considered. In general, the linear penalized regression model was determined to perform the best.

Model 1: Forward Stepwise Ordinary Least Square Regression

See Example 1 for a description of the forward stepwise ordinary least square regression model.

Model 2: Penalized Regressions

See Example 1 for a description of the penalized regressions model.

Coefficients Representative of a DAI Model

The following coefficients represent the terms of the respective DAI models: $DAI_k=\Sigma\beta_i x_{ik}$, where $DAI_{ik}$ is the calculated DAI for the kth subject, $x_{ik}$ represents the standardized ith biomarker concentration for the kth subject (usually log transformed and plate-to-plate normalized), and $\beta_i$ is the coefficient for the ith biomarker.

Cross-validation

A random subset of 70% of the total study population was selected without replacement. The model was fitted using this subset, then evaluated against the remaining 30% of the study population, using AUC and correlation. Cross-validation was repeated 100 times, and the resulting accuracy estimates were averaged to predict future performance.

Results

The DAI score in the present example was computed using the following formula:

DAI=(−16.16)−(0.06*calprotectin)+(0.22*CHI3L1)+
(1.19*ICAM1)+(2.77*IL6)+(0.73*MMP1)−
(0.83*MMP3)+(1.03*pyridinoline)+
(1.18*SAA1)+(2.44*TNFRSF1A)+
(0.33*VEGFA).

This formula exhibited a correlation of 0.65 and AUC of 0.84 in predicting DAS28 in the independent cohort, CAMERA.

The analyses demonstrated that the DAI scores correlate well with DAS28 scores, and also discriminate between subjects with high and low DAS28 scores, thus allowing for classification of subjects by disease activity.

Correlations of the DAI scores with DAS28 were r=0.75 to r=0.78, as estimated using 100 test set cross-validations. Specifically, the DAS28 correlation of the DAI score derived using the Lasso method was 0.776, the DAS28 correlation of the DAI score derived using the Elastic Net method was 0.762, and the DAS28 correlation of the DAI score derived using the forward variable selection method was 0.746. (Forward selection is a method of finding the "best" combination of variables by starting with a single variable, that which results in the best fit for the dependent variable Y, and increasing the number of variables used, step by step, testing all combinations of the original variable with the remaining variables in order to find the "best" pair of variables, continuing until either all variables are used up or some stopping criterion is met.)

These results show that the DAI scores derived using each of these modeling methods, and using different subsets of the protein biomarkers, all yield good correlation with DAS28 scores.

DAI scores can also be used to discriminate between subjects with high and low DAS28 scores, as demonstrated by the value of the area under the ROC curve, estimated using 100 cross-validation test sets. For subjects dichotomized on a DAS of 4.1, which is the median DAS value of this study, the area under the ROC curve for the DAI score derived using the Lasso method was 0.896. The area under the ROC curve for the DAI score derived using the Elastic Net method was 0.881. These results show that the DAI scores derived using each of these methods all yield good areas under the ROC curves for discriminating subjects with high and low DAS28 scores.

Example 8

Association of DAI Scores with DAS28 Scores by AUC is not Dependent on Subgroup

Example 8 demonstrates that the correlation of DAI scores with DAS by AUC, and thus the usefulness of DAI scores to classify subjects by disease activity, are not significantly affected by subject subgroupings, such as by CCP status, sex, age, etc.

The performance of the 10-marker DAI algorithm (described in Example 7) relative to DAS28-CRP was further evaluated in patient subgroups from the CAMERA cohort (see Example 7 for a description of the CAMERA study) defined by several major clinical variables; namely, sex, RF status, CCP status, and age. Table 10 presents the correlation and classification (AUC) results of this analysis.

TABLE 10

| | AUC | |
|---|---|---|
| Sex (M; F) | 0.828 | 0.849 |
| RF status (Neg; Pos) | 0.8 | 0.852 |
| CCP status (Neg; Pos) | 0.820 | 0.837 |
| Age (under 53; over 53) | 0.858 | 0.851 |

This analysis indicates that the capability of DAI scores to classify subjects by disease activity, as demonstrated by AUC values, are not significantly affected by the subject subgroupings of sex, RF status, CCP status, and age.

Example 9

Change in DAI Scores not Strictly Correlated with Single Biomarker Levels

Example 9 demonstrates that changes in subjects' disease activity, as evidenced by changes in their DAI or DAS scores between first and second clinical visits, do not strictly correlate with changes in the levels of the single biomarker CHI3L1. In other words, univariate analysis of the DAIMRK biomarker CHI3L1, which is positively weighted in an exemplary DAI algorithm (see, e.g., example 7), indicated that despite its positive weight, an increase in CHI3L1 level does not statistically correlate with an increase in disease activity, and vice versa.

The Index for Rheumatoid Arthritis Measurement (INFORM) study is a large multi-center observational study of the North American RA population. Patients were recruited between April and September 2009 from 25 sites in the U.S. and Canada. Inclusion criteria were: age>18 years with a diagnosis of RA made by a board-certified rheumatologist. Patients concurrently enrolled in a therapeutic drug trial involving a biologic agent and a placebo arm were excluded.

At their first study visit, 512 patients were selected for biomarker analysis. The average age of these patients was 58.9 years (range 20-91), and 76% were female. The mean SJC and TJC were 4.28 and 5.49, respectively. Of these 512 patients, 128 were tested for CHI3L1 at both the first and second study visits, which were separated by around 3 months. Of these patients, 53% had increased DAI values at the second visit. Among the patients with increased DAI values, 57% also demonstrated an increase in CHI3L1 values. See Table 11.

TABLE 11

| | No. patients DAI decreased/stayed same | No. patients DAI increased |
|---|---|---|
| No. patients CHI3L1 decrease/stayed same | 36 | 29 |
| No. patients CHI3L1 increased | 24 | 39 |

These results indicate that in the example of the DAIMRK biomarker CHI3L1, weighted positively in the DAI algorithm of Example 7, for example, an increase in CHI3L1 level does not necessarily correlate with an increase in RA disease activity, as measured by DAI, and vice versa.

The same holds true when the change in levels of CHI3L1 is compared to change in disease activity as measured by DAS. In a study of the INFORM cohort, 44% of the patients demonstrated an increase in DAS values in second visits, among which 43% demonstrated an increase in CHI3L1 values. See Table 12.

TABLE 12

| | No. patients DAS decreased/stayed same | No. patients DAS increased |
|---|---|---|
| No. patients CHI3L1 decreased/stayed same | 33 | 32 |
| No. patients CHI3L1 increased | 39 | 24 |

In another analysis, the change in CHI3L1 levels from the first to second visit was compared to DAI change, where the DAI change from visit 1 to visit 2 was at least by a magnitude of 10%. The results are shown in Table 13.

TABLE 13

| | No. patients DAI decreased by <=10% | No. patients DAI increased by >10% |
|---|---|---|
| No. patients CHI3L1 decreased/stayed same | 58 | 7 |
| No. patients CHI3L1 increased | 44 | 19 |

These results demonstrate that among patients demonstrating a DAI decrease of at least 10% in the subsequent visits, 43% of these demonstrated an increase in CHILI levels.

Changes in CHI3L1 levels were likewise analyzed against changes in DAS values, where DAS changed by at least 10%. Results from the INFORM study showed that among all patients where DAS increased by at least 10%, only 41% also showed an increase in CHI3L1 level. See Table 14.

TABLE 14

|  | No. patients DAS decreased by <=10% | No. patients DAS increased by >10% |
|---|---|---|
| No. patients CHI3L1 decreased/stayed same | 42 | 23 |
| No. patients CHI3L1 increased | 47 | 16 |

Taken together, these results demonstrate that in the example of the DAIMRK biomarker CHI3L1, weighted positively in the DAI algorithm of Example 7, for example, an increase in CHI3L1 level does not necessarily correlate with an increase in RA disease activity, as measured by DAI or by DAS, and vice versa.

Example 10

Performance of Univariate Models Across Various Cohorts

This example demonstrates that the predictive value univariate (single biomarker) models are weaker across various cohorts than are the multivariate models of the present teachings.

The ability of each single DAIMRK biomarker to predict disease activity was analyzed for the cohorts indicated in Table 15, and the correlation values obtained. (For a description of BRASS, see Example 1; for CAMERA, see Example 7; for INFORM, see Example 9).

TABLE 15

| DAIMRK | BRASS correlation | BRASS p-value | CAMERA correlation | CAMERA p-value | INFORM correlation | INFORM p-value |
|---|---|---|---|---|---|---|
| calprotectin | 0.42 | 0 | 0.557 | 0 | 0.251 | 0 |
| CCL22 | 0.167 | 0.034 | N/D* | N/D | 0.123 | 0.005 |
| CHI3L1 | 0.498 | 0 | 0.423 | 0 | 0.207 | 0 |
| CRP | 0.803 | 0 | 0.685 | 0 | 0.421 | 0 |
| EGF | −0.218 | 0.005 | N/D | N/D | N/D | N/D |
| ICAM1 | 0.366 | 0 | 0.23 | 0.012 | 0.186 | 0 |
| ICTP | N/D | N/D | N/D | N/D | 0.162 | 0 |
| IL1B | N/D | N/D | 0.454 | 0 | 0.161 | 0.001 |
| IL1RA | 0.31 | 0 | N/D | N/D | 0.183 | 0 |
| IL6 | 0.597 | 0 | 0.693 | 0 | 0.325 | 0 |
| IL6R | 0.224 | 0.004 | N/D | N/D | 0.132 | 0.003 |
| IL8 | N/D | N/D | 0.466 | 0 | 0.139 | 0.002 |
| LEP | 0.176 | 0.023 | N/D |  | 0.151 | 0.001 |
| MMP1 | 0.411 | 0 | 0.364 | 0 | 0.135 | 0.003 |
| MMP3 | 0.562 | 0 | 0.509 | 0 | 0.189 | 0 |
| pyridinoline | 0.379 | 0 | 0.228 | 0.013 | 0.115 | 0.01 |
| RETN | 0.236 | 0.002 | 0.219 | 0.016 | N/D | N/D |
| SAA1 | 0.746 | 0 | 0.658 | 0 | 0.318 | 0 |
| TNFRSF1A | 0.506 | 0 | 0.363 | 0 | 0.201 | 0 |
| VCAM1 | 0.291 | 0 | N/D | N/D | N/D | N/D |
| VEGFA | 0.43 | 0 | 0.293 | 0.001 | 0.17 | 0 |

*N/D: "Not Done"

As is evident from this table, these univariate markers cannot be used with consistency to predict disease activity across cohort populations. By comparison, the 10-marker panel of Example 7 demonstrated, in CAMERA, a correlation of 0.65 and an AUROC of 0.84; in BRASS, representative Lasso models achieved an average correlation of 0.76 and AUROC of 0.88; and, in INFORM, representative Lasso models in the 512 samples achieved an average correlation of 0.44 and AUROC of 0.67 in cross-validation.

Example 11

Alternative Modeling for Deriving DAI Score

This example demonstrates another, alternative method of deriving a Disease Activity Index score, based on a dataset of quantitative data for biomarkers. In this example, a DAI score is determined from the biomarker data using an interpretation function that is based on a set of predictive models, where each predictive model is predictive of a component of the DAS28-CRP, in this example TJC, SJC and patient global health assessment (GHA).

DAI Algorithm Development and Evaluation
Training Data

A DAI algorithm was trained using clinical and biomarker data for patients in the InFoRM and BRASS studies. The InFoRM study (Index For Rheumatoid Arthritis Measurement) is a multi-center observational study of the North American RA population. The patients used in algorithm training were recruited between April and September 2009 from 25 sites in the U.S. and Canada. Inclusion criteria were: age>18 years with a diagnosis of RA made by a board-certified rheumatologist. Patients concurrently enrolled in therapeutic drug trials involving a biologic agent and a placebo arm were excluded. The study includes three visits for each patient, each with clinical data and biological sample collection, at approximately three-month intervals.

BRASS is an observational study of approximately 1,000 RA patients receiving care at the RB Brigham Arthritis and Musculoskeletal Diseases Clinical Research Center, at the Brigham and Women's Hospital, Boston, Mass. Inclusion criteria were: age>18 years with a diagnosis of RA made by a board-certified rheumatologist. The study includes annual visits with clinical data and biological sample collection, and patient questionnaires between visits.

The first data set used in training consisted of visit 1 data for 512 InFoRM patients. The 512 patient visits were chosen to have clinical characteristics representative of the entire study population at the time of selection, and also to have been evaluated by a limited number of joint assessors. The number of joint assessors was limited to 12 so that assessor-specific biases could be evaluated and taken into account in algorithm development. The average age of these patients was 58.9 years (range 20-91), and 76% were female. The mean SJC and TJC were 4.28 and 5.49, respectively.

Assays for 25 candidate biomarkers were run on serum from the 512 InFoRM visits. Those biomarkers were SAA1, IL6, TNFRSF1A, VEGFA, PYD, MMP1, ICAM1, calprotectin, CHI3L1, MMP3, EGF, IL1RA, VCAM1, LEP, RETN, CRP, IL8, APOA1, APOC3, CCL22, IL1B, IL6R, IL18, keratan sulfate and ICTP. All the biomarker assays were run on the Meso Scale Discovery (MSD®) platform. See Example 1 for specifics of biomarker assay development and evaluation.

The biomarkers were prioritized based on (1) univariate association with disease activity, (2) contribution to multi-variate models for disease activity, and (3) assay performance.

The assays for 20 candidate biomarkers were run in a second set of patient samples, comprising 167 samples from BRASS and 29 from InFoRM. These 20 candidate biomarkers were SAA1, IL6, TNFRSF1A, VEGFA, PYD, MMP1, ICAM1, calprotectin, YKL40, MMP3, EGF, IL1RA, VCAM1, leptin, resistin, CRP, IL8, CCL22, IL1B and IL6R. The samples were selected to enrich the overall training data for extremes of disease activity, while also having good representation of patients with moderate disease activity. Enriching for extreme phenotypes can result in improved algorithm training, as long as the resulting training population still fully represents the types of patients on which the algorithm will used in independent validation and intended use populations. The 167 BRASS samples were intended to represent similar numbers of patients with low, moderate and high disease activity. The 29 InFoRM samples were selected to represent patients with high disease activity, since low and moderate activity patients were already well represented by the first 512 training samples.

Data Analysis

Prior to statistical analyses, all assay data were reviewed for pass/fail criteria on parameters including inter-assay CV, intra-assay CV, percent of samples within the measureable range of the calibration curve, and four serum process controls within the range of the calibration curve. The biomarker values that were not in the measureable range of the calibration curves were marked as missing data, and imputed with the lowest/highest detected value across all the samples within a given biomarker assay during the data export process. If the intra-assay CV of the biomarker concentration, computed from two replicates, was greater than 30%, it was also considered missing and excluded from univariate analyses. For multivariate analysis, individual biomarkers were excluded entirely if more than 20% of their data values were missing, and other missing data were imputed by the KNN algorithm (with k=5 nearest neighbors). In the data used for algorithm training, no biomarkers were excluded from multivariate analysis because they all had less than 20% missing values. Concentration values were transformed as x0.1 prior to further analysis in order to make the distribution of values for each biomarker more normal. This transformation has a similar effect to log transformation but avoids the generation of negative values. The transformed, imputed biomarker dataset is denoted as X_(n×m), where X is the protein data from n markers and m samples.

In univariate analysis, the Pearson correlations between the levels of each biomarker and disease activity measures including DAS28-CRP4, DAS28-ESR4, SJC, TJC, GHA, SDAI and CDAI were calculated.

In multivariate analysis, statistical models were developed by five different regression methods. In the first regression method (1), forward stepwise ordinary least square regression, the equation $Y=X\beta+\epsilon$ applies, where Y is the column vector with observed values, $\beta$ is the vector of coefficients, and $\epsilon$ is the residuals. The forward selection begins with no variables in the model. Then, given a collection of predictors X, the one having the largest absolute correlation with the response Y is selected and a simple linear regression of Y on X1 is performed. The residual vector is now orthogonal to X1, and is taken to be the new response variable. The other predictors are then projected orthogonally to X1 and the forward selection process is repeated.

In the second method (2), Lasso is used to prioritize biomarkers (based on $R^2$ values) and to obtain a Lasso model. The "lasso" in this model minimizes the residual sum of squares, subject to the sum of the absolute value of the coefficients being less than a constant. This method produces interpretable models and exhibits the stability of ridge regression. See R. Tibshirani, *J. Royal Stat. Soc. B* 1996, 58(1):267-288.

In the third method (3), the Elastic Net, mixtures of Lasso and ridge penalties are applied. It encourages a grouping effect, where strongly correlated predictors segregate together, either tending to be in or out of the model together. See T. Zou, *J. Royal Stat. Soc. B* 2005, 67(2):301-320. For each of the above three methods, the marker selected at each step is recorded.

The fourth method (4) is Multivariate Response with Curds and Whey (CW) using ordinary least squares (OLS). See L. Breiman and JH Friedman, *J. Royal. Stat. Soc. B* 1997, 59(1): 3-54. This method takes advantage of the correlations between the response variables (e.g., components of DAS) to improve predictive accuracy, compared with the usual procedure of performing an individual regression of each response variable on the common set of predictor variables X. In CW, $Y=XB^*S$, where $Y=(y_{kj})$ with k for the $k^{th}$ patient and j for $j^{th}$ response (j=1 for TJC, j=2 for SJC, etc.), B is obtained using OLS, and S is the shrinkage matrix computed from the canonical co-ordinate system. Hence, this approach will yield sub-models corresponding to each component of DAS.

The fifth method (5) is Curds and Whey and Lasso in combination (CW-Lasso). Instead of using OLS to obtain B as in CW, Lasso was used, and the parameters were adjusted accordingly for the Lasso approach.

The performance of the five regression methods was compared in 70/30 cross validation (repeatedly training in a randomly selected 70% of the data and testing in the remaining 30%). The number of markers in each regression model was chosen by using nested 10-fold cross-validation once the number of markers was selected for a given analysis method the best-fitting model of that size was used to represent the method. In the CW approaches (methods 4 and 5), nested 10 fold cross validation was used for each sub-model corresponding to each component of DAS. The models developed using the CW-Lasso method performed best overall. The following sections consist of results mainly using CW-Lasso approach.

The 20 candidate biomarkers examined in all training samples were prioritized according to a number of criteria, including: strength of association with disease activity and contribution to multivariate models; consistency of correlation with disease activity across feasibility and training data sets; CRP was excluded from any sub-models for TJC, SJC, and PGA both because it is included in the DAS28-CRP4 and because it did not increase sub-model prediction accuracy in independent test samples (CRP is used, however, in the final DAI score calculation as part of the DAI formula); robust assay performance (IL1B was excluded from final modeling because its concentrations too frequently fall below the limits of detection of immunoassays); known drug effects (IL6R was excluded from final modeling because it is known to be strongly affected by tocilizumab, independently of the effects of the drug on disease activity); and, stability (IL8 was excluded from final modeling because its measurable levels are known to rise dramatically when serum samples are not kept cold). These criteria led to 15 candidate biomarkers being considered for inclusion in the final algorithm. See Table 16.

TABLE 16

| Biomarker | Functional Category |
|---|---|
| calprotectin | cytokines and receptors |
| CHI3L1 | skeletal |
| EGF | growth factors |
| ICAM1 | adhesion molecules |
| IL1RA | cytokines and receptors |
| IL6 | cytokines and receptors |
| LEP | hormones |
| MMP1 | matrix metalloproteinases |
| MMP3 | matrix metalloproteinases |
| PYD | skeletal |
| RETN | hormones |

TABLE 16-continued

| Biomarker | Functional Category |
|---|---|
| SAA1 | acute phase response |
| TNFRSF1A | cytokines and receptors |
| VCAM1 | adhesion molecules |
| VEGFA | growth factors |

Training the Algorithm

While all data was used in prioritizing biomarkers, a subset was used for training the final algorithm. This subset was selected to have a broad range of disease activity levels, so that patients at all levels of disease activity were well represented. A comparison was made of the performance of models trained using: only BRASS samples (167 total); BRASS samples plus InFoRM samples (167+~100) selected to have a uniform disease activity distribution; or, BRASS samples plus InFoRM samples (167+~100) with a disease activity distribution like that of the BRASS samples.

The model performance was evaluated in an independent set of BRASS and InFoRM samples (70 total) set aside for this purpose. The DAS28-CRP distribution of this independent test set was similar to that of past studies (approximately normal). As shown below, correlation (r) to the DAS28-CRP and area under the ROC curve (AUROC) for predicting high and low DAS using median cut off were higher when training used BRASS samples plus "BRASS-like" InFoRM samples, although the differences were not statistically significant. The following Table 17 uses the Lasso regression method.

TABLE 17

| Training Set | r | AUROC |
|---|---|---|
| BRASS only | 0.53 | 0.68 |
| BRASS + Uniform InFoRM | 0.54 | 0.69 |
| BRASS + BRASS-like InFoRM | 0.55 | 0.71 |

For final training, the combination of BRASS plus "BRASS-like" InFoRM samples was selected. The CW-Lasso regression method was chosen for development of the final algorithm because of its superior performance in cross validation within the training set and in testing using InFoRM 512 patients and CAMERA patients (see below, DAI algorithm performance, for a description of algorithm testing in another cohort of samples). In the application of this method, the shrinkage matrix was applied to the predictions of TJC and SJC. Ten-fold cross-validation indicated that the following 13 markers were optimal for performance. See Table 18.

TABLE 18

| Marker | TJC | SJC | PGA |
|---|---|---|---|
| calprotectin | X | | |
| CHI3L1 | X | X | |
| EGF | X | X | X |
| IL6 | X | X | X |
| LEP | X | | X |
| MMP1 | | | X |
| MMP3 | | | X |
| PYD | X | X | |
| RETN | | | X |
| SAA1 | X | X | X |
| TNFRSF1A | X | | X |
| VCAM1 | X | | X |
| VEGF1 | X | | X |

From this set, PYD and calprotectin were excluded due to elevated assay failure rates. The remaining 11 biomarkers gave very similar algorithm performance to the full set of 13. An algorithm was chosen for validation that was developed by CW-Lasso regression using this 11-marker to estimate the DAS28-CRP in data from the BRASS+BRASS-like InFoRM samples. The estimates of TJC, SJC and PGHA were combined with a CRP test result in a formula similar to that used to calculate the DAS28-CRP.

$$DAS28CRP = 0.56\sqrt{TJC} + 0.28\sqrt{SJC} + 0.14\,PGHA + 0.36\log\left(\frac{CRP}{10^6} + 1\right) + 0.96$$

$$PDAS = 0.56\sqrt{IPTJC} + 0.28\sqrt{IPSJC} + 0.14\,PPGHA + 0.36\log\left(\frac{CRP}{10^6} + 1\right) + 0.96$$

Here IPTJC=Improved Prediction of TJC, IPSJC=Improved Prediction of SJC, PPGHA=Predicted PGHA, and PDAS is Predicted DAS28-CRP. (Details are defined below; see Selected algorithm.) The DAI score is the result from this formula.

Table 19 demonstrates the correlation of the values predicted by the PDAS algorithm with actual values for TJC, SJC, PGHA and DAS28-CRP, in the two cohorts studied, CAMERA and InFoRM.

TABLE 19

| Study | TJC | SJC | PGHA | DAS28-CRP |
|---|---|---|---|---|
| CAMERA | 0.445 | 0.536 | 0.427 | 0.726 |
| InFoRM (512 subjects) | 0.223 | 0.328 | 0.388 | 0.53 |

Selected Algorithm

The 11-marker+CRP Lasso model selected from the training process is as follows:

PTJC=−38.564+3.997*(SAA1)$^{1/10}$+17.331*(IL6)$^{1/10}$+ 4.665*(CHI3L1)$^{1/10}$−15.236*(EGF)$^{1/10}$+2.651* (TNFRSF1A)$^{1/10}$+2.641*(LEP)$^{1/10}$+4.026* (VEGFA)$^{1/10}$−1.47*(VCAM1)$^{1/10}$;

PSJC=−25.444+4.051*(SAA1)$^{1/10}$+16.154*(IL6)$^{1/10}$− 11.847*(EGF)$^{1/10}$+3.091*(CHI3L1)$^{1/10}$+0.353* (TNFRSF1A)$^{1/10}$;

PPGHA=−13.489+5.474*(IL6)$^{1/10}$+0.486* (SAA1)$^{1/10}$+2.246*(MMP1)$^{1/10}$+1.684* (leptin)$^{1/10}$+4.14*(TNFRSF1A)$^{1/10}$+2.292* (VEGFA)$^{1/10}$−1.898*(EGF)$^{1/10}$+0.028* (MMP3)$^{1/10}$−2.892*(VCAM1)$^{1/10}$−0.506* (RETN)$^{1/10}$;

IPTJC=max(0.1739*PTJC+0.7865*PSJC,0);

IPSJC=max(0.1734*PTJC+0.7839*PSJC,0);

DAI score=round(max(min((0.56*sqrt(IPTJC)+ 0.28*sqrt(IPSJC)+0.14*PPGA+0.36*ln(CRP/ 10$^6$+1))*10.53+1,100),1)).

For the final DA algorithm, the results from the 11-marker+ CRP CW-Lasso model were scaled and rounded to be integers on a scale of 1-100 such that a DAI score of 1 would be equivalent to a DAS28-CRP value of 0, and a DAI score of 100 would be equivalent to a DAS28-CRP value of 9.4.

Gene names in the above formulas correspond to serum protein concentrations, as obtained by the MSD® platform. Biomarker concentrations were obtained in the ranges shown in Table 20 (95% interval).

TABLE 20

| Biomarker | pg/ml Lower Limit | pg/ml Upper Limit |
|---|---|---|
| IL6 | 2.2 | 104 |
| EGF | 20 | 383 |
| VEGFA | 83 | 776 |
| LEP | 2,226 | 139,885 |
| SAA1 | 636,889 | 99,758,140 |
| VCAM1 | 354,026 | 1,054,681 |
| CRP | 245,332 | 76,399,801 |
| MMP1 | 3,047 | 39,373 |

TABLE 20-continued

| Biomarker | pg/ml Lower Limit | pg/ml Upper Limit |
|---|---|---|
| MMP3 | 9,203 | 134,262 |
| TNFRSF1A | 1,139 | 4,532 |
| RETN | 3,635 | 19,308 |
| CHI3L1 | 25,874 | 442,177 |

DAI Algorithm Performance

In order to independently test the performance of the algorithm developed above in this Example, a total of 120 serum samples were analyzed, obtained from the CAMERA study (see Example 7 for a description of the CAMERA study). Of these, 72 samples were taken from subject baseline visits, and 48 were from visits six months subsequent to baseline. The concentrations of 23 serum protein biomarkers were measured in each sample: APOA1, APOC3, calprotectin, CCL22, CHI3L1 (YKL40), CRP, EGF, ICAM1, IL18, IL1B, IL1RA, IL6, IL6R, IL8, LEP, MMP1, MMP3, PYD, RETN, SAA1, TNFRSF1A, VCAM1, and VEGFA. The concentrations of the markers were determined by customized immunoassays using either the Meso Scale Discovery SECTOR® Imager 6000 or individual ELISAs.

The associations between individual biomarkers and the clinical assessment measurements of DAS28-CRP, SJC28 and TJC28 were assessed by Pearson correlation (r) for log-transformed concentrations. The correlation p-values were adjusted for multiple hypothesis testing by estimating false discovery rates (FDR) using the method of Benjamini and Hochberg. See *J. Royal Stat. Soc. B* 1995 57(1):289-300.

Of the 23 proteins examined, fourteen were statistically significantly correlated with DAS28-CRP, eleven with SJC28 and nine with TJC28 (FDR <0.05). See Table 22, which shows the Pearson correlations (r) between individual biomarkers and each clinical disease activity measure. The q-values reflect the FDRs, and were calculated by adjusting the p-values for multiple hypothesis testing. Statistically significant associations (q<0.05) are in bold. As Table 21 shows, the individual biomarkers associated with disease activity represented a range of pathways associated with RA disease pathophysiology (Functional Category).

TABLE 21

| Biomarker | Functional Category | DAS28-CRP r | DAS28-CRP q-val | SJC28 r | SJC28 q-val | TJC28 r | TJC28 q-val |
|---|---|---|---|---|---|---|---|
| calprotectin | cytokines and receptors | 0.56 | <0.01 | 0.38 | <0.01 | 0.33 | <0.01 |
| CHI3L1 | Skeletal | 0.42 | <0.01 | 0.35 | <0.01 | 0.30 | <0.01 |
| CCL22 | cytokines and receptors | −0.04 | 0.75 | −0.13 | 0.19 | −0.03 | 0.73 |
| CRP | acute phase response | 0.69 | <0.01 | 0.41 | <0.01 | 0.36 | <0.01 |
| EGF | growth factors | −0.07 | 0.46 | −0.08 | 0.42 | −0.12 | 0.28 |
| ICAM1 | adhesion molecules | 0.23 | 0.02 | 0.13 | 0.20 | 0.08 | 0.44 |
| IL1B | cytokines and receptors | 0.45 | <0.01 | 0.34 | <0.01 | 0.31 | <0.01 |
| IL6 | cytokines and receptors | 0.69 | <0.01 | 0.50 | <0.01 | 0.41 | <0.01 |
| IL6R | cytokines and receptors | 0.01 | 0.97 | 0.03 | 0.71 | 0.02 | 0.89 |
| IL8 | cytokines and receptors | 0.47 | <0.01 | 0.46 | <0.01 | 0.30 | <0.01 |
| IL1RA | cytokines and receptors | 0.01 | 0.97 | 0.05 | 0.58 | −0.09 | 0.44 |
| LEP | hormones | 0.00 | 0.97 | −0.07 | 0.53 | −0.06 | 0.56 |
| MMP1 | MMPs | 0.36 | <0.01 | 0.29 | <0.01 | 0.19 | 0.06 |
| MMP3 | MMPs | 0.51 | <0.01 | 0.40 | <0.01 | 0.26 | <0.01 |
| PYD | skeletal | 0.23 | 0.04 | 0.29 | <0.01 | 0.21 | 0.09 |
| RETN | hormones | 0.22 | 0.03 | 0.13 | 0.20 | 0.13 | 0.28 |
| SAA1 | acute phase response | 0.66 | <0.01 | 0.43 | <0.01 | 0.37 | <0.01 |
| TNFRSF1A | cytokines and receptors | 0.36 | <0.01 | 0.30 | <0.01 | 0.24 | 0.02 |
| VCAM1 | adhesion molecules | 0.13 | 0.24 | 0.14 | 0.20 | 0.08 | 0.56 |
| VEGFA | growth factors | 0.29 | <0.01 | 0.18 | 0.12 | 0.07 | 0.56 |

Two pre-specified algorithms, a prototype and a final algorithm, using subsets of these 23 biomarkers were applied to calculate a total DAI score for each subject at each visit (baseline and six-month). These algorithms were trained in prior studies using independent samples from other clinical cohorts. Algorithm performance was evaluated by Pearson correlation (r) and area under the ROC curve (AUROC) for identifying high and low disease activity at the baseline and six-month visits. The reference classification for ROC analysis was based on a DAS28-CRP of 2.67, the threshold separating remission/low disease activity from moderate and high disease activity.

Prototype Algorithm for Multivariate Model

The first algorithm, or "prototype algorithm," using a linear combination of protein biomarkers, was trained on subject samples to estimate the DAS28 directly and was provided by the formula described elsewhere herein according to:

$$DAI = b_0 + b_1 * DAIMRK_1^x - b_2 * DAIMRK_2^x - b_3 * DAIMRK_3^x \ldots - b_n * DAIMRK_n^x;$$

where DAI is the DAI score, $b_{0-n}$ are constants, and $DAIMRK_{1-n}^x$ are the serum concentrations, transformed to the $x^{th}$ power, of n different biomarkers selected from the DAIMRK panel.

The prototype algorithm used in this Example was:

$$DAI = (-16.1564) - (0.0606 * Calprotectin^{1/10}) + (0.2194 * CHI3L1^{1/10}) + (1.1886 * ICAM1^{1/10}) + (2.7738 * IL6^{1/10}) + (0.7254 * MMP1^{1/10}) - (0.8348 * MMP3^{1/10}) + (1.0296 * PYD^{1/10}) + (1.1792 * SAA1^{1/10}) + (2.4422 * TNFRSF1A^{1/10}) + (0.3272 * VEGFA^{1/10}).$$

The prototype algorithm achieved a Pearson correlation (r) of 0.65 and an AUROC of 0.84 relative to the DAS28-CRP.

Biomarker Selection for Final Algorithm

The second algorithm was derived using serum biomarker concentrations to separately estimate the three clinical assessments of TJC28, SJC28 and PGHA. Note that all of these are components of the formula used in calculating DAS28-CRP:

$$DAS28\text{-}CRP = 0.56 * sqrt(TJC28) + 0.28 * sqrt(SJC28) + 0.36 * ln(CRP+1) + (0.014 * PGHA) + 0.96.$$

Figure 22:
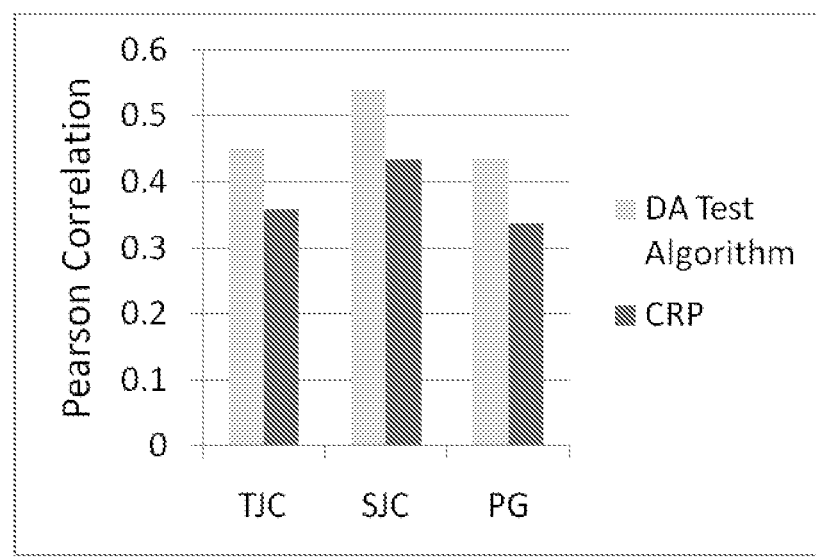
FIG. 22 depicts correlations of the DAI algorithm predictions and CRP with clinical assessments of disease activity, as described in Example 11.

Biomarkers were then selected to predict and estimate clinical assessments of disease activity, specifically PGHA, TJC28 and SJC28. The resulting estimates were combined with a serum CRP concentration measurement to calculate an overall DAI score. See FIG. 22, which indicates the three panels of biomarkers predictive of clinical disease activity measurements, the union thereof, and CRP. The CW-Lasso method was used to predict the individual components of the DAS28; i.e., TJC28, SJC28 and PGHA. Note that biomarker terms are included in the CW-Lasso if they help to improve cross-validated model performance, and this criterion does not imply that each term is statistically significant by univariate analysis. A biomarker could make a significant contribution to a multivariate model even if it does not have a significant univariate correlation, and could not make a significant contribution to a multivariate model even though it has a significant univariate correlation. Indeed, a comparison of each algorithm predictive for a clinical assessment, (a)-(c) above, with the biomarkers of Table 18 shows that not all biomarkers in each algorithm were individually statistically correlated with that clinical assessment. For example, values for serum concentrations of EGF, LEP, VEGFA and VCAM1 are all included in the algorithm for predicting TJC28, yet each of these markers individually demonstrated a q-value for correlation with TJC of ≥0.28. Including these markers, however, improves multivariate model performance in independent cross-validation test sets.

The overall DAI score derived according to the methods of the present Example was given as a whole number between 1 and 100. The formula used to derive this score was provided by:

$$DAI\ Score = ((0.56 * sqrt(PTJC) + 0.28 * sqrt(PSJC) + 0.36 * log(CRP/10^6 + 1) + (0.14 * PPGHA) + 0.96) * 10.53) + 1,$$

where PTJC=predicted TJC28, PSJC=predicted SJC28, and PPGHA=predicted PGA. Unlike other formulas to derive DAI scores described herein, in the formula of this Example the measurements of individual biomarkers were weighted based on information such as that depicted in FIG. 22, and removing redundancy of biomarkers, so as to derive the best prediction of and correlation with particular clinical disease activity measurements (TJC28, SJC28, PGHA). This resulted in the inclusion of data from the following set of biomarkers: SAA1, IL6, CHI3L1, EGF, TNFRSF1A, LEP, VEGFA and VCAM1 for PTJC; SAA1, IL6, EGF, CHI3L1 and TNFRSF1A for PSJC; SAA1, MMP1, LEP, TNFRSF1A, VEGFA, EGF, MMP3, VCAM1 and RETN for PPGHA; plus CRP. In total, therefore, data from the following set of 12 markers was used to derive a DAI score: CHI3L1, CRP, EGF, IL6, LEP, MMP1, MMP3, RETN, SAA1, TNFRSF1A, VCAM1 and VEGFA. The predicted clinical assessments of disease activity were developed according to the following formulas:

$$PTJC = -38.564 + (3.997 * SAA1^{1/10}) + (17.331 * IL6^{1/10}) + (4.665 * CHI3L1^{1/10}) - (15.236 * EGF^{1/10}) + (2.651 *^{1/10}) + (2.641 * LEP^{1/10}) + (4.026 * VEGFA^{1/10}) - (1.47 * VCAM1^{1/10}); \quad (a)$$

$$PSJC = -25.444 + (4.051 * SAA1^{1/10}) + (16.154 * IL6^{1/10}) - (11.847 * EGF^{1/10}) + (3.091 * CHI3L1^{1/10}) + (0.353 * TNFRSF1A^{1/10}); \quad (b)$$

and, $$PPGHA = -13.489 + (5.474 * IL6^{1/10}) + (0.486 * SAA1^{1/10}) + (2.246 * MMP1^{1/10}) + (1.684 * LEP^{1/10}) + (4.14 * TNFRSF1A^{1/10}) + (2.292 * VEGFA^{1/10}) - (1.898 * EGF^{1/10}) + (0.028 * MMP3^{1/10}) - (2.892 * VCAM1^{1/10}) - (0.506 * RETN^{1/10}). \quad (c)$$

The performance of the above algorithm in deriving a DAI score was evaluated by Pearson correlation (r) and area under the ROC curve (AUROC) for identifying high and low disease activity at the baseline and six-month visits. The Pearson correlation was 0.73, and the AUROC was 0.87, with the reference classification for ROC analysis based on a threshold DAS28-CRP of 2.67, the threshold separating remission/low disease activity from moderate and high disease activity. The changes in biomarker-based DAI scores between the baseline and six-month visits were assessed by the paired Wilcoxon rank sum test.

To ensure that performance of the second algorithm was not overestimated due to the inclusion of two samples for some patients, subsets of samples were also analyzed that included only one randomly selected visit for each subject. The algorithm performed equally well in these subsets. Possible bias in the AUROC due to an imbalance in numbers between low and high disease activity groups was also analyzed using a DAS28-CRP cutoff of 2.67. When the cutoff was set at the median DAS28-CRP of 4.6, the AUROC was 0.83.

Figure 23:
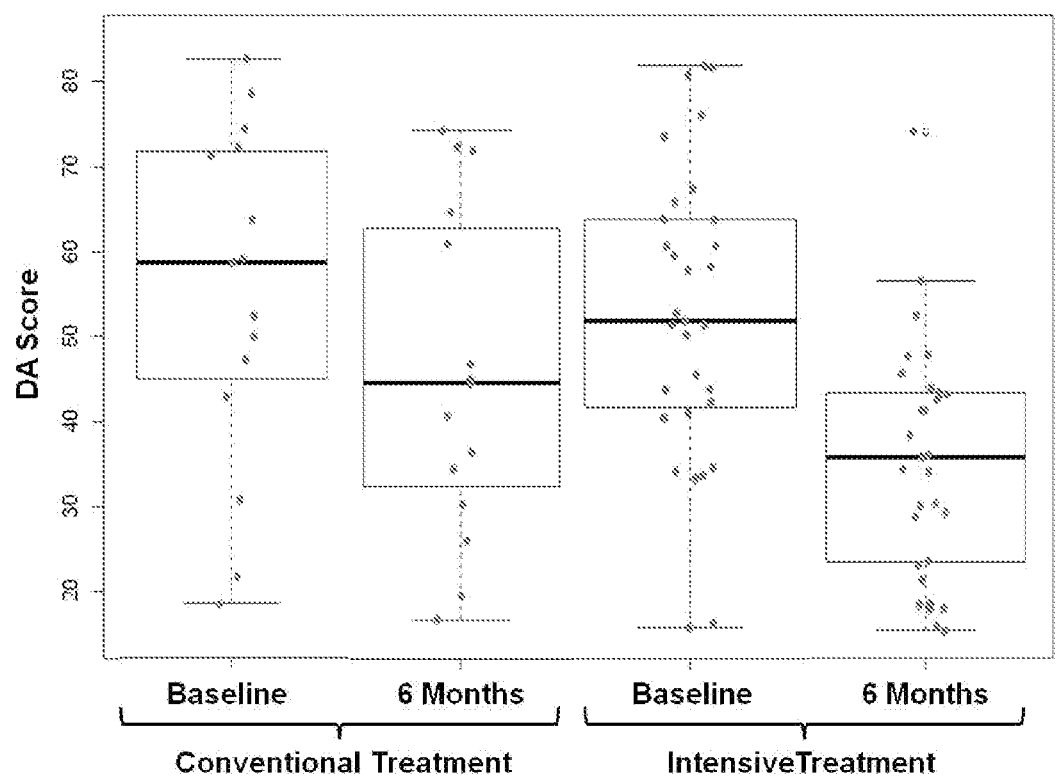
FIG. 23 depicts the DAI scores for subjects at baseline and six-month visits, according to the description in Example 11. DAI scores are shown by treatment arm and time point. Only subjects with DAI scores available at both baseline and six months are shown.

When the predictions of the individual components of the DAS28 generated by the DAI algorithm were correlated to the actual TJC28, SJC28 and PGHA, the correlation coefficients were seen to trend higher (and thus provide better correlation with clinical disease activity measurements) than the coefficients for CRP, a marker commonly used alone as an indicator of RA disease activity. See FIG. 23.

An analysis was then done to determine whether the DAI score changed in response to the treatment protocols used in the CAMERA study. For all subjects for whom DAI Scores were available for both visits (baseline and six-month), the median score dropped from 52 to 37 (p=2.2E-6; n=46). See FIG. 24. The intensive and conventional treatment arms were considered separately. There was also a significant decrease in median DAI Score in the intensive treatment arm, from 52 to 36 (p=2.5E-5; n=31). In the conventional treatment arm, the median DAI Score decreased from 59 to 45 (p=0.06; n=15).

In conclusion, this Example demonstrates that serum protein biomarkers representing a variety of biological pathways were consistently associated with RA disease activity. A pre-specified DAI algorithm combining information from several of these biomarkers performed well in predicting RA disease activity when evaluated in an independent test set. The algorithm's estimates of TJC, SJC and PGHA correlated to actual clinical measures of disease activity. Furthermore, subsequent DAI scores of the subjects analyzed decreased compared to initial DAI scores following and in response to treatment.

Example 12

Use of DAI to Predict Joint Damage Progression

Example 12 demonstrates the use of the DAI score to predict joint damage progression in RA subjects. In this Example serum samples were analyzed from 89 subject participants in the BeSt (Dutch, "Behandelstrategieen") study. The BeSt study is a multicenter, randomized, controlled study designed to compare the clinical efficacy and radiologic outcomes of four different treatment strategies in patients with early onset RA. See Y P Goekoop-Ruiterman et al., *Arth. Rheum.* 2005, 52:3381-3390. Serum biomarkers were evaluated in serum collected at year 1. Total Van der Heijde modified Sharp scores (TSS) from year 1 and year 2 were used.

The DAI score at year 1 was evaluated for its ability to predict the change in TSS from year 1 to year 2. Identifying patients at risk of increase in TSS is a clinical question of great importance. The DAI score was correlated with change in TSS($P<0.001$). See Table 22. Moreover, the observed correlation coefficient for DAI score was greater than for any clinical variable examined except year 1 TSS. Since TSS is only evaluated in clinical trials and not available in routine clinical practice, this suggests that the DAI score has the potential to outperform conventional clinical variables at predicting progressive joint damage. DAI score also had a higher observed area under the receiver operating characteristic curve for identifying patients with increases in TSS than other clinical variables except year 1 TSS.

TABLE 22

|  | P value | Correlation | AUROC |
| --- | --- | --- | --- |
| TSS | <0.001 | 0.541 | 0.765 |
| DAI | <0.001 | 0.435 | 0.686 |
| CRP | <0.001 | 0.366 | 0.64 |
| ESR | 0.027 | 0.216 | 0.527 |
| DAS-ESR | 0.001 | 0.33 | 0.567 |
| DAS-CRP | 0.001 | 0.351 | 0.595 |
| TJC28 | 0.012 | 0.252 | 0.492 |
| SJC28 | 0.003 | 0.3 | 0.653 |
| RAI | 0.164 | 0.11 | 0.485 |
| SJC44 | 0.106 | 0.14 | 0.56 |
| VAS | 0.06 | 0.174 | 0.554 |

Example 13

DAI Score Unaffected by Comorbidities 512 subjects were selected from the InFoRM cohort, to be representative of the entire cohort in age, sex, DAS28CRP (DAS28) and disease duration. The ratios in the median CRP, CDAI, DAS28 and DAI in patients with co-morbidities were compared to patients without the co-morbidity to assess the robustness of the DAI. To calculate the DAI, the concentrations of IL-6, EGF, VEGF-A, Leptin, SAA, CRP, VCAM-1, MMP-1, MMP-3, Resistin, YKL-40, and TNF-RI were measured using multiplex immunoassays and combined in the algorithm identified in Example 11. Co-morbidities of interest included hypertension, osteoarthritis, prior fracture, diabetes, psychiatric illness, peptic ulcer, Sjogren's syndrome, fibromyalgia, COPD, and asthma. The significance of differences was determined by Wilcoxon rank sum test with a multiple testing correction applied. The multiple testing correction is described in Benjamini and Hochberg. *J. Royal Stat. Soc. B* 1995 57(1):289-300. Results are reported as the ratio of the median value of the measure (e.g. CDAI) among people with the condition compared to those without the condition.

The results showed that several co-morbidities were associated with differences, mostly increases, in median disease activity measures. Comparing people with each comorbidity to those without the comorbidity, the ratios in the median scores were generally larger for CRP [range 0.8-2.1] and CDAI [range 1.0-1.8] than for DAS28 [range 1.0-1.4] and DAI [range 1.0-1.2]. Across the 4 outcome measures, the greatest number of significant differences in median scores was seen in patients with fibromyalgia, psychiatric illness, Sjogren's, and hypertension (Table 1). The DAI was not significantly different in males versus females (median: 41.7 vs. 42.3, p-value: 0.46) or in current smokers versus non-smokers (median: 38.5 vs. 42.7, p-value: 0.13). The score did vary significantly with BMI: median DAI score for subjects with BMI ≤30 was 38.7, while the median for subjects with a BMI >30 was 46.3.

TABLE 23

Ratios in Disease Activity Measure's Median Value

| Subgroup | N (%) | CRP | CDAI | DAS28 | DAI |
| --- | --- | --- | --- | --- | --- |
| Fibromyalgia | 33 (6) | 1.6* | 1.6* | 1.3* | 1.1 |
| Psychiatric illness | 24 (5) | 1.7 | 1.7* | 1.4* | 1.1 |
| Sjogren's | 20 (4) | 1.0 | 1.8* | 1.3* | 1.1 |
| Hypertension | 223 (44) | 1.0 | 1.3* | 1.1* | 1.1 |
| Peptic Ulcer | 19 (4) | 0.8 | 1.5* | 1.2 | 1.0 |
| Osteoarthritis | 173 (34) | 1.0 | 1.2 | 1.1 | 1.0 |
| Osteoporotic bone fracture | 131 (26) | 0.9 | 1.0 | 1.0 | 1.0 |
| Diabetes | 72 (14) | 0.9 | 1.1 | 1.1 | 1.1 |
| Asthma | 50 (10) | 1.5 | 1.2 | 1.1 | 1.1 |
| COPD | 20 (4) | 2.1 | 1.1 | 1.0 | 1.2 |

A value of 1.0 implies that there is no difference in the median value of the measure for people with versus those without the comorbidity
*Significant difference from the population without the co-morbidity, False Discovery Rate <10%.

In conclusion, DAI has been validated to assess and monitor rheumatoid arthritis ("RA") disease activity. When assessing the RA disease activity of patients with common co-morbidities, the DAI appears to be less confounded by the presence of co-morbidities than the other measures tested. This may be due to its inclusion of multiple biomarkers representing biologic pathways in RA.

Example 14

DAI Score to Measure Disease Activity in Undifferentiated Arthritis

It has been shown that DAS is a valid measure of disease activity in undifferentiated arthritis ("UA"). See Fransen, J. et al. *Arthritis Care and Research,* 62(10):1392-8, 2010. Thus, the model in example 11, which estimates the DAS, calculates a DAI score which is a measure of UA disease activity. Alternatively a model similar to that in example 11 is trained such that the DAI score is a measure of UA disease activity.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the invention as defined in the appended claims.

The invention claimed is:

1. A method for generating quantitative data for a first subject comprising:
performing at least one immunoassay on a first sample from the first subject to generate a first dataset comprising the quantitative data, wherein the quantitative data represents at least twelve protein markers comprising: chitinase 3-like 1 (cartilage glycoprotein-39) (CHI3L1); C-reactive protein, pentraxin-related (CRP); epidermal growth factor (beta-urogastrone) (EGF); interleukin 6 (interferon, beta 2) (IL6); leptin (LEP); matrix metallopeptidase 1 (interstitial collagenase) (MMP1); matrix metallopeptidase 3 (stromelysin 1, progelatinase) (MMP3); resistin (RETN); serum amyloid A1 (SAA1); tumor necrosis factor receptor superfamily, member 1A (TNFRSF1A); vascular cell adhesion molecule 1 (VCAM1); and, vascular endothelial growth factor A (VEGFA); and
wherein the first subject has rheumatoid arthritis (RA) or is suspected of having RA.

2. The method of claim 1, wherein the at least twelve protein markers consist of: IL6, EGF, VEGFA, LEP, SAA1, VCAM1, CRP, MMP1, MMP3, TNFRSF1A, RETN, and CHI3L1.

3. The method of claim 1, wherein performance of the at least one immunoassay comprises:
obtaining the first sample, wherein the first sample comprises the protein markers;

contacting the first sample with a plurality of distinct reagents;

generating a plurality of distinct complexes between the reagents and markers; and detecting the complexes to generate the data.

4. The method of claim 1, wherein the at least one immunoassay comprises a multiplex assay.

* * * * *

UNITED STATES PATENT AND TRADEMARK OFFICE
CERTIFICATE OF CORRECTION

| | | |
|---|---|---|
| PATENT NO. | : 9,200,324 B2 | Page 1 of 1 |
| APPLICATION NO. | : 12/905984 | |
| DATED | : December 1, 2015 | |
| INVENTOR(S) | : Cavet et al. | |

It is certified that error appears in the above-identified patent and that said Letters Patent is hereby corrected as shown below:

ON THE TITLE PAGE ITEM 56 SHOULD READ

Afuwape et al. (Histol. Hisopathol. (2002) vol. 17, pp. 961-972.

Signed and Sealed this
Eighth Day of March, 2016

Michelle K. Lee
*Director of the United States Patent and Trademark Office*